(12) United States Patent
Patel et al.

(10) Patent No.: US 8,785,425 B2
(45) Date of Patent: Jul. 22, 2014

(54) 11β-HYDROXYANDROSTA-4-ENE-3-ONES

(75) Inventors: Jiten Ranchhodbhai Patel, Baroda (IN); Gopalkumar Chimanlal Patel, Baroda (IN); Gaurav Sanjivkumar Sheth, Baroda (IN); Samir Rameshchandra Shah, Baroda (IN); Sanjay Nandlal Mandhane, Baroda (IN); Trinadha Rao Chitturi, Baroda (IN); Rajamannar Thennati, Baroda (IN)

(73) Assignee: Sun Pharma Advanced Research Company Ltd., Andheri (E), Mumbai ( * ) Notice: Subject to any disclaimer, the term of this patent is extended or adjusted under 35 U.S.C. 154(b) by 1101 days.

(21) Appl. No.: 12/180,257

(22) Filed: Jul. 25, 2008

(65) Prior Publication Data
US 2009/0054388 A1 Feb. 26, 2009

Related U.S. Application Data

(63) Continuation of application No. PCT/IN2007/000039, filed on Jan. 29, 2007.

(30) Foreign Application Priority Data

Jan. 27, 2006 (IN) .................. 131MUM06

(51) Int. Cl.
C07J 3/00 (2006.01)
A61K 31/56 (2006.01)

(52) U.S. Cl.
USPC ........... 514/179; 514/172; 514/174; 514/175; 514/178; 552/610; 540/2; 540/114; 540/115

(58) Field of Classification Search
USPC ............... 552/610; 540/2, 114, 115; 514/172, 514/174, 175, 178
See application file for complete search history.

(56) References Cited

U.S. PATENT DOCUMENTS

| | | | |
|---|---|---|---|
| 3,007,923 A | | 11/1961 | Muller et al. |
| 3,929,768 A | | 12/1975 | Brattsand et al. |
| 4,335,121 A | | 6/1982 | Phillipps et al. |
| 4,472,393 A | | 9/1984 | Shapiro |
| 4,996,335 A | * | 2/1991 | Bodor .......................... 552/610 |
| 6,197,761 B1 | * | 3/2001 | Biggadike et al. ............. 514/174 |
| 6,610,675 B1 | * | 8/2003 | Bodor .......................... 514/178 |
| 7,208,613 B2 | * | 4/2007 | Jadav et al. ................... 552/610 |
| 7,405,206 B2 | * | 7/2008 | Biggadike et al. ............. 514/172 |

FOREIGN PATENT DOCUMENTS

| | | |
|---|---|---|
| WO | WO-9901467 A2 | 1/1999 |
| WO | WO-2004001369 A2 | 12/2003 |
| WO | WO-2004039827 A2 | 5/2004 |
| WO | WO-2007099548 A2 | 9/2007 |

* cited by examiner

Primary Examiner — Sabiha N Qazi
(74) Attorney, Agent, or Firm — Schwegman Lundberg & Woessner, P.A.

(57) ABSTRACT

The invention provides 11β-hydroxyandrosta-4-ene-3-one compounds of Formula I, or physiologically acceptable salts or solvates thereof:

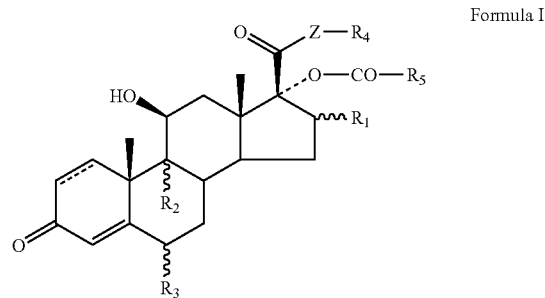

Formula I wherein $R^4$ represents a moiety selected from a group consisting of (A), (B) and (C), with a proviso that when $R^4$ represents moiety (C), Z is S:

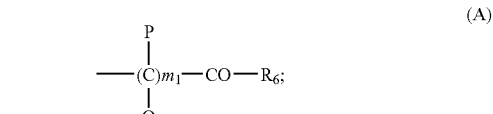

(A)

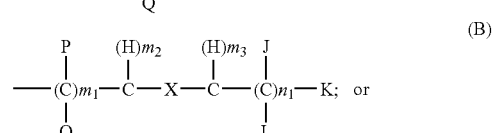

(B)

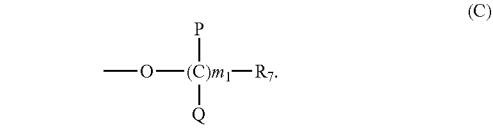

(C)

14 Claims, No Drawings

11β-HYDROXYANDROSTA-4-ENE-3-ONES

RELATED APPLICATIONS

This application is a continuation under 35 U.S.C. 111(a) of International Application No. PCT/IN2007/000039 filed Jan. 29, 2007 and published in English as WO 2007/099548 on Sep. 7, 2007, which claimed priority from Indian National Application Serial No. 131/MUM/06 filed Jan. 27, 2006, which applications and publication are incorporated herein by reference.

FIELD OF THE INVENTION

The invention relates to novel anti-inflammatory and anti-allergic analogues of the 11β-hydroxyandrosta-4-ene-3-ones, including compounds of formula I having insignificant or no noteworthy systemic effects at multiples of an efficacious dose.

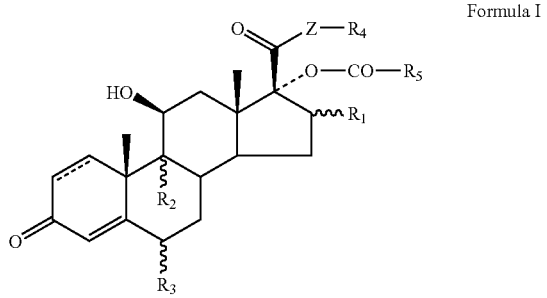

Formula I

BACKGROUND OF THE INVENTION

Corticosteroids (or glucocorticoids) having anti-inflammatory properties are widely used for the treatment of inflammatory conditions or disorders of skin, airways, eye, GI tract, joints, CNS etc., and several autoimmune disorders. Some of the inflammatory skin disorders where treatment with glucocorticoids is prescribed are eczema, psoriasis, allergic dermatitis, pruritis, hypersensitivity reactions etc. Inflammatory or allergic conditions of the airways for which glucocorticoids are used include disorders of nose, throat or lungs such as rhinitis (including hay fever), nasal polyps, asthma (including allergen-induced asthmatic reaction), chronic obstructive pulmonary disease, interstitial lung disease, fibrosis, etc. Glucocorticoid administration is also used for inflammatory bowel disorders such as ulcerative colitis and Crohn's diseases; and inflammatory joint disorders such as rheumatoid arthritis which are autoimmune diseases.

However, administration of corticosteroids in general may cause, in addition to the desired pharmacological effect, undesirable or adverse side effects at sites distant from the target tissue, the so-called systemic effects. Some of the undesired systemic effects encountered include widespread immunosuppression, increased bone turnover, impaired growth, skin thinning, diabetes, obesity, water retention, and progesterone and estrogen related disorders. It is therefore desirable to have glucocorticoids that possess potent anti-inflammatory activity at the target tissue, with minimal or no systemic activity at therapeutic doses when used for chronic treatment.

Classical glucocorticoids are described in U.S. Pat. No. 4,335,121 (e.g., (S)-fluoromethyl 6α,9α-difluoro-11β-hydroxy-16α-methyl-17α-propionyloxy-3-oxoandrosta-1,4-diene-17β-carbothioate (Fluticasone)); U.S. Pat. No. 3,007,923 (e.g., 16α-methyl-9α-fluoro-1,4-pregnadiene-11β,17α,21-triol-3,20-dione (Dexamethasone)); U.S. Pat. No. 3,929,768 (e.g., (11β,16α)-16,17-[Butylidenebis(oxy)]-11,21-dihydroxypregna-1,4-diene-3,20-dione (Budesonide)); and U.S. Pat. No. 4,472,393 (e.g., (11β,16α)-9,21-Dichloro-17-[(2-furanylcarbonyl)oxy]-11-hydroxy-16-methylpregna-1,4-diene-3,20-dione (Mometasone furoate)). These drugs are potent glucocorticoids that are already in clinical use. However, at high multiples of efficacy dose these drugs have the potential to cause adverse systemic side effects.

PCT publication WO 99/01467 describes therapeutically active steroidal compounds or salts or solvates having lactone group connected to the cyclopentane ring of the steroid nucleus (as given below).

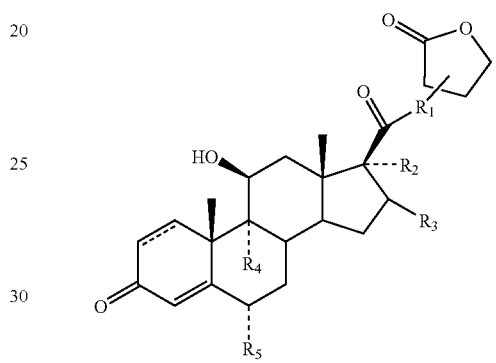

These compounds have been described to have reduced potential for systemic activity due to the relative instability of the lactone system in plasma. The compounds of the present invention do not possess a lactone group connected to the cyclopentane ring.

DESCRIPTION OF THE INVENTION

Our interest to develop compounds that act at the specific site of inflammation with insignificant or no noteworthy side effects has led us to the discovery of novel, safe 11β-hydroxyandrosta-4-ene-3-one compounds described in this disclosure. These compounds possess useful anti-inflammatory activity whilst having insignificant or no noteworthy systemic effects at multiples of an efficacious dose.

The present invention provides 11β-hydroxyandrosta-4-ene-3-one compounds of formula I, and physiologically acceptable salts and solvates thereof:

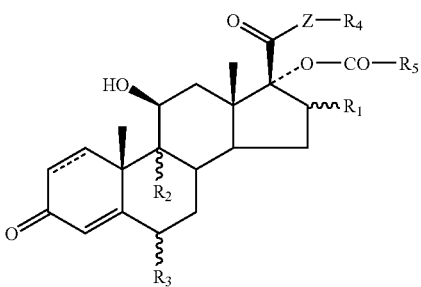

wherein

═══ represents a single or double bond;

∼∼∼ represents either the α or β-configuration;

Z represents O or S;

$R_1$ represents hydrogen or methyl which may be either in α or β-configuration, or methylene;

$R_2$ and $R_3$ are the same or different and each independently represents hydrogen, halogen or a methyl group;

$R_5$ represents a group selected from $(C_1-C_{10})$-alkyl, $(C_3-C_{13})$-cycloalkyl, —O—$(C_1-C_{10})$-alkyl, aryl or heterocyclic ring, wherein the ring or ring system is unsubstituted or substituted by one or more (e.g., 1, 2, 3, 4, or 5) halogen, —OH, $(C_1-C_3)$-alkyl, —O—$(C_1-C_3)$-alkyl, or $(C_3-C_{13})$-cycloalkyl; wherein the alkyl or cycloalkyl groups can optionally contain one or more (e.g., 1, 2, 3, 4, or 5) unsaturations and/or can have one or more (e.g., 1, 2, 3, 4, or 5) hetero atoms incorporated therein, and optionally in each case have one or more (e.g., 1, 2, 3, 4, or 5) hydrogen atoms replaced by halogen, —OH, $(C_1-C_3)$-alkyl, —O—$(C_1-C_3)$-alkyl, $(C_3-C_{13})$-cycloalkyl;

$R_4$ represents a moiety selected from the group consisting of (A), (B) and (C), with a proviso that when $R_4$ represents moiety (C), Z is S:

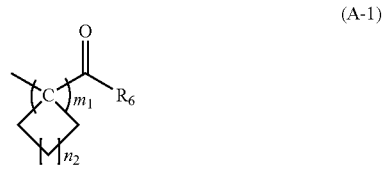

(A)

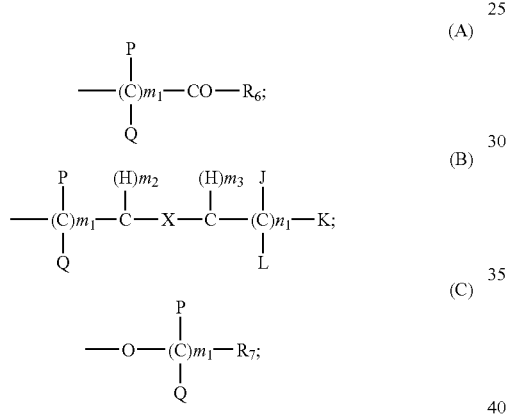

(B)

(C)

wherein $m_1$ is 1, 2 or 3;

$m_2$ is 0 or 1;

$m_3$ is 0 or 1;

$n_1$ is 0, 1 or 2;

$R_6$ represents a group selected from $(C_1-C_8)$-alkyl, $(C_3-C_{13})$-cycloalkyl, aryl and a heterocyclic radical, where the ring or ring system is unsubstituted or substituted by one or more (e.g., 1, 2, 3, 4, or 5) substituents selected from $(C_1-C_8)$-alkyl, $(C_3-C_{13})$-cycloalkyl, halogen, O—$(C_1-C_8)$-alkyl, O—$(C_3-C_{13})$-cycloalkyl, OCO—$(C_1-C_3)$-alkyl, $S(O)_{0-2}(C_1-C_8)$-alkyl, COO—$(C_1-C_8)$-alkyl, —OCO—O—$(C_1-C_3)$-alkyl, —OCO—CO—O—$(C_1-C_3)$-alkyl, $CONH_2$, CONH—$(C_1-C_8)$-alkyl, CON—$[(C_1-C_8)$-alkyl$]_2$, —NHCO—$(C_1-C_8)$-alkyl, N—$(C_1-C_8)$-alkyl-CO—$(C_1-C_8)$-alkyl, —NHCO—O—$(C_1-C_8)$-alkyl, —N—$(C_1-C_8)$-alkyl-CO—O—$(C_1-C_8)$-alkyl, —NHCONH—$(C_1-C_8)$-alkyl, —N—$(C_1-C_8)$-alkyl-CONH—$(C_1-C_8)$-alkyl, —NHCONH—$SO_2$—$(C_1-C_8)$-alkyl, —N—$(C_1-C_8)$-alkyl-CONH—$SO_2$—$(C_1-C_8)$-alkyl, $—NO_2$, or —CN;

wherein the alkyl or cycloalkyl groups can optionally contain one or more (e.g., 1, 2, 3, 4, or 5) unsaturations and/or can have one or more hetero atoms incorporated therein and optionally, in each case have one or more (e.g., 1, 2, 3, 4, or 5) hydrogen atoms replaced by halogen, —OH, $(C_1-C_3)$-alkyl, —OCO—$(C_1-C_3)$-alkyl or $(C_3-C_{13})$-cycloalkyl;

with a proviso that when $R_4$ represents moiety (A) wherein $R_6$ represents $(C_3-C_{13})$-cycloalkyl optionally containing one or more hetero atoms incorporated therein, the hetero atom is not nitrogen;

P and Q are independently selected from hydrogen and $C_1$ to $C_3$ alkyl; or

P and Q can be joined together with the carbon atom to which they are attached to form a $(C_3-C_8)$-cycloalkyl as represented by moiety (A-1):

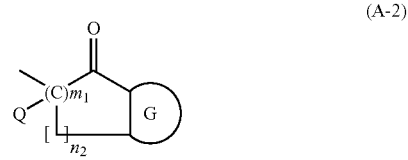

(A-1)

wherein $m_1$ is 1 and $n_2$ is 0, 1, 2, 3, 4 or 5 and $R_6$ is an aryl as defined above; or P and $R_6$ can be joined together to form a cyclic system as represented by moiety (A-2):

(A-2)

wherein $m_1$ is 1 and $n_2$ is 0, 1, 2, 3 or 4 and ring G is an aryl as defined above;

X represents either a double bond or a triple bond; and

J, K and L are each independently selected from a group consisting of hydrogen, halogen, $(C_1-C_{10})$-alkyl, $(C_3-C_{13})$-cycloalkyl, —OH, —O—$(C_1-C_{10})$-alkyl, —O—$(C_3-C_{13})$-cycloalkyl, —OCO—$(C_1-C_{10})$-alkyl, —OCO—$(C_3-C_{13})$-cycloalkyl, —OCO—CO—O—$(C_1-C_{10})$-alkyl, —OCO—CO—O—$(C_3-C_{13})$-cycloalkyl, —OCO—O—$(C_1-C_{10})$-alkyl, —OCO—O—$(C_3-C_{13})$-cycloalkyl, —OCO—NH—$(C_1-C_{10})$-alkyl, —OCO—NH—$(C_3-C_{13})$-cycloalkyl, —OCO—N—$[(C_1-C_{10})$-alkyl$]_2$, —OCO—N—$[(C_3-C_{13})$-cycloalkyl$]_2$, —OCO—$NHSO_2$—$(C_1-C_{10})$-alkyl, —OCO—$NHSO_2$—$(C_3-C_{13})$-cycloalkyl, $—NH_2$, —NH—$(C_1-C_8)$-alkyl, —N—$[(C_1-C_8)$-alkyl$]_2$, $—NO_2$ and —CN;

wherein the alkyl or cycloalkyl groups can optionally contain one or more (e.g., 1, 2, 3, 4, or 5) unsaturations and/or can have one or more (e.g., 1, 2, 3, 4, or 5) hetero atom incorporated therein and optionally, in each case have one or more (e.g., 1, 2, 3, 4, or 5) hydrogen atoms replaced by halogen, —OH, $(C_1-C_3)$-alkyl, —O—$(C_1-C_3)$-alkyl, —OCO—$(C_1-C_3)$-alkyl, —COOH, —COO—$(C_1-C_5)$-alkyl, —COO—$(C_1-C_5)$-haloalkyl, —NHCO—$(C_1-C_8)$-alkyl, $—ONO_2$, —NH—$(C_1-C_8)$-alkyl, —N—$[(C_1-C_8)$-alkyl$]_2$, $—NO_2$, —CN, $(C_3-C_{13})$-cycloalkyl, aryl or heterocyclic radical; or J and K can be joined together with the carbon atom to which they are attached to form a $(C_3-C_{13})$-cycloalkyl or —CO— group and L is as defined above; or J, K and L are absent when $n_1$ is 0; and $R_7$ represents a group selected from hydrogen, halogen, aryl and CO-aryl, wherein the ring or ring system is unsubstituted or substituted as defined above.

The invention further includes 11β-hydroxyandrosta-4-ene-3-one compounds of formula I-B, and physiologically acceptable salts thereof:

Formula I-B

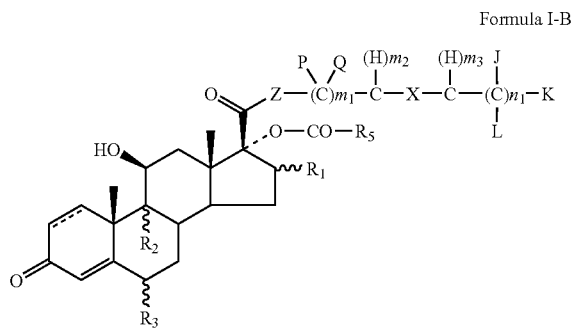

wherein

Z represents O or S;

$R_1$ represents hydrogen or methyl which may be either in α or β-configuration, or methylene;

$R_2$ and $R_3$ are the same or different and each independently represents hydrogen, halogen or a methyl group;

$R_5$ represents a group selected from $(C_1-C_{10})$-alkyl, $(C_3-C_{13})$-cycloalkyl, —O—$(C_1-C_{10})$-alkyl, aryl or heterocyclic ring wherein the ring or ring system is unsubstituted or substituted by one or more halogen, —OH, $(C_1-C_3)$-alkyl, —O—$(C_1-C_3)$-alkyl, $(C_3-C_{13})$-cycloalkyl; wherein the alkyl or cycloalkyl groups can optionally contain one or more unsaturations and/or can have one or more hetero atom incorporated therein and optionally in each case have one or more hydrogen atoms replaced by halogen, —OH, $(C_1-C_3)$-alkyl, —O—$(C_1-C_3)$-alkyl, $(C_3-C_{13})$-cycloalkyl;

$m_1$ is 1;

$m_2$ is 0 or 1;

$m_3$ is 0 or 1;

$n_1$ is 0, 1 or 2;

P and Q are hydrogen;

X represents either a double bond or a triple bond; and

J, K and L are independently selected from a group consisting of hydrogen, halogen, $(C_1-C_{10})$-alkyl, $(C_3-C_{13})$-cycloalkyl, —OH, —O—$(C_1-C_{10})$-alkyl, —O—$(C_3-C_{13})$-cycloalkyl, —OCO—$(C_1-C_{10})$-alkyl, —OCO—$(C_3-C_{13})$-cycloalkyl, —OCO—CO—O—$(C_1-C_{10})$-alkyl, —OCO—CO—O—$(C_3-C_{13})$-cycloalkyl, —OCO—O—$(C_1-C_{10})$-alkyl, —OCO—O—$(C_3-C_{13})$-cycloalkyl, —OCO—NH—$(C_1-C_{10})$-alkyl, —OCO—NH—$(C_3-C_{13})$-cycloalkyl, —OCO—N—$[(C_1-C_{10})$-alkyl$]_2$, —OCO—N—$[(C_3-C_{13})$-cycloalkyl$]_2$, —OCO—NHSO$_2$—$(C_1-C_{10})$-alkyl, —OCO—NHSO$_2$—$(C_3-C_{13})$-cycloalkyl, —NH$_2$, —NH—$(C_1-C_8)$-alkyl, —N—$[(C_1-C_8)$-alkyl$]_2$, —NO$_2$ and —CN.

The invention further includes 11β-hydroxyandrosta-4-ene-3-one compounds of formula I-B, and physiologically acceptable salts thereof:

Formula I-B

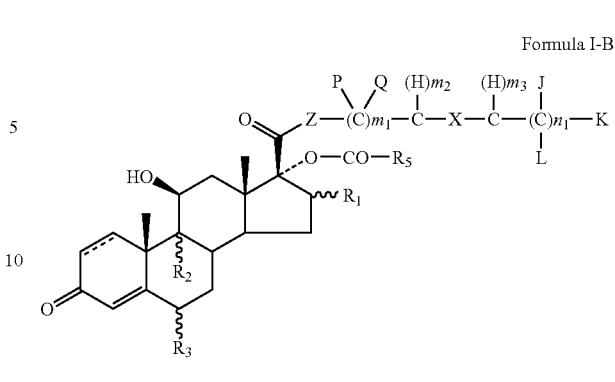

wherein

Z represents S;

$R_1$ represents hydrogen or methyl which may be either in α or β-configuration, or methylene;

$R_2$ and $R_3$ are the same or different and each independently represents hydrogen, halogen or a methyl group;

$R_5$ represents a group selected from $(C_1-C_{10})$-alkyl, $(C_3-C_{13})$-cycloalkyl, —O—$(C_1-C_{10})$-alkyl, aryl or heterocyclic ring wherein the ring or ring system is unsubstituted or substituted by one or more halogen, —OH, $(C_1-C_3)$-alkyl, —O—$(C_1-C_3)$-alkyl, $(C_3-C_{13})$-cycloalkyl; wherein the alkyl or cycloalkyl groups can optionally contain one or more unsaturations and/or can have one or more hetero atom incorporated therein and optionally in each case have one or more hydrogen atoms replaced by halogen, —OH, $(C_1-C_3)$-alkyl, —O—$(C_1-C_3)$-alkyl, $(C_3-C_{13})$-cycloalkyl; and $m_1$ is 1;

$m_2$ is 0;

$m_3$ is 0;

$n_1$ is 0, 1 or 2;

P and Q are hydrogen;

X represents a triple bond; and

J, K and L are each independently selected from a group consisting of hydrogen, halogen, (C1-C10)-alkyl, (C3-C13)-cycloalkyl, —OH, —O—(C1-C10)-alkyl, —O—(C3-C13)-cycloalkyl, —OCO—(C1-C10)-alkyl, —OCO—(C3-C13)-cycloalkyl, —OCO—CO—O—(C1-C10)-alkyl, —OCO—CO—O—(C3-C13)-cycloalkyl, —OCO—O—(C1-C10)-alkyl, —OCO—O—(C3-C3C3-C13)-cycloalkyl, —OCO—NH—(C1-C10)-alkyl, —OCO—NH—(C3-C13)-cycloalkyl, —OCO—N—[(C1-C10)-alkyl]2, —OCO—N—[(C3-C13)-cycloalkyl]2, —OCO—NHSO2-(C1-C10)-alkyl, —OCO—NHSO2-(C3-C13)-cycloalkyl, —NH2, —NH—(C1-C8)-alkyl, —N—[(C1-C8)-alkyl]2, —NO2 and —CN.

DETAILED DESCRIPTION OF THE INVENTION

The present invention relates to novel, safe 11β-hydroxyandrosta-4-ene-3-one compounds of formula I, and physiologically acceptable salts or solvates thereof.

Compounds of formula I, may be in the form of diastereomers and mixtures thereof. As used herein, any stereoisomeric form includes diastereomers and mixtures thereof.

Reference to compound of formula I hereinafter includes a compound of formula I and physiologically acceptable salt or solvate thereof.

With respect to the various groups encompassed by the generic terms used here and throughout this specification, the following definitions and explanations are applicable:

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X.

The term "about" can refer to a variation of ±5%, 10%, or 20% of the value specified. For example, "about 50" percent can in some embodiments carry a variation from 45 to 55 percent. For integer ranges, the term "about" can include one or two integers greater than and less than a recited integer.

As used herein, "contacting" refers to the act of touching, making contact, or of bringing to immediate or close proximity, including at the molecular level, such as in solution, in vitro, or in vivo.

Compounds and pharmaceutical compositions suitable for use in the present invention include those wherein the active agent is administered in an effective amount to achieve its intended purpose. The phrase "therapeutically effective amount" refers to an amount effective to treat the disease, disorder, and/or condition, for example, an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., to treat or prevent a disease or disorder, or to treat the symptoms of the disease or disorder, in a host.

Thus the terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

The term "mammal" refers to an animal of the class Mammalia, e.g., a human, dog, cat, or horse.

The term "solvate" refers to a solid compound that has one or more solvent molecules associated with its solid structure. Solvates can form when a compound is crystallized from a solvent, wherein one or more solvent molecules become integral part(s) of the crystalline matrix. The compounds of the formulas described herein can be solvates, for example, ethanol solvates. Likewise, a "hydrate" refers to a solid compound that has one or more water molecules associated with its solid structure. A hydrate is a subgroup of solvates. Hydrates can form when a compound is crystallized from water, wherein one or more water molecules become integral part(s) of the crystalline matrix. The compounds of the formulas described herein can be hydrates.

As used herein 'alkyl' can be straight-chain or branched and can optionally contain one or more unsaturations and/or can have one or more hetero atom incorporated therein and optionally, in each case have one or more hydrogen atoms replaced by —F, —Cl, —Br, —I, —OH, —OCO—($C_1$-$C_3$)-alkyl, ($C_3$-$C_{13}$)-cycloalkyl, aryl or heterocyclic radical.

As used herein 'alkyl including one or more unsaturations' is to be understood as meaning 'alkenyl' and/or 'alkynyl'. Exemplary alkyl groups include methyl, ethyl, n-propyl, i-propyl, n-butyl, t-butyl, n-pentyl, 3-pentyl, 2-octyl and the like. Exemplary alkenyl groups include ethenyl, propenyl, 1-butenyl, (Z)-2-butenyl, (E)-3-methylbut-2-enyl, (E)-2,4-pentadienyl, (Z)-3-heptenyl and the like. Exemplary alkynyl groups include ethynyl, propynyl, 1-butynyl, 2-butynyl, 4-methyl-2-pentynyl, 2,4-hexadiynyl and the like.

As used herein 'cycloalkyl' is to be understood as meaning monocyclic, bicyclic, tricyclic and polycyclic ring systems such as norbornyl, adamantly and the like. The term 'cycloalkyl' as used herein can optionally contain one or more unsaturations and/or can have one or more hetero atom incorporated therein —F, —Cl, —Br, —I, —OH, —OCO—($C_1$-$C_3$)-alkyl, ($C_3$-$C_{13}$)-cycloalkyl, aryl or heterocyclic radical.

As used herein 'halogen' or 'halo group' refers to fluorine, chlorine, bromine or iodine.

As used herein aryl is to be understood as meaning ring systems such as phenyl, naphthyl, anthracenyl, phenanthryl, preferably aryl is phenyl.

As used herein heterocyle or heterocyclic ring is to be understood as meaning ring systems which, in addition to carbon, also contain hetero atoms, such as, for example, nitrogen, oxygen or sulfur. This definition furthermore includes ring systems in which the heterocycle or heterocyclic radical is fused with benzene rings. Examples of heterocycles or heterocyclic rings include but are not limited to: heteroaryls, such as
benzimidazolyl,
1-[($C_1$-$C_6$)-alkyl]benzimidazolyl,
imidazolyl,
2- or 3-thienyl,
2- or 3-furyl,
benzoxazolyl,
benzothiazolyl,
2-, 3- or 4-pyridyl,
pyrimidinyl,
4-, 5- or 6-pyridazin-2H-yl-3-one,
4-, 5- or 6-pyridazin-2-($C_1$-$C_8$)-alkyl-2H-yl-3-one,
2-benzyl-4-, -5- or -6-pyridazin-2H-yl-3-one,
3- or 4-pyridazinyl,
2-, 3-, 4- or 8-quinolinyl,
1-, 3- or 4-isoquinolinyl,
1-phthalazinyl,
3- or 4-cinnolinyl,
2- or 4-quinazolinyl,
2-pyrazinyl,
2-quinoxalinyl,
2-, 4- or 5-oxazolyl,
3-, 4- or 5-isoxazolyl,
2-, 4- or 5-thiazolyl,
3-, 4- or 5-isothiazolyl,
1-[($C_1$-$C_6$)-alkyl]-2-, -4- or -5-imidazolyl,
3-, 4- or 5-pyrazolyl,
1-[($C_1$-$C_6$)-alkyl]-3-, -4- or -5-pyrazolyl,
1- or 4-[1,2,4]-triazolyl,
4- or 5-[1,2,3]-triazolyl,
1-[($C_1$-$C_6$)-alkyl]-4- or -5-[1,2,3]triazolyl,
3-, 4- or 7-indolyl,
N—[($C_1$-$C_6$)-alkyl]-3-, -4- or -7-indolyl
2-[($C_1$-$C_6$)-alkyl]-3(2H)-indazolyl,
1-[($C_1$-$C_6$)-alkyl]-3(1H)-indazolyl,
5-tetrazolyl,
1-[($C_1$-$C_6$)-alkyl]-1H-tetrazolyl, or
2-[($C_1$-$C_6$)-alkyl]-2H-tetrazolyl.

In one embodiment the preferred compounds of formula I are selected from the compounds wherein $m_1$ is 1.

In one embodiment the preferred compounds of formula I are selected from the compounds wherein $m_1$ is 1 and P and Q are hydrogen.

In one embodiment the compounds of formula I are selected from the compounds wherein $R_4$ represents moiety (A).

In one embodiment the compounds of formula I are selected from the compounds wherein $R_4$ represents moiety (B).

In one embodiment the compounds of formula I are selected from the compounds wherein $R_4$ represents moiety (C).

In one embodiment the compounds of formula I are selected from the compounds wherein $m_1$ is 1; P and Q are both hydrogen and $R_4$ represents moiety (A).

In one embodiment the compounds of formula I are selected from the compounds wherein $m_1$ is 1; P and Q are both hydrogen and $R_4$ represents moiety (B).

In one embodiment the compounds of formula I are selected from the compounds wherein $m_1$ is 1; P and Q are both hydrogen and $R_4$ represents moiety (C).

In one embodiment the compounds of formula I are selected from the compounds wherein $R_6$ is selected from a group consisting of $(C_1-C_8)$-alkyl, aryl and a heterocyclic radical wherein the ring or ring system is unsubstituted or substituted as defined above.

In one embodiment the compounds of formula I are selected from the compounds wherein $R_5$ represents a group selected from $R_6$, wherein $R_6$ is selected from a group consisting of $(C_1-C_8)$-alkyl and a heterocyclic radical wherein the ring or ring system is unsubstituted or substituted as defined above.

In one embodiment the present invention provides 11β-hydroxyandrosta-4-ene-3-one, a compound of formula I-A and physiologically acceptable salt, thereof:

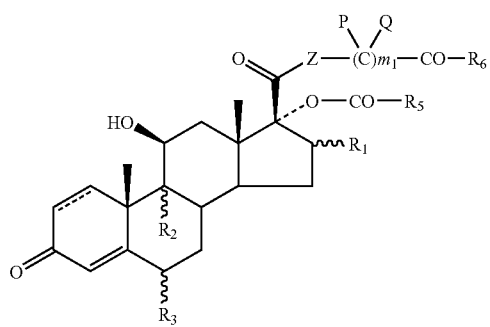

Formula I-A wherein
----- represents a single or double bond and 〜〜 represents α or β-configuration;
Z represents O, S;
$R_1$ represents hydrogen or methyl which may be either in α or β-configuration, or methylene;
$R_2$ and $R_3$ are the same or different and each independently represents hydrogen, halogen or a methyl group;
$m_1$ is 1, 2 or 3;
$R_6$ represents a group selected from $(C_1-C_8)$-alkyl, $(C_3-C_{13})$-cycloalkyl, aryl and a heterocyclic radical, where the ring or ring system is unsubstituted or substituted by one or more substituents selected from $(C_1-C_8)$-alkyl, $(C_3-C_{13})$-cycloalkyl, halogen, O—$(C_1-C_8)$-alkyl, O—$(C_3-C_{13})$-cycloalkyl, OCO—$(C_1-C_3)$-alkyl, $S(O)_{0-2}(C_1-C_8)$-alkyl, COO—$(C_1-C_8)$-alkyl, —OCO—O—$(C_1-C_3)$-alkyl, —OCO—CO—O—$(C_1-C_3)$-alkyl, $CONH_2$, CONH—$(C_1-C_8)$-alkyl, CON—[$(C_1-C_8)$-alkyl]$_2$, —NHCO—$(C_1-C_8)$-alkyl, N—$(C_1-C_8)$-alkyl-CO—$(C_1-C_8)$-alkyl, —NHCO—O—$(C_1-C_8)$-alkyl, —N—$(C_1-C_8)$-alkyl-CO—O—$(C_1-C_8)$-alkyl, —NHCONH—$(C_1-C_8)$-alkyl, —N—$(C_1-C_8)$-alkyl-CONH—$(C_1-C_8)$-alkyl, —NHCONH—$SO_2$—$(C_1-C_8)$-alkyl, —N—$(C_1-C_8)$-alkyl-CONH—$SO_2$—$(C_1-C_8)$-alkyl, —$NO_2$, —CN;

wherein the alkyl or cycloalkyl groups can optionally contain one or more unsaturations and/or can have one or more hetero atom incorporated therein and optionally, in each case have one or more hydrogen atoms replaced by —F, —Cl, —Br, —I, —OH, —OCO—$(C_1-C_3)$-alkyl, $(C_3-C_{13})$-cycloalkyl, aryl or heterocyclic radical;

with a proviso that when $R_4$ represents moiety A wherein $R_6$ represents $(C_3-C_{13})$-cycloalkyl optionally containing one or more hetero atom incorporated therein, the hetero atom is not nitrogen;

P and Q are independently selected from hydrogen, halogen and $C_1$ to $C_3$ alkyl; or P and Q can be joined together with the carbon atom to which they are attached to form $(C_3-C_8)$-cycloalkyl as represented by moiety (A-1):

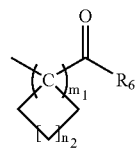

(A-1)

wherein $m_1$ is 1 and $n_2$ is 0, 1, 2, 3, 4 or 5; or

P and $R_6$ can be joined together to form a cyclic system as represented by moiety (A-2):

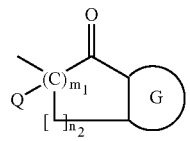

(A-2)

wherein $m_1$ is 1 and $n_2$ is 0, 1, 2, 3 or 4 and ring G is optionally present, wherein G represents a $(C_3-C_8)$-cycloalkyl, aryl or a heterocyclic radical as defined above; and $R_5$ represents a group selected from $R_6$, —O—$R_6$ or —N($R_8$)$R_6$, wherein $R_6$ is as defined above and $R_8$ represents hydrogen, $(C_1-C_6)$-alkyl or $(C_3-C_6)$-cycloalkyl.

In one embodiment the compounds of formula I-A are selected from the compounds wherein $m_1$ is 1; P and Q are both hydrogen; $R_6$ is selected from group consisting of $(C_1-C_8)$-alkyl, aryl and a heterocyclic radical; or wherein $m_1$ is 1; P and Q are both hydrogen; $R_6$ is aryl wherein the ring or ring system is unsubstituted or substituted as defined above; or wherein $R_6$ is phenyl wherein the ring or ring system is unsubstituted or substituted as defined above.

In one embodiment the present invention provides 11β-hydroxyandrosta-4-ene-3-one, a compound of formula I-B and physiologically acceptable salt thereof:

Formula I-B

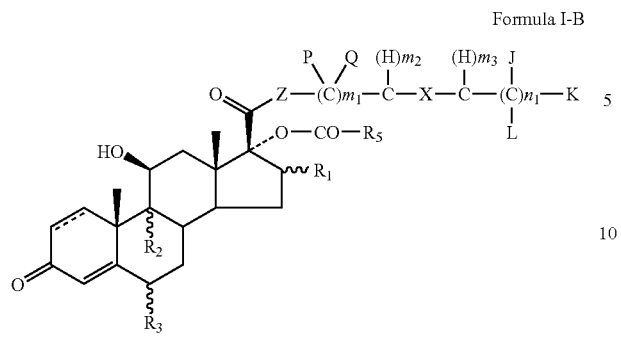

wherein

═══ represents a single bond or double bond and ∿∿∿ represents α or β-configuration;

Z represents O, S;

$R_1$ represents hydrogen or methyl which may be either in α or β-configuration, or methylene;

$R_2$ and $R_3$ are the same or different and each independently represents hydrogen, halogen or a methyl group;

$m_1$ is 1, 2 or 3;

$m_2$ is 0 or 1;

$m_3$ is 0 or 1;

$n_1$ is 0, 1 or 2;

P and Q are independently selected from hydrogen, halogen and $C_1$ to $C_3$ alkyl;

X represents either a double bond or a triple bond; and

J, K and L are independently selected from a group consisting of hydrogen, halogen, $(C_1-C_{10})$-alkyl, $(C_3-C_{13})$-cycloalkyl, —OH, —O—$(C_1-C_{10})$-alkyl, —O—$(C_3-C_{13})$-cycloalkyl, —OCO—$(C_1-C_{10})$-alkyl, —OCO—$(C_3-C_{13})$-cycloalkyl, —OCO—CO—O—$(C_1-C_{10})$-alkyl, —OCO—CO—O—$(C_3-C_{13})$-cycloalkyl, —OCO—O—$(C_1-C_{10})$-alkyl, —OCO—O—$(C_3-C_{13})$-cycloalkyl, —OCO—NH—$(C_1-C_{10})$-alkyl, —OCO—NH—$(C_3-C_{13})$-cycloalkyl, —OCO—N—$[(C_1-C_{10})$-alkyl$]_2$, —OCO—N—$[(C_3-C_{13})$-cycloalkyl$]_2$, —OCO—NHSO$_2$—$(C_1-C_{10})$-alkyl, —OCO—NHSO$_2$—$(C_3-C_{13})$-cycloalkyl, —CO—$[(C_3-C_{10})$N-cyclo], —OCO—$[(C_3-C_{10})$N-cyclo], —NH$_2$, —NH—$(C_1-C_8)$-alkyl, —N—$[(C_1-C_8)$-alkyl$]_2$, —NO$_2$, —CN, aryl and a heterocyclic radical as defined above; or J and K can be joined together with the carbon atom to which they are attached to represent a $(C_3-C_{13})$-cycloalkyl or —CO— group and L is as defined above; and $R_5$ represents a group selected from $R_6$, —O—$R_6$ or —N$(R_8)R_6$, wherein $R_6$ is as defined above and $R_8$ represents hydrogen, $(C_1-C_6)$-alkyl or $(C_3-C_6)$-cycloalkyl.

In one embodiment the compounds of formula I-B are selected from the compounds wherein, $m_1$ is 1; P and Q are both hydrogen; X represents either a double bond or a triple bond; $m_2$ is 0; $m_3$ is 0; $n_1$ is 1 and J, K and L are independently selected from hydrogen, halogen, —OH, —OCO—$(C_1-C_{10})$-alkyl and —OCO—O—$(C_1-C_{10})$-alkyl.

The invention also includes 11β-hydroxyandrosta-4-ene-3-one compounds of formula I-B, and physiologically acceptable salts or solvates thereof:

Formula I-B wherein

Z represents O or S;

$R_1$ represents hydrogen or methyl which may be either in α or β-configuration, or methylene;

$R_2$ and $R_3$ are the same or different and each independently represents hydrogen, halogen or a methyl group;

$R_5$ represents a group selected from $(C_1-C_{10})$-alkyl, $(C_3-C_{13})$-cycloalkyl, —O—$(C_1-C_{10})$-alkyl, aryl or heterocyclic ring wherein the ring or ring system is unsubstituted or substituted by one or more halogen, —OH, $(C_1-C_3)$-alkyl, —O—$(C_1-C_3)$-alkyl, $(C_3-C_{13})$-cycloalkyl;

wherein the alkyl or cycloalkyl groups can optionally contain one or more unsaturations and/or can have one or more hetero atom incorporated therein and optionally in each case have one or more hydrogen atoms replaced by halogen, —OH, $(C_1-C_3)$-alkyl, —O—$(C_1-C_3)$-alkyl, $(C_3-C_{13})$-cycloalkyl; and $m_1$ is 1;

$m_2$ is 0 or 1;

$m_3$ is 0 or 1;

$n_1$ is 0, 1 or 2;

P and Q are hydrogen;

X represents either a double bond or a triple bond; and

J, K and L are independently selected from a group consisting of hydrogen, halogen, $(C_1-C_{10})$-alkyl, $(C_3-C_{13})$-cycloalkyl, —OH, —O—$(C_1-C_{10})$-alkyl, —O—$(C_3-C_{13})$-cycloalkyl, —OCO—$(C_1-C_{10})$-alkyl, —OCO—$(C_3-C_{13})$-cycloalkyl, —OCO—CO—O—$(C_1-C_{10})$-alkyl, —OCO—CO—O—$(C_3-C_{13})$-cycloalkyl, —OCO—O—$(C_1-C_{10})$-alkyl, —OCO—O—$(C_3-C_{13})$-cycloalkyl, —OCO—NH—$(C_1-C_{10})$-alkyl, —OCO—NH—$(C_3-C_{13})$-cycloalkyl, —OCO—N—$[(C_1-C_{10})$-alkyl$]_2$, —OCO—N—$[(C_3-C_{13})$-cycloalkyl$]_2$, —OCO—NHSO$_2$—$(C_1-C_{10})$-alkyl, —OCO—NHSO$_2$—$(C_3-C_{13})$-cycloalkyl, —NH$_2$, —NH—$(C_1-C_8)$-alkyl, —N—$[(C_1-C_8)$-alkyl$]_2$, —NO$_2$ and —CN.

The invention further provides 11β-hydroxyandrosta-4-ene-3-one compounds of formula I-B, and physiologically acceptable salt thereof:

Formula I-B

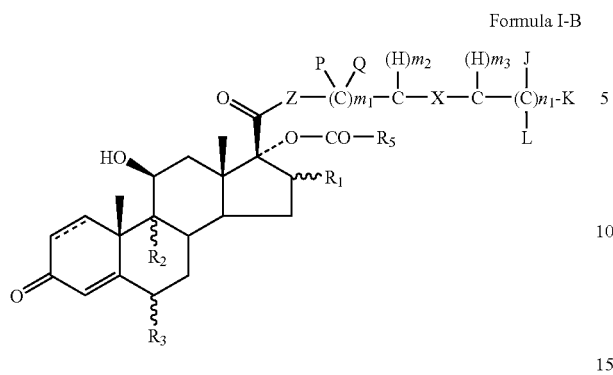

Formula I-C

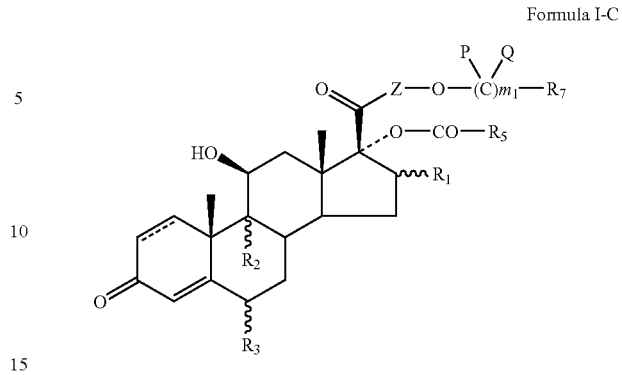

wherein

Z represents S;

$R_1$ represents hydrogen or methyl which may be either in α or β-configuration, or methylene;

$R_2$ and $R_3$ are the same or different and each independently represents hydrogen, halogen or a methyl group;

$R_5$ represents a group selected from $(C_1-C_{10})$-alkyl, $(C_3-C_{13})$-cycloalkyl, —O—$(C_1-C_{10})$-alkyl, aryl or heterocyclic ring wherein the ring or ring system is unsubstituted or substituted by one or more halogen, —OH, $(C_1-C_3)$-alkyl, —O—$(C_1-C_3)$-alkyl, $(C_3-C_{13})$-cycloalkyl;

wherein the alkyl or cycloalkyl groups can optionally contain one or more unsaturations and/or can have one or more hetero atom incorporated therein and optionally in each case have one or more hydrogen atoms replaced by halogen, —OH, $(C_1-C_3)$-alkyl, —O—$(C_1-C_3)$-alkyl, $(C_3-C_{13})$-cycloalkyl; and $m_1$ is 1;

$m_2$ is 0;

$m_3$ is 0;

$n_1$ is 0, 1 or 2;

P and Q are hydrogen;

X represents a triple bond; and

J, K and L are independently selected from a group consisting of hydrogen, halogen, $(C_1-C_{10})$-alkyl, $(C_3-C_{13})$-cycloalkyl, —OH, —O—$(C_1-C_{10})$-alkyl, —O—$(C_3-C_{13})$-cycloalkyl, —OCO—$(C_1-C_{10})$-alkyl, —OCO—$(C_3-C_{13})$-cycloalkyl, —OCO—CO—O—$(C_1-C_{10})$-alkyl, —OCO—CO—O—$(C_3-C_{13})$-cycloalkyl, —OCO—O—$(C_1-C_{10})$-alkyl, —OCO—O—$(C_3-C_{13})$-cycloalkyl, —OCO—NH—$(C_1-C_{10})$-alkyl, —OCO—NH—$(C_3-C_{13})$-cycloalkyl, —OCO—N—$[(C_1-C_{10})$-alkyl$]_2$, —OCO—N—$[(C_3-C_{13})$-cycloalkyl$]_2$, —OCO—NHSO$_2$—$(C_1-C_{10})$-alkyl, —OCO—NHSO$_2$—$(C_3-C_{13})$-cycloalkyl, —NH$_2$, —NH—$(C_1-C_8)$-alkyl, —N—$[(C_1-C_8)$-alkyl$]_2$, —NO$_2$ and —CN.

In one embodiment the present invention provides 11β-hydroxyandrosta-4-ene-3-one, a compound of formula I-C or physiologically acceptable salts thereof:

wherein

----- represents a single or double bond and ⁓⁓⁓ represents α or β-configuration;

Z represents S;

$R_1$ represents hydrogen or methyl which may be either in α or β-configuration, or methylene;

$R_2$ and $R_3$ are the same or different and each independently represents hydrogen, halogen or a methyl group;

$m_1$ is 1, 2 or 3;

P and Q are independently selected from hydrogen, halogen and $C_1$ to $C_3$ alkyl;

$R_7$ represents a group selected from halogen, CO-aryl and $R_6$, wherein the aryl ring of CO-aryl is unsubstituted or substituted by one or more substituents as defined above for the ring or ring system;

$R_6$ represents a group selected from $(C_1-C_8)$-alkyl, $(C_3-C_{13})$-cycloalkyl, aryl and a heterocyclic radical, where the ring or ring system is unsubstituted or substituted by one or more substituents selected from $(C_1-C_8)$-alkyl, $(C_3-C_{13})$-cycloalkyl, halogen, O—$(C_1-C_8)$-alkyl, O—$(C_3-C_{13})$-cycloalkyl, OCO—$(C_1-C_3)$-alkyl, $S(O)_{0-2}(C_1-C_8)$-alkyl, COO—$(C_1-C_8)$-alkyl, —OCO—O—$(C_1-C_3)$-alkyl, —OCO—CO—O—$(C_1-C_3)$-alkyl, CONH$_2$, CONH—$(C_1-C_8)$-alkyl, CON—$[(C_1-C_8)$-alkyl$]_2$, —NHCO—$(C_1-C_8)$-alkyl, N—$(C_1-C_8)$-alkyl-CO—$(C_1-C_8)$-alkyl, —NHCO—O—$(C_1-C_8)$-alkyl, —N—$(C_1-C_8)$-alkyl-CO—O—$(C_1-C_8)$-alkyl, —NHCONH—$(C_1-C_8)$-alkyl, —N—$(C_1-C_8)$-alkyl-CONH—$(C_1-C_8)$-alkyl, —NHCONH—SO$_2$—$(C_1-C_8)$-alkyl, —N—$(C_1-C_8)$-alkyl-CONH—SO$_2$—$(C_1-C_8)$-alkyl, —NO$_2$, —CN;

wherein the alkyl or cycloalkyl groups can optionally contain one or more unsaturations and/or can have one or more hetero atom incorporated therein and optionally, in each case have one or more hydrogen atoms replaced by —F, —Cl, —Br, —I, —OH, —OCO—$(C_1-C_3)$-alkyl, $(C_3-C_{13})$-cycloalkyl, aryl or heterocyclic radical; and $R_5$ represents a group selected from $R_6$, —O—$R_6$ or —N($R_8$)$R_6$, wherein $R_6$ and $R_8$ are as defined above.

In one embodiment the compounds of formula I-C are selected from the compounds wherein $m_1$ is 1; P and Q are both hydrogen and $R_7$ represents $R_6$ wherein, $R_6$ is selected from group consisting of $(C_1-C_8)$-alkyl or aryl wherein the ring or ring system is unsubstituted or substituted as defined above.

Physiologically acceptable salts are particularly suitable for medical applications, due to their greater solubility in water compared with the starting or base compounds. Suitable physiologically acceptable acid addition salts of the compounds of the invention may be salts of inorganic acids such as hydrochloric acid, hydrobromic acid, phosphoric acid, and the like or of organic acids such as, for example, acetic acid, behenic acid, benzenesulfonic acid, benzoic acid, citric acid and the like. Examples of suitable physiologically acceptable basic salts are ammonium salts, alkali metal salts such as sodium salts and potassium salts and alkaline earth metal salts such as magnesium salts and calcium salts.

The compounds of formula I are useful in human or veterinary medicine, in particular as anti-inflammatory and anti-allergic agents.

The compounds of formula I have potentially beneficial anti-inflammatory or antiallergic effects, which are demonstrated by, for example, their ability to bind to the glucocorticoid receptor in vitro; and inhibit croton oil induced ear edema, cotton pellet induced granuloma, sephadex induced lung edema in vivo models, without causing systemic side effects like involution of thymus, enhanced deposition of glycogen in the liver, or appreciable change in body weight.

All references to compound(s) of the formula I herein refer to a compound/compounds of the formula (I) and to a salt or solvate thereof.

The present invention provides processes for preparation of the compounds of the formula I, comprising reacting a compound of formula II, with $R_4$—Y, a compound of formula III (Scheme-I):

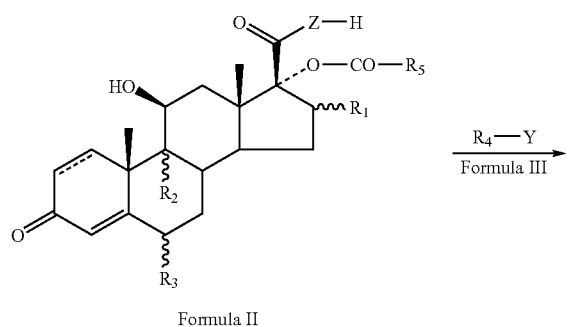

wherein ----- represents a single or double bond and ∧∧∧ represents α or β-configuration;

Z represents O or S;

$R_1, R_2, R_3, R_4$ and $R_5$ are as defined above; and Y represents a leaving group.

In the compound of formula III, Y represents a suitable leaving group. A suitable leaving group is any group which upon reaction of a compound of formula II with the compound of formula III, facilitates formation of a compound of formula I. For example, Y may be halogen, alkylsulfonate or arylsulfonate group, like methanesulfonate, p-toluenesulfonate or trifluoromethanesulfonate group.

In one embodiment the present invention also provides a compound of formula I-A and a process for preparation of compound of formula IA comprising reacting a carboxylic acid compound of formula II-A (a compound of formula II, wherein Z is O) or a carbothioic acid compound of formula II-B (a compound of formula II, wherein Z is S) with a compound of formula III-A (Scheme-II):

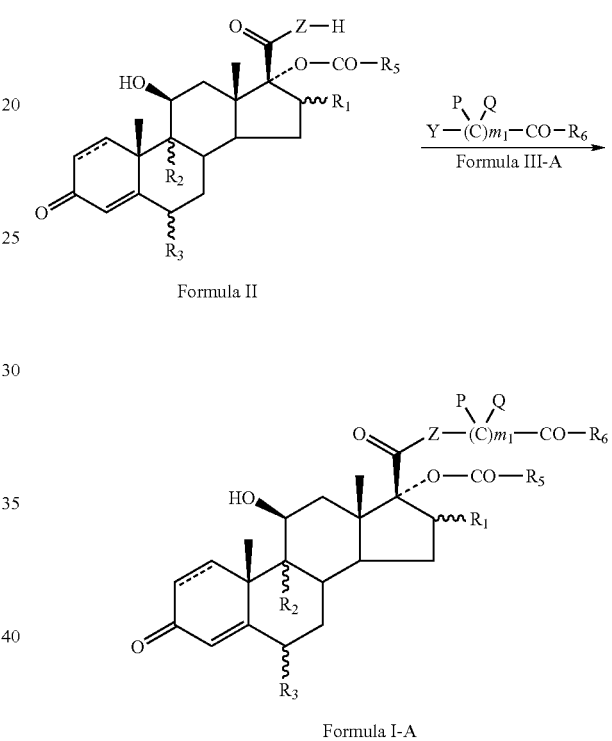

wherein ----- represents a single or double bond and ∧∧∧ represents α or β-configuration;

Z represents O, S; and $R_1, R_2, R_3, R_5, R_6, Y, P, Q$ and $m_1$ are as defined above.

The reactions represented by Schemes I or II can be advantageously carried out in a suitable inert organic polar solvent or solvent system, for example, acetone, acetonitrile, N,N-dimethylformamide, N,N-dimethylacetamide, dimethyl sulfoxide and the like or mixture thereof, in presence of a suitable base, for example, alkali or alkaline earth metal carbonates like potassium carbonate, sodium carbonate, sodium bicarbonate and the like.

The starting compounds of formula II are either known in the art or can be prepared by following known methods, for example, Gordon J. Phillips et al., J. Med. Chem., 37, 3717-3729 (1994); U.S. Pat. No. 4,335,121; PCT publication No. WO 04/001369 or WO 04/039827, incorporated herein by reference.

Scheme-III represents a reaction sequence following which compound of formula II can be prepared.

Scheme-III

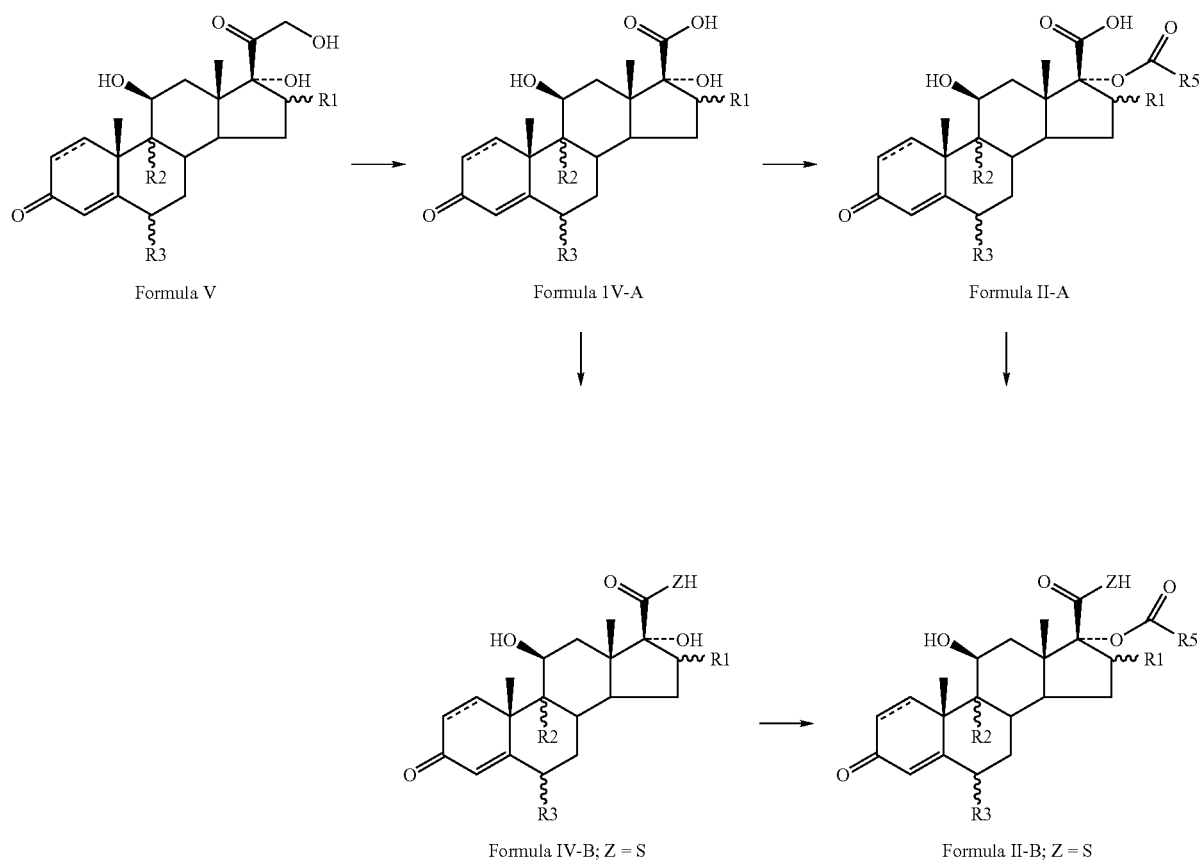

Preferably, the compounds of formula II-A (compound of formula II, wherein Z is O) may be prepared by treating a compound of formula IV-A with compounds of formula $R_5COOH$ or an active derivative thereof such as an activated ester, anhydride or halide thereof, especially an acid halide, for example, an acid chloride, in the presence of an organic base like triethylamine or an inorganic base like potassium carbonate. To obtain compounds of formula II-A, wherein $R_5$ represents —O—$R_6$ or —N($R_8$)$R_6$, the compound of formula IV-A is reacted with corresponding $R_6$—O—CO—Y' or $R_6(R_8)$N—CO—Y' where Y' represents a leaving group such as a halide, 4-nitrophenolate etc, in the presence of an organic base like triethylamine or an inorganic base like potassium carbonate. To obtain compounds of formula II-A, where $R_5$ represents —N($R_8$)$R_6$, and $R_8$ is hydrogen, the compound of formula IV-A can be reacted with the corresponding isocyanate OCN—$R_6$. The compounds of formula IV-A may be prepared by oxidation of compounds of formula V in presence of a chemical oxidizing agent like periodic acid or sodium periodate.

Preferably, the compounds of formula II-B (compound of formula II, wherein Z is S) may be prepared from compound formula II-A by initial reaction with N,N-dimethylthiocarbamoyl chloride, followed by aminolysis of the resulting rearranged mixed anhydride with diethylamine, or methanolysis by methanol and potassium carbonate, or reaction with sodium hydrosulfide in a suitable solvent, for example, N,N-dimethylformamide.

The compounds of formula II-B, where Z is S may also be prepared by treating a compound of formula IV-B with compounds of formula $R_5COOH$ or an active derivative thereof such as an activated ester, anhydride or halide thereof, especially an acid halide, for example, an acid chloride, in the presence of an organic base like triethylamine or an inorganic abse like potassium carbonate. In compounds of formula II-B wherein $R_5$ represents —O—$R_6$ or —N($R_8$)$R_6$, the compound of formula IV-B is reacted with corresponding $R_6$—O—CO—Y' or $R_6(R_8)$N—CO—Y' where Y' represents a leaving group such as a halide, 4-nitrophenolate etc, in the in the presence of an organic base like triethylamine or an inorganic base like potassium carbonate.

The compounds of formula IV-B, where Z is S may be prepared from compound formula IV-A by carbonyl activation with 1,1'-carbonyldiimidazole and reaction with hydrogen sulfide or sodium hydrosulfide in a suitable solvent, for example, N,N-dimethylformamide.

The compounds of formula II may be conveniently used as acid addition salts thereof, preferably in crystalline form. Any suitable base addition salts can be used, for example, sodium or potassium salt.

The compound of formula III-A are known or may be prepared by methods known in the art.

In one embodiment the present invention provides a compound of formula I-B and a process for preparation thereof comprising reacting a carboxylic acid compound of formula II-A (a compound of formula II, wherein Z is O) or carbothioic acid compound of formula II-B (a compound of formula II, wherein Z is S) with a compound of formula III-B (Scheme-IV):

Scheme-IV

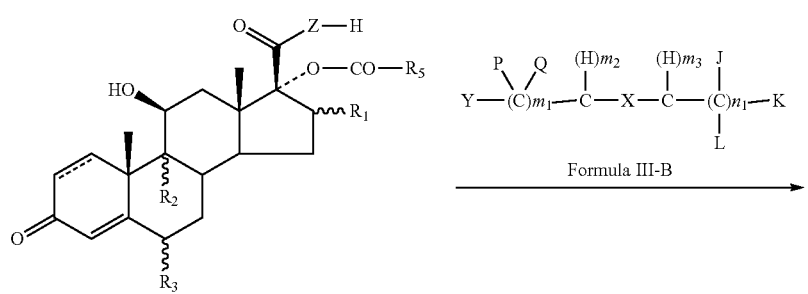

Formula II

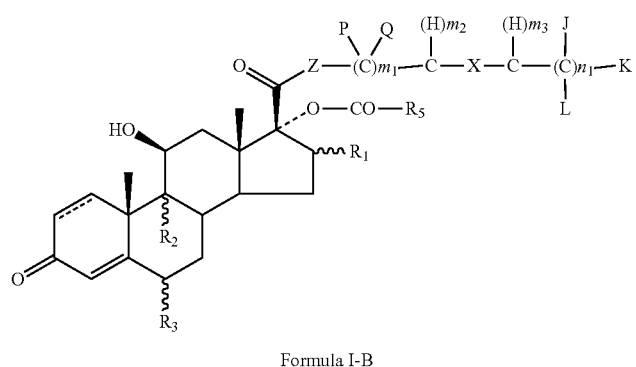

Formula I-B wherein ===== represents a single or double bond and ⌇⌇⌇ represents α or β-configuration;

Z represents O or S;

$R_1$, $R_2$, $R_3$, $R_5$, Y, P, Q, J, K, L, $m_1$ and $n_1$ are as defined above, X represents either a double bond or a triple bond, $m_2$ is 0 or 1, and $m_3$ is 0 or 1.

The compound of formula I-B can be prepared by alkylation of compound of formula II with compound of formula III-B, advantageously carried out in an inert organic polar solvent, for example, acetone, acetonitrile, N,N-dimethylformamide, N,N-dimethylacetamide, dimethyl sulfoxide and the like in presence of a suitable base, for example, alkali or alkaline earth metal carbonates like potassium carbonate, sodium carbonate, sodium bicarbonate and the like. The compound of formula III-B are known or can be prepared by methods known in the art.

In one preferred embodiment, the present invention provides a compound of formula I-C and a process for preparation thereof comprising reacting a compound of formula VI with a compound of formula III-C (Scheme-V):

Scheme-V

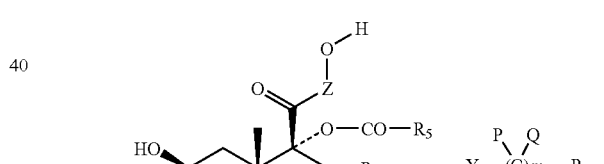

Formula VI

Formula I-C wherein ----- represents a single or double bond and ∼∼∼ represents α or β-configuration;

Z represents S; and $R_1$, $R_2$, $R_3$, $R_5$, $R_7$, Y, P, Q and $m_1$ are as defined above.

The compound of formula I-C can be prepared by the alkylation of compound of formula VI with compound of formula III-C, advantageously carried out in an inert organic polar solvent, for example, acetone, acetonitrile, N,N-dimethylformamide, N,N-dimethylacetamide, dimethyl sulfoxide and the like in presence of a suitable base, for example, alkali or alkaline earth metal carbonates like potassium carbonate, sodium carbonate, sodium bicarbonate and the like. The compound of formula III-C are known or can be prepared by methods known in the art.

The compound of formula VI may be prepared by oxidation of compound of formula II-B with oxidizing agent, for example, hydrogen peroxide, urea-hydrogen peroxide, peracetic acid, m-chloroperbenzoic acid, sodium periodate and the like in a polar organic solvent such as methanol, ethanol, 2-propanol, acetic acid and the like.

The compound of formula I and physiologically acceptable salt thereof can also be used as intermediates for preparation of derivatives thereof, for example, the —OH group can be converted to halo group or acetylated, sulfonated, etc. Additionally, the intermediates described herein that are used for the preparation of the compounds of the formulas described herein can be useful for the preparation of other compounds or pharmaceutical compositions.

The present invention also relates to the dosage forms for local application depends on the precise type of formulation to be prepared but generally may be within the range of 0.001 to 10% by weight. Generally, however for most types of preparations advantageously the proportion used will be within the range of 0.005 to 1% and preferably 0.01 to 0.5%. However, in powders for inhalation or insufflation the proportion used may be within the range of 0.1 to 5%. The daily dose may vary and would be dependent on the condition being treated, and the duration of treatment desired.

In one embodiment, the amount of a compound according to formula I used to attain the desired biological effect depends on a number of factors, for example the specific compound selected, the intended use, the type of administration and the clinical state of the patient. In general, the daily dose is in the range of 0.01 mg to 500 mg (typically from 0.1 mg to 10 mg). Orally administrable individual dose formulations such as, for example, tablets or capsules can contain, for example, from 0.1 mg to 500 mg, typically from 1 mg to 100 mg.

In the case of physiologically acceptable salts, the above mentioned masses relate to the mass of the free compound on which the addition salt is based. The compounds used for the prophylaxis or therapy may be the compounds according to formula I themselves, or, in one embodiment, they are present in the form of a pharmaceutical composition together with an acceptable carrier. In one embodiment, the carrier must be naturally acceptable, in the sense that it is compatible with the other ingredients of said composition and is not harmful to the patient's health. The carrier may be a solid or a liquid or both and is preferably formulated with the compound as an individual dose, for example as a tablet that may contain from 0.05% to 95% by weight of the active compound. The pharmaceutical compositions of the invention may be prepared according to any of the known pharmaceutical methods which essentially comprise mixing the ingredients with pharmacologically acceptable carriers and/or excipients.

Another aspect of the present invention relates to formulation of compounds of formula I in a suitable form for administration to a subject.

Pharmaceutical compositions of the invention are those which are suitable for oral, rectal, topical, peroral (e.g. sublingual) and parenteral (e.g. subcutaneous, intradermal or intraarticular) administration, although the most suitable manner of administration depends in each individual case on the nature and severity of the condition to be treated and on the nature of the compound according to formula I used in each case. Sugar-coated formulations and sugar-coated delayed-release formulations, too, are included within the scope of the invention. In one embodiment, preference is given to acid-resistant and enteric formulations. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be present in separate units as, for example, capsules, cachets, lozenges or tablets, which in each case contain a particular amount of the compound according to formula I; as powders or granules; as solution or suspension in an aqueous or non-aqueous liquid; or as an oil-in-water or water-in-oil emulsion. These compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine.

Pharmaceutical compositions which are suitable for peroral (sublingual) administration include lozenges which contain a compound according to formula I with a flavoring agent, usually sucrose and gum arabic or tragacanth, and pastilles which comprise the compound in an inert base such as gelatin and glycerol or sucrose and gum arabic.

Suitable pharmaceutical compositions for parenteral administration may, for example, comprise sterile preparations of a compound according to formula I. These preparations may be administered intradermally, although they may also be administered subcutaneously, intramuscularly or intraarticularly as an injection. These preparations may be prepared by mixing the compound with water and rendering the obtained solution sterile. Injectable compositions of the invention generally contain from 0.01 to 5% by weight of the active compound.

Suitable pharmaceutical compositions for rectal administration are present as individual dose suppositories. These may be prepared by mixing a compound according to formula I with one or more conventional solid carriers, for example cocoa butter, and shaping the resulting mixture.

Suitable pharmaceutical compositions for topical application to the skin may be present as ointment, cream, lotion, paste, spray, aerosol or oil. The carriers which may be used include, for example, petroleum jelly, lanolin, polyethylene glycols, alcohols and combinations of two or more of these substances. In one embodiment, the active compound is present at a concentration ranging from 0.1 to 15%, for example from 0.5 to 2%, by weight of the composition.

Transdermal administration is also possible. Suitable pharmaceutical compositions for transdermal administration may be present as individual patches, which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 0.1% to 35%, preferably approx. 1 to 15%. A particular possibility is the release of the active compound by electro-transport or ionophoresis, as described, for example, in Pharmaceutical Research, 2(6): 318 (1986).

In one preferred embodiment the compounds of formula I are adapted for local administration. Local administration as used herein includes administration by insufflations and inhalation. The various types of dosage forms useful for local administration include ointments, lotions, creams, gels, foams, preparations for transdermal delivery by patches, powders, sprays, aerosols, capsules or cartridges for use in inhaler or insufflator or drops (for example, eye or nose drops), solution/suspensions for nebulisation, suppositories, pessaries, retention enemas and chewable or suckable tablets or pellets or microencapsulation preparations.

Ointments, creams and gels, may for example, be formulated with an aqueous or oily base with the addition of suitable thickening and/or gelling agent and/or solvents. Such bases may thus, for example, include water and/or oil such as liquid paraffin or a vegetable oil such as arachis oil or caster oil, or a solvent such as polyethylene glycol. Thickening agents and gelling agents which may be used according to the nature of the base include soft paraffin, aluminum stearate, cetostearyl alcohol, polyethylene glycols, woolfat, beewax, carboxypolymethylene and cellulose derivatives, and/or glyceryl monosterate and non-ionic emulsifying agents.

Powders for external application may be formed with the aid of any suitable powder base, for example, talc, lactose or starch. Drops may be formulated with an aqueous or non aqueous base also comprising agents, solubilizing agents, suspending agents or preservatives.

Spray compositions may for example be formulated as aqueous solution or suspensions or as aerosols delivered from pressurized packs, such as a metered dose inhaler, with the use of a suitable liquefied propellant. Aerosol compositions suitable for inhalation can be either a suspension or a solution and generally contain a compound of formula I and suitable propellant such as a fluorocarbon or hydrogen containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and co solvents e.g. ethanol.

Advantageously, the formulations of the invention may be buffered by the addition of suitable buffering agents.

Capsules and cartridges for use in an inhaler or insufflator, for example gelatine, may be formulated containing a powder mix or for inhalation of a compound of the invention suitable powder base such as lactose or starch. Each capsule or cartridge may generally contain between 20 µg-1000 µg of the compound of formula I. Alternatively, the compound of the invention may be presented without excipients such as lactose.

The proportion of the active compound of formula I in the local compositions according to the invention depends on the precise type of formulation to be prepared but will generally be within the range of form 0.001 to 10% by weight. Generally, however for most types of preparations advantageously the proportion used will be within the range of form 0.005 to 1% and preferably 0.01 to 0.5%. However, in powders for inhalation or insufflation the proportion used will be within the range of from 0.1 to 5%.

Aerosol formulations are preferably arranged so that each metered dose or "puff" of aerosol contains 20 µg-2000 µg, preferably about 20 µg-500 µg of a compound of formula I. Administration may be once daily or several times daily, for example 2, 3, 4 or 8 times, giving for example 1, 2 or 3 doses each time. The overall daily dose with an aerosol will be within the range 100 µg-1000 µg preferably, 200 µg-2000 µg. The overall daily dose and the metered dose delivered by capsules and cartridges in an inhaler or insufflator will generally be double those with aerosol formulations.

Topical preparation may be administrated by one or more applications per day to the affected area, occlusive dressing may advantageously be used. A continuous or prolonged delivery may be achieved by an adhesive reservoir system.

A pharmaceutical composition may be a solution or suspension comprising a therapeutically effective concentration of compound of formula I, with or without other bioactives in pharmaceutically effective concentrations. The composition may additionally comprise of various pharmaceutically acceptable excipients such as chelating agents, pH modifiers, buffers, viscosity enhancers, isotonicity agents, solubilizers, preservatives, antioxidants and the like.

A compound of formula I may be formulated in the form of drug delivery systems such as gel forming solutions.

For internal administration the compounds according to the invention may, for example, be formulated in conventional manner for oral, parenteral or rectal administration. Formulation for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents as appropriate. Dosage unit forms are, however, preferred as described below.

Slow release or enteric coated formulations may be advantageous, particularly for inflammatory bowel disorders.

Preferred forms of preparation for internal administration are dosage unit forms i.e. tablets and capsules. Such dosage unit forms contain from 0.01 mg to 20 mg preferably from 2.5 mg to 10 mg of the compounds of the invention.

The present invention provides a pharmaceutical composition comprising 11β-hydroxyandrosta-4-ene-3-one, a compound of formula I and physiologically acceptable salt thereof.

The present invention in one embodiment provides a pharmaceutical composition comprising 11β-hydroxyandrosta-4-ene-3-one, a compound of formula I-A, and physiologically acceptable salt thereof.

The present invention in one embodiment provides a pharmaceutical composition comprising 11β-hydroxy androsta-4-ene-3-one, a compound of formula I-B, physiologically acceptable salt thereof.

The present invention in one embodiment provides a pharmaceutical composition comprising 11β-hydroxyandrosta-4-ene-3-one, a compound of formula I-C, and physiologically acceptable salt thereof.

The invention is illustrated but not restricted by the description in the following examples.

EXAMPLES

Example 1

9,11-Epoxy-17α-hydroxy-16α-methyl-3-oxandrosta-1,4-diene-17β-carboxylic acid

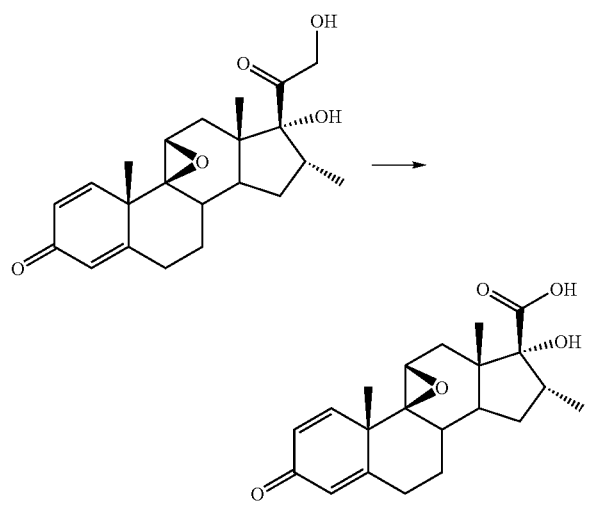

A solution of periodic acid (4.59 g, 0.0201 mol) in water (25 ml) (prepared by heating to 50-55° C. and then cooling to 30-35° C.) was added dropwise to a stirred suspension of 17α,21-dihydroxy-9,11-epoxy-16α-methylpregna-1,4-diene-3,20-dione (5.0 g, 0.0134 mol) in tetrahydrofuran (25 ml) at 0-5°. The reaction mixture was stirred at 0-5° C. for 2 hrs, water was added to the reaction mixture at 0-5° C. The precipitated product was filtered, washed with water, and dried to yield the title compound as white solid (4.75 g, 98.7%).

$^1$H NMR (400 MHz in CDCl$_3$), δ: 0.92 (d, J=6.99 Hz, 3H), 1.04 (s, 3H), 1.29-1.36 (m, 1H), 1.44 (s, 3H), 1.41-1.82 (m, 4H), 2.12-2.94 (m, 6H), 3.19 (s, 1H), 3.55-3.65 (m, 1H), 6.11 (s, 1H), 6.14 (dd, J$_1$=10.09 Hz, J$_2$=1.68 Hz, 1H), 6.60 (d, J=10.06 Hz, 1H).

Example 2

9,11-Epoxy-17α-[(2-furanylcarbonyl)oxy]16α-methyl-3-oxoandrosta-1,4-diene-17β-carboxylic acid

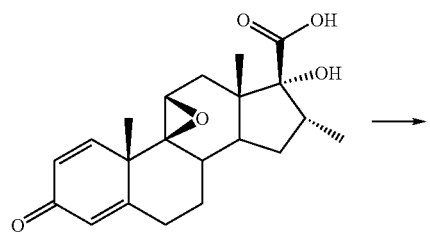

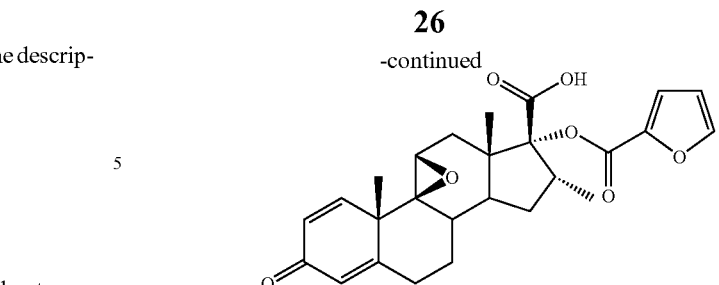

To suspension of 9,11-epoxy-17α-hydroxy-16α-methyl-3-oxoandrosta-1,4-diene-17β-carboxylic acid. (4.5 g, 0.012 mol) in acetone (25 ml) at 10-15° C. was added sequentially triethylamine (5.3 ml, 0.038 mol) and 2-furoyl chloride (4.96 g, 0.038 mol). After stirring for 4 hrs at 25-30° C., diethylamine (2.63 ml, 0.025 mol) was added dropwise at 10-15° C. and then stirred at ambient temperature for 1 hr. Thereafter the reaction mixture was acidified to pH 1.0-1.5 at 0-5° C., the precipitated product was filtered, washed with water, and dried to yield the title compound as white solid (5.96 g, 99%).

$^1$H NMR (400 MHz in CDCl$_3$+DMSO-d6), δ: 0.98 (d, J=7.09 Hz, 3H), 1.07 (s, 3H), 1.25-1.48 (m, 2H), 1.46 (s, 3H), 1.66-1.81 (m, 3H), 2.02-2.74 (m, 6H), 3.26 (s, 1H), 3.26-3.32 (m, 1H), 6.19 (s, 1H), 6.22 (dd, J$_1$=10.13 Hz, J$_2$=1.76 Hz, 1H), 6.53 (dd, J$_1$=3.44 Hz, J$_2$=1.61 Hz, 1H), 6.64 (d, J=10.04 Hz, 1H), 7.15 (d, J=3.37 Hz, 1H), 7.62 (d, J=0.81 Hz, 1H).

Example 3

17β-[(N,N-Dimethylcarbamoyl)thio]carbonyl-9,11-epoxy-17α-[(2-furanylcarbonyl)oxy]-16α-methyl-3-oxoandrosta-1,4-diene A solution of 9,11-epoxy-17α-[(2-furanylcarbonyl)oxy] 16α-methyl-3-oxoandrosta-1,4-diene-17β-carboxylic acid (7.0 g, 0.0129 mol) and N,N-dimethylthiocarbamoyl chloride (2.74 g, 0.0259 mol) in tetrahydrofuran (35 ml) was cooled to 10 to 15° C. and treated with triethylamine (2.86 g, 0.0283 mol) and tetrabutylammonium iodide (0.5 g). The reaction mixture was then warmed to ambient temperature, stirred for 4 hrs and then added N,N-dimethylacetamide (21 ml) followed by water (140 ml). The resultant mixture was cooled to 0° C., the product filtered, washed with water and dried to yield the title compound as light yellow solid. (6.6 g, 79.1%).

¹H NMR (400 MHz in CDCl₃+DMSO-d6), δ: 1.01 (d, J=7.11 Hz, 3H), 1.15 (s, 3H), 1.41-1.49 (m, 2H), 1.46 (s, 3H), 1.72-1.87 (m, 3H), 2.19-2.73 (m, 6H), 3.06 (s, 3H), 3.16 (s, 3H), 3.30 (s, 1H), 3.30-3.32 (m, 1H), 6.19 (s, 1H), 6.22 (dd, J₁=10.02 Hz, J₂=1.74 Hz, 1H), 6.58 (dd, J₁=3.51 Hz, J₂=1.68 Hz, 1H), 6.64 (d, J=10.09 Hz, 1H), 7.22 (d, J=3.51 Hz), 7.67 (d, J=0.90 Hz, 1H).

Example 4

9,11-Epoxy-17α-[(2-furanylcarbonyl)oxy]-17α-hydroxy-16α-methyl-3-oxoandrosta-1,4-diene-17β-carbothioic acid

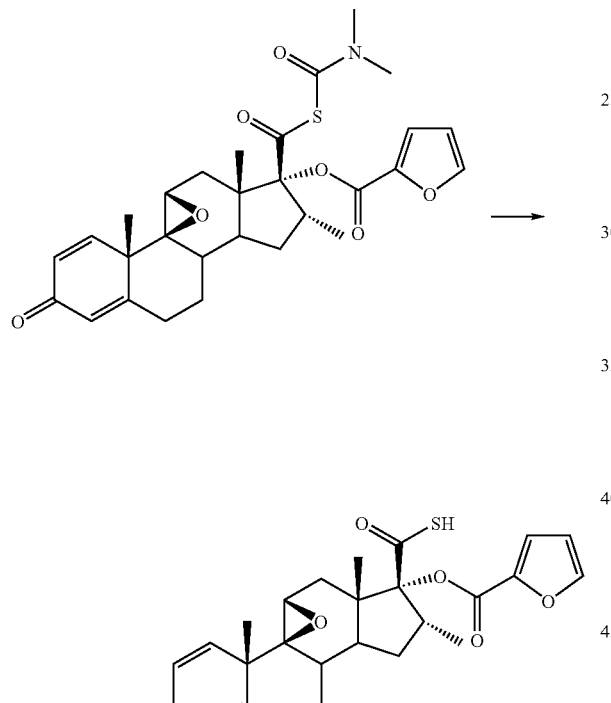

A suspension of 17β-[(N,N-dimethylcarbamoyl)thio]carbonyl-9,11-epoxy-17α-[(2-furanylcarbonyl)oxy]-16α-methyl-3-oxoandrosta-1,4-diene (5.0 g, 0.0106 mol) and potassium carbonate (2.94 g, 0.0213 mol) in methanol (25 ml) was stirred at ambient temperature for 5 hrs under a blanket of nitrogen. Thereafter, water was added to the reaction mixture and the resultant clear solution was washed with toluene. The aqueous layer containing the product was charcolized and then acidified with 2N HCl until pH was 1.5 to 2.0. The precipitated product was filtered, washed with water, and dried to yield the title compound as an off-white solid (3.6 g, 83%).

¹H NMR (400 MHz in CDCl₃), δ: 1.01 (d, J=7.11 Hz, 3H), 1.12 (s, 3H), 1.36-1.48 (m, 2H), 1.46 (s, 3H), 1.72-1.81 (m, 3H), 2.18-2.69 (m, 6H), 3.28-3.31 (m, 1H), 3.31 (s, 1H), 6.21 (s, 1H), 6.25 (dd, J₁=10.08 Hz, J₂=1.76 Hz, 1H), 6.55 (dd, J₁=3.48 Hz, J₂=1.61 Hz, 1H), 6.63 (d, J=10.06 Hz, 1H), 7.23 (dd, J₁=3.45 Hz, J₂=0.58 Hz, 1H), 7.64 (d, J=0.97 Hz, 1H).

Example 5

17β-[(N,N-Dimethylcarbamoyl)thio]carbonyl-6α,9α-difluoro-17α-[(2-furanyl-carbonyl)oxy]-11β-hydroxy-16α-methyl-3-oxoandrosta-1,4-diene

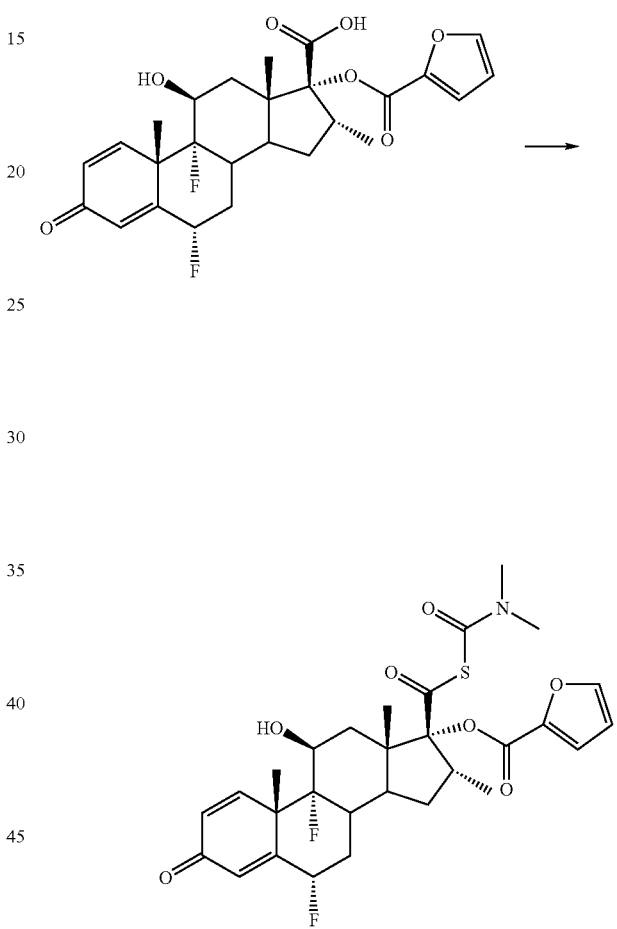

To a solution of 6α,9α-difluoro-17α-[(2-furanylcarbonyl)oxy]-11β-hydroxy-16α-methyl-3-oxoandrosta-1,4-diene-17β-carboxylic acid (12.3 g, 0.025 mol) and N,N-dimethylthiocarbamoyl chloride (9.29 g, 0.075 mol) in tetrahydrofuran (60 ml) was added triethylamine (10.48 ml, 0.075 mol) at 10-15° C. and tetrabutylammonium iodide (0.92 g) and the mixture stirred for 4 hrs at ambient temperature. Dimethylacetamide (37 ml) and water (310 ml) were added to the reaction mixture and stirred for 2 hrs at 0° C. The solid obtained was filtered, washed with water and dried to yield the title compound as a white solid (14.3 g, 99%).

¹H NMR (400 MHz in CDCl₃+DMSO-d6), δ: 1.00 (d, J=7.10 Hz, 3H), 1.19 (s, 3H), 1.30-1.36 (m, 1H), 1.54 (s, 3H), 1.63-2.00 (m, 3H), 2.22-2.60 (m, 4H), 3.03 (s, 3H), 3.16 (s, 3H), 3.31-3.36 (m, 1H), 4.29 (d, J=8.91 Hz, 1H), 5.39 (br-s, 1H), 5.43-5.59 (m, 1H), 6.22 (s, 1H), 6.27 (dd, J₁=10.15 Hz, $J_2$=1.75 Hz, 1H), 6.60 (dd, $J_1$=3.49 Hz, $J_2$=1.70 Hz, 1H), 7.15 (d, J=3.46 Hz, 1H), 7.26 (d, J=9.85 Hz, 1H), 7.80 (d, J=0.92 Hz, 1H).

Example 6

6α,9α-Difluoro-11β-hydroxy-16β-methyl-3-oxo-17α-propionyloxyandrosta-1,4-diene-17β-carbothioic acid

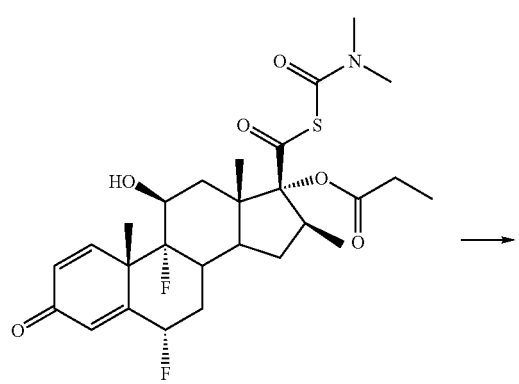

A suspension of 17β-[(N,N-dimethylcarbamoyl)thio]carbonyl-6α,9α-difluoro-11β-hydroxy-16β-methyl-3-oxo-17α-propionyloxyandrosta-1,4-diene (5.0 g, 9.27 mmol) in 75 ml diethylamine was heated under reflux for 8 hrs. The cooled reaction mixture was poured in to ice-water acidified with 2N HCl to pH 2 and extracted with ethyl acetate. The ethyl acetate extract was washed with water, dried, and concentrated in vacuo. The residue obtained was crystallized from ethyl acetate to give the title compound as light yellow solid (3.2 g, 73.7%).

$^1$H NMR (400 MHz in CDCl$_3$), δ: 1.06 (s, 3H), 1.16 (t, J=7.52 Hz, 3H), 1.20-1.25 (m, 1H), 1.39 (d, J=7.23 Hz, 3H), 1.54 (s, 3H), 1.67-2.05 (m, 4H), 2.22-2.80 (m, 4H), 2.39 (q, J=7.69 Hz, 2H), 4.45 (br-d, J=7.69 Hz, 1H), 5.30-5.50 (m, 1H), 6.38 (d, J=9.93 Hz, 1H), 6.43 (s, 1H), 7.15 (dd, J=10.17 Hz, 1H).

In an analogous manner was prepared 6α,9α-difluoro-17α-[(2-furanylcarbonyl)oxy]-11β-hydroxy-16β-methyl-3-oxoandrosta-1,4-diene-17β-carbothioic acid.

Example 7

6α,9α-Difluoro-17α-[(2-furanylcarbonyl)oxy]-11β-hydroxy-16α-methyl-3-oxoandrosta-1,4-diene-17β-carbothioic acid

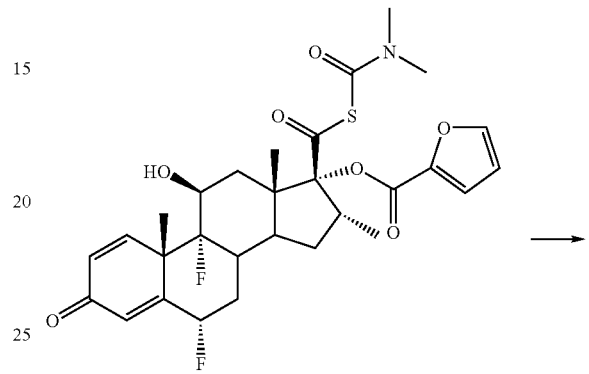

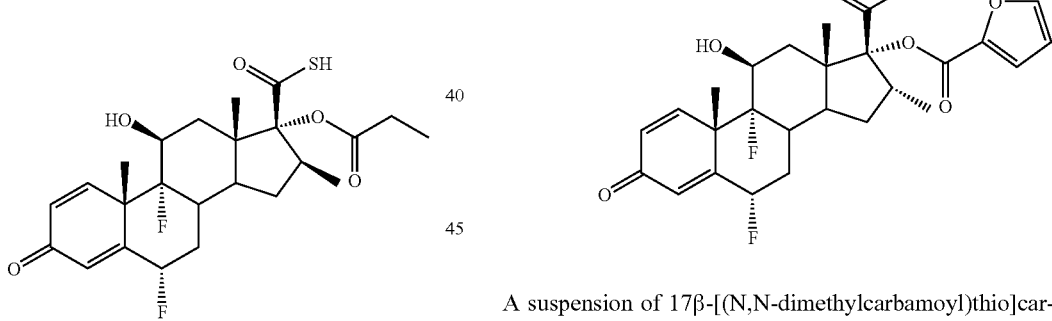

A suspension of 17β-[(N,N-dimethylcarbamoyl)thio]carbonyl-6α,9α-difluoro-17α-[(2-furanylcarbonyl)oxy]-11β-hydroxy-16α-methyl-3-oxoandrosta-1,4-diene (14.2 g, 0.024 mol) and potassium carbonate (6.78 g, 0.0491 mol) in methanol (70 ml) was stirred at ambient temperature for 6 hrs under a blanket of nitrogen. Thereafter, water was added to the reaction mixture and the resultant clear solution was washed with toluene. The aqueous layer containing the product was charcolized and then acidified with 2N HCl until pH was 1.5 to 2.0. The precipitated product was filtered, washed with water, and dried to yield the title compound as white solid (11.8 g, 94.8%).

$^1$H NMR (400 MHz in CDCl$_3$+DMSO-d6), δ: 1.03 (d, J=7.17 Hz, 3H), 1.20 (s, 3H), 1.31-1.37 (m, 1H), 1.56 (s, 3H), 1.73-2.03 (m, 3H), 2.28-2.59 (m, 4H), 3.37-3.42 (m, 1H), 4.35-4.38 (br-d, 1H), 4.89 (d, J=1.22 Hz, 1H), 5.34-5.51 (m, 1H), 6.34 (dd, $J_1$=10.06 Hz, $J_2$=1.88 Hz, 1H), 6.39 (s, 1H), 6.53 (dd, $J_1$=3.45 Hz, $J_2$=1.73 Hz, 1H), 7.14 (dd, $J_1$=3.28 Hz, $J_2$=0.49 Hz, 1H), 7.25 (dd, $J_1$=10.12 Hz, $J_2$=1.30 Hz, 1H), 7.63 (dd, $J_1$=1.73 Hz, $J_2$=0.63 Hz, 1H).

The following 17β-carbothioic acids were prepared by an analogous method to example 7:

9α-Fluoro-17α-[(2-furanylcarbonyl)oxy]-11β-hydroxy-16α-methyl-3-oxoandrosta-1,4-diene-17β-carbothioic acid.

6α,9α-Difluoro-11β-hydroxy-16α-methyl-17α-[[(3-methyl-2-furanyl)carbonyl]oxy]-3-oxoandrosta-1,4-diene-17β-carbothioic acid.

6α,9α-Difluoro-17α-[(3-furanylcarbonyl)oxy]-11β-hydroxy-16α-methyl-3-oxoandrosta-1,4-diene-17β-carbothioic acid.

6α,9α-Difluoro-11β-hydroxy-16α-methyl-3-oxo-17α-[(2-thienylcarbonyl)oxy]-androsta-1,4-diene-17β-carbothioic acid.

17α-[[(5-Chloro-2-thioenyl)carbonyl]oxy]-6α,9α-difluoro-11β-hydroxy-16α-methyl-3-oxoandrosta-1,4-diene-17β-carbothioic acid.

17α-Cyclopropylcarbonyloxy-6α,9α-difluoro-11β-hydroxy-16α-methyl-3-oxoandrosta-1,4-diene-17β-carbothioic acid.

17α-Cyclobutylcarbonyloxy-6α,9α-difluoro-11β-hydroxy-16α-methyl-3-oxoandrosta-1,4-diene-17β-carbothioic acid.

17α-Cyclopentylcarbonyloxy-6α,9α-difluoro-11β-hydroxy-16α-methyl-3-oxoandrosta-1,4-diene-17β-carbothioic acid.

17α-Cyclohexylcarbonyloxy-6α,9α-difluoro-11β-hydroxy-16α-methyl-3-oxoandrosta-1,4-diene-17β-carbothioic acid.

17α-Cyclohexylmethylcarbonyloxy-6α,9α-difluoro-11β-hydroxy-16α-methyl-3-oxoandrosta-1,4-diene-17β-carbothioic acid.

9α-Fluoro-11β-hydroxy-16α-methyl-3-oxo-17α-propionyloxyandrosta-1,4-diene-17β-carbothioic acid.

9α-Fluoro-11β-hydroxy-16β-methyl-3-oxo-17α-propionyloxyandrosta-1,4-diene-17β-carbothioic acid.

6α,9α-Difluoro-11β-hydroxy-16α-methyl-3-oxo-17α-propionyloxyandrosta-1,4-diene-17β-carbothioic acid.

6α,9α-Difluoro-11β-hydroxy-16β-methyl-3-oxo-17α-propionyloxyandrosta-1,4-diene-17β-carbothioic acid.

17α-Butryloxy-6α,9α-difluoro-11β-hydroxy-16α-methyl-3-oxoandrosta-1,4-diene-17β-carbothioic acid.

6α,9α-difluoro-11β-hydroxy-16α-methyl-3-oxo-17α-valeryloxyandrosta-1,4-diene-17β-carbothioic acid.

6α,9α-Difluoro-11β-hydroxy-16α-methyl-17α-(2-methylpropionyl)oxy-3-oxoandrosta-1,4-diene-17β-carbothioic acid.

17α-Dichloroacetoxy-6α,9α-difluoro-11β-hydroxy-16α-methyl-3-oxoandrosta-1,4-diene-17β-carbothioic acid.

6α,9α-Difluoro-11β-hydroxy-17α-(methoxymethylcarbonyl)oxy-16α-methyl-3-oxoandrosta-1,4-diene-17β-carbothioic acid.

6α,9α-Difluoro-17α-(ethoxymethylcarbonyl)oxy-11β-hydroxy-16α-methyl-3-oxoandrosta-1,4-diene-17β-carbothioic acid.

17α-(Ethoxycarbonyl)oxy-11β-hydroxy-16α-methyl-3-oxoandrosta-1,4-diene-17β-carbothioic acid.

6α,9α-Difluoro-17α-(ethoxycarbonyl)oxy-11β-hydroxy-16α-methyl-3-oxoandrosta-1,4-diene-17β-carbothioic acid.

Example 8

Compound IA.44

2-Phenyl-2-oxoethyl 6α,9α-difluoro-11β-hydroxy-16α-methyl-3-oxo-17α-propionyloxyandrosta-1,4-diene-17β-carboxylate 2-Bromo-1-phenylethanone (0.438 g, 2.2 mmol) and sodium iodide (50 mg) were added to a stirred mixture of 6α,9α-difluoro-11β-hydroxy-16α-methyl-3-oxo-17α-propionyloxy-androsta-1,4-diene-17β-carboxylic acid (1.0 g, 2.20 mmol) and anhydrous potassium carbonate (0.360 g, 2.6 mmol) in acetone (15 ml). The mixture was stirred under a blanket of nitrogen at 25 to 30° C. for 8 hrs, then poured into water and extracted with ethyl acetate. The organic layer was washed twice with water, dried, and concentrated in vacuo. The residue was purified by column chromatography (40% ethyl acetate in hexane) to yield the title compound as a white solid.

The following compounds were prepared in a manner similar to example 8 using an appropriate carboxylic acid of formula II and compound of formula III-A:

IA.1, IA.2, IA.4, IA.5, IA.7 to IA.10, IA.12, IA.15 to IA.19, IA.21, IA.23 to 25, IA.28 to 30, IA.32, IA.33, IA.36, IA.37, IA.42, IA.46, IA.48, IA50, IA.52, IA.54, IA.57, IA.60, IA.62

Example 9

Compound IA.38

S-[2-Oxo-2-(4-trifluoromethylphenyl)ethyl]6α,9α-difluoro-11β-hydroxy-16α-methyl-3-oxo-17α-propionyloxyandrosta-1,4-diene-17β-carbothioate

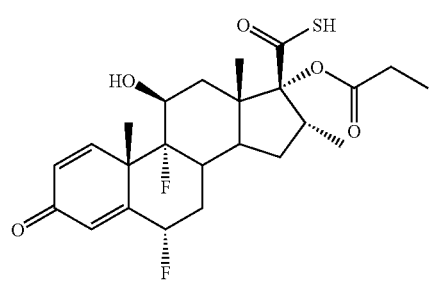

A mixture of 2-bromo-1-(4-trifluoromethylphenyl)ethan-1-one (0.569 g, 2.13 mmol), 6α,9α-difluoro-11β-hydroxy-16α-methyl-3-oxo-17α-propionyloxyandrosta-1,4-diene-17β-carbothioic acid (1.0 g, 2.13 mmol) and anhydrous potassium carbonate (0.295 g, 2.13 mmol) in acetone (25 ml) was stirred under a blanket of nitrogen at 25 to 30° C. for 3 hrs. The reaction mixture was then poured into water and extracted with ethyl acetate. The organic layer was washed with water, dried, and concentrated in vacuo. The residue was purified by column chromatography (40% ethyl acetate in hexane) to yield the title compound as a white solid.

The following compounds were prepared in a manner similar to example 9 using an appropriate thioic acid of formula II and compound of formula III-A:

IA.3, IA.6, IA.11, IA.13, IA.14, IA.20, IA.22, IA.26, IA.27, IA.31, IA.34, IA.35, IA.39, IA.40, IA.43, IA.45, IA.47, IA.49, IA.51, IA.53, IA.55, IA.56, IA.58, IA.59, IA.61, IA.63, IA.68 to IA.70, IA.73, IA.75, IA.78, IA.79, IA.81, IA.83, IA.85, IA.86, IA.88 to IA.90, IA.92 to IA.102, IA.104 to IA.67, IA.71, IA.72, IA.74, IA.76, IA.77, IA.80, IA.82, IA.84, IA.87, IA.91, IA.103, IA.115, IA.118, IA.121, IA.133.

Example 10

Compound IA.59

S-[1,1-Dimethyl-2-oxo-2-phenylethyl]6α,9α-difluoro-11β-hydroxy-16α-methyl-3-oxo-17α-propionyloxyandrosta-1,4-diene-17β-carbothioate

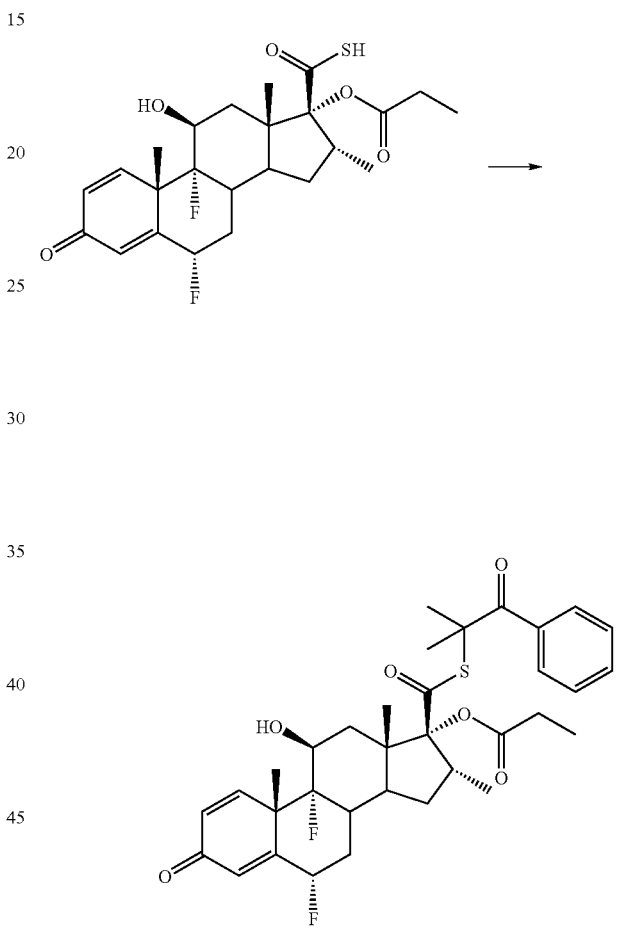

2-Bromo-2-methyl-1-phenyl-propan-1-one (0.483 g, 2.13 mmol) was added to a stirred mixture of 6α,9α-difluoro-11β-hydroxy-16α-methyl-3-oxo-17α-propionyloxyandrosta-1,4-diene-17β-carbothioic acid (1.0 g, 2.13 mmol) and anhydrous potassium carbonate (0.295 g, 2.13 mmol) in acetone (20 ml) and the mixture was stirred under a blanket of nitrogen at 25 to 30° C. for 3 hrs. The reaction mixture was then poured into water and extracted with ethyl acetate. The organic layer was washed with water, dried, and concentrated in vacuo. The residue was purified by column chromatography (40% ethyl acetate in hexane) to yield the title compound as a white solid.

The following compounds were prepared in a manner similar to example 10 using an appropriate thioic acid of formula II and compound of formula III-A:

IA.109, IA.187 to IA.197.

Example 11

Compound IA-1.2

S-(1-Benzoylcyclopentyl) 6α,9α-difluoro-11β-hydroxy-16α-methyl-3-oxo-17α-propionyloxyandrosta-1,4-diene-17β-carbothioate

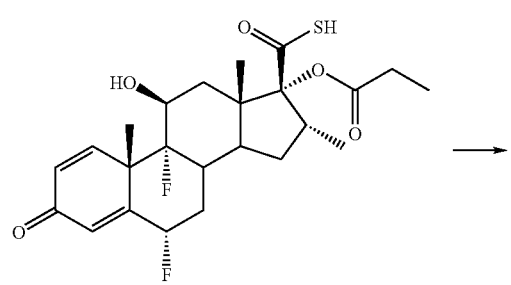

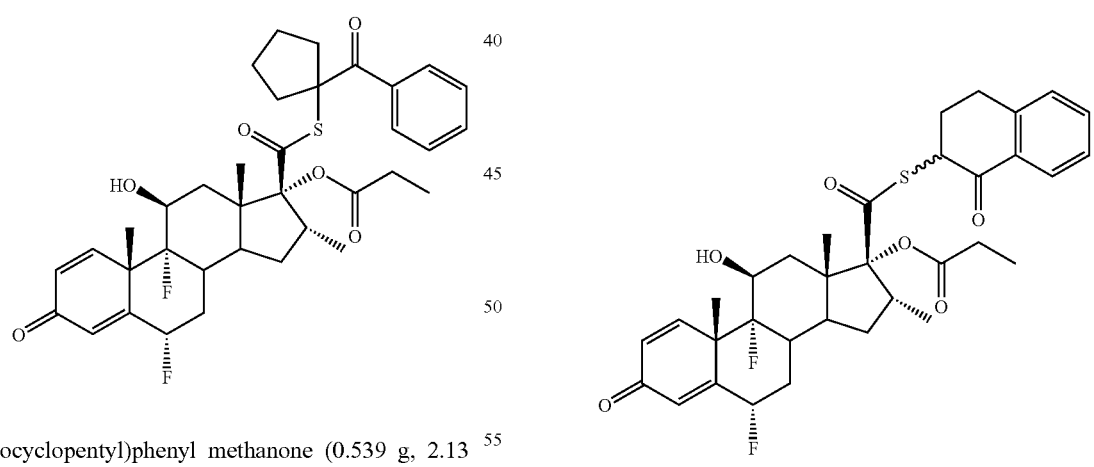

(1-Bromocyclopentyl)phenyl methanone (0.539 g, 2.13 mmol) was added to a stirred mixture of 6α,9α-difluoro-11β-hydroxy-16α-methyl-3-oxo-17α-propionyloxyandrosta-1,4-diene-17β-carbothioic acid (1.0 g, 2.13 mmol) and anhydrous potassium carbonate (0.295 g, 2.13 mmol) in acetone (25 ml), and the mixture was stirred under a blanket of nitrogen at 25 to 30° C. for 3 hrs. The reaction mixture was then poured into water and extracted with ethyl acetate. The organic layer was washed with water, dried, and concentrated in vacuo. The residue was purified by column chromatography (35% ethyl acetate in hexane) to yield the title compound as a white solid.

The compound IA-1.1 was prepared in a manner similar to example 11.

Example 12

Compound IA-2.1

S-(1-Oxo-1,2,3,4-tetrahydronapthalen-2-yl) 6α,9α-difluoro-11β-hydroxy-16α-methyl-17α-propionyloxy-3-oxoandrosta-1,4-diene-17β-carbothioate

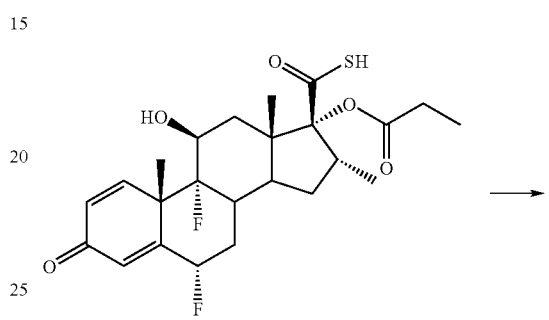

2-Bromo-1-tetralone (0.395 g, 1.75 mmol) was added to a stirred mixture of 6α,9α-difluoro-11β-hydroxy-16α-methyl-3-oxo-17α-propionyloxyandrosta-1,4-diene-17β-carbothioic acid (0.500 g, 1.06 mmol) and anhydrous potassium carbonate (0.161 g, 1.17 mmol) in acetone (10 ml) and the mixture was stirred under a blanket of nitrogen at 25 to 30° C. for 3 hrs. The reaction mixture was then poured into water and extracted with ethyl acetate. The organic layer was washed with water, dried, and concentrated in vacuo. The residue was purified by column chromatography (40% ethyl acetate in hexane) to yield the title compound as a white solid.

Example 13

Compound IA.41

S-[2-Oxo-2-(2,4,6-Trimethylphenyl)ethyl]9α-chloro-17α-[(2-furanylcarbonyl)oxy]-11β-hydroxy-16α-methyl-3-oxoandrosta-1,4-diene-17β-carbothioate

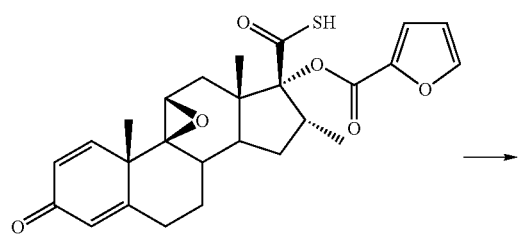

purified by column chromatography (35% ethyl acetate in hexane) to yield the title compound as a white solid.

Example 14

Compound IB.45

S-[4-Hydroxy-but-2-ynyl]9α-chloro-17α-[(2-furanylcarbonyl)oxy]-11β-hydroxy-16α-methyl-3-oxoandrosta-1,4-diene-17β-carbothioate

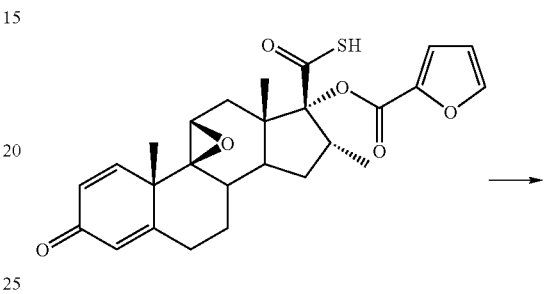

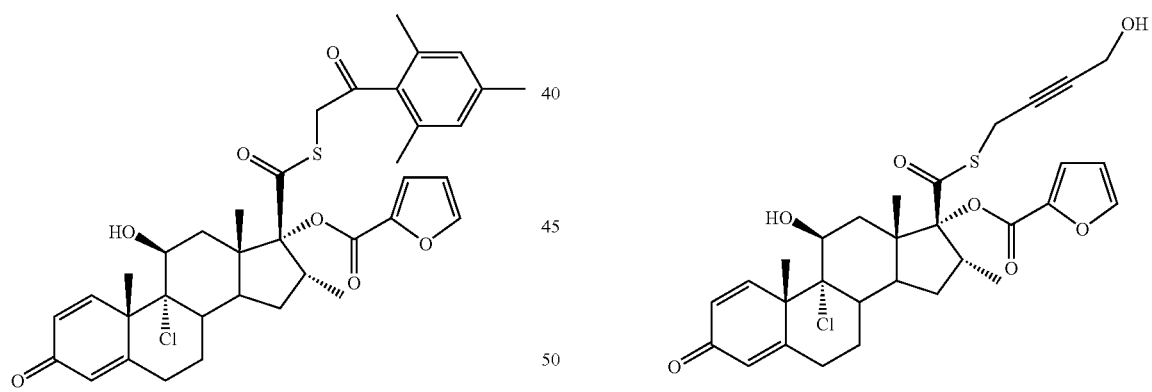

2-Bromo-1-(2,4,6-trimethylphenyl)ethanone (0.287 g, 1.13 mmol) was added to a stirred mixture of 9,11-epoxy-17α-[(2-furanylcarbonyl)oxy]-16α-methyl-3-oxoandrosta-1,4-diene-17β-carbothioic acid (0.600 g, 1.28 mmol) and anhydrous potassium carbonate (0.194 g, 1.40 mmol) in acetone (25 ml) and the mixture was stirred under a blanket of nitrogen at 25 to 30° C. for 2.5 hrs. The reaction mixture was then poured into water and extracted with ethyl acetate. The organic layer was washed with water, dried, and concentrated in vacuo. The crude solid was dissolved in glacial acetic acid (10 ml) and concentrated hydrochloric acid (1 ml) was added at 10-15° C. The mixture was stirred at 15-20° C. for 30 min, poured into ice-water (400 ml), the product filtered, washed with water, and finally dried in air oven. The crude solid was 4-(Tetrahydropyran-2-yloxy)-but-2-ynyl toluene-4-sulfonic acid ester (0.727 g, 2.24 mmol) was added to a stirred mixture of 9,11-epoxy-17α-[(2-furanylcarbonyl)oxy]-17α-hydroxy-16α-methyl-3-oxoandrosta-1,4-diene-17β-carbothioic acid (1.0 g, 2.13 mmol) and anhydrous potassium carbonate (0.300 g, 2.34 mmol) in acetone (20 ml) and the mixture was stirred under a blanket of nitrogen at 25 to 30° C. for 4 hrs. The reaction mixture was then poured into water and extracted with ethyl acetate. The organic layer was washed with water, dried, and concentrated in vacuo. The crude solid was dissolve in methanol (15 ml) and concentrated hydrochloric acid (4 ml) was added at 10-15° C. The mixture was stirred at 25-30 for 30 min and then heated at 60° C. for 4 hrs. The mixture was then cooled and poured in to ice-water. The solid was filtered, washed with water, and dried. The crude solid was purified by column chromatography (3% methanol in dichloromethane) to yield the title compound as a white solid.

Example 15

Compound IB.2

S-(4-Hydroxy-but-2-ynyl) 6α,9α-difluoro-11β-hydroxy-16α-methyl-3-oxo-17α-propionyloxyandrosta-1,4-diene-17β-carbothioate

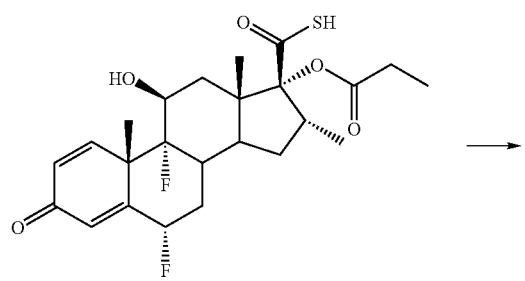

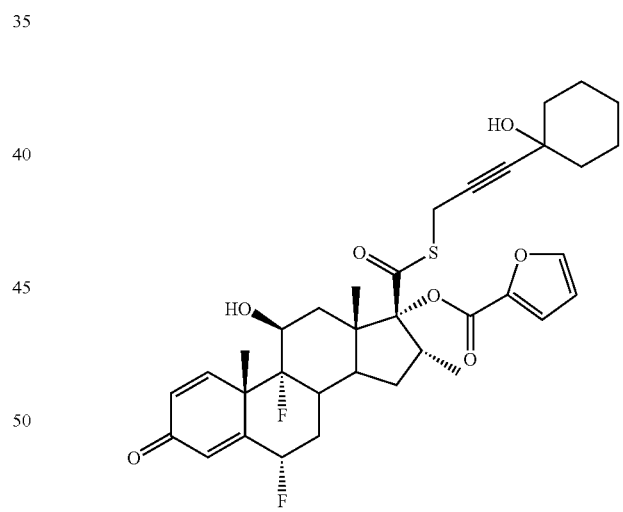

4-Chloro-but-2-yne-1-ol (0.169 g, 1.62 mmol) was added to a stirred mixture of 6α,9α-difluoro-11β-hydroxy-16α-methyl-3-oxo-17α-propionyloxyandrosta-1,4-diene-17β-carbothioic acid (0.800 g, 1.54 mmol) and anhydrous potassium carbonate (0.234 g, 1.70 mmol) in acetone (20 ml) and the mixture was stirred under a blanket of nitrogen at 25 to 30° C. for 3 hrs. The reaction mixture was then poured into water and extracted with ethyl acetate. The organic layer was washed with water, dried, and concentrated in vacuo. The residue was purified by column chromatography (3% methanol in dichloromethane) to yield the title compound as a white solid.

The following compounds were prepared in a manner similar to example 15 using an appropriate thioic acid of formula II and compound of formula III-B:

IB.1, IB.4, IB.5, IB.7 to IB.11, IB.20 to IB.24, IB.26 to IB.29, IB.38, IB.39, IB.61, IB.62, IB.132.

Example 16

Compound IB.25

S-[3-(1-Hydroxycyclohexyl)prop-2-ynyl]6α,9α-difluoro-17α-[(2-furanylcarbonyl)oxy]-11β-hydroxy-16α-methyl-3-oxoandrosta-1,4-diene-17β-carbothioate

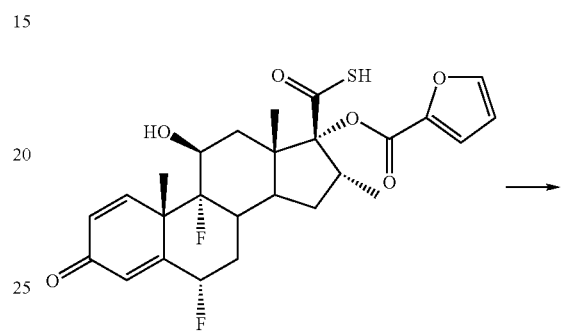

4-Methyl-[3-(hydroxycyclohexyl)prop-2-ynyl]benzenesulfonate (0.222 g, 0.72 mmol) was added to a stirred mixture of 6α,9α-difluoro-17α-[(2-furanylcarbonyl)oxy]-11β-hydroxy-16α-methyl-3-oxoandrosta-1,4-diene-17β-carbothioic acid (0.350 g, 0.688 mmol) and anhydrous potassium carbonate (0.104 g, 0.756 mmol) in acetone (20 ml) and the mixture was stirred under a blanket of nitrogen at 25 to 30° C. for 3 hrs. The reaction mixture was then poured into water and extracted with ethyl acetate. The organic layer was washed with water, dried, and concentrated in vacuo. The residue was purified by column chromatography (35% ethyl acetate in hexane) to yield the title compound as a white solid.

Compound IB.40 was prepared in a manner similar to example 16.

Example 17

Compound IB.35

S-[4-n-Butylcarbonyloxy-but-2-ynyl]6α,9α-difluoro-11β-hydroxy-16α-methyl-3-oxo-17α-propionyloxyandrosta-1,4-diene-17β-carbothioate

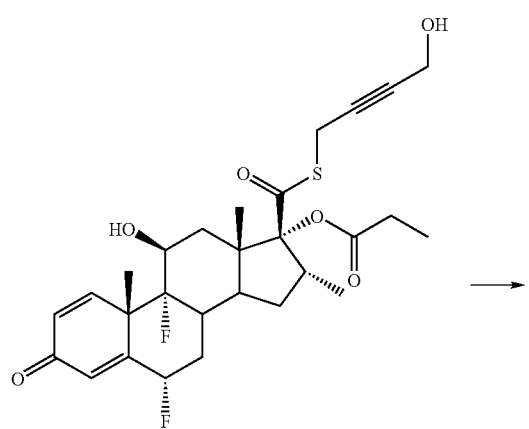

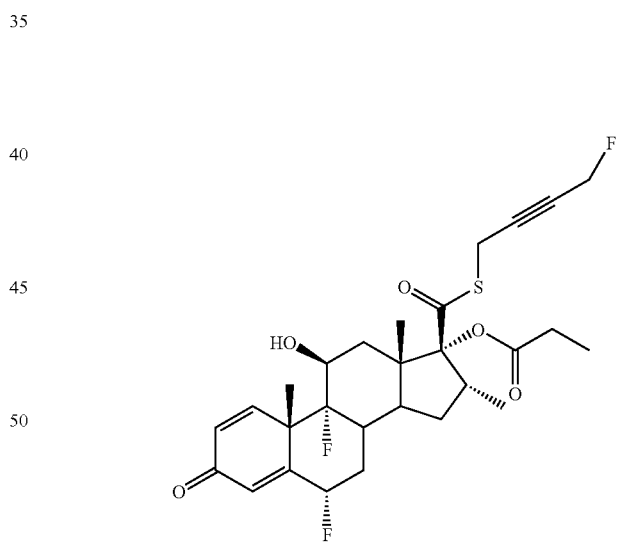

Valeryl chloride (0.337 g, 2.79 mmol) was added at 10-15° C. in to a stirred mixture of S-(4-hydroxy-but-2-ynyl)6α,9α-difluoro-11β-hydroxy-16α-methyl-3-oxo-17α-propionyloxyandrosta-1,4-diene-17β-carbothioate (0.5 g, 0.93 mmol) and triethylamine (0.282 g, 2.79 mmol) in acetone (20 ml) and the mixture was stirred under a blanket of nitrogen at 25-30° C. for 8 hrs. The reaction mixture was then poured into water and extracted with ethyl acetate. The organic layer was washed with water, dried, and concentrated in vacuo. The residue was purified by column chromatography (35% ethyl acetate in hexane) to yield the title compound as a white solid.

The following compounds were prepared with similar manner to example 17:
IB.31 to IB.37, IB.48 to IB.53, IB.55 to IB.60, IB.67 to IB.73, IB.75 to IB.86, IB.88, IB.92-IB.102, IB.104 to IB.122, IB.124, IB.133, IB.135, IB.148, IB.155, IB.157.

Example 18

Compound IB.3

S-(4-Fluorobut-2-ynyl) 6α,9α-difluoro-11β-hydroxy-16α-methyl-3-oxo-17α-propionyl-oxyandrosta-1,4-diene-17β-carbothioate

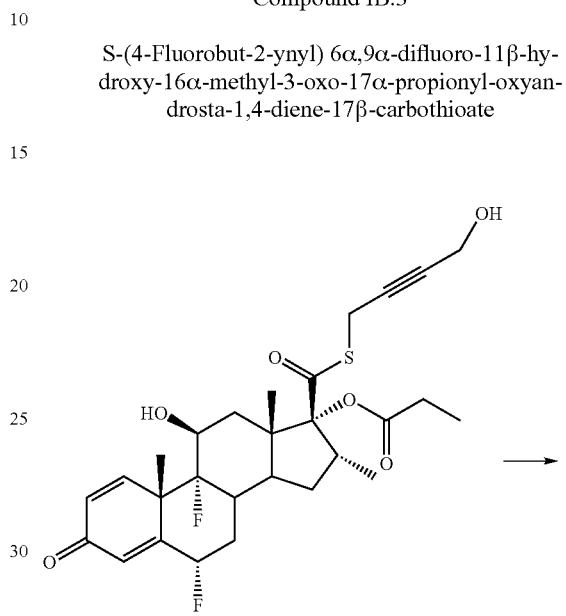

Diethylaminosulfur trifluoride (DAST) (0.151 g, 0.93 mmol) was added to a stirred solution of S-(4-hydroxy-but-2-ynyl) 6α,9α-difluoro-11β-hydroxy-16α-methyl-3-oxo-17α-propionyloxyandrosta-1,4-diene-17β-carbothioate (0.450 g, 0.783 mmol) in dry dichloromethane (20 ml) at 25-30° C. and the mixture was stirred under a blanket of nitrogen at 25-30° C. for 2 hrs. The reaction mixture was washed with sodium bicarbonate solution (25 ml), water, dried, and concentrated in vacuo. The residue was purified by column chromatography (40% ethyl acetate in hexane) to yield the title compound as a white solid.

The compound IB.6 was prepared in a manner similar to example 18.

Example 19

Compound IB.15

S-(4-Hydroxy-(Z)-but-2-enyl) 6α,9α-difluoro-17α-[(2-furanylcarbonyl)oxy]-11β-hydroxy-16α-methyl-3-oxoandrosta-1,4-diene-17β-carbothioate

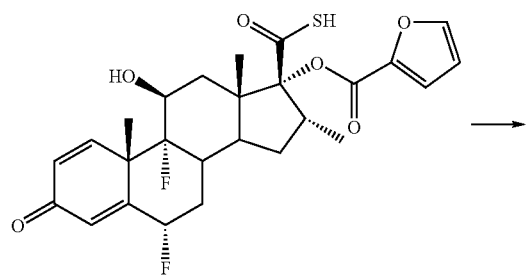

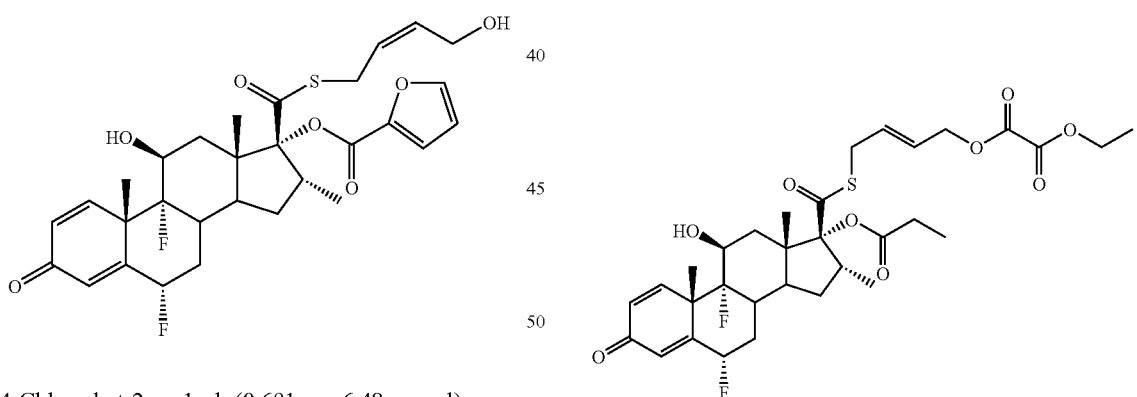

(Z)-4-Chloro-but-2-en-1-ol (0.691 g, 6.48 mmol) was added to a stirred mixture of 6α,9α-difluoro-17α-[(2-furanylcarbonyl)oxy]-11β-hydroxy-16α-methyl-3-oxoandrosta-1,4-diene-17β-carbothioic acid (3.0 g, 5.87 mmol) and anhydrous potassium carbonate (0.895 g, 6.48 mmol) in acetone (60 ml) and the mixture was stirred under a blanket of nitrogen at 25 to 30° C. for 3 hrs. The reaction mixture was then poured into water and extracted with ethyl acetate. The organic layer was washed with water, dried, and concentrated in vacuo. The residue was purified by column chromatography (1% methanol in dichloromethane) to yield the title compound as a white solid.

The compounds IB.16, IB.30 were prepared with similar manner to example 19. The compounds IB.13, IB.14, IB.17 were prepared by similar manner using (E)-4-bromo-but-2-en-1-ol and an appropriate thioic acid of formula II.

Example 20

Compound IB.44

S-[4-(2-Ethoxy-1,2-dioxoethyl)oxy-(E)-but-2-enyl] 6α,9α-difluoro-11β-hydroxy-16α-methyl-3-oxo-17α-propionyloxyandrosta-1,4-diene-17β-carbothioate

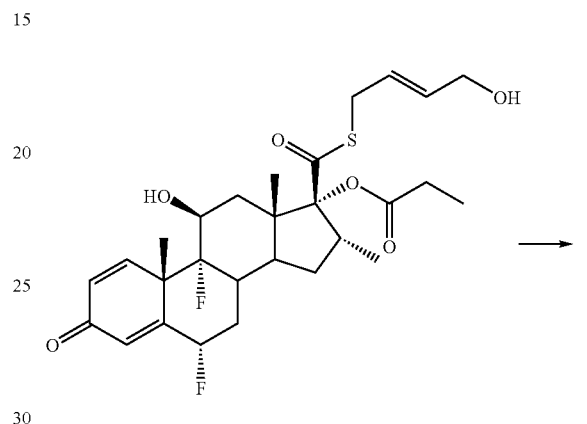

Ethyl oxalyl chloride (0.352 g, 2.58 mmol) was added at 10-15° C. in to a stirred mixture of S-(4-hydroxy-(E)-but-2-enyl)-6α,9α-difluoro-11β-hydroxy-16α-methyl-3-oxo-17α-propionyloxyandrosta-1,4-diene-17β-carbothioate (0.7 g, 1.29 mmol) and triethylamine (0.260 g, 2.58 mmol) in acetone (20 ml) and the mixture was stirred under a blanket of nitrogen at 25-30° C. for 8 hrs. The reaction mixture was then poured into water and extracted with ethyl acetate. The organic layer was washed with water, dried, and concentrated in vacuo. The residue was purified by column chromatography (35% ethyl acetate in hexane) to yield the title compound as a white solid.

The compound IB.46 was prepared in a similar manner to example 20. The compounds IB.47 and IB.54 were prepared from IB.15 and IB.4 respectively, in a similar manner to example 20.

Example 21

Compound IB.42

4-Methoxy-4-oxo-(E)-but-2-enyl 6α,9α-difluoro-11β-hydroxy-16α-methyl-3-oxo-17α-propionyloxyandrosta-1,4 diene-17β-carbothioate

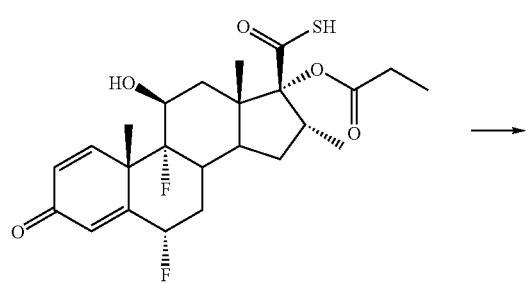

Methyl 4-bromocrotonate (0.191 g, 1.06 mmol) was added at 25-30° C. in to a stirred mixture of 6α,9α-difluoro-11β-hydroxy-16α-methyl-3-oxo-17α-propionyloxyandrosta-1,4-diene-17β-carbothioic acid (0.5 g, 1.06 mmol) and anhydrous potassium carbonate (0.146 g, 1.06 mmol) in N,N-dimethylformamide (10 ml) and the mixture was stirred under a blanket of nitrogen at 25-30° C. for 1.5 hrs. The reaction mixture was then poured into water and extracted with ethyl acetate. The organic layer was washed with water, dried, and concentrated in vacuo. The residue was purified by column chromatography (40% ethyl acetate in hexane) to yield the title compound as a white solid.

Compounds IB.41 and IB.43 were prepared in a manner similar to example 21.

Example 22

6α,9α-Difluoro-17α-[(2-furanylcarbonyl)oxy]-11β-hydroxy-16α-methyl-3-oxoandrosta-1,4-diene-17β-carbonylsulfenic acid

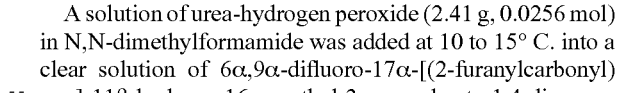

A solution of urea-hydrogen peroxide (2.41 g, 0.0256 mol) in N,N-dimethylformamide was added at 10 to 15° C. into a clear solution of 6α,9α-difluoro-17α-[(2-furanylcarbonyl)oxy]-11β-hydroxy-16α-methyl-3-oxoandrosta-1,4-diene-17β-carbothioic acid (13.0 g, 0.0256 mol) in N,N-dimethylformamide (40 ml). The reaction mixture was stirred at 10-15° C. for 30 min, then poured into ice-water. The solid was filtered, washed with water, and dried at 50-60° C. to yield the title compound as white solid (12.0 g, 89.48%).

$^1$H NMR (400 MHz in CDCl$_3$+DMSO-d6), δ: 1.06 (d, J=7.09 Hz, 3H), 1.19 (s, 3H), 1.33-1.38 (m, 1H), 1.55 (s, 3H), 1.58-1.98 (m, 4H), 2.26-2.52 (m, 4H), 3.02-3.06 (m, 1H), 4.32-(br-d, J=8.76 Hz, 1H), 5.14-5.19 (br-s, 1H), 5.38-5.54 (m, 1H), 6.29 (s, 1H), 6.30 (d, J=8.71 Hz, 1H), 6.54 (dd, $J_1$=3.32 Hz, $J_2$=1.53 Hz, 1H), 7.08 (d, J=3.37 Hz, 1H), 7.27 (d, J=10.30 Hz, 1H), 7.67 (s, 1H).

Example 23

6α,9α-Difluoro-11β-hydroxy-16α-methyl-3-oxo-17α-propionyloxyandrosta-1,4-diene-17β-carbonylsulfenic acid

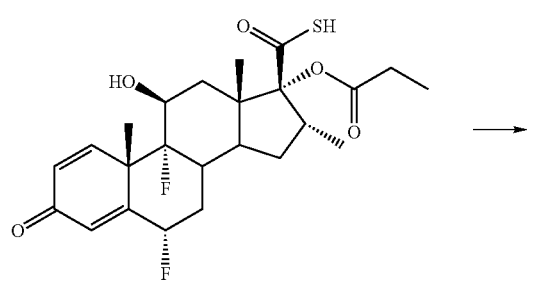

Hydrogen peroxide (30 vol, 60 ml) was added to a suspension of 6α,9α-difluoro-11β-hydroxy-16α-methyl-3-oxo-17α-propionyloxyandrosta-1,4-diene-17β-carbothioic acid (20.0 g, 42.68 mmol) in methanol (120 ml) at 10 to 15° C. The reaction mixture was stirred at ambient temperature for 1 hr. Excess peroxide was neutralized with 10% sodium metabisulfite solution, the product was filtered, washed with water, and dried to yield the title compound as white solid (19.9 g, 96.22%).

$^1$H NMR (400 MHz in CDCl$_3$+DMSO-d6), δ: 0.98 (d, J=7.10 Hz, 3H), 1.08 (t, J=7.55 Hz, 3H), 1.12 (s, 3H), 1.25-1.33 (m, 1H), 1.53 (s, 3H), 1.58-1.93 (m, 4H), 2.12-2.47 (m, 4H), 2.33 (q, J=7.57 Hz, 2H), 2.95-2.99 (m, 1H), 4.24-4.27 (br-d, 1H), 5.15 (br-s, 1H), 5.36-5.53 (m, 1H), 6.26 (s, 1H), 6.27 (dd, $J_1$=10.21 Hz, $J_2$=1.68 Hz, 1H), 7.24 (d, J=9.73 Hz, 1H).

The following 17β-carbonylsulfenic acids were prepared by an analogous method to example 23:

9α-Fluoro-17α-[(2-furanylcarbonyl)oxy]-11β-hydroxy-16α-methyl-3-oxoandrosta-1,4-diene-17β-carbonylsulphenic acid.

6α,9α-Difluoro-11β-hydroxy-16α-methyl-17α-penatanoyloxy-3-oxoandrosta-1,4-diene-17β-carbonylsulphenic acid.

Example 24

Compound IC.3

6α,9α-Difluoro-11β-hydroxy-16α-methyl-3-oxo-17α-propionyloxyandrosta-1,4-diene-17β-carbonylsulfenic acid fluoromethyl ester

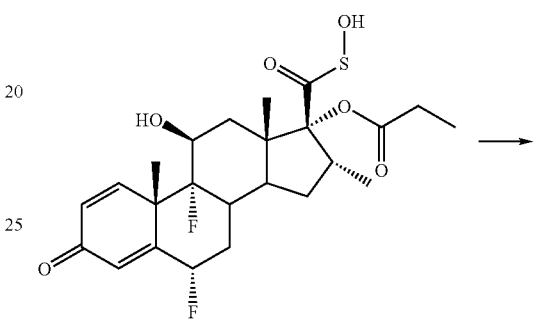

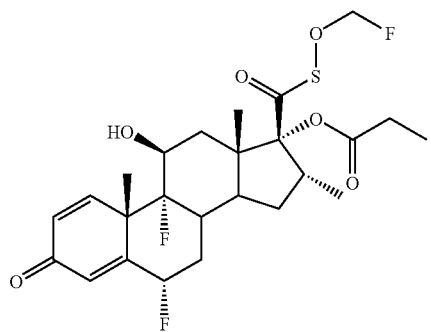

Bromofluoromethane (1.5 ml) was added at 0° C. in to a stirred mixture of 6α,9α-difluoro-11β-hydroxy-16α-methyl-17α-propionyloxy-3-oxoandrosta-1,4-diene-17β-carbonylsulphenic acid (1.5 g, 3.1 mmol) and anhydrous potassium carbonate (0.427 g, 3.1 mmol) in acetone (50 ml). The mixture was stirred under a blanket of nitrogen at 5 to 10° C. for 1 hr. The reaction mixture was then poured into water and extracted with ethyl acetate. The organic layer was washed with water, dried, and concentrated in vacuo. The residue was purified by preparative HPLC to yield the title compound as a white solid.

Structure of compound IC.3 was confirmed by single crystal X-Ray as shown below:

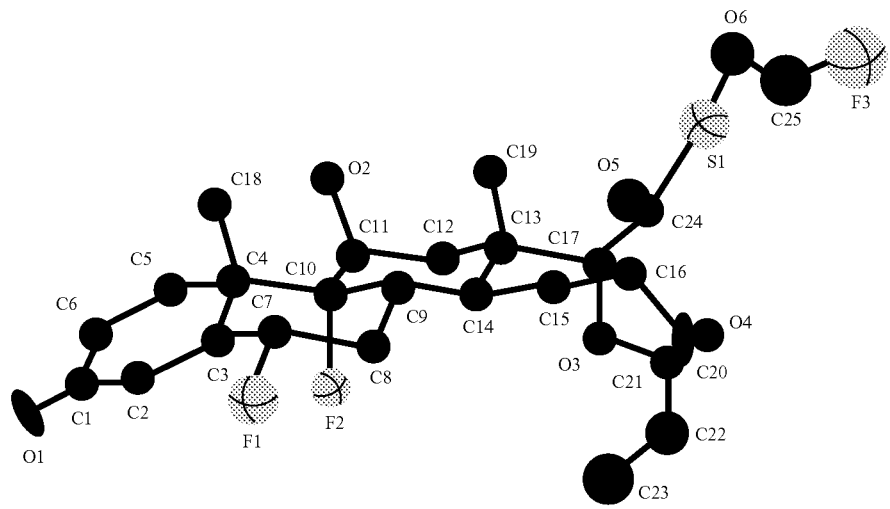

The compounds IC.4, IC.11 to IC.14 were prepared in a similar manner to example 24 using appropriate carbonyl sulfenic acid of formula VI and compound of III-C.

Example 25

Compound IC.5

6α,9α-Difluoro-17α-[(2-furanylcarbonyl)oxy]-11β-hydroxy-16α-methyl-3-oxoandrosta-1,4-diene-17β-carbonylsulfenic acid (4-fluorophenyl)methyl ester

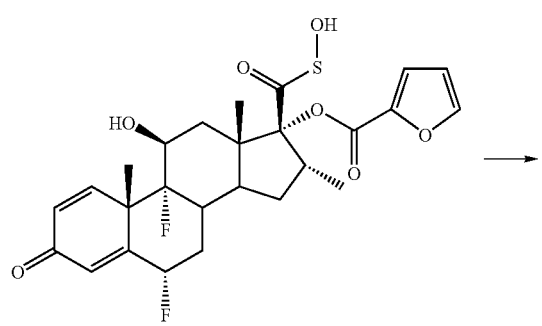

→

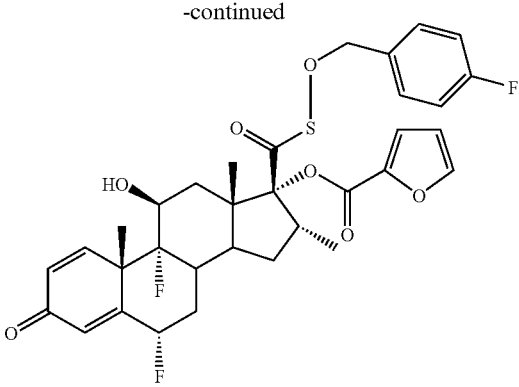

4-Fluorobenzyl chloride (0.277 g, 1.91 mmol) was added at 25-30° C. in to a stirred mixture of 6α,9α-difluoro-17α-[(2-furanylcarbonyl)oxy]-11β-hydroxy-16α-methyl-3-oxoandrosta-1,4-diene-17β-carbonylsulfenic acid (1.0 g, 1.91 mmol) and anhydrous potassium carbonate (0.344 g, 2.49 mmol) in N,N-dimethylformamide (15 ml), and the mixture was stirred under a blanket of nitrogen at 25-30° C. for 2 hrs. The reaction mixture was then poured into water and extracted with ethyl acetate. The organic layer was washed with water, and concentrated in vacuo. The residue was purified by crystallization from acetone to yield the title compound as a white solid.

The compounds IC.1, IC.2, IC.6 to IC.9, IC.15, IC.16, IC.18 to IC.23 were prepared in a manner similar to example 25.

Example 26

Compound IC.10

6α,9α-Difluoro-11β-hydroxy-16α-methyl-3-oxo-17α-propionyloxyandrosta-1,4-diene-17β-carbonylsulfenic acid [2-(4-chlorophenyl)-2-oxoethyl]ester

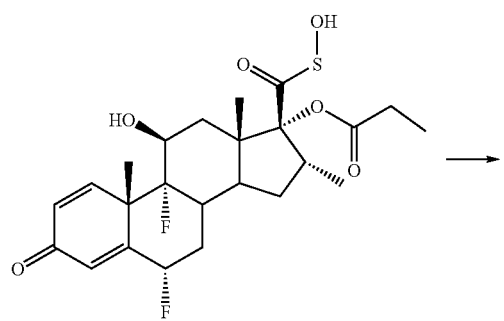

2-Bromo-1-(4-chlorophenyl)ethanone (0.120 g, 0.51 mmol) was added at 25-30° C. in to a stirred mixture of 6α,9α-difluoro-11β-hydroxy-16α-methyl-3-oxo-17α-propionyloxyandrosta-1,4-diene-17β-carbonylsulfenic acid (0.25 g, 0.51 mmol) and anhydrous potassium carbonate (0.070 g, 0.51 mmol) in acetone (20 ml) and the mixture was stirred under a blanket of nitrogen at 25-30° C. for 2 hrs. The reaction mixture was then poured into water and extracted with ethyl acetate. The organic layer was washed with water, dried, and concentrated in vacuo. The residue was purified by column chromatography (35% ethyl acetate in hexane) to yield the title compound as a white solid.

Compound IC.17 was prepared in a similar manner to example 26.

Example 27

Compound IB.63

S-(4-Methoxycarbonyloxy-but-2-ynyl) 6α,9α-difluoro-17α-[(2-furanylcarbonyl)-oxy]-11β-hydroxy-16α-methyl-3-oxoandrosta-1,4-diene-17β-carbothioate

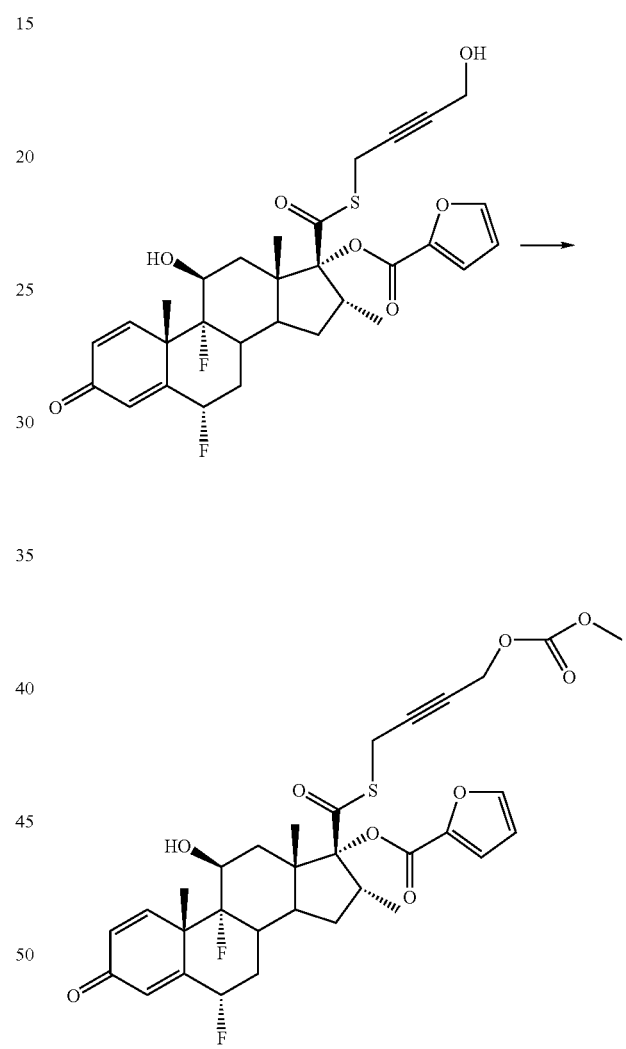

Methyl chloroformate (0.33 g, 3.48 mmol) was added at 25-30° C. in to a stirred mixture of S-(4-hydroxy-but-2-ynyl) 6α,9α-difluoro-17α-[(2-furanylcarbonyl)oxy]-11β-hydroxy-16α-methyl-3-oxoandrosta-1,4-diene-17β-carbothioate (1.0 g, 1.74 mmol) and triethylamine (0.70 g, 6.96 mmol) in dry dichloromethane (30 ml). The mixture was stirred at 25 to 30° C. for 6 hrs, then washed with water and concentrated in vacuo. The residue was purified by column chromatography (30% ethyl acetate in hexane) to yield the title compound as a white solid.

The compounds IB.12, IB.18, IB.19, IB.64 to IB.66, IB.89, IB.91, IB.123, IB.125 to IB.129, IB.131, IB.134, IB.137 to IB.147, IB.149, IB.150, IB.153, IB.154, IB.156 were prepared in a manner similar to example 27.

Example 28

Compound IB.103

S-[4-(N,N-Dimethylaminocarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate

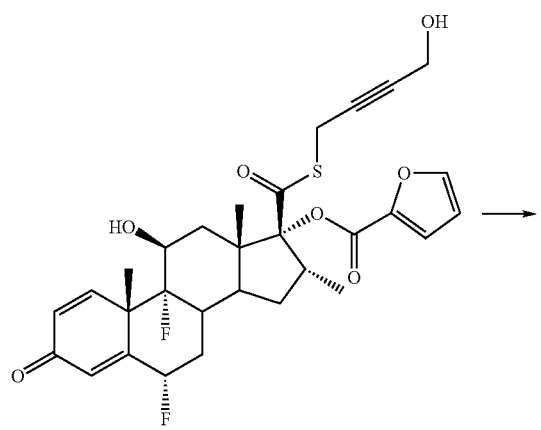

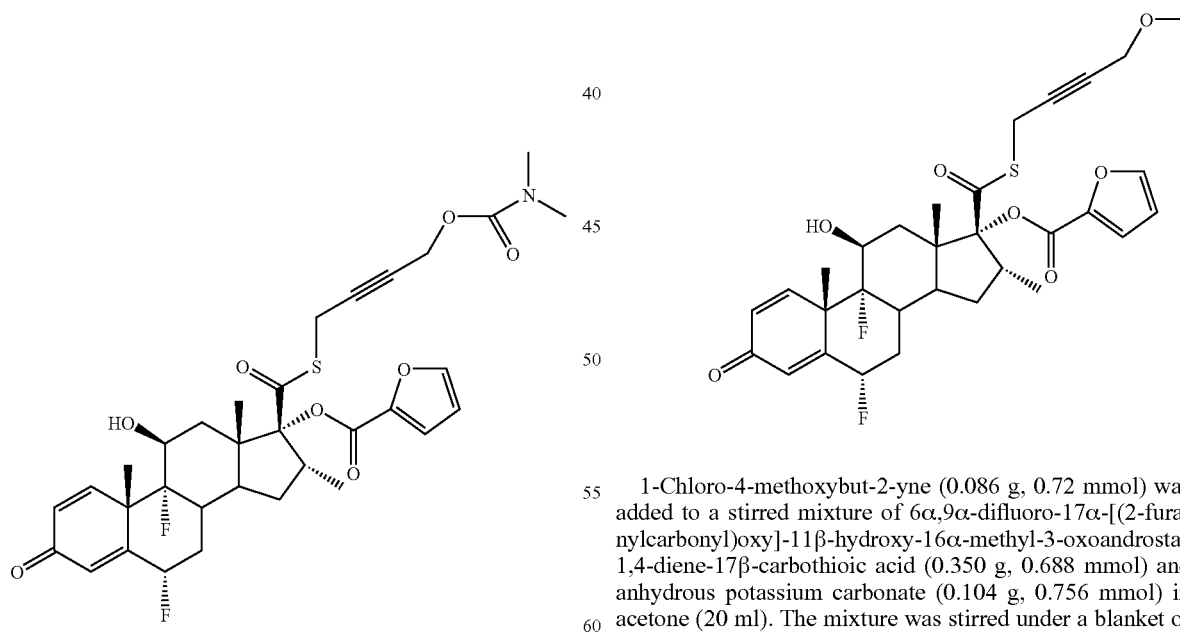

N,N-Dimethylcarbamoyl chloride (0.23 g, 2.0 mmol) was added at 25-30° C. to a stirred mixture of S-(4-hydroxy-but-2-ynyl) 6α,9α-difluoro-17α-[(2-furanylcarbonyl)oxy]-11β-hydroxy-16α-methyl-3-oxoandrosta-1,4-diene-17β-carbothioate (1.0 g, 1.74 mmol) and triethylamine (0.70 g, 6.96 mmol) in dichloromethane (30 ml). The mixture was stirred at 25 to 30° C. for 4 hrs, then washed with water and concentrated in vacuo. The residue was purified by column chromatography (40% ethyl acetate in hexane) to yield the title compound as a white solid.

The compounds IB.129 to IB.131 were prepared in a manner similar to example 28.

Example 29

Compound IB.158

S-[4-Methoxybut-2-ynyl]6α,9α-difluoro-17α-[(2-furanylcarbonyl)oxy]-11β-hydroxy-16α-methyl-3-oxoandrosta-1,4-diene-17β-carbothioate

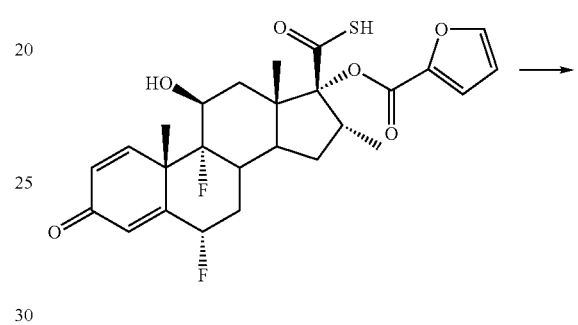

1-Chloro-4-methoxybut-2-yne (0.086 g, 0.72 mmol) was added to a stirred mixture of 6α,9α-difluoro-17α-[(2-furanylcarbonyl)oxy]-11β-hydroxy-16α-methyl-3-oxoandrosta-1,4-diene-17β-carbothioic acid (0.350 g, 0.688 mmol) and anhydrous potassium carbonate (0.104 g, 0.756 mmol) in acetone (20 ml). The mixture was stirred under a blanket of nitrogen at 25 to 30° C. for 3 hrs., then poured into water and extracted with ethyl acetate. The organic layer was washed with water, dried, and concentrated in vacuo. The residue was purified by column chromatography (35% ethyl acetate in hexane) to yield the title compound as a white solid.

Compounds IB.159, IB.160 were prepared in a manner similar to example 29.

TABLE 1

Lists the compound of formula I-A which have been synthesized.

Formula I-A

| No. | $R_1$ | $R_2$ | $R_3$ | $R_5$ | $R_6$ | P | Q | $m_1$ | Z | Chemical Name |
|---|---|---|---|---|---|---|---|---|---|---|
| IA.1 | H | H | H | Ethoxy | 4-Chlorophenyl | H | H | 1 | O | 2-(4-Chlorophenyl)-2-oxoethyl 17α-ethoxycarbonyloxy-11β-hydroxy-3-oxoandrosta-1,4-diene-17β-carboxylate. |
| IA.2 | α-CH$_3$ | F | F | Ethyl | 4-Chlorophenyl | H | H | 1 | O | 2-(4-Chlorophenyl)-2-oxoethyl 6α,9α-difluoro-11β-hydroxy-16α-methyl-3-oxo-17α-propionyloxyandrosta-1,4-diene-17β-carboxylate. |
| IA.3 | α-CH$_3$ | F | F | Ethyl | 4-Chlorophenyl | H | H | 1 | S | S-[2-(4-Chlorophenyl)-2-oxoethyl] 6α,9α-difluoro-11β-hydroxy-16α-methyl-3-oxo-17α-propionyloxyandrosta-1,4-diene-17β-carbothioate. |
| IA.4 | H | H | H | Ethoxy | 4-Fluorophenyl | H | H | 1 | O | 2-(4-Fluorophenyl)-2-oxoethyl 17α-ethoxycarbonyloxy-11β-hydroxy-3-oxoandrosta-1,4-diene-17β-carboxylate. |
| IA.5 | α-CH$_3$ | F | F | Ethyl | 4-Fluorophenyl | H | H | 1 | O | 2-(4-Fluorophenyl)-2-oxoethyl 6α,9α-difluoro-11β-hydroxy-16α-methyl-3-oxo-17α-propionyloxyandrosta-1,4-diene-17β-carboxylate. |
| IA.6 | α-CH$_3$ | F | F | Ethyl | 4-Fluorophenyl | H | H | 1 | S | S-[2-(4-Fluorophenyl)-2-oxoethyl] 6α,9α-difluoro-11β-hydroxy-16α-methyl-3-oxo-17α-propionyloxyandrosta-1,4-diene-17β-carbothioate. |
| IA.7 | H | H | H | Ethoxy | 2,4-Difluorophenyl | H | H | 1 | O | 2-(2,4-Difluorophenyl)-2-oxoethyl 17α-(ethoxycarbonyl)oxy-11β-hydroxy-3-oxoandrosta-1,4-diene-17β-carboxylate. |
| IA.8 | H | H | H | Ethoxy | 2,4-Dichlorophenyl | H | H | 1 | O | 2-(2,4-Dichlorophenyl)-2-oxoethyl 17α-(ethoxycarbonyl)oxy-11β-hydroxy-3-oxoandrosta-1,4-diene-17β-carboxylate. |
| IA.9 | α-CH$_3$ | F | F | Ethyl | 2,4-Difluorophenyl | H | H | 1 | O | 2-(2,4-Difluorophenyl)-2-oxoethyl 6α,9α-difluoro-11β-hydroxy-16α-methyl-3-oxo-17α-propionyloxyandrosta-1,4-diene-17β-carboxylate. |
| IA.10 | α-CH$_3$ | F | F | Ethyl | 2,4-Dichlorophenyl | H | H | 1 | O | 2-(2,4-Dichlorophenyl)-2-oxoethyl 6α,9α-difluoro-11β-hydroxy-16α-methyl-3-oxo-17α-propionyloxyandrosta-1,4-diene-17β-carboxlate. |
| IA.11 | α-CH$_3$ | F | F | Ethyl | 2,4-Difluorophenyl | H | H | 1 | S | S-2-[(2,4-Difluorophenyl)-2-oxoethyl] 6α,9α-difluoro-11β-hydroxy-16α-methyl-3-oxo-17α-propionyloxyandrosta-1,4-diene-17β-carbothioate. |
| IA.12 | H | H | H | Ethoxy | 3,4-Dichlorophenyl | H | H | 1 | O | 2-(3,4-Dichlorophenyl)-2-oxoethyl 17α-ethoxycarbonyloxy-11β-hydroxy-3-oxoandrosta-1,4-diene-17β-carboxylate. |
| IA.13 | α-CH$_3$ | F | F | Ethyl | 2,4-Dichlorophenyl | H | H | 1 | S | S-[2-(2,4-Dichlorophenyl)-2-oxoethyl] 6α,9α-difluoro-11β-hydroxy-16α-methyl-3-oxo-17α-propionyloxyandrosta-1,4-diene-17β-carbothioate. |
| IA.14 | α-CH$_3$ | F | F | Ethyl | 3,4-Dichlorophenyl | H | H | 1 | S | S-[2-(3,4-Dichlorophenyl)-2-oxoethyl] 6α,9α-difluoro-11β-hydroxy-16α-methyl-3-oxo-17α-propionyloxyandrosta-1,4 diene-17β-carbothioate. |
| IA.15 | α-CH$_3$ | F | F | Ethyl | 3,4-Dichlorophenyl | H | H | 1 | O | 2-(3,4-Dichlorophenyl)-2-oxoethyl 6α,9α-difluoro-11β-hydroxy-16α-methyl-3-oxo-17α-propionyloxyandrosta-1,4 diene-17β-carboxylate. |
| IA.16 | H | H | H | Ethoxy | 2-Thienyl | H | H | 1 | O | 2-Oxo-2-(thiophen-2-yl)ethyl 17α-(ethoxycarbonyl)oxy-11β-hydroxy-3-oxoandrosta-1,4-diene-17β-carboxylate. |

TABLE 1-continued

Lists the compound of formula I-A which have been synthesized.

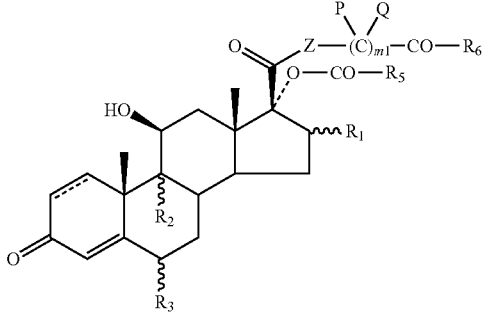

Formula I-A

| No. | $R_1$ | $R_2$ | $R_3$ | $R_5$ | $R_6$ | P | Q | $m_1$ | Z | Chemical Name |
|---|---|---|---|---|---|---|---|---|---|---|
| IA.17 | H | H | H | Ethoxy | 5-Chloro-2-thienyl | H | H | 1 | O | 2-(5-Chlorothiophen-2-yl)-2-oxoethyl 17α-(ethoxycarbonyl)oxy-11β-hydroxy-3-oxoandrosta-1,4-diene-17β-carboxylate. |
| IA.18 | α-CH$_3$ | F | F | Ethyl | 5-Chloro-2-thienyl | H | H | 1 | O | 2-(5-Chlorothiophen-2-yl)-2-oxoethyl 6α,9α-difluoro-11β-hydroxy-16α-methyl-3-oxo-17α-propionyloxyandrosta-1,4-diene-17β-carboxylate. |
| IA.19 | H | H | H | Ethoxy | 5-Methyl-2-furyl | H | H | 1 | O | 2-(5-Methylfuran-2-yl)-2-oxoethyl 17α-(ethoxycarbonyl)oxy-11β-hydroxy-3-oxoandrosta-1,4-diene-17β-carboxylate. |
| IA.20 | α-CH$_3$ | F | F | Ethyl | 5-Chloro-2-thienyl | H | H | 1 | S | S-[2-(5-Chlorothiophen-2-yl)-2-oxoethyl] 6α,9α-difluoro-11β-hydroxy-16α-methyl-3-oxo-17α-propionyloxyandrosta-1,4-diene-17β-carbothioate. |
| IA.21 | α-CH$_3$ | F | F | Ethyl | 5-Methyl-2-furyl | H | H | 1 | O | 2-(5-Methylfuran-2-yl)-2-oxoethyl 6α,9α-difluoro-11β-hydroxy-16α-methyl-3-oxo-17α-propionyloxyandrosta-1,4-diene-17β-carboxylate. |
| IA.22 | α-CH$_3$ | F | F | Ethyl | 5-Methyl-2-furyl | H | H | 1 | S | S-[2-(5-Methylfuran-2-yl)-2-oxoethyl] 6α,9α-difluoro-11β-hydroxy-16α-methyl-3-oxo-17α-propionyloxyandrosta-1,4-diene-17β-carbothioate. |
| IA.23 | H | H | H | Ethoxy | t-Butyl | H | H | 1 | O | 3,3-Dimethyl-2-oxobutyl 17α-(ethoxycarbonyl)oxy-11β-hydroxy-3-oxoandrosta-1,4-diene-17β-carboxylate. |
| IA.24 | H | H | H | Ethoxy | Methyl | H | H | 1 | O | 2-Oxopropyl 17α-(ethoxycarbonyl)oxy-11β-hydroxy-3-oxoandrosta-1,4-diene-17β-carboxylate. |
| IA.25 | α-CH$_3$ | F | F | Ethyl | t-Butyl | H | H | 1 | O | 3,3-Dimethyl-2-oxobutyl 6α,9α-difluoro-11β-hydroxy-16α-methyl-3-oxo-17α-propionyloxyandrosta-1,4-diene-17β-carboxylate. |
| IA.26 | α-CH$_3$ | F | F | Ethyl | t-Butyl | H | H | 1 | S | S-(3,3-Dimethyl-2-oxobutyl) 6α,9α-difluoro-11β-hydroxy-16α-methyl-3-oxo-17α-propionyloxyandrosta-1,4-diene-17β-carbothioate. |
| IA.27 | α-CH$_3$ | F | F | Ethyl | Methyl | H | H | 1 | S | S-[2-Oxopropyl] 6α,9α-difluoro-11β-hydroxy-16α-methyl-3-oxo-17α-propionyloxyandrosta-1,4-diene-17β-carbothioate. |
| IA.28 | α-CH$_3$ | F | F | Ethyl | Methyl | H | H | 1 | O | 2-Oxopropyl 6α,9α-difluoro-11β-hydroxy-16α-methyl-3-oxo-17α-propionyloxyandrosta-1,4-dien-17β-carboxylate. |
| IA.29 | H | H | H | Ethoxy | 4-Methoxyphenyl | H | H | 1 | O | 2-(4-Methoxyphenyl)-2-oxoethyl 17α-(ethoxycarbonyl)oxy-11β-hydroxy-3-oxoandrosta-1,4-dien-17β-carboxylate. |
| IA.30 | α-CH$_3$ | F | F | Ethyl | 4-Methoxyphenyl | H | H | 1 | O | 2-(4-Methoxyphenyl)-2-oxoethyl 6α,9α-difluoro-11β-hydroxy-16α-methyl-3-oxo-17α-propionyloxyandrosta-1,4-diene-17β-carboxylate. |
| IA.31 | α-CH$_3$ | F | F | Ethyl | 4-Methoxyphenyl | H | H | 1 | S | S-[2-(4-Methoxyphenyl)-2-oxoethyl] 6α,9α-difluoro-11β-hydroxy-16α-methyl-3-oxo-17α-propionyloxyandrosta-1,4-diene-17β-carbothioate. |
| IA.32 | H | H | H | Ethoxy | 1-Adamantyl | H | H | 1 | O | 2-(Adamantan-1-yl)-2-oxoethyl 17α-(ethoxycarbonyl)oxy-11β-hydroxy-3-oxoandrosta-1,4-diene-17β-carboxylate. |
| IA.33 | α-CH$_3$ | F | F | Ethyl | 1-Adamantyl | H | H | 1 | O | 2-(Adamantan-1-yl)-2-oxoethyl 6α,9α-difluoro-11β-hydroxy-16α-methyl-3-oxo-17α- |

TABLE 1-continued

Lists the compound of formula I-A which have been synthesized.

Formula I-A

| No. | R₁ | R₂ | R₃ | R₅ | R₆ | P | Q | m₁ | Z | Chemical Name |
|---|---|---|---|---|---|---|---|---|---|---|
| IA.34 | α-CH₃ | F | F | Ethyl | 1-Adamantyl | H | H | 1 | S | S-[2-(Adamantan-1-yl)-2-oxoethyl] 6α,9α-difluoro-11β-hydroxy-16α-methyl-3-oxo-17α-propionyloxyandrosta-1,4-diene-17β-carbothioate. |
| IA.35 | α-CH₃ | F | F | Ethyl | 4-Trifluoromethyloxyphenyl | H | H | 1 | S | S-[2-Oxo-2-(4-trifluoromethyloxyphenyl)ethyl] 6α,9α-difluoro-11β-hydroxy-16α-methyl-3-oxo-17α-propionyloxyandrosta-1,4-diene-17β-carbothioate. |
| IA.36 | α-CH₃ | F | F | Ethyl | 4-Trifluoromethyloxyphenyl | H | H | 1 | O | 2-Oxo-2-(4-trifluoromethyloxyphenyl)ethyl 6α,9α-difluoro-11β-hydroxy-16α-methyl-3-oxo-17α-propionyloxyandrosta-1,4-diene-17β-carboxylate. |
| IA.37 | H | H | H | Ethoxy | 4-Trifluoromethyloxyphenyl | H | H | 1 | O | 2-Oxo-2-(4-trifluoromethyloxyphenyl)ethyl 17α-(ethoxycarbonyl)oxy-11β-hydroxy-3-oxoandrosta-1,4-diene-17β-carboxylate. |
| IA.38 | α-CH₃ | F | F | Ethyl | 4-Trifluoromethylphenyl | H | H | 1 | S | S-[2-Oxo-2-(4-trifluoromethylphenyl)ethyl] 6α,9α-difluoro-11β-hydroxy-16α-methyl-3-oxo-17α-propionyloxyandrosta-1,4-diene-17β-carbothioate. |
| IA.39 | α-CH₃ | F | F | 5-Chloro-2-thienyl | 4-Trifluoromethylphenyl | H | H | 1 | S | S-[2-Oxo-2-(4-trifluoromethylphenyl)ethyl] 17α-[[(5-chloro2-thienyl)carbonyl]oxy]-6α,9α-difluoro-11β-hydroxy-16α-methyl-3-oxoandrosta-1,4-diene-17β-carbothioate. |
| IA.40 | α-CH₃ | F | F | 5-Chloro-2-thienyl | 2,4,6-Trimethylphenyl | H | H | 1 | S | S-[2-Oxo-2-(2,4,6-trimethylphenyl)ethyl] 17α-[[(5-chloro2-thienyl)carbonyl]oxy]-6α,9α-difluoro-11β-hydroxy-16α-methyl-3-oxoandrosta-1,4-diene-17β-carbothioate. |
| IA.41 | α-CH₃ | Cl | H | 2-Furyl | 2,4,6-Trimethylphenyl | H | H | 1 | S | S-[2-Oxo-2-(2,4,6-trimethylphenyl)ethyl] 9α-chloro-17α-[(2-furanylcarbonyl)oxy]-11β-hydroxy-16α-methyl-3-oxoandrosta-1,4-diene-17β-carbothioate. |
| IA.42 | α-CH₃ | F | F | Ethyl | 4-Methanesulfonylphenyl | H | H | 1 | O | 2-(4-Methanesulphonylphenyl)-2-oxoethyl 6α,9α-difluoro-11β-hydroxy-16α-methyl-3-oxo-17α-propionyloxyandrosta-1,4-diene-17β-carboxylate. |
| IA.43 | α-CH₃ | F | F | Ethyl | 4-Methanesulfonylphenyl | H | H | 1 | S | S-[2-(4-Methanesulphonylphenyl)-2-oxoethyl] 6α,9α-difluoro-11β-hydroxy-16α-methyl-3-oxo-17α-propionyloxyandrosta-1,4-diene-17β-carbothioate. |
| IA.44 | α-CH₃ | F | F | Ethyl | Phenyl | H | H | 1 | O | 2-Oxo-2-phenylethyl 6α,9α-difluoro-11β-hydroxy-16α-methyl-3-oxo-17α-propionyloxyandrosta-1,4-diene-17β-carboxylate. |
| IA.45 | α-CH₃ | F | F | Ethyl | Phenyl | H | H | 1 | S | S-[2-Oxo-2-phenylethyl] 6α,9α-difluoro-11β-hydroxy-16α-methyl-3-oxo-17α-propionyloxyandrosta-1,4-diene-17β-carbothioate. |
| IA.46 | α-CH₃ | F | F | Ethyl | 4-Methylphenyl | H | H | 1 | O | 2-(4-Methylphenyl)-2-oxoethyl 6α,9α-difluoro-11β-hydroxy-16α-methyl-3-oxo-17α-propionyloxyandrosta-1,4-diene-17β-carboxylate. |
| IA.47 | α-CH₃ | F | F | Ethyl | 4-Methylphenyl | H | H | 1 | S | S-[2-(4-Methylphenyl)-2-oxoethyl] 6α,9α-difluoro-11β-hydroxy-16α-methyl-3-oxo-17α-propionyloxyandrosta-1,4-diene-17β-carbothioate. |

TABLE 1-continued

Lists the compound of formula I-A which have been synthesized.

Formula I-A

| No. | $R_1$ | $R_2$ | $R_3$ | $R_5$ | $R_6$ | P | Q | $m_1$ | Z | Chemical Name |
|---|---|---|---|---|---|---|---|---|---|---|
| IA.48 | α-CH₃ | F | F | Ethyl | 2,6-Dichlorophenyl | H | H | 1 | O | 2-(2,6-Dichlorophenyl)-2-oxoethyl 6α,9α-difluoro-11β-hydroxy-16α-methyl-3-oxo-17α-propionyloxyandrosta-1,4-diene-17β-carboxylate. |
| IA.49 | α-CH₃ | F | F | Ethyl | 2,6-Dichlorophenyl | H | H | 1 | S | S-[2-(2,6-Dichlorophenyl)-2-oxoethyl] 6α,9α-difluoro-11β-hydroxy-16α-methyl-3-oxo-17α-propionyloxyandrosta-1,4-diene-17β-carbothioate. |
| IA.50 | α-CH₃ | F | F | Ethyl | 2,3-Dichlorophenyl | H | H | 1 | O | 2-(2,3-Dichlorophenyl)-2-oxoethyl 6α,9α-difluoro-11β-hydroxy-16α-methyl-3-oxo-17α-propionyloxyandrosta-1,4-diene-17β-carboxylate. |
| IA.51 | α-CH₃ | F | F | Ethyl | 2,3-Dichlorophenyl | H | H | 1 | S | S-[2-(2,3-Dichlorophenyl)-2-oxoethyl] 6α,9α-difluoro-11β-hydroxy-16α-methyl-3-oxo-17α-propionyloxyandrosta-1,4-diene-17β-carbothioate. |
| IA.52 | α-CH₃ | F | F | Ethyl | 2,6-Difluorophenyl | H | H | 1 | O | 2-(2,6-Difluorophenyl)-2-oxoethyl 6α,9α-difluoro-11β-hydroxy-16α-methyl-3-oxo-17α-propionyloxyandrosta-1,4-diene-17β-carboxylate. |
| IA.53 | α-CH₃ | F | F | Ethyl | 2,6-Difluorophenyl | H | H | 1 | S | S-[2-(2,6-Difluorophenyl)-2-oxoethyl] 6α,9α-difluoro-11β-hydroxy-16α-methyl-3-oxo-17α-propionyloxyandrosta-1,4-diene-17β-carbothioate. |
| IA.54 | α-CH₃ | F | F | Ethyl | 2,3-Difluorophenyl | H | H | 1 | O | 2-(2,3-Difluorophenyl)-2-oxoethyl 6α,9α-difluoro-11β-hydroxy-16α-methyl-3-oxo-17α-propionyloxyandrosta-1,4-diene-17β-carboxylate. |
| IA.55 | α-CH₃ | F | F | Ethyl | 2,3-Difluorophenyl | H | H | 1 | S | S-[2-(2,3-Difluorophenyl)-2-oxoethyl] 6α,9α-difluoro-11β-hydroxy-16α-methyl-3-oxo-17α-propionyloxyandrosta-1,4-diene-17β-carbothioate. |
| IA.56 | α-CH₃ | F | F | 5-Chloro-2-thienyl | 4-Chlorophenyl | H | H | 1 | S | S-[2-(4-Chlorophenyl)-2-oxoethyl] 17α-[[(5-chloro-2-thienyl)carbonyl]oxy]-6α,9α-difluoro-11β-hydroxy-16α-methyl-3-oxoandrosta-1,4-diene-17β-carbothioate. |
| IA.57 | α-CH₃ | F | F | Ethyl | 2,4,6-Trimethylphenyl | H | H | 1 | O | 2-Oxo-2-(2,4,6-trimethylphenyl)ethyl 6α,9α-difluoro-11β-hydroxy-16α-methyl-3-oxo-17α-propionyloxyandrosta-1,4-diene-17β-carboxylate. |
| IA.58 | α-CH₃ | F | F | Ethyl | 2,4,6-Trimethylphenyl | H | H | 1 | S | S-[2-Oxo-2-(2,4,6-trimethylphenyl)ethyl] 6α,9α-difluoro-11β-hydroxy-16α-methyl-3-oxo-17α-propionyloxyandrosta-1,4-diene-17β-carbothioate. |
| IA.59 | α-CH₃ | F | F | Ethyl | Phenyl | CH₃ | CH₃ | 1 | S | S-[1,1-Dimethyl-2-oxo-2-phenylethyl] 6α,9α-difluoro-11β-hydroxy-16α-methyl-3-oxo-17α-propionyloxyandrosta-1,4-diene-17β-carbothioate. |
| IA.60 | α-CH₃ | F | F | Ethyl | 2-Thienyl | H | H | 1 | O | 2-Oxo-2-(thiophen-2-yl)ethyl 6α,9α-difluoro-11β-hydroxy-16α-methyl-3-oxo-17α-propionyloxy-androsta-1,4-diene-17β-carboxylate. |
| IA.61 | α-CH₃ | F | F | Ethyl | 2-Thienyl | H | H | 1 | S | S-[2-Oxo-2-(thiophen-2-yl)ethyl] 6α,9α-difluoro-11β-hydroxy-16α-methyl-3-oxo-17α-propionyloxyandrosta-1,4-diene-17β-carbothioate. |
| IA.62 | α-CH₃ | F | F | Ethyl | 3,4-Difluoro- | H | H | 1 | O | 2-(3,4-Difluorophenyl)-2-oxoethyl 6α,9α-difluoro-11β-hydroxy-16α-methyl-3-oxo-17α- |

TABLE 1-continued

Lists the compound of formula I-A which have been synthesized.

Formula I-A

| No. | R₁ | R₂ | R₃ | R₅ | R₆ | P | Q | m₁ | Z | Chemical Name |
|---|---|---|---|---|---|---|---|---|---|---|
| | | | | | phenyl | | | | | propionyloxyandrosta-1,4-diene-17β-carboxylate. |
| IA.63 | α-CH₃ | F | F | Ethyl | 3,4-Difluorophenyl | H | H | 1 | S | S-[2-(3,4-Difluorophenyl)-2-oxoethyl] 6α,9α-difluoro-11β-hydroxy-16α-methyl-3-oxo-17α-propionyloxyandrosta-1,4-diene-17β-carbothioate. |
| IA.64 | α-CH₃ | F | F | Ethyl | 2-Furyl | H | H | 1 | O | 2-(Furan-2-yl)-2-oxoethyl 6α,9α-difluoro-11β-hydroxy-16α-methyl-3-oxo-17α-propionyloxy-androsta-1,4-diene-17β-carboxylate. |
| IA.65 | α-CH₃ | F | F | Dichloromethyl | 4-Fluorophenyl | H | H | 1 | O | 2-(4-Fluorophenyl)-2-oxoethyl 17α-dichloromethyl-carbonyloxy-6α,9α-difluoro-11β-hydroxy-16α-methyl-3-oxoandrosta-1,4-diene-17β-carboxylate. |
| IA.66 | α-CH₃ | F | F | Dichloromethyl | 2,4-Difluorophenyl | H | H | 1 | O | 2-(2,4-Difluorophenyl)-2-oxoethyl 17α-dichloromethylcarbonyloxy-6α,9α-difluoro-11β-hydroxy-16α-methyl-3-oxoandrosta-1,4-diene-17β-carboxylate. |
| IA.67 | α-CH₃ | F | F | Ethyl | 2-Benzofuryl | H | H | 1 | O | 2-(Benzofuran-2-yl)-2-oxoethyl 6α,9α-difluoro-11β-hydroxy-16α-methyl-3-oxo-17α-propionyloxyandrosta-1,4-diene-17β-carboxylate. |
| IA.68 | α-CH₃ | F | F | Ethyl | 2-Furyl | H | H | 1 | S | S-[2-(Furan-2-yl)-2-oxoethyl] 6α,9α-difluoro-11β-hydroxy-16α-methyl-3-oxo-17α-propionyloxyandrosta-1,4-diene-17β-carbothioate. |
| IA.69 | α-CH₃ | F | F | Ethyl | 2-Benzofuryl | H | H | 1 | S | S-[2-(Benzofuran-2-yl)-2-oxoethyl] 6α,9α-difluoro-11β-hydroxy-16α-methyl-3-oxo-17α-propionyloxyandrosta-1,4-diene-17β-carbothioate. |
| IA.70 | α-CH₃ | F | F | Ethyl | 4-t-Butyl-phenyl | H | H | 1 | S | S-[2-(4-t-Butylphenyl)-2-oxoethyl] 6α,9α-difluoro-11β-hydroxy-16α-methyl-3-oxo-17α-propionyloxyandrosta-1,4-diene-17β-carbothioate. |
| IA.71 | α-CH₃ | F | F | Ethyl | 7-Methoxy-2-benzofuryl | H | H | 1 | O | 2-(7-Methoxybenzofuran-2-yl)-2-oxoethyl 6α,9α-difluoro-11β-hydroxy-16α-methyl-3-oxo-17α-propionyloxyandrosta-1,4-diene-17β-carboxylate. |
| IA.72 | α-CH₃ | F | F | Ethyl | 4-t-Butyl-phenyl | H | H | 1 | O | 2-(4-t-Butylphenyl)-2-oxoethyl 6α,9α-difluoro-11β-hydroxy-16α-methyl-3-oxo-17α-propionyloxyandrosta-1,4-diene-17β-carboxylate. |
| IA.73 | α-CH₃ | F | F | Ethyl | 7-Methoxy-2-benzofuryl | H | H | 1 | S | S-[2-(7-Methoxybenzofuran-2-yl)-2-oxoethyl] 6α,9α-difluoro-11β-hydroxy-16α-methyl-3-oxo-17α-propionyloxyandrosta-1,4-diene-17β-carbothioate. |
| IA74 | α-CH₃ | F | F | Ethyl | 2-Fluoro-4-methoxy-phenyl | H | H | 1 | O | 2-(2-Fluoro-4-methoxyphenyl)-2-oxoethyl 6α,9α-difluoro-11β-hydroxy-16α-methyl-3-oxo-17α-propionyloxy-androsta-1,4-diene-17β-carboxylate. |
| IA.75 | α-CH₃ | F | F | Ethyl | 2-Fluoro-4-methoxy-phenyl | H | H | 1 | S | S-[2-(2-Fluoro-4-methoxyphenyl)-2-oxoethyl] 6α,9α-difluoro-11β-hydroxy-16α-methyl-3-oxo-17α-propionyloxyandrosta-1,4-diene-17β-carbothioate. |
| IA.76 | α-CH₃ | F | F | Ethyl | 2-Methoxy-phenyl | H | H | 1 | O | 2-(2-Methoxyphenyl)-2-oxoethyl 6α,9α-difluoro-11β-hydroxy-16α-methyl-3-oxo-17α-propionyloxyandrosta-1,4-diene-17β-carboxylate. |
| IA.77 | α-CH₃ | F | F | Ethyl | 2,4-Dimethoxy- | H | H | 1 | O | 2-(2,4-Dimethoxyphenyl)-2-oxoethyl 6α,9α-difluoro-11β-hydroxy-16α-methyl-3-oxo-17α- |

TABLE 1-continued

Lists the compound of formula I-A which have been synthesized.

Formula I-A

| No. | $R_1$ | $R_2$ | $R_3$ | $R_5$ | $R_6$ | P | Q | $m_1$ | Z | Chemical Name |
|---|---|---|---|---|---|---|---|---|---|---|
| | | | | | phenyl | | | | | propionyloxyandrosta-1,4-diene-17β-carboxylate. |
| IA.78 | α-CH$_3$ | F | F | Ethyl | 2,4-Dimethoxy-phenyl | H | H | 1 | S | S-[2-(2,4-Dimethoxyphenyl)-2-oxoethyl] 6α,9α-difluoro-11β-hydroxy-16α-methyl-3-oxo-17α-propionyloxyandrosta-1,4-diene-17β-carbothioate. |
| IA.79 | α-CH$_3$ | F | F | Ethyl | 2-Methoxy-phenyl | H | H | 1 | S | S-[2-(2-Methoxyphenyl)-2-oxoethyl] 6α,9α-difluoro-11β-hydroxy-16α-methyl-3-oxo-17α-propionyloxyandrosta-1,4-diene-17β-carbothioate. |
| IA.80 | α-CH$_3$ | F | F | Ethyl | 2-Trifluoro-methylphenyl | H | H | 1 | O | 2-Oxy-2-(2-trifluoromethylphenyl)ethyl 6α,9α-difluoro-11β-hydroxy-16α-methyl-3-oxo-17α-propionyloxy-androsta-1,4-diene-17β-carboxylate. |
| IA.81 | α-CH$_3$ | F | F | Ethyl | 2-Trifluoro-methylphenyl | H | H | 1 | S | S-[2-Oxy-2-(2-trifluoromethylphenyl)ethyl] 6α9α-difluoro-11β-hydroxy-16α-methyl-3-oxo-17α-propionyloxyandrosta-1,4-diene-17β-carbothioate. |
| IA.82 | α-CH$_3$ | F | F | 2-Furyl | 4-Fluoro-phenyl | H | H | 1 | O | 2-(4-Fluorophenyl)-2-oxoethyl 6α,9α-difluoro-17α-[(2-furanylcarbonyl)oxy]-11β-hydroxy-16α-methyl-3-oxoandrosta-1,4-diene-17β-carbothioate. |
| IA.83 | α-CH$_3$ | F | F | 2-Furyl | 4-Fluoro-phenyl | H | H | 1 | S | S-[2-(4-Fluorophenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.84 | α-CH$_3$ | F | F | 2-Furyl | 2,4-Difluoro-phenyl | H | H | 1 | O | 2-(2,4-Difluorophenyl)-2-oxoethyl 6α,9α-difluoro-17α-[(2-furanylcarbonyl)oxy]-11β-hydroxy-16α-methyl-3-oxo-androsta-1,4-diene-17β-carboxylate. |
| IA.85 | α-CH$_3$ | F | F | 2-Furyl | 2,4-Difluoro-phenyl | H | H | 1 | S | S-[2-(2,4-Difluorophenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.86 | α-CH$_3$ | F | H | Ethyl | 4-Fluoro-phenyl | H | H | 1 | S | S-[2-(4-Fluorophenyl)-2-oxoethyl] 9α-fluoro-11β-hydroxy-16α-methyl-3-oxo-17α-propionyloxy-androsta-1,4-diene-17β-carbothioate. |
| IA.87 | α-CH$_3$ | F | H | Ethyl | 4-Fluoro-phenyl | H | H | 1 | O | 2-(4-Fluorophenyl)-2-oxoethyl 9α-fluoro-11β-hydroxy-16α-methyl-3-oxo-17α-propionyloxy-androsta-1,4-diene-17β-carboxylate. |
| IA.88 | α-CH$_3$ | F | F | Ethyl | 3,5-Bis(trifluoro-methyl)phenyl | H | H | 1 | S | S-[2-[3,5-Bis(trifluoromethyl)phenyl]-2-oxoethyl] 6α,9α-difluoro-11β-hydroxy-16α-methyl-3-oxo-17α-propionyloxyandrosta-1,4-diene-17β-carbothioate. |
| IA.89 | α-CH$_3$ | F | F | Ethyl | 3-Trifluoro-methylphenyl | H | H | 1 | S | S-[2-Oxo-2-(3-trifluoromethyl)phenylethyl] 6α,9α-difluoro-11β-hydroxy-16α-methyl-3-oxo-17α-propionyloxyandrosta-1,4-diene-17β-carbothioate. |
| IA.90 | α-CH$_3$ | F | F | Ethyl | 4-Isobutyl-phenyl | H | H | 1 | S | S-[2-(4-Isobutylphenyl)-2-oxoethyl] 6α,9α-difluoro-11β-hydroxy-16α-methyl-3-oxo-17α-propionyloxy-androsta-1,4-diene-17β-carbothioate. |
| IA.91 | β-CH$_3$ | F | H | Ethyl | 4-Fluoro-phenyl | H | H | 1 | O | 2-(4-Fluorophenyl)-2-oxoethyl 9α-fluoro-11β-hydroxy-16β-methyl-3-oxo-17α-propionyloxy-androsta-1,4-diene-17β-carboxylate. |
| IA.92 | α-CH$_3$ | F | F | Ethyl | 4-Ethyl-phenyl | H | H | 1 | S | S-[2-(4-Ethylphenyl)-2-oxoethyl] 6α,9α-difluoro-11β-hydroxy-16α-methyl-3-oxo-17α- |

TABLE 1-continued

Lists the compound of formula I-A which have been synthesized.

Formula I-A

| No. | R₁ | R₂ | R₃ | R₅ | R₆ | P | Q | m₁ | Z | Chemical Name |
|---|---|---|---|---|---|---|---|---|---|---|
| | | | | | | | | | | propionyloxy-androsta-1,4-diene-17β-carbothioate. |
| IA.93 | α-CH₃ | F | F | Ethyl | 4-Cyclohexylphenyl | H | H | 1 | S | S-[2-(4-Cyclohexylphenyl)-2-oxoethyl] 6α,9α-difluoro-11β-hydroxy-16α-methyl-3-oxo-17α-propionyloxyandrosta-1,4-diene-17β-carbothioate. |
| IA.94 | β-CH₃ | F | H | Ethyl | 2,4-Difluorophenyl | H | H | 1 | S | S-[2-(2,4-Difluorophenyl)-2-oxoethyl] 9α-fluoro-11β-hydroxy-16β-methyl-3-oxo-17α-propionyloxy-androsta-1,4-diene-17β-carbothioate. |
| IA.95 | α-CH₃ | F | F | Ethyl | 4-Isopropylphenyl | H | H | 1 | S | S-[2-(4-Isopropylphenyl)-2-oxoethyl] 6α,9α-difluoro-11β-hydroxy-16α-methyl-3-oxo-17α-propionyloxyandrosta-1,4-diene-17β-carbothioate. |
| IA.96 | α-CH₃ | F | F | Ethyl | 4-Cyclopentyloxyphenyl | H | H | 1 | S | S-[2-(4-Cyclopentyloxyphenyl)-2-oxoethyl] 6α,9α-difluoro-11β-hydroxy-16α-methyl-3-oxo-17α-propionyloxyandrosta-1,4-diene-17β-carbothioate. |
| IA.97 | α-CH₃ | F | H | Ethyl | 4-Methylsulfonylphenyl | H | H | 1 | S | S-[2-(4-Methylsulfonylphenyl)-2-oxoethyl] 9α-fluoro-11β-hydroxy-16α-methyl-3-oxo-17α-propionyloxyandrosta-1,4-diene-17β-carbothioate. |
| IA.98 | α-CH₃ | F | H | Ethyl | 2,4-Difluorophenyl | H | H | 1 | S | S-[2-(2,4-Difluorophenyl)-2-oxoethyl] 9α-fluoro-11β-hydroxy-16α-methyl-3-oxo-17α-propionyloxy-androsta-1,4-diene-17β-carbothioate. |
| IA.99 | β-CH₃ | F | H | Ethyl | 4-Methylsulfonylphenyl | H | H | 1 | S | S-[2-(4-Methylsulfonylphenyl)-2-oxoethyl] 9α-fluoro-11β-hydroxy-16β-methyl-3-oxo-17α-propionyloxyandrosta-1,4-diene-17β-carbothioate. |
| IA.100 | α-CH₃ | F | H | Ethyl | 4-Chlorophenyl | H | H | 1 | S | S-[2-(4-Chlorophenyl)-2-oxoethyl] 9α-fluoro-11β-hydroxy-16α-methyl-3-oxo-17α-propionyloxyandrosta-1,4-diene-17β-carbothioate. |
| IA.101 | β-CH₃ | F | H | Ethyl | 4-Chlorophenyl | H | H | 1 | S | S-[2-(4-Chlorophenyl)-2-oxoethyl] 9α-fluoro-11β-hydroxy-16β-methyl-3-oxo-17α-propionyloxyandrosta-1,4-diene-17β-carbothioate. |
| IA.102 | α-CH₃ | F | F | Ethoxy | 4-Trifluoromethylphenyl | H | H | 1 | S | S-[2-Oxo-2-(4-trifluoromethylphenyl)ethyl] 6α,9α-difluoro-17α-(ethoxycarbonyl)oxy-11β-hydroxy-16α-methyl-3-oxoandrosta-1,4-diene-17β-carbothioate. |
| IA.103 | α-CH₃ | F | F | Cyclopropyl | 4-Fluorophenyl | H | H | 1 | O | 2-(4-Fluorophenyl)-2-oxoethyl 17α-cyclopropylcarbonyloxy-6α,9α-difluoro-11β-hydroxy-16α-methyl-3-oxoandrosta-1,4-diene-17β-carboxylate. |
| IA.104 | α-CH₃ | F | F | Cyclopropyl | 2,4-Difluorophenyl | H | H | 1 | S | S-[2-(2,4-Difluorophenyl)-2-oxoethyl] 17α-cyclopropylcarbonyloxy-6α,9α-difluoro-11β-hydroxy-16α-methyl-3-oxoandrosta-1,4-diene-17β-carbothioate. |
| IA.105 | α-CH₃ | F | F | Ethoxy | 4-Chlorophenyl | H | H | 1 | S | S-[2-(4-Chlorophenyl)-2-oxoethyl] 6α,9α-difluoro-17α-(ethoxycarbonyl)oxy-11β-hydroxy-16α-methyl-3-oxoandrosta-1,4-diene-17β-carbothioate. |
| IA.106 | α-CH₃ | F | F | Cyclopropyl | 4-Chlorophenyl | H | H | 1 | S | S-[2-(4-Chlorophenyl)-2-oxoethyl] 17α-cyclopropyl-carbonyloxy-6α,9α-difluoro-11β-hydroxy-16α-methyl-3-oxoandrosta-1,4-diene-17β-carbothioate. |

TABLE 1-continued

Lists the compound of formula I-A which have been synthesized.

Formula I-A

| No. | R₁ | R₂ | R₃ | R₅ | R₆ | P | Q | m₁ | Z | Chemical Name |
|---|---|---|---|---|---|---|---|---|---|---|
| IA.107 | β-CH₃ | F | H | Ethyl | 4-Methoxy-phenyl | H | H | 1 | S | S-[2-(4-Methoxyphenyl)-2-oxoethyl] 9α-fluoro-11β-hydroxy-16β-methyl-3-oxo-17α-propionyloxy-androsta-1,4-diene-17β-carbothioate. |
| IA.108 | α-CH₃ | F | H | Ethyl | 4-Trifluoro-methylphenyl | H | H | 1 | S | S-[2-Oxo-2-(4-trifluoromethylphenyl)-2-oxoethyl] 9α-fluoro-11β-hydroxy-16α-methyl-3-oxo-17α-propionyloxyandrosta-1,4-diene-17β-carbothioate. |
| IA.109 | α-CH₃ | F | F | Ethyl | 4-Methoxy-phenyl | CH₃ | CH₃ | 1 | S | S-[1,1-Dimethyl-2-(4-methoxyphenyl)-2-oxoethyl] 6α,9α-difluoro-11β-hydroxy-16α-methyl-3-oxo-17α-propionyloxyandrosta-1,4-diene-17β-carbothioate. |
| IA.110 | α-CH₃ | F | F | Ethoxy | 4-Fluoro-phenyl | H | H | 1 | S | S-[2-(4-Fluorophenyl)-2-oxoethyl] 6α,9α-difluoro-17α-(ethoxycarbonyl)oxy-11β-hydroxy-16α-methyl-3-oxoandrosta-1,4-diene-17β-carbothioate. |
| IA.111 | β-CH₃ | F | H | Ethyl | 4-Trifluoro-methylphenyl | H | H | 1 | S | S-[2-Oxo-2-(4-trifluoromethylphenyl)-2-oxoethyl] 9α-fluoro-11β-hydroxy-16β-methyl-3-oxo-17α-propionyloxyandrosta-1,4-diene-17β-carbothioate. |
| IA.112 | α-CH₃ | F | F | Cyclo-hexyl | 4-Trifluoro-methylphenyl | H | H | 1 | S | S-[2-Oxo-2-(4-trifluoromethylphenyl)ethyl] 17α-cyclohexylcarbonyloxy-6α,9α-difluoro-11β-hydroxy-16α-methyl-3-oxoandrosta-1,4-diene-17β-carbothioate. |
| IA.113 | α-CH₃ | F | F | Cyclo-hexyl | 4-Chloro-phenyl | H | H | 1 | S | S-[2-(4-Chlorophenyl)-2-oxoethyl] 17α-cyclohexylcarbonyloxy-6α,9α-difluoro-11β-hydroxy-16α-methyl-3-oxoandrosta-1,4-diene-17β-carbothioate. |
| IA.114 | α-CH₃ | F | F | Cyclo-hexyl | 2,4-Difluoro-phenyl | H | H | 1 | S | S-[2-(2,4-Difluorophenyl)-2-oxoethyl] 17α-cyclohexylcarbonyloxy-6α,9α-difluoro-11β-hydroxy-16α-methyl-3-oxoandrosta-1,4-diene-17β-carbothioate. |
| IA.115 | α-CH₃ | F | F | Cyclo-hexyl | 4-Fluoro-phenyl | H | H | 1 | O | 2-(4-Fluorophenyl)-2-oxoethyl 17α-cyclohexylcarbonyloxy-6α,9α-difluoro-11β-hydroxy-16α-methyl-3-oxoandrosta-1,4-diene-17β-carboxylate. |
| IA.116 | α-CH₃ | F | F | Cyclo-hexyl | 4-Methoxy-phenyl | H | H | 1 | S | S-[2-(4-Methoxyphenyl)-2-oxoethyl] 17α-cyclohexylcarbonyloxy-6α,9α-difluoro-11β-hydroxy-16α-methyl-3-oxo-androsta-1,4-diene-17β-carbothioate. |
| IA.117 | α-CH₃ | F | F | Cyclo-pentyl | 4-Chloro-phenyl | H | H | 1 | S | S-[2-(4-Chlorophenyl)-2-oxoethyl] 17α-cyclopentylcarbonyloxy-6α,9α-difluoro-11β-hydroxy-16α-methyl-3-oxoandrosta-1,4-diene-17β-carbothioate. |
| IA.118 | α-CH₃ | F | F | Cyclo-pentyl | 4-Fluoro-phenyl | H | H | 1 | O | S-[2-(4-Fluorophenyl)-2-oxoethyl] 17α-cyclopentylcarbonyloxy-6α,9α-difluoro-11β-hydroxy-16α-methyl-3-oxoandrosta-1,4-diene-17β-carboxylate. |
| IA.119 | α-CH₃ | F | F | Isopropyl | 4-Trifluoro-methylphenyl | H | H | 1 | S | S-[2-Oxo-2-(4-trifluoromethylphenyl)ethyl] 6α,9α-difluoro-11β-hydroxy-16α-methyl-17α-(2-methylpropionyloxy)-3-oxoandrosta-1,4-diene-17β-carbothioate. |
| IA.120 | α-CH₃ | F | F | Cyclo-pentyl | 2,4-Difluoro-phenyl | H | H | 1 | S | S-[2-(2,4-Difluorophenyl)-2-oxoethyl] 17α-cyclopentylcarbonyloxy-6α,9α-difluoro-11β-hydroxy-16α-methyl-3-oxoandrosta-1,4-diene-17β-carbothioate. |
| IA.121 | α-CH₃ | F | F | Isopropyl | 4-Fluoro-phenyl | H | H | 1 | O | 2-(4-Fluorophenyl)-2-oxoethyl 6α,9α-difluoro-11β-hydroxy-16α-methyl-17α-(2- |

TABLE 1-continued

Lists the compound of formula I-A which have been synthesized.

Formula I-A

| No. | R₁ | R₂ | R₃ | R₅ | R₆ | P | Q | m₁ | Z | Chemical Name |
|---|---|---|---|---|---|---|---|---|---|---|
| IA.122 | α-CH₃ | F | F | Isopropyl | 4-Methoxyphenyl | H | H | 1 | S | S-[2-(4-Methoxyphenyl)-2-oxoethyl] 6α,9α-difluoro-11β-hydroxy-16α-methyl-17α-(2-methylpropionyloxy)-3-oxoandrosta-1,4-diene-17β-carboxylate. methylpropionyloxy)-3-oxoandrosta-1,4-diene-17β-carbothioate. |
| IA.123 | α-CH₃ | F | F | Isopropyl | 2,4-Difluorophenyl | H | H | 1 | S | S-[2-(2,4-Difluorophenyl)-2-oxoethyl] 6α,9α-difluoro-11β-hydroxy-16α-methyl-17α-(2-methylpropionyloxy)-3-oxoandrosta-1,4-diene-17β-carbothioate. |
| IA.124 | α-CH₃ | F | F | 2-Furyl | 4-Trifluoromethylphenyl | H | H | 1 | S | S-[2-Oxo-2-(4-trifluoromethylphenyl)ethyl] 6α,9α-difluoro-17α-[(2-furanylcarbonyl)oxy]-11β-hydroxy-16α-methyl-3-oxoandrosta-1,4-diene-17β-carbothioate. |
| IA.125 | α-CH₃ | F | F | Ethyl | 4-Chlorophenyl | CH₃ | CH₃ | 1 | S | S-[1,1-Dimethyl-2-(4-chlorophenyl)-2-oxoethyl] 6α,9α-difluoro-11β-hydroxy-16α-methyl-3-oxo-17α-propionyloxyandrosta-1,4-diene-17β-carbothioate. |
| IA.126 | α-CH₃ | F | F | Ethoxy | 4-Methoxyphenyl | H | H | 1 | S | S-[2-(4-Methoxyphenyl)-2-oxoethyl] 6α,9α-difluoro-17α-(ethoxycarbonyl)oxy-11β-hydroxy-16α-methyl-3-oxoandrosta-1,4-diene-17β-carbothioate. |
| IA.127 | α-CH₃ | F | F | 2-Furyl | 4-Methoxyphenyl | H | H | 1 | S | S-[2-(4-Methoxyphenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.128 | α-CH₃ | F | F | n-Butyl | 4-Trifluoromethylphenyl | H | H | 1 | S | S-[2-Oxo-2-(4-trifluoromethylphenyl)ethyl] 17α-n-butylcarbonyloxy-6α,9α-difluoro-11β-hydroxy-16α-methyl-3-oxoandrosta-1,4-diene-17β-carbothioate. |
| IA.129 | α-CH₃ | F | F | n-Butyl | 4-Chlorophenyl | H | H | 1 | S | S-[2-(4-Chlorophenyl)-2-oxoethyl] 17α-n-butylcarbonyloxy-6α,9α-difluoro-11β-hydroxy-16α-methyl-3-oxoandrosta-1,4-diene-17β-carbothioate. |
| IA.130 | α-CH₃ | F | F | n-Butyl | 2,4-Difluorophenyl | H | H | 1 | S | S-[2-(2,4-Difluorophenyl)-2-oxoethyl] 17α-n-butylcarbonyloxy-6α,9α-difluoro-11β-hydroxy-16α-methyl-3-oxoandrosta-1,4-diene-17β-carbothioate. |
| IA.131 | α-CH₃ | F | F | n-Butyl | 4-Fluorophenyl | H | H | 1 | S | S-[2-(4-Fluorophenyl)-2-oxoethyl] 17α-n-butylcarbonyloxy-6α,9α-difluoro-11β-hydroxy-16α-methyl-3-oxoandrosta-1,4-diene-17β-carbothioate. |
| IA.132 | α-CH₃ | F | F | Isopropyl | 4-Chlorophenyl | H | H | 1 | S | S-[2-(4-Chlorophenyl)-2-oxoethyl] 6α,9α-difluoro-11β-hydroxy-16α-methyl-17α-(2-methylpropionyl-oxy)-3-oxoandrosta-1,4-diene-17β-carbothioate. |
| IA.133 | α-CH₃ | F | F | Cyclobutyl | 4-Fluorophenyl | H | H | 1 | O | S-[2-(4-Fluorophenyl)-2-oxoethyl] 17α-cyclobutyl-carbonyloxy-6α,9α-difluoro-11β-hydroxy-16α-methyl-3-oxoandrosta-1,4-diene-17β-carboxylate. |
| IA.134 | α-CH₃ | F | F | Cyclopentyl | 4-Trifluoromethylphenyl | H | H | 1 | S | S-[2-Oxo-2-(4-trifluoromethylphenyl)ethyl] 17α-cyclopentylcarbonyloxy-6α,9α-difluoro-11β-hydroxy-16α-methyl-3-oxoandrosta-1,4-diene-17β-carbothioate. |
| IA.135 | α-CH₃ | F | F | Cyclobutyl | 4-Chlorophenyl | H | H | 1 | S | S-[2-(4-Chlorophenyl)-2-oxoethyl] 17α-cyclobutylcarbonyloxy-6α,9α-difluoro-11β-hydroxy-16α-methyl-3-oxoandrosta-1,4-diene-17β-carbothioate. |

TABLE 1-continued

Lists the compound of formula I-A which have been synthesized.

Formula I-A

| No. | $R_1$ | $R_2$ | $R_3$ | $R_5$ | $R_6$ | P | Q | $m_1$ | Z | Chemical Name |
|---|---|---|---|---|---|---|---|---|---|---|
| IA.136 | α-CH$_3$ | F | F | Cyclo-butyl | 4-Trifluoro-methylphenyl | H | H | 1 | S | S-[2-Oxo-2-(4-trifluoromethylphenyl)ethyl] 17α-cyclobutylcarbonyloxy-6α,9α-difluoro-11β-hydroxy-16α-methyl-3-oxoandrosta-1,4-diene-17β-carbothioate. |
| IA.137 | α-CH$_3$ | F | F | Cyclo-butyl | 2,4-Difluoro-phenyl | H | H | 1 | S | S-[2-(2,4-Difluorophenyl)-2-oxoethyl] 17α-cyclobutylcarbonyloxy-6α,9α-difluoro-11β-hydroxy-16α-methyl-3-oxoandrosta-1,4-diene-17β-carbothioate. |
| IA.138 | α-CH$_3$ | F | F | Cyclo-butyl | 4-Methoxy-phenyl | H | H | 1 | S | S-[2-(4-Methoxyphenyl)-2-oxoethyl] 17α-cyclobutylcarbonyloxy-6α,9α-difluoro-11β-hydroxy-16α-methyl-3-oxoandrosta-1,4-diene-17β-carbothioate. |
| IA.139 | α-CH$_3$ | F | H | 2-Furyl | 4-Trifluoro-methylphenyl | H | H | 1 | S | S-[2-Oxo-2-(4-trifluoromethylphenyl)ethyl] 9α-fluoro-17α-[(2-furanylcarbonyl)oxy]-11β-hydroxy-16α-methyl-3-oxoandrosta-1,4-diene-17β-carbothioate. |
| IA.140 | α-CH$_3$ | F | H | 2-Furyl | 2,4-Difluoro-phenyl | H | H | 1 | S | S-[2-(2,4-Difluorophenyl)-2-oxoethyl] 9α-fluoro-17α-[(2-furanylcarbonyl)oxy]-11β-hydroxy-16α-methyl-3-oxoandrosta-1,4-diene-17β-carbothioate. |
| IA.141 | α-CH$_3$ | F | H | 2-Furyl | 4-Chloro-phenyl | H | H | 1 | S | S-[2-(4-Chlorophenyl)-2-oxoethyl] 9α-fluoro-17α-[(2-furanylcarbonyl)oxy]-11β-hydroxy-16α-methyl-3-oxoandrosta-1,4-diene-17β-carbothioate. |
| IA.142 | α-CH$_3$ | F | H | 2-Furyl | 4-Methox-yphenyl | H | H | 1 | S | S-[2-(4-Methoxyphenyl)-2-oxoethyl] 9α-fluoro-17α-[(2-furanylcarbonyl)oxy]-11β-hydroxy-16α-methyl-3-oxoandrosta-1,4-diene-17β-carbothioate. |
| IA.143 | α-CH$_3$ | F | H | 2-Furyl | 4-Fluoro-phenyl | H | H | 1 | S | S-[2-(4-Fluorophenyl)-2-oxoethyl] 9α-fluoro-17α-[(2-furanylcarbonyl)oxy]-11β-hydroxy-16α-methyl-3-oxoandrosta-1,4-diene-17β-carbothioate. |
| IA.144 | α-CH$_3$ | F | F | Isopropyl | 2,4,6-Trimethyl-phenyl | H | H | 1 | S | S-[2-Oxo-2-(2,4,6-trimethylphenyl)ethyl] 6α,9α-difluoro-11β-hydroxy-16α-methyl-17α-(2-methyl-propionyloxy)-3-oxoandrosta-1,4-diene-17β-carbothioate. |
| IA.145 | α-CH$_3$ | F | F | Cyclo-hexyl | 2,4,6-Trimethyl-phenyl | H | H | 1 | S | S-[2-Oxo-2-(2,4,6-trimethylphenyl)ethyl] 17α-cyclohexylcarbonyloxy-6α,9α-difluoro-11β-hydroxy-16α-methyl-3-oxoandrosta-1,4-diene-17β-carbothioate. |
| IA.146 | α-CH$_3$ | F | F | Cyclo-pentyl | 2,4,6-Trimethyl-phenyl | H | H | 1 | S | S-[2-Oxo-2-(2,4,6-trimethylphenyl)ethyl] 17α-cyclopentylcarbonyloxy-6α,9α-difluoro-11β-hydroxy-16α-methyl-3-oxoandrosta-1,4-diene-17β-carbothioate. |
| IA.147 | α-CH$_3$ | F | F | Cyclo-butyl | 2,4,6-Trimethyl-phenyl | H | H | 1 | S | S-[2-Oxo-2-(2,4,6-trimethylphenyl)ethyl] 17α-cyclobutylcarbonyloxy-6α,9α-difluoro-11β-hydroxy-16α-methyl-3-oxoandrosta-1,4-diene-17β-carbothioate. |
| IA.148 | α-CH$_3$ | F | F | Cyclo-hexyl-methyl | 2,4,6-Trimethyl-phenyl | H | H | 1 | S | S-[2-Oxo-2-(2,4,6-trimethylphenyl)ethyl] 17α-cyclohexylmethylcarbonyloxy-6α9α-difluoro-11β-hydroxy-16α-methyl-3-oxoandrosta-1,4-diene-17β-carbothioate. |
| IA.149 | α-CH$_3$ | F | F | 2-Thienyl | 2,4,6-Trimethyl-phenyl | H | H | 1 | S | S-[2-Oxo-2-(2,4,6-trimethylphenyl)ethyl] 6α,9α-difluoro-11β-hydroxy-16α-methyl-3-oxo-17α-[(2-thienylcarbonyl)oxyandrosta-1,4-diene-17β-carbothioate. |
| IA.150 | α-CH$_3$ | F | F | Cyclo-hexyl- | 2,4-Difluoro- | H | H | 1 | S | S-[2-(2,4-Difluorophenyl)-2-oxoethyl] 17α-cyclohexylmethylcarbonyloxy-6α,9α-difluoro- |

TABLE 1-continued

Lists the compound of formula I-A which have been synthesized.

Formula I-A

| No. | R₁ | R₂ | R₃ | R₅ | R₆ | P | Q | m₁ | Z | Chemical Name |
|---|---|---|---|---|---|---|---|---|---|---|
| | | | | methyl | phenyl | | | | | 11β-hydroxy-16α-methyl-3-oxoandrosta-1,4-diene-17β-carbothioate. |
| IA.151 | α-CH₃ | F | F | Cyclohexylmethyl | 4-Chlorophenyl | H | H | 1 | S | S-[2-(4-Chlorophenyl)-2-oxoethyl] 17α-cyclohexylmethylcarbonyloxy-6α,9α-difluoro-11β-hydroxy-16α-methyl-3-oxoandrosta-1,4-diene-17β-carbothioate. |
| IA.152 | α-CH₃ | F | F | Cyclohexylmethyl | 4-Trifluoromethylphenyl | H | H | 1 | S | S-[2-Oxo-2-(4-trifluoromethylphenyl)ethyl] 17α-cyclohexylmethylcarbonyloxy-6α,9α-difluoro-11β-hydroxy-16α-methyl-3-oxoandrosta-1,4-diene-17β-carbothioate. |
| IA.153 | α-CH₃ | F | F | Cyclohexylmethyl | 4-methoxyphenyl | H | H | 1 | S | S-[2-(4-Methoxyphenyl)-2-oxoethyl] 17α-cyclohexylmethylcarbonyloxy-6α,9α-difluoro-11β-hydroxy-16α-methyl-3-oxoandrosta-1,4-diene-17β-carbothioate. |
| IA.154 | α-CH₃ | F | F | n-Butyl | 2,4,6-Trimethylphenyl | H | H | 1 | S | S-[2-Oxo-2-(2,4,6-trimethylphenyl)ethyl] 17α-n-butylcarbonyloxy-6α,9α-difluoro-11β-hydroxy-16α-methyl-3-oxoandrosta-1,4-diene-17β-carbothioate. |
| IA.155 | α-CH₃ | F | F | Ethoxy | 2,4,6-Trimethylphenyl | H | H | 1 | S | S-[2-Oxo-2-(2,4,6-trimethylphenyl)ethyl] 6α,9α-difluoro-17α-(ethoxycarbonyl)oxy-11β-hydroxy-16α-methyl-3-oxo-androsta-1,4-diene-17β-carbothioate. |
| IA.156 | α-CH₃ | F | F | 2-Furyl | 2,4,6-Trimethylphenyl | H | H | 1 | S | S-[2-Oxo-2-(2,4,6-trimethylphenyl)ethyl] 6α,9α-difluoro-17α-[(2-furanylcarbonyl)oxy]-11β-hydroxy-16α-methyl-3-oxoandrosta-1,4-diene-17β-carbothioate. |
| IA.157 | α-CH₃ | F | F | 2-Furyl | 4-Chlorophenyl | H | H | 1 | S | S-[2-(4-Chlorophenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.158 | β-CH₃ | F | F | Ethyl | 4-Chlorophenyl | H | H | 1 | S | S-[2-(4-Chlorophenyl)-2-oxoethyl] 6α,9α-difluoro-11β-hydroxy-16β-methyl-3-oxo-17α-propionyloxyandrosta-1,4-diene-17β-carbothioate. |
| IA.159 | α-CH₃ | F | F | 2-Thienyl | 4-Trifluoromethylphenyl | H | H | 1 | S | S-[2-Oxo-2-(4-trifluoromethylphenyl)ethyl] 6α,9α-difluoro-17α-[(2-thienylcarbonyl)oxy]-11β-hydroxy-16α-methyl-3-oxoandrosta-1,4-diene-17β-carbothioate. |
| IA.160 | α-CH₃ | F | F | Ethyl | 3-Nitrophenyl | H | H | 1 | S | S-[2-(3-Nitrophenyl)-2-oxoethyl] 6α,9α-difluoro-11β-hydroxy-16α-methyl-3-oxo-17α-propionyloxyandrosta-1,4-diene-17β-carbothioate. |
| IA.161 | α-CH₃ | F | F | Ethyl | 3,4-Dimethylphenyl | H | H | 1 | S | S-[2-(3,4-Dimethylphenyl)-2-oxoethyl] 6α,9α-difluoro-11β-hydroxy-16α-methyl-3-oxo-17α-propionyloxyandrosta-1,4-diene-17β-carbothioate. |
| IA.162 | β-CH₃ | F | F | Ethyl | 4-Trifluoromethylphenyl | H | H | 1 | S | S-[2-Oxo-2-(4-trifluoromethylphenyl)ethyl] 6α,9α-difluoro-11β-hydroxy-16β-methyl-3-oxo-17α-propionyloxyandrosta-1,4-diene-17β-carbothioate. |
| IA.163 | α-CH₃ | F | F | n-Propyl | 4-Trifluoromethylphenyl | H | H | 1 | S | S-[2-Oxo-2-(4-trifluoromethylphenyl)ethyl] 6α,9α-difluoro-11β-hydroxy-16α-methyl-3-oxo-17α-n-propylcarbonyloxyandrosta-1,4-diene-17β-carbothioate. |
| IA.164 | α-CH₃ | F | F | n-Propyl | 4-Chlorophenyl | H | H | 1 | S | S-[2-(4-Chlorophenyl)-2-oxoethyl] 6α,9α-difluoro-11β-hydroxy-16α-methyl-3-oxo-17α-n-propylcarbonyloxyandrosta-1,4-diene-17β-carbothioate. |

TABLE 1-continued

Lists the compound of formula I-A which have been synthesized.

Formula I-A

| No. | R$_1$ | R$_2$ | R$_3$ | R$_5$ | R$_6$ | P | Q | m$_1$ | Z | Chemical Name |
|---|---|---|---|---|---|---|---|---|---|---|
| IA.165 | α-CH$_3$ | F | F | n-Propyl | 2,4-Difluorophenyl | H | H | 1 | S | S-[2-(2,4-Difluorophenyl)-2-oxoethyl] 6α,9α-difluoro-11β-hydroxy-16α-methyl-3-oxo-17α-n-propylcarbonyloxyandrosta-1,4-diene-17β-carbothioate. |
| IA.166 | α-CH$_3$ | F | F | n-Propyl | 4-Fluorophenyl | H | H | 1 | S | S-[2-(4-Fluorophenyl)-2-oxoethyl] 6α,9α-difluoro-11β-hydroxy-16α-methyl-3-oxo-17α-n-propylcarbonyloxyandrosta-1,4-diene-17β-carbothioate. |
| IA.167 | α-CH$_3$ | F | F | n-Propyl | 4-Methoxyphenyl | H | H | 1 | S | S-[2-(4-Methoxyphenyl)-2-oxoethyl] 6α,9α-difluoro-11β-hydroxy-16α-methyl-3-oxo-17α-n-propylcarbonyloxyandrosta-1,4-diene-17β-carbothioate. |
| IA.168 | α-CH$_3$ | F | F | 2-Furyl | 3-Chlorophenyl | H | H | 1 | S | S-[2-(3-Chlorophenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.169 | β-CH$_3$ | F | F | 2-Furyl | 4-Trifluoromethylphenyl | H | H | 1 | S | S-[2-Oxo-2-(4-trifluoromethylphenyl)ethyl] 6α,9α-difluoro-17α-[(2-furanylcarbonyl)oxy]-11β-hydroxy-16β-methyl-3-oxoandrosta-1,4-diene-17β-carbothioate. |
| IA.170 | α-CH$_3$ | F | F | 2-Furyl | 3,5-Dimethoxyphenyl | H | H | 1 | S | S-[2-(3,5-Dimethoxyphenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.171 | α-CH$_3$ | F | F | 2-Furyl | 4-Nitrophenyl | H | H | 1 | S | S-[2-(4-Nitrophenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.172 | α-CH$_3$ | F | F | Methoxymethyl | 4-Trifluoromethylphenyl | H | H | 1 | S | S-[2-Oxo-2-(4-trifluoromethylphenyl)ethyl] 6α,9α-difluoro-11β-hydroxy-17α-(methoxymethyl-carbonyl)oxy-16α-methyl-3-oxoandrosta-1,4-diene-17β-carbothioate. |
| IA.173 | α-CH$_3$ | F | F | Methoxymethyl | 2,4,6-Trimethylphenyl | H | H | 1 | S | S-[2-Oxo-2-(2,4,6-trimethylphenyl)ethyl] 6α,9α-difluoro-11β-hydroxy-17α-(methoxymethyl-carbonyl)oxy-16α-methyl-3-oxoandrosta-1,4-diene-17β-carbothioate. |
| IA.174 | α-CH$_3$ | F | F | Ethyl | 3-Chloro-4-fluorophenyl | H | H | 1 | S | S-[2-(3-Chloro-4-fluorophenyl)-2-oxoethyl] 6α,9α-difluoro-11β-hydroxy-16α-methyl-3-oxo-17α-propionyloxy-androsta-1,4-diene-17β-carbothioate. |
| IA.175 | β-CH$_3$ | F | F | 2-Furyl | 2,4,6-Trimethylphenyl | H | H | 1 | S | S-[2-Oxo-2-(2,4,6-trimethylphenyl)ethyl] 6α,9α-difluoro-17α-[(2-furanylcarbonyl)oxy]-11β-hydroxy-16β-methyl-3-oxoandrosta-1,4-diene-17β-carbothioate. |
| IA.176 | α-CH$_3$ | F | F | Ethoxymethyl | 2,4,6-Trimethylphenyl | H | H | 1 | S | S-[2-Oxo-2-(2,4,6-trimethylphenyl)ethyl] 6α,9α-difluoro-17α-(ethoxymethylcarbonyl)oxy-11β-hydroxy-16α-methyl-3-oxoandrosta-1,4-diene-17β-carbothioate. |
| IA.177 | α-CH$_3$ | F | F | Ethoxymethyl | 4-Trifluoromethylphenyl | H | H | 1 | S | S-[2-Oxo-2-(4-trifluoromethylphenyl)ethyl] 6α,9α-difluoro-17α-(ethoxymethylcarbonyl)oxy-11β-hydroxy-16α-methyl-3-oxoandrosta-1,4-diene-17β-carbothioate. |
| IA.179 | α-CH$_3$ | F | F | 2-Furyl | 2-Naphthyl | H | H | 1 | S | S-[2-(Naphthalen-2-yl)-2-oxoethyl] 6α,9α-difluoro-17α-[(2-furanylcarbonyl)oxy]-11β-hydroxy-16α-methyl-3-oxoandrosta-1,4-diene-17β-carbothioate. |

TABLE 1-continued

Lists the compound of formula I-A which have been synthesized.

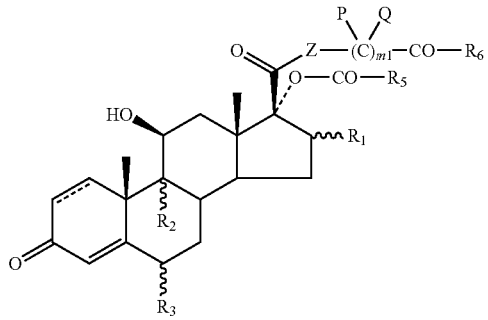

Formula I-A

| No. | $R_1$ | $R_2$ | $R_3$ | $R_5$ | $R_6$ | P | Q | $m_1$ | Z | Chemical Name |
|---|---|---|---|---|---|---|---|---|---|---|
| IA.180 | α-CH$_3$ | F | F | 2-Furyl | 1-Naphthyl | H | H | 1 | S | S-[2-(Naphthalen-1-yl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.181 | α-CH$_3$ | F | F | 3-Methyl-2-furyl | 4-Trifluoro-methylphenyl | H | H | 1 | S | S-[2-Oxo-2-(4-trifluoromethylphenyl)ethyl] 6α,9α-difluoro-11β-hydroxy-17α-[[(3-methyl-2-furanyl)-carbonyl]oxy]-16α-methyl-3-oxoandrosta-1,4-diene-17β-carbothioate. |
| IA.182 | α-CH$_3$ | F | F | 3-Methyl-2-furyl | 2,4,6-Trimethyl-phenyl | H | H | 1 | S | S-[2-Oxo-2-(2,4,6-trimethylphenyl)ethyl] 6α,9α-difluoro-11β-hydroxy-17α-[[(3-methyl-2-furanyl)-carbonyl]oxy]-16α-methyl-3-oxoandrosta-1,4-diene-17β-carbothioate. |
| IA.183 | α-CH$_3$ | F | F | 2-Furyl | 3-Nitro-4-methoxy-phenyl | H | H | 1 | S | S-[2-(3-Nitro-4-methoxyphenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.184 | α-CH$_3$ | F | F | 2-Furyl | 3,4-Dimethyl-phenyl | H | H | 1 | S | S-[2-(3,4-Dimethylphenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.185 | α-CH$_3$ | F | F | 3-Furyl | 4-Trifluoro-methylphenyl | H | H | 1 | S | S-[2-Oxo-2-(4-trifluoromethylphenyl)ethyl] 6α,9α-difluoro-17α-[(3-furanylcarbonyl)oxy]-11β-hydroxy-16α-methyl-3-oxoandrosta-1,4-diene-17β-carbothioate. |
| IA.186 | α-CH$_3$ | F | F | 3-Furyl | 2,4,6-Trimethyl-phenyl | H | H | 1 | S | S-[2-Oxo-2-(2,4,6-trimethylphenyl)ethyl] 6α,9α-difluoro-17α-[(3-furanylcarbonyl)oxy]-11β-hydroxy-16α-methyl-3-oxoandrosta-1,4-diene-17β-carbothioate. |
| IA.187 | α-CH$_3$ | F | F | Ethyl | 4-Trifluoro-methylphenyl | CH$_3$ | CH$_3$ | 1 | S | S-[1,1-Dimethyl-2-oxo-2-(4-trifluoromethylphenyl)-ethyl] 6α,9α-difluoro-11β-hydroxy-16α-methyl-3-oxo-17α-propionyloxyandrosta-1,4-diene-17β-carbothioate. |
| IA.188 | α-CH$_3$ | F | F | Ethyl | 4-Fluoro-phenyl | CH$_3$ | CH$_3$ | 1 | S | S-[1,1-Dimethyl-2-(4-fluorophenyl)-2-oxoethyl] 6α,9α-difluoro-11β-hydroxy-16α-methyl-3-oxo-17α-propionyloxyandrosta-1,4-diene-17β-carbothioate. |
| IA.189 | α-CH$_3$ | F | H | Ethyl | Phenyl | CH$_3$ | CH$_3$ | 1 | S | S-[1,1-Dimethyl-2-phenyl-2-oxoethyl] 9α-fluoro-11β-hydroxy-16α-methyl-3-oxo-17α-propionyloxy-androsta-1,4-diene-17β-carbothioate. |

TABLE 1-continued

Lists the compound of formula I-A which have been synthesized.

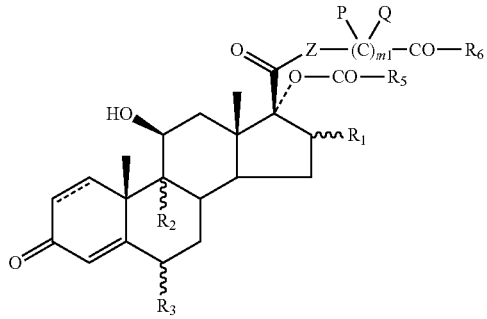

Formula I-A

| No. | $R_1$ | $R_2$ | $R_3$ | $R_5$ | $R_6$ | P | Q | $m_1$ | Z | Chemical Name |
|---|---|---|---|---|---|---|---|---|---|---|
| IA.190 | α-$CH_3$ | F | F | Cyclohexyl | Phenyl | $CH_3$ | $CH_3$ | 1 | S | S-[1,1-Dimethyl-2-phenyl-2-oxoethyl] 17α-cyclohexylcarbonyloxy-6α,9α-difluoro-11β-hydroxy-16α-methyl-3-oxoandrosta-1,4-diene-17β-carbothioate. |
| IA.191 | α-$CH_3$ | F | F | Cyclopentyl | Phenyl | $CH_3$ | $CH_3$ | 1 | S | S-[1,1-Dimethyl-2-phenyl-2-oxoethyl] 17α-cyclopentylcarbonyloxy-6α,9α-difluoro-11β-hydroxy-16α-methyl-3-oxoandrosta-1,4-diene-17β-carbothioate. |
| IA.192 | α-$CH_3$ | F | F | Isopropyl | Phenyl | $CH_3$ | $CH_3$ | 1 | S | S-[1,1-Dimethyl-2-phenyl-2-oxoethyl] 6α,9α-difluoro-11β-hydroxy-16α-methyl-17α-(2-methylpropionyloxy)-3-oxoandrosta-1,4-diene-17β-carbothioate. |
| IA.193 | α-$CH_3$ | F | F | Cyclobutyl | Phenyl | $CH_3$ | $CH_3$ | 1 | S | S-[1,1-Dimethyl-2-phenyl-2-oxoethyl] 17α-cyclobutylcarbonyloxy-6α,9α-difluoro-11β-hydroxy-16α-methyl-3-oxoandrosta-1,4-diene-17β-carbothioate. |
| IA.194 | α-$CH_3$ | F | H | 2-Furyl | Phenyl | $CH_3$ | $CH_3$ | 1 | S | S-[1,1-Dimethyl-2-phenyl-2-oxoethyl] 9α-fluoro-17α-[(2-furanylcarbonyl)oxy]-11β-hydroxy-16α-methyl-3-oxoandrosta-1,4-diene-17β-carbothioate. |
| IA.195 | α-$CH_3$ | F | F | Cyclohexylmethyl | Phenyl | $CH_3$ | $CH_3$ | 1 | S | S-[1,1-Dimethyl-2-phenyl-2-oxoethyl] 17α-cyclohexylmethylcarbonyloxy-6α,9α-difluoro-11β-hydroxy-16α-methyl-3-oxoandrosta-1,4-diene-17β-carbothioate. |
| IA.196 | α-$CH_3$ | F | F | 2-Furyl | 4-Fluorophenyl | $CH_3$ | $CH_3$ | 1 | S | S-[1,1-Dimethyl-2-(4-fluorophenyl)-2-oxoethyl] 6α,9α-difluoro-17α-[(2-furanylcarbonyl)oxy]-11β-hydroxy-16α-methyl-3-oxoandrosta-1,4-diene-17β-carbothioate. |
| IA.197 | α-$CH_3$ | F | F | 2-Furyl | 4-Trifluoromethylphenyl | $CH_3$ | $CH_3$ | 1 | S | S-[1,1-Dimethyl-2-oxo-2-(4-trifluoromethylphenyl)ethyl] 6α,9α-difluoro-17α-[(2-furanylcarbonyl)oxy]-11β-hydroxy-16α-methyl-3-oxoandrosta-1,4-diene-17β-carbothioate. |
| IA.198 | α-$CH_3$ | F | F | 5-Chloro-2-thienyl | 3,4-Dimethylphenyl | H | H | 1 | S | S-[2-(3,4-Dimethylphenyl)-2-oxoethyl] 17α-[[(5-chloro-2-thienyl)carbonyl]oxy]-6α,9α-difluoro-11β-hydroxy-16α-methyl-3-oxoandrosta-1,4-diene-17β-carbothioate. |

TABLE 2

Lists the compound of formula I-A-1 and Table-3 lists the compound of formula I-A-2 which have been synthesized

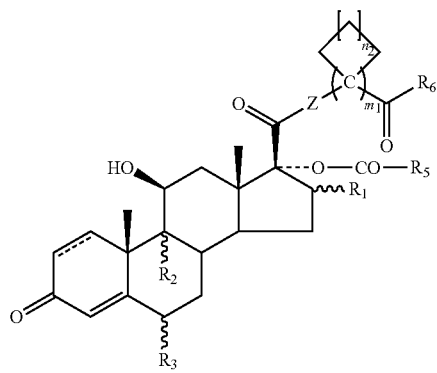

Formula I-A-1

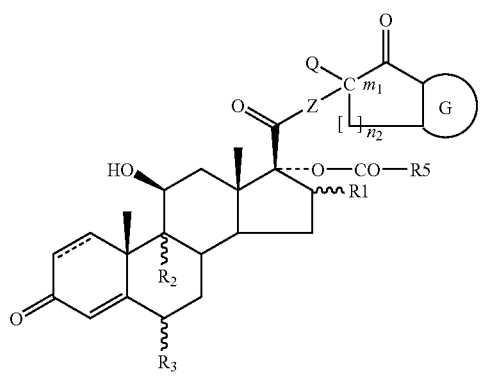

Formula I-A-2

| Sr. No | $R_1$ | $R_2$ | $R_3$ | $R_5$ | $R_6$ | $n_2$ | $m_1$ | Z | Chemical Name |
|---|---|---|---|---|---|---|---|---|---|
| IA-1.1 | α-CH$_3$ | F | F | Ethyl | 4-Fluorophenyl | 2 | 1 | S | S-[1-(4-Fluorobenzoyl)cyclopentyl]6α,9α-difluoro-11β-hydroxy-16α-methyl-3-oxo-17α-propionyloxy-androsta-1,4-diene-17β-carbothioate. |
| IA-1.2 | α-CH$_3$ | F | F | Ethyl | Phenyl | 2 | 1 | S | S-[1-Benzoylcyclopentyl]6α,9α-difluoro-11β-hydroxy-16α-methyl-3-oxo-17α-propionyloxyandrosta-1,4-diene-17β-carbothioate. |

TABLE 3

| Sr. No | $R_1$ | $R_2$ | $R_3$ | $R_5$ | $n_2$ | Q | G | $m_1$ | Z | Chemical Name |
|---|---|---|---|---|---|---|---|---|---|---|
| IA-2.1 | α-CH$_3$ | F | F | Ethyl | 2 | H | Phenyl | 1 | S | S-(1-oxo-1,2,3,4-tetrahydronapthalen-2-yl) 6α,9α-difluoro-11β-hydroxy-16α-methyl-3-oxo-17α-propionyloxyandrosta-1,4-diene-17β-carbothioate. |

TABLE 4

Lists the compound of formula I-B which have been synthesized

Formula I-B

| Sr. No | $R_1$ | $R_2$ | $R_3$ | $R_5$ | P | Q | J | K | Z | X | $m_1$ | $m_2$ | $m_3$ | $n_1$ |
|---|---|---|---|---|---|---|---|---|---|---|---|---|---|---|
| IB.1 | α-CH₃ | F | F | Ethyl | H | H | H | H | O | ═ | 1 | 0 | 0 | 1 |
| IB.2 | α-CH₃ | F | F | Ethyl | H | H | H | H | S | ═ | 1 | 0 | 0 | 1 |
| IB.3 | α-CH₃ | F | F | Ethyl | H | H | H | H | S | ═ | 1 | 0 | 0 | 1 |
| IB.4 | α-CH₃ | F | F | 2-Furyl | H | H | H | H | S | ═ | 1 | 0 | 0 | 1 |
| IB.5 | α-CH₃ | F | H | Ethyl | H | H | H | H | S | ═ | 1 | 0 | 0 | 1 |
| IB.6 | α-CH₃ | F | F | 2-Furyl | H | H | H | H | S | ═ | 1 | 0 | 0 | 1 |
| IB.7 | α-CH₃ | F | F | Isopropyl | H | H | H | H | S | ═ | 1 | 0 | 0 | 1 |
| IB.8 | α-CH₃ | F | F | Cyclo-butyl | H | H | H | H | S | ═ | 1 | 0 | 0 | 1 |
| IB.9 | α-CH₃ | F | H | 2-Furyl | H | H | H | H | S | ═ | 1 | 0 | 0 | 1 |
| IB.10 | α-CH₃ | F | F | 2-Thienyl | H | H | H | H | S | ═ | 1 | 0 | 0 | 1 |
| IB.11 | α-CH₃ | F | F | Ethyl | H | H | — | — | S | ═ | 1 | 0 | 1 | 0 |
| IB.12 | α-CH₃ | F | F | 2-Furyl | H | H | H | H | S | ═ | 1 | 0 | 0 | 1 |
| IB.13 | α-CH₃ | F | F | Ethyl | H | H | H | H | S | ═(E) | 1 | 1 | 1 | 1 |
| IB.14 | α-CH₃ | F | F | 2-Furyl | H | H | H | H | S | ═(E) | 1 | 1 | 1 | 1 |
| IB.15 | α-CH₃ | F | F | 2-Furyl | H | H | H | H | S | ═(Z) | 1 | 1 | 1 | 1 |
| IB.16 | α-CH₃ | F | F | 2-Thienyl | H | H | H | H | S | ═(Z) | 1 | 1 | 1 | 1 |
| IB.17 | α-CH₃ | F | F | 2-Thienyl | H | H | H | H | S | ═(E) | 1 | 1 | 1 | 1 |
| IB.18 | α-CH₃ | F | F | 2-Furyl | H | H | H | H | S | ═ | 1 | 0 | 0 | 1 |
| IB.19 | α-CH₃ | F | F | 2-Furyl | H | H | H | H | S | ═ | 1 | 0 | 0 | 1 |
| IB.20 | α-CH₃ | F | F | 5-Chloro-2-Thienyl | H | H | H | H | S | ═ | 1 | 0 | 0 | 1 |
| IB.21 | α-CH₃ | F | F | 2-Furyl | H | H | H | H | S | ═ | 1 | 0 | 0 | 1 |
| IB.22 | α-CH₃ | F | F | 3-Methyl-2-furyl | H | H | H | H | S | ═ | 1 | 0 | 0 | 1 |
| IB.23 | α-CH₃ | F | F | Ethoxy-methyl | H | H | H | H | S | ═ | 1 | 0 | 0 | 1 |
| IB.24 | α-CH₃ | F | F | Methoxy-methyl | H | H | H | H | S | ═ | 1 | 0 | 0 | 1 |
| IB.25 | α-CH₃ | F | F | 2-Furyl | H | H | (CH₂)₅ | | S | ═ | 1 | 0 | 0 | 1 |
| IB.26 | α-CH₃ | F | F | Cyclo-Hexyl-methyl | H | H | H | H | S | ═ | 1 | 0 | 0 | 1 |
| IB.27 | α-CH₃ | F | F | n-Butyl | H | H | H | H | S | ═ | 1 | 0 | 0 | 1 |
| IB.28 | α-CH₃ | F | F | Ethyl | H | H | — | — | O | ═ | 1 | 0 | 1 | 0 |
| IB.29 | α-CH₃ | F | F | Cyclo-pentyl | H | H | H | H | S | ═ | 1 | 0 | 0 | 1 |
| IB.30 | α-CH₃ | F | F | Ethyl | H | H | H | H | S | ═(Z) | 1 | 1 | 1 | 1 |
| IB.31 | α-CH₃ | F | F | Ethyl | H | H | H | H | S | ═ | 1 | 0 | 0 | 1 |
| IB.32 | α-CH₃ | F | F | Ethyl | H | H | H | H | S | ═ | 1 | 0 | 0 | 1 |
| IB.33 | α-CH₃ | F | F | Ethyl | H | H | H | H | S | ═ | 1 | 0 | 0 | 1 |
| IB.34 | α-CH₃ | F | F | Ethyl | H | H | H | H | S | ═ | 1 | 0 | 0 | 1 |
| IB.35 | α-CH₃ | F | F | Ethyl | H | H | H | H | S | ═ | 1 | 0 | 0 | 1 |
| IB.36 | α-CH₃ | F | F | Ethyl | H | H | H | H | S | ═ | 1 | 0 | 0 | 1 |
| IB.37 | α-CH₃ | F | F | Ethyl | H | H | H | H | S | ═ | 1 | 0 | 0 | 1 |
| IB.38 | β-CH₃ | F | H | Ethyl | H | H | H | H | S | ═ | 1 | 0 | 0 | 1 |
| IB.39 | β-CH₃ | F | F | Ethyl | H | H | H | H | S | ═ | 1 | 0 | 0 | 1 |
| IB.40 | α-CH₃ | F | F | 2-Furyl | H | H | CH₃ | CH₃ | S | ═ | 1 | 0 | 0 | 1 |
| IB.41 | α-CH₃ | F | F | Ethyl | H | H | | O | O | ═(E) | 1 | 1 | 1 | 1 |
| IB.42 | α-CH₃ | F | F | Ethyl | H | H | | O | S | ═(E) | 1 | 1 | 1 | 1 |
| IB.43 | — | H | H | Ethoxy | H | H | | O | O | ═(E) | 1 | 1 | 1 | 1 |
| IB.44 | α-CH₃ | F | F | Ethyl | H | H | H | H | S | ═(E) | 1 | 1 | 1 | 1 |
| IB.45 | α-CH₃ | Cl | H | 2-Furyl | H | H | H | H | S | ═ | 1 | 0 | 0 | 1 |
| IB.46 | α-CH₃ | F | F | 2-Furyl | H | H | H | H | S | ═(E) | 1 | 1 | 1 | 1 |
| IB.47 | α-CH₃ | F | F | 2-Furyl | H | H | H | H | S | ═(Z) | 1 | 1 | 1 | 1 |
| IB.48 | α-CH₃ | F | F | 2-Furyl | H | H | H | H | S | ═ | 1 | 0 | 0 | 1 |
| IB.49 | α-CH₃ | F | F | 2-Furyl | H | H | H | H | S | ═ | 1 | 0 | 0 | 1 |
| IB.50 | α-CH₃ | F | F | 2-Furyl | H | H | H | H | S | ═ | 1 | 0 | 0 | 1 |

TABLE 4-continued

Lists the compound of formula I-B which have been synthesized

Formula I-B

| | | | | | | | | | | | | | | |
|---|---|---|---|---|---|---|---|---|---|---|---|---|---|---|
| IB.51 | α-CH₃ | F | F | 2-Furyl | H | H | H | H | S | = | | 1 | 0 | 0 | 1 |
| IB.52 | α-CH₃ | F | F | Ethyl | H | H | H | H | S | = | | 1 | 0 | 0 | 1 |
| IB.53 | α-CH₃ | F | F | 2-Furyl | H | H | H | H | S | =(Z) | 1 | 1 | 1 | 1 |
| IB.54 | α-CH₃ | F | F | 2-Furyl | H | H | H | H | S | = | | 1 | 0 | 0 | 1 |
| IB.55 | α-CH₃ | F | F | 2-Thienyl | H | H | H | H | S | = | | 1 | 0 | 0 | 1 |
| IB.56 | α-CH₃ | F | F | 5-Cl-2-Thienyl | H | H | H | H | S | = | | 1 | 0 | 0 | 1 |
| IB.57 | α-CH₃ | F | F | 2-Furyl | H | H | H | H | S | = | | 1 | 0 | 0 | 1 |
| IB.58 | α-CH₃ | F | F | 2-Furyl | H | H | H | H | S | = | | 1 | 0 | 0 | 1 |
| IB.59 | α-CH₃ | F | F | 2-Furyl | H | H | H | H | S | = | | 1 | 0 | 0 | 1 |
| IB.60 | α-CH₃ | F | F | 2-Furyl | H | H | H | H | S | =(E) | 1 | 1 | 1 | 1 |
| IB.61 | α-CH₃ | F | F | 4-Cl-phenyl | H | H | H | H | S | = | | 1 | 0 | 0 | 1 |
| IB.62 | α-CH₃ | F | F | 3-Cl-phenyl | H | H | H | H | S | = | | 1 | 0 | 0 | 1 |
| IB.63 | α-CH₃ | F | F | 2-Furyl | H | H | H | H | S | = | | 1 | 0 | 0 | 1 |
| IB.64 | α-CH₃ | F | F | 2-Furyl | H | H | H | H | S | = | | 1 | 0 | 0 | 1 |
| IB.65 | α-CH₃ | F | F | 2-Furyl | H | H | H | H | S | = | | 1 | 0 | 0 | 1 |
| IB.66 | α-CH₃ | F | F | 2-Furyl | H | H | H | H | S | = | | 1 | 0 | 0 | 1 |
| IB.67 | α-CH₃ | F | F | 2-Furyl | H | H | H | H | S | = | | 1 | 0 | 0 | 1 |
| IB.68 | α-CH₃ | F | F | 2-Furyl | H | H | H | H | S | =(Z) | 1 | 1 | 1 | 1 |
| IB.69 | α-CH₃ | F | F | 2-Furyl | H | H | H | H | S | =(E) | 1 | 1 | 1 | 1 |
| IB.70 | α-CH₃ | F | F | 2-Furyl | H | H | H | H | S | = | | 1 | 0 | 0 | 1 |
| IB.71 | α-CH₃ | F | F | 2-Furyl | H | H | H | H | S | = | | 1 | 0 | 0 | 1 |
| IB.72 | α-CH₃ | F | F | 2-Furyl | H | H | H | H | S | = | | 1 | 0 | 0 | 1 |
| IB.73 | α-CH₃ | F | F | 2-Furyl | H | H | H | H | S | = | | 1 | 0 | 0 | 1 |
| IB.74 | α-CH₃ | F | F | Cyclo-butyl | H | H | H | H | S | = | | 1 | 0 | 0 | 1 |
| IB.75 | α-CH₃ | F | F | Cyclo-butyl | H | H | H | H | S | = | | 1 | 0 | 0 | 1 |
| IB.76 | α-CH₃ | F | F | 2-Furyl | H | H | H | H | S | = | | 1 | 0 | 0 | 1 |
| IB.77 | α-CH₃ | F | F | 2-Furyl | H | H | H | H | S | = | | 1 | 0 | 0 | 1 |
| IB.78 | α-CH₃ | F | F | 2-Furyl | H | H | H | H | S | = | | 1 | 0 | 0 | 1 |
| IB.79 | α-CH₃ | F | F | 2-Furyl | H | H | H | H | S | = | | 1 | 0 | 0 | 1 |
| IB.80 | α-CH₃ | F | F | 2-Furyl | H | H | H | H | S | = | | 1 | 0 | 0 | 1 |
| IB.81 | α-CH₃ | F | F | 2-Furyl | H | H | H | H | S | = | | 1 | 0 | 0 | 1 |
| IB.82 | α-CH₃ | F | F | 2-Furyl | H | H | H | H | S | =(E) | 1 | 1 | 1 | 1 |
| IB.83 | α-CH₃ | F | F | 2-Furyl | H | H | H | H | S | =(Z) | 1 | 1 | 1 | 1 |
| IB.84 | α-CH₃ | F | F | Cyclo-butyl | H | H | H | H | S | = | | 1 | 0 | 0 | 1 |
| IB.85 | α-CH₃ | F | F | 2-Furyl | H | H | H | H | S | = | | 1 | 0 | 0 | 1 |
| IB.86 | α-CH₃ | F | F | 2-Furyl | H | H | H | H | S | = | | 1 | 0 | 0 | 1 |
| IB.87 | α-CH₃ | F | F | 2-Furyl | H | H | H | H | S | = | | 1 | 0 | 0 | 1 |
| IB.88 | α-CH₃ | F | F | 2-Furyl | H | H | H | H | S | = | | 1 | 0 | 0 | 1 |
| IB.89 | α-CH₃ | F | F | 2-Furyl | H | H | H | H | S | = | | 1 | 0 | 0 | 1 |
| IB.90 | α-CH₃ | F | F | 2-Furyl | H | H | H | H | S | = | | 1 | 0 | 0 | 1 |
| IB.91 | α-CH₃ | F | F | 5-Chloro-2-Thienyl | H | H | H | H | S | = | | 1 | 0 | 0 | 1 |
| IB.92 | α-CH₃ | F | F | 5-Chloro-2-Thienyl | H | H | H | H | S | = | | 1 | 0 | 0 | 1 |
| IB.93 | α-CH₃ | F | F | 2-Furyl | H | H | H | H | S | = | | 1 | 0 | 0 | 1 |
| IB.94 | α-CH₃ | F | F | 2-Furyl | H | H | H | H | S | = | | 1 | 0 | 0 | 1 |
| IB.95 | α-CH₃ | F | F | 2-Furyl | H | H | H | H | S | = | | 1 | 0 | 0 | 1 |
| IB.96 | α-CH₃ | F | F | 2-Furyl | H | H | H | H | S | = | | 1 | 0 | 0 | 1 |
| IB.97 | α-CH₃ | F | F | 2-Furyl | H | H | H | H | S | = | | 1 | 0 | 0 | 1 |
| IB.98 | α-CH₃ | F | F | 2-Furyl | H | H | H | H | S | = | | 1 | 0 | 0 | 1 |
| IB.99 | α-CH₃ | F | F | 2-Furyl | H | H | H | H | S | = | | 1 | 0 | 0 | 1 |
| IB.100 | α-CH₃ | F | F | 2-Furyl | H | H | H | H | S | = | | 1 | 0 | 0 | 1 |
| IB.101 | α-CH₃ | F | F | 2-Furyl | H | H | H | H | S | = | | 1 | 0 | 0 | 1 |
| IB.102 | α-CH₃ | F | F | 2-Furyl | H | H | H | H | S | = | | 1 | 0 | 0 | 1 |

TABLE 4-continued

Lists the compound of formula I-B which have been synthesized

Formula I-B

| | | | | | | | | | | | | | | |
|---|---|---|---|---|---|---|---|---|---|---|---|---|---|---|
| IB.103 | α-CH$_3$ | F | F | 2-Furyl | H | H | H | H | S | = | 1 | 0 | 0 | 1 |
| IB.104 | α-CH$_3$ | F | F | 2-Furyl | H | H | H | H | S | = | 1 | 0 | 0 | 1 |
| IB.105 | α-CH$_3$ | F | F | 2-Furyl | H | H | H | H | S | = | 1 | 0 | 0 | 1 |
| IB.106 | α-CH$_3$ | F | F | 2-Furyl | H | H | H | H | S | = | 1 | 0 | 0 | 1 |
| IB.107 | α-CH$_3$ | F | F | 2-Furyl | H | H | H | H | S | = | 1 | 0 | 0 | 1 |
| IB.108 | α-CH$_3$ | F | F | 2-Furyl | H | H | H | H | S | = | 1 | 0 | 0 | 1 |
| IB.109 | α-CH$_3$ | F | F | 2-Furyl | H | H | H | H | S | = | 1 | 0 | 0 | 1 |
| IB.110 | α-CH$_3$ | F | F | 2-Furyl | H | H | H | H | S | = | 1 | 0 | 0 | 1 |
| IB.111 | α-CH$_3$ | F | F | 2-Furyl | H | H | H | H | S | = | 1 | 0 | 0 | 1 |
| IB.112 | α-CH$_3$ | F | F | 2-Furyl | H | H | H | H | S | = | 1 | 0 | 0 | 1 |
| IB.113 | α-CH$_3$ | F | F | 2-Furyl | H | H | H | H | S | = | 1 | 0 | 0 | 1 |
| IB.114 | α-CH$_3$ | F | F | 2-Furyl | H | H | H | H | S | = | 1 | 0 | 0 | 1 |
| IB.115 | α-CH$_3$ | F | F | 2-Furyl | H | H | H | H | S | = | 1 | 0 | 0 | 1 |
| IB.116 | α-CH$_3$ | Cl | H | 2-Furyl | H | H | H | H | S | = | 1 | 0 | 0 | 1 |
| IB.117 | α-CH$_3$ | F | F | 2-Furyl | H | H | H | H | S | = | 1 | 0 | 0 | 1 |
| IB.118 | α-CH$_3$ | F | F | 2-Furyl | H | H | H | H | S | = | 1 | 0 | 0 | 1 |
| IB.119 | α-CH$_3$ | F | F | 2-Furyl | H | H | H | H | S | = | 1 | 0 | 0 | 1 |
| IB.120 | α-CH$_3$ | F | F | 2-Furyl | H | H | H | H | S | = | 1 | 0 | 0 | 1 |
| IB.121 | α-CH$_3$ | F | F | 2-Furyl | H | H | H | H | S | = | 1 | 0 | 0 | 1 |
| IB.122 | α-CH$_3$ | F | F | 2-Furyl | H | H | H | H | S | = | 1 | 0 | 0 | 1 |
| IB.123 | α-CH$_3$ | F | F | 2-Furyl | H | H | H | H | S | = | 1 | 0 | 0 | 1 |
| IB.124 | α-CH$_3$ | F | F | 2-Furyl | H | H | H | H | S | = | 1 | 0 | 0 | 1 |
| IB.125 | α-CH$_3$ | F | F | 2-Furyl | H | H | H | H | S | = | 1 | 0 | 0 | 1 |
| IB.126 | α-CH$_3$ | F | F | 2-Furyl | H | H | H | H | S | = | 1 | 0 | 0 | 1 |
| IB.127 | α-CH$_3$ | Cl | H | 2-Furyl | H | H | H | H | S | = | 1 | 0 | 0 | 1 |
| IB.128 | α-CH$_3$ | F | F | 2-Furyl | H | H | H | H | S | = | 1 | 0 | 0 | 1 |
| IB.129 | α-CH$_3$ | F | F | 2-Furyl | H | H | H | H | S | = | 1 | 0 | 0 | 1 |
| IB.130 | α-CH$_3$ | F | F | 2-Furyl | H | H | H | H | S | = | 1 | 0 | 0 | 1 |
| IB.131 | α-CH$_3$ | F | F | 2-Furyl | H | H | H | H | S | = | 1 | 0 | 0 | 1 |
| IB.132 | β-CH$_3$ | F | F | 2-Furyl | H | H | H | H | S | = | 1 | 0 | 0 | 1 |
| IB.133 | β-CH$_3$ | F | F | 2-Furyl | H | H | H | H | S | = | 1 | 0 | 0 | 1 |
| IB.134 | β-CH$_3$ | F | F | 2-Furyl | H | H | H | H | S | = | 1 | 0 | 0 | 1 |
| IB.135 | α-CH$_3$ | F | F | 2-Furyl | H | H | H | H | S | = | 1 | 0 | 0 | 1 |
| IB.136 | α-CH$_3$ | F | F | 2-Furyl | H | H | H | H | S | = | 1 | 0 | 0 | 1 |
| IB.137 | α-CH$_3$ | F | F | 2-Furyl | H | H | H | H | S | = | 1 | 0 | 0 | 1 |
| IB.138 | α-CH$_3$ | F | F | 2-Furyl | H | H | H | H | S | = | 1 | 0 | 0 | 1 |
| IB.139 | α-CH$_3$ | F | F | 2-Furyl | H | H | H | H | S | = | 1 | 0 | 0 | 1 |
| IB.140 | α-CH$_3$ | F | F | 2-Furyl | H | H | H | H | S | = | 1 | 0 | 0 | 1 |
| IB.141 | α-CH$_3$ | F | F | 2-Furyl | H | H | H | H | S | = | 1 | 0 | 0 | 1 |
| IB.142 | α-CH$_3$ | F | F | 2-Furyl | H | H | H | H | S | = | 1 | 0 | 0 | 1 |
| IB.143 | α-CH$_3$ | F | F | 2-Furyl | H | H | H | H | S | = | 1 | 0 | 0 | 1 |
| IB.144 | α-CH$_3$ | F | F | 2-Furyl | H | H | H | H | S | = | 1 | 0 | 0 | 1 |
| IB.145 | α-CH$_3$ | F | F | 2-Furyl | H | H | H | H | S | = | 1 | 0 | 0 | 1 |
| IB.146 | α-CH$_3$ | F | F | 2-Furyl | H | H | H | H | S | = | 1 | 0 | 0 | 1 |
| IB.147 | α-CH$_3$ | F | F | 2-Furyl | H | H | H | H | S | = | 1 | 0 | 0 | 1 |
| IB.148 | α-CH$_3$ | F | F | 2-Furyl | H | H | H | H | S | = | 1 | 0 | 0 | 1 |
| IB.149 | α-CH$_3$ | F | F | 2-Furyl | H | H | H | H | S | = | 1 | 0 | 0 | 1 |
| IB.150 | α-CH$_3$ | F | F | 2-Furyl | H | H | H | H | S | = | 1 | 0 | 0 | 1 |
| IB.151 | α-CH$_3$ | F | F | 2-Furyl | H | H | H | H | S | = | 1 | 0 | 0 | 1 |
| IB.152 | α-CH$_3$ | F | F | 2-Furyl | H | H | H | H | S | = | 1 | 0 | 0 | 1 |
| IB.153 | α-CH$_3$ | F | F | 2-Furyl | H | H | H | H | S | = | 1 | 0 | 0 | 1 |
| IB.154 | α-CH$_3$ | F | F | 2-Furyl | H | H | H | H | S | = | 1 | 0 | 0 | 1 |
| IB.155 | α-CH$_3$ | F | F | 2-Furyl | H | H | H | H | S | = | 1 | 0 | 0 | 1 |
| IB.156 | α-CH$_3$ | F | F | 2-Furyl | H | H | H | H | S | = | 1 | 0 | 0 | 1 |
| IB.157 | α-CH$_3$ | F | F | 2-Furyl | H | H | H | H | S | = | 1 | 0 | 0 | 1 |
| IB.158 | α-CH$_3$ | F | F | 2-Furyl | H | H | H | H | S | = | 1 | 0 | 0 | 1 |
| IB.159 | α-CH$_3$ | F | F | 2-Furyl | H | H | H | H | S | = | 1 | 0 | 0 | 1 |
| IB.160 | α-CH$_3$ | F | F | 2-Furyl | H | H | H | H | S | = | 1 | 0 | 0 | 1 |

TABLE 4-continued

Lists the compound of formula I-B which have been synthesized

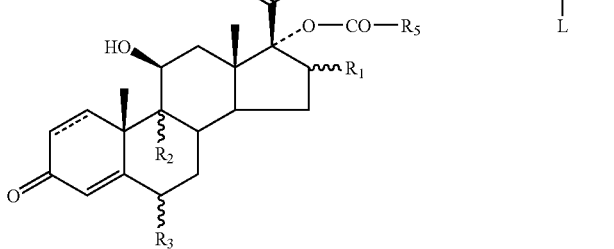

Formula I-B

| | L | Chemical Name |
|---|---|---|
| IB.1 | OH | 2 4-Hydroxy-but-2-ynyl 6α,9α-difluoro-11β-hydroxy-16α-methyl-3-oxo-17α-propionyloxyandrosta-1,4-diene-17β-carboxylate. |
| IB.2 | OH | S-(4-Hydroxy-but-2-ynyl) 6α,9α-difluoro-11β-hydroxy-16α-methyl-3-oxo-17α-propionyloxyandrosta-1,4-diene-17β-carbothioate. |
| IB.3 | F | S-(4-Fluoro-but-2-ynyl) 6α-,9α-difluoro-11β-hydroxy-16α-methyl-3-oxo-17α-propionyloxyandrosta-1,4-diene-17β-carbothioate. |
| IB.4 | OH | S-(4-Hydroxy-but-2-ynyl) 6α-,9α-difluoro-17α-[(2-furanylcarbonyl)oxy]-11β-hydroxy-16α-methyl-3-oxoandrosta-1,4-diene-17β-carbothioate. |
| IB.5 | OH | S-(4-Hydroxy-but-2-ynyl) 9α-fluoro-11β-hydroxy-16α-methyl-3-oxo-17α-propionyloxyandrosta-1,4-diene-17β-carbothioate. |
| IB.6 | F | S-(4-Fluoro-but-2-ynyl) 6α-,9α-difluoro-17α-[(2-furanylcarbonyl)oxy]-11β-hydroxy-16α-methyl-3-oxoandrosta-1,4-diene-17β-carbothioate. |
| IB.7 | OH | S-(4-Hydroxy-but-2-ynyl) 6α-,9α-difluoro-11β-hydroxy-16α-methyl-17α-(2-methyl-propionyloxy)-3-oxoandrosta-1,4-diene-17β-carbothioate. |
| IB.8 | OH | S-(4-Hydroxy-but-2-ynyl) 17α-cyclobutylcarbonyloxy-6α-,9α-difluoro-11β-hydroxy-16α-methyl-3-oxoandrosta-1,4-diene-17β-carbothioate. |
| IB.9 | OH | S-(4-Hydroxy-but-2-ynyl) 9α-fluoro-17α-[(2-furanylcarbonyl)oxy]-11β-hydroxy-16α-methyl-3-oxoandrosta-1,4-diene-17β-carbothioate. |
| IB.10 | OH | S-(4-Hydroxy-but-2-ynyl) 6α-,9α-difluoro-11β-hydroxy-16α-methyl-3-oxo-17α-[(2-thienylcarbonyl)oxy]-androsta-1,4-diene-17β-carbothioate. |
| IB.11 | — | S-(Prop-2-ynyl) 6α-,9α-difluoro-11β-hydroxy-16α-methyl-3-oxo-17α-propionyl-oxyandrosta-1,4-diene-17β-carbothioate. |
| IB.12 | 1,4-Dioxa-spiro[4,5]decan-2-ylmethoxy carbonyloxy | S-[4-(1,4-Dioxa-spiro[4,5]decan-2-ylmethoxycarbonyloxy)-but-2-ynyl] 6α,9α-difluoro-17α-[(2-furanyl-carbonyl)oxy]-11β-hydroxy-16α-methyl-3-oxoandrosta-1,4-dione-17β-carbothioate. |
| IB.13 | OH | S-[4-Hydroxy-(E)-but-2-enyl] 6α,9α-difluoro-11β-hydroxy-16α-methyl-3-oxo-17α-propionyloxyandrosta-1,4-diene-17β-carbothioate. |
| IB.14 | OH | S-[4-Hydroxy-(E)-but-2-enyl] 6α,9α-difluoro-17α-[(2-furanylcarbonyl)oxy]-11-β-hydroxy-16α-methyl-3-oxoandrosta-1,4-diene-17β-carbothioate. |
| IB.15 | OH | S-[4-Hydroxy-(Z)-but-2-enyl] 6α-,9α-difluoro-17α-[(2-furanylcarbonyl)oxy]-11- |

TABLE 4-continued

Lists the compound of formula I-B which have been synthesized

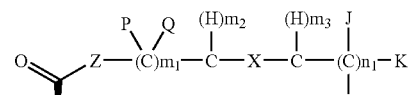

Formula I-B

| | | β-hydroxy-16α-methyl-3-oxoandrosta-1,4-diene-17β-carbothioate. |
|---|---|---|
| IB.16 | OH | S-[4-Hydroxy-(Z)-but-2-enyl] 6α,9α-difluoro-11β-hydroxy-16α-methyl-3-oxo-17α-[(2-thienylcarbonyl)oxy-]androsta-1,4-diene-17β-carbothioate. |
| IB.17 | OH | S-[4-Hydroxy-(E)-but-2-enyl] 6α,9α-difluoro-11β-hydroxy-16α-methyl-3-oxo-17α-[(2-thienylcarbonyl)oxy]-androsta-1,4-diene-17β-carbothioate. |
| IB.18 | 1,4-Dioxa-spiro[4,4]nonan-2-ylmethoxy carbonyloxy | S-[4-(1,4-Dioxa-spiro[4,4]nonan-2-ylmethoxycarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.19 | OCO—O(CH$_2$)$_4$—ONO$_2$ | S-(4-(4-Nitroxybutyloxycarbonyloxy)-but-2-ynyl) 6α,9α-difluoro-17α-[(2-furanylcarbonyl)oxy]-11β-hydroxy-16α-methyl-3-oxoandrosta-1,4-diene-17β-carbothioate. |
| IB.20 | OH | S-[4-Hydroxy-but-2-ynyl] 17α-[[(5-chloro-2-thienyl)carbonyl]oxy]-6α,9α-difluoro-11β-hydroxy-16α-methyl-3-oxoandrosta-1,4-diene-17β-carbothioate. |
| IB.21 | H | S-[But-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.22 | OH | S-[4-Hydroxy-but-2-ynyl] 6α,9α-difluoro-11β-hydroxy-17α-[[(3-methyl-2-furanyl)-carbonyl]oxy]-16α-methyl-3-oxoandrosta-1,4-diene-17β-carbothioate. |
| IB.23 | OH | S-[4-Hydroxy-but-2-ynyl] 6α-,9α-difluoro-17α-(ethoxymethylcarbonyl)oxy-11β-hydroxy-16α-methyl-3-oxoandrosta-1,4-diene-17β-carbothioate. |
| IB.24 | OH | S-[4-Hydroxy-but-2-ynyl] 6α,9α-difluoro-11β-hydroxy-17α-(methoxymethyl-carbonyl)oxy-16α-methyl-3-oxoandrosta-1,4-diene-17β-carbothioate. |
| IB.25 | OH | S-[3-(1-Hydroxycyclohexyl)prop-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.26 | OH | S-[4-Hydroxy-but-2-ynyl] 17α-cyclohexylmethylcarbonyloxy-6α,9α-difluoro-11β-hydroxy-16α-methyl-3-oxoandrosta-1,4-diene-17β-carbothioate. |
| IB.27 | OH | S-[4-Hydroxy-but-2-ynyl] 17α-n-butylcarbonyloxy-6α,9α-difluoro-11β-hydroxy-16α-methyl-3-oxoandrosta-1,4-diene-17β-carbothioate. |
| IB.28 | — | Prop-2-ynyl 6α,9α-difluoro-11β-hydroxy-16α-methyl-3-oxo-17α-propionyloxy-androsta-1,4-diene-17β-carboxylate. |
| IB.29 | OH | S-[4-Hydroxy-but-2-ynyl] 17α-cyclopentylcarbonyloxy-6α,9α-difluoro-11β-hydroxy-16α-methyl-3-oxoandrosta-1,4-diene-17β-carbothioate. |

TABLE 4-continued

Lists the compound of formula I-B which have been synthesized

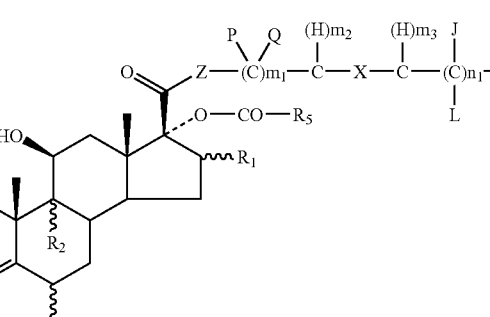

Formula I-B

| | | |
|---|---|---|
| IB.30 | OH | S-[4-Hydroxy-(Z)-but-2-enyl] 6α,9α-difluoro-11β-hydroxy-16α-methyl-3-oxo-17α-propionyloxyandrosta-1,4-diene-17β-carbothioate. |
| IB.31 | OCOC$_2$H$_5$ | S-[4-Propionyloxy-but-2-ynyl] 6α,9α-difluoro-11β-hydroxy-16α-methyl-3-oxo-17α-propionyloxyandrosta-1,4-diene-17β-carbothioate. |
| IB.32 | OCOCH$_3$ | S-[4-Acetoxy-but-2-ynyl] 6α,9α-difluoro-11β-hydroxy-16α-methyl-3-oxo-17α-propionyloxyandrosta-1,4-diene-17β-carbothioate. |
| IB.33 | OCO-n-C$_3$H$_7$ | S-[4-n-Propylcarbonyloxy-but-2-ynyl] 6α,9α-difluoro-11β-hydroxy-16α-methyl-3-oxo-17α-propionyloxyandrosta-1,4-diene-17β-carbothioate. |
| IB.34 | OCO—CH(CH$_3$)$_2$ | S-[4-(2-Methylpropionyloxy)-but-2-ynyl] 6α,9α-difluoro-11β-hydroxy-16α-methyl-3-oxo-17α-propionyloxyandrosta-1,4-diene-17β-carbothioate. |
| IB.35 | OCO-n-C$_4$H$_9$ | S-[4-n-Butylcarbonyloxy-but-2-ynyl] 6α,9α-difluoro-11β-hydroxy-16α-methyl-3-oxo-17α-propionyloxyandrosta-1,4-diene-17β-carbothioate. |
| IB.36 | OCO-cyclobutyl | S-[4-Cyclobutylcarbonyloxy-but-2-ynyl] 6α,9α-difluoro-11β-hydroxy-16α-methyl-3-oxo-17α-propionyloxyandrosta-1,4-diene-17β-carbothioate. |
| IB.37 | OCO-n-C$_5$H$_{11}$ | S-[4-n-Pentylcarbonyloxy-but-2-ynyl] 6α,9α-difluoro-11β-hydroxy-16α-methyl 3-oxo-17α-propionyloxyandrosta-1,4-diene-17β-carbothioate. |
| IB.38 | OH | S-[4-Hydroxy-but-2-ynyl] 9α-fluoro-11β-hydroxy-16β-methyl-3-oxo-17α-propionyloxyandrosta-1,4-diene-17β-carbothioate. |
| IB.39 | OH | S-[4-Hydroxy-but-2-ynyl] 6α,9α-difluoro-11β-hydroxy-16β-methyl-3-oxo-17α-propionyloxyandrosta-1,4-diene-17β-carbothioate. |
| IB.40 | OH | S-[4-Hydroxy-4-methyl-pent-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.41 | OCH$_3$ | 4-Methoxy-4-oxo-(E)-but-2-enyl 6α,9α-difluoro-11β-hydroxy-16α-methyl-3-oxo-17α-propionyloxyandrosta-1,4 diene-17β-carboxylate. |
| IB.42 | OCH$_3$ | S-[4-Methoxy-4-oxo-(E)-but-2-enyl] 6α,9α-difluoro-11β-hydroxy-16α-methyl-3-oxo-17α-propionyloxyandrosta-1,4 diene-17β-carbothioate. |
| IB.43 | OCH$_3$ | 4-Methoxy-4-oxo-(E)-but-2-enyl 17α-(ethoxycarbonyl)oxy-11β-hydroxy-3-oxoandrosta-1,4-diene-17β-carboxylate. |
| IB.44 | OCOCO—OC$_2$H$_5$ | S-[4-(2-Ethoxy-1,2-dioxoethyl-(E)-but-2-enyl] 6α,9α-difluoro-11β-hydroxy-16α-methyl-3-oxo-17α-propionyloxyandrosta-1,4-diene-17β-carbothioate. |

TABLE 4-continued

Lists the compound of formula I-B which have been synthesized

Formula I-B

| | | |
|---|---|---|
| IB.45 | OH | S-[4-Hydroxy-but-2-ynyl] 9α-chloro-17α-[(2-furanylcarbonyl)oxy]-11β-hydroxy-16α-methyl-3-oxoandrosta-1,4-diene-17β-carbothioate. |
| IB.46 | OCOCO—OC$_2$H$_5$ | S-[4-(2-Ethoxy-1,2-dioxoethyl)oxy-(E)-but-2-enyl] 6α,9α-difluoro-17α-[(2-furanylcarbonyl)oxy]-11β-hydroxy-16α-methyl-3-oxoandrosta-1,4-diene-17β-carbothioate. |
| IB.47 | OCOCO—OC$_2$H$_5$ | S-[4-(2-Ethoxy-1,2-dioxoethyl)oxy-(Z-but-2-enyl] 6α,9α-difluoro-17α-[(2-furanylcarbonyl)oxy]-11β-hydroxy-16α-methyl-3-oxoandrosta-1,4-diene-17β-carbothioate. |
| IB.48 | (S)-(−)-2-Acetoxy-propionyl-oxy | S-[4-((s)-(−)2-Acetoxypropionyloxy)but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.49 | OCO-n-C$_3$H$_7$ | S-[4-n-Propylcarbonyloxy-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.50 | OCO—CH(CH$_3$)$_2$ | S-[4-(2-Methylpropionyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.51 | OCO—C(CH$_3$)$_3$ | S-[4-(2,2-Dimethylpropionyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.52 | OCO—C(CH$_3$)$_3$ | S-[4-(2,2-Dimethylpropionyloxy)-but-2-ynyl] 6α,9α-difluoro-11β-hydroxy-16α-methyl-3-oxo-17α-propionyloxyandrosta-1,4-diene-17β-carbothioate. |
| IB.53 | OCO-n-C$_3$H$_7$ | S-[4-n-Propylcarbonyloxy-(Z)-but-2-enyl] 6α,9α-difluoro-17α-[(2-furanylcarbonyl)-oxy]-11β-hydroxy-16α-methyl-3-oxoandrosta-1,4-diene-17β-carbothioate. |
| IB.54 | OCOCO—OC$_2$H$_5$ | S-[4-(2-Ethoxy-1,2-dioxoethyl)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.55 | OCO-n-C$_3$H$_7$ | S-[4-n-Propylcarbonyloxy-but-2-ynyl] 6α,9α-difluoro-11β-hydroxy-16α-methyl-3-oxo-17α-[(2-thienylcarbonyl)oxy]androsta-1,4-diene-17β-carbothioate. |
| IB.56 | OCO-n-C$_3$H$_7$ | S-[4-n-Propylcarbonyloxy-but-2-ynyl] 17α-[[(5-chloro2-thienyl)carbonyl]-oxy]-6α,9α-difluoro-11β-hydroxy-16α-methyl-3 oxo-androsta-1,4-diene-17β-carbothioate. |
| IB.57 | OCO-cyclopropyl | S-[(4-cyclopropylcarbonyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.58 | OCO-cyclobutyl | S-[(4-cyclobutylcarbonyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.59 | OCO-cyclopentyl | S-[(4-cyclopentylcarbonyloxy)-but-2-ynyl] 6α,9α-difluoro-17α-[(2-furanylcarbonyl)- |

TABLE 4-continued

Lists the compound of formula I-B which have been synthesized

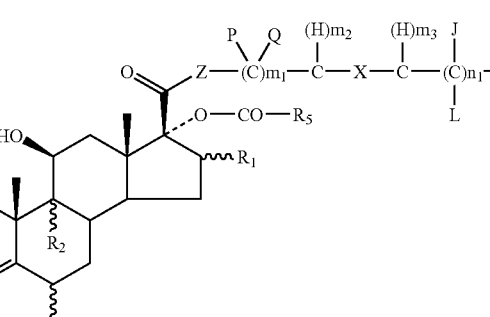

Formula I-B

| | | |
|---|---|---|
| IB.60 | OCO-n-C$_3$H$_7$ | S-[4-n-Propylcarbonyloxy-(E)-but-2-enyl] 6α,9α-difluoro-17α-[(2-furanylcarbonyl)-oxy]-11β-hydroxy-16α-methyl-3-oxoandrosta-1,4-diene-17β-carbothioate. |
| IB.61 | OH | S-[4-Hydroxy-but-2-ynyl] 17α-(4-chloro-phenyl)carbonyloxy-6α,9α-difluoro-11β-hydroxy-16α-methyl-3-oxoandrosta-1,4-diene-17β-carbothioate. |
| IB.62 | OH | S-[4-Hydroxy-but-2-ynyl] 17α-(3-chlorophenyl)carbonyloxy-6α,9α-difluoro-11β-hydroxy-16α-methyl-3-oxoandrosta-1,4-diene-17β-carbothioate. |
| IB.63 | OCO—OCH$_3$ | S-[(4-Methoxycarbonyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.64 | OCO—C$_3$H$_5$ | S-[(4-Ethoxycarbonyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.65 | OCO—OC(CH$_3$)$_3$ | S-[4-(2,2-Dimethylethyloxycarbonyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.66 | OCO—OCH$_2$CH—(CH$_3$)$_2$ | S-[4-(2-Methylpropyloxycarbonyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.67 | OCO—(CH$_2$)$_2$CH$_2$Cl | S-[4-(3-Chloropropylcarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.68 | OCO—C(CH$_3$)$_3$ | S-[4-(2,2-Dimethylpropionyloxy)-(Z)-but-2-enyl] 6α,9α-difluoro-17α-[(2-furanyl-carbonyl)oxy]-11β-hydroxy-16α-methyl-3-oxoandrosta-1,4-diene-17β-carbothioate. |
| IB.69 | OCO—C(CH$_3$)$_3$ | S-[4-(2,2-Dimethylpropionyloxy)-(E)-but-2-enyl] 6α,9α-difluoro-17α-[(2-furanyl-carbonyl)oxy]-11β-hydroxy-16α-methyl-3 oxoandrosta-1,4-diene-17β-carbothioate. |
| IB.70 | OCOCHCl$_2$ | S-[4-Dichloroacetoxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.71 | 2-methyl propyl-carbonyloxy | S-[4-(2-methylpropylcarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.72 | OCOCH$_2$—C(CH$_3$)$_3$ | S-[4-(3,3-dimethylpropyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.73 | OCO—CH$_2$CH$_3$ | S-[4-Propionyloxy-but-2-ynyl] 6α,9α-difluoro-11β-hydroxy-17α-[(2-furanyl- |

TABLE 4-continued

Lists the compound of formula I-B which have been synthesized

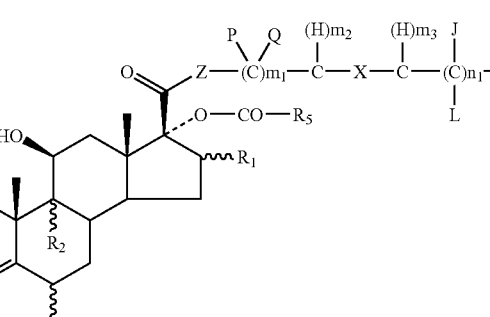

Formula I-B

| | | |
|---|---|---|
| | | carbonyl)oxy]-16α-methyl-3-oxoandrosta-1,4-diene-17β-carbothioate. |
| IB.74 | OCO—COOCH$_2$CH$_3$ | S-[4-(2-Ethoxy-1,2-dioxoethyl)oxy-but-2-ynyl] 17α-cyclobutylcarbonyl-oxy-6α,9α-difluoro-11β-hydroxy-16α-methyl-3-oxoandrosta-1,4-diene-17β-carbothioate. |
| IB.75 | OCO—CH(CH$_3$)$_2$ | S-(4-(2-Methylpropionyloxy)-but-2-ynyl) 17α-cyclobutylcarbonyloxy-6α,9α-difluoro-11β-hydroxy-16α-methyl-3-oxoandrosta-1,4-diene-17β-carbothioate. |
| IB.76 | Adamantyl-carbonyloxy | S-[4-(Adamantylcarbonyloxy)-but-2-ynyl] 6α,9α-difluoro-17α-[(2-furanyl-carbonyl)oxy]-11β-hydroxy-16α-methyl-3 oxoandrosta-1,4-diene-17β-carbothioate. |
| IB.77 | OCOCH$_2$—CF$_3$ | S-(4-(3,3,3-Trifluoropropionyloxy)-but-2-ynyl) 6α,9α-difluoro-17α-[(2-furanylcarbonyl)oxy]-11β-hydroxy-16α-methyl-3-oxo-androsta-1,4-diene-17β-carbothioate. |
| IB.78 | OCOCH$_2$—OCH$_3$ | S-(4-(Methoxyacetyloxy)-but-2-ynyl) 6α,9α-difluoro-17α-[(2-furanyl-carbonyl)oxy]-11β-hydroxy-16α-methyl-3-oxoandrosta-1,4-diene-17β-carbothioate. |
| IB.79 | OCOCH$_2$—OCH$_2$CH$_3$ | S-(4-(Ethoxyacetyloxy)-but-2-ynyl) 6α,9α-difluoro-17α-[(2-furanyl-carbonyl)oxy]-11β-hydroxy-16α-methyl-3-oxoandrosta-1,4-diene-17β-carbothioate. |
| IB.80 | OCOCH$_2$—CH$_2$COOH | S-[4-(4-Hydroxybutyl-1,4-dione)oxy-but-2-ynyl] 6α,9α-difluoro-11β-hydroxy-16α-methyl-17α-[(2-furanylcarbonyl)oxy]-3-oxoandrosta-1,4-diene-17β-carbothioate. |
| IB.81 | OCOCH$_3$ | S-[4-Acetoxy-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.82 | OCO—CH(CH$_3$)$_2$ | S-[4-(2-Methylpropionyloxy)-(E)-but-2-enyl] 6α,9α-difluoro-17α-[(2-furanylcarbonyl)oxy]-11β-hydroxy-16α-methyl-3-oxoandrosta-1,4-diene-17β-carbothioate. |
| IB.83 | OCO—CH(CH$_3$)$_2$ | S-[4-(2-Methylpropionyloxy)-(Z)-but-2-enyl] 6α,9α-difluoro-17α-[(2-furanylcarbonyl)oxy]-11β-hydroxy-16α-methyl-3-oxoandrosta-1,4-diene-17β-carbothioate. |
| IB.84 | OCO—C(CH$_3$)$_3$ | S-[4-(2,2-Dimethylpropionyloxy)-but-2-ynyl] 17α-cyclobutylcarbonyloxy-6α,9α-difluoro-11β-hydroxy-16α-methyl-3-oxoandrosta-1,4-diene-17β-carbothioate. |
| IB.85 | 2,2-Dimethyl-butylcarbonyl-oxy | S-[4-(2,2-Dimethylbutylcarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.86 | (1S)-Camphanyl-carbonyloxy | S-[4-(1S)-Camphanylcarbonyloxy-but-2-ynyl] 6α,9α-difluoro-17α-[(2-furanyl-carbonyl)oxy]-11β-hydroxy-16α-methyl-3-oxoandrosta-1,4-diene-17β-carbo-thioate. |
| IB.87 | OCONH—C(CH$_3$)$_3$ | S-[4-(1,1-Dimethylethylcarbamoyloxy)-but-2-ynyl] 6α,9α-difluoro-17α-[(2-furanyl- |

TABLE 4-continued

Lists the compound of formula I-B which have been synthesized

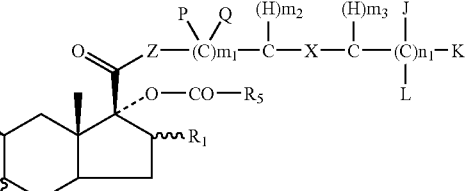

Formula I-B

| | | |
|---|---|---|
| IB.88 | OCO(CH$_2$)$_3$—COOC$_2$H$_5$ | carbonyl)oxy]-11β-hydroxy-16α-methyl-3-oxoandrosta-1,4-diene-17β-carbothioate.<br>S-[4-(4-Ethoxybutyl-1,4-dione)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.89 | Menthyl-carbonyloxy | S-[4-Menthylcarbonyloxy-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.90 | OCOCH$_2$NH—COCH$_3$ | S-[4-Acetamidoacetoxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.91 | OCOOCH$_2$—CH(CH$_3$)$_2$ | S-[4-(2-Methylpropyloxycarbonyloxy)-but-2-ynyl] 17α-[[(5-chloro-2-thienyl)carbonyl]-oxy]-6α,9α-difluoro-11β-hydroxy-16α-methyl-3-oxoandrosta-1,4-diene-17β-carbothioate. |
| IB.92 | OCO—CH(CH$_3$)$_2$ | S-[4-(2-Methylpropionyloxy)-but-2-ynyl] 17α-[[(5-chloro-2-thienyl)-carbonyl]oxy]-oxy-6α,9α-difluoro-11β-hydroxy-16α-methyl-3-oxoandrosta-1,4-diene-17β-carbothioate. |
| IB.93 | OCOCH=CH—COOC$_2$H$_5$ | S-[4-(4-Ethyloxy-(Z)-but-2-en-1,4-dione)oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.94 | OCO(CH$_2$)$_2$—COOCH$_3$ | S-[4-(4-Methoxybutyl-1,4-dione)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.95 | OCO(CH$_2$)$_2$—COOCH—(CH$_3$)$_2$ | S-[4-(4-Isopropyloxybutyl-1,4-dione)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.96 | OCO(CH$_2$)$_2$—COOCH$_2$CH—(CH$_3$)$_2$ | S-[4-(4-Isobutyloxybutyl-1,4-dione)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.97 | OCO(CH$_2$)$_2$—COO(CH$_2$)$_3$—CH$_3$ | S-[4-(4-n-Butyloxybutyl-1,4-dione)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.98 | 3-Chloro-2,2-dimethyl-propionyloxy | S-[4-(3-Chloro-2,2-dimethylpropionyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.99 | OCOCH=CH—COOCH$_2$CH—(CH$_3$)$_2$ | S-[4-(4-Isobutyloxy-(Z)-but-2-en-1,4-dione)oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.100 | OCOCH=CH—COOCH$_3$ | S-[4-(4-Methoxy-(E)-but-2-en-1,4-dione)oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |

TABLE 4-continued

Lists the compound of formula I-B which have been synthesized

Formula I-B

| IB.101 | OCO—CH$_2$CH(CH$_3$)$_2$ | S-[4-(3-Methyl-1-oxobutyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
|---|---|---|
| IB.102 | OCO—CH(C$_2$H$_5$)$_2$ | S-[4-(2-Ethyl-1-oxobutyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.103 | OCON(CH$_3$)$_2$ | S-[4-(N,N-Dimethylaminocarbonyl-oxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.104 | OCO—CCl(CH$_3$)$_2$ | S-[4-(2-Chloro-2-methylpropionyl-oxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.105 | OCO(CH$_2$)$_2$—CH(CH$_3$)$_2$ | S-[4-(4-Methyl-1-oxopentyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.106 | OCO(CH$_2$)$_2$—COOCH$_2$F | S-[4-(4-Fluoromethoxy-1,4-dioxo-butyl)oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.107 | OCOCH=CH—COOCH$_2$F | S-[4-(4-Fluoromethyloxy-1,4-dioxo-(Z)-but-2-en)oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.108 | OCOCH$_2$—COOCH$_3$ | S-[4-(3-Methoxypropyl-1,3-dione)oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.109 | OCOC(CH$_3$)$_2$—COOCH$_3$ | S-[4-(3-Methoxy-2,2-dimethylpropyl-1,3-dione)oxy-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.110 | OCOC(OH)—(CH$_3$)$_2$ | S-[4-(2-Hydroxy-2-methylpropionyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.111 | OCOCF(CH$_3$)$_2$ | S-[4-(2-Fluoro-2-methylpropionyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.112 | OCOCH=CH—COOCH$_3$ | S-[4-(4-Methoxy-(Z)-but-2-en-1,4-dione)-oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.113 | OCOCH=CH—COOC$_2$H$_5$ | S-[4-(4-Ethoxy-(E)-but-2-en-1,4-dione)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |

TABLE 4-continued

Lists the compound of formula I-B which have been synthesized

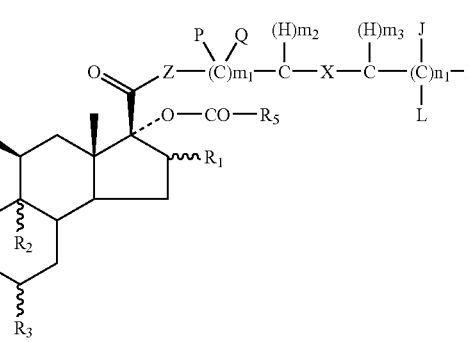

Formula I-B

| | | |
|---|---|---|
| IB.114 | OCOCH=CH—COOCH$_2$—CH(CH$_3$)$_2$ | S-[4-(4-Isobutyloxy-1,4-dioxo-(E)-but-2-en)oxy-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.115 | OCOCH=CH—COO(CH$_2$)$_3$—CH$_3$ | S-[4-(4-n-butyloxy-1-4-dioxo-(E)-but-2-en)oxy-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.116 | OCOCH—(CH$_3$)$_2$ | S-[4-(2-Methylpropionyloxy)-but-2-ynyl] 9α-chloro-17α-[(2-furanylcarbonyl)oxy]-11β-hydroxy-16α-methyl-3-oxoandrosta-1,4-diene-17β-carbothioate. |
| IB.117 | 2-(S)-Methyl-butyryloxy | S-[4-(2-(S)-methylbutyryloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.118 | OCO-(2-Furyl) | S-[4-((furan-2-yl)carbonyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.119 | OCOCH=CH—COOCH—(CH$_3$)$_2$ | S-[4-(4-Isopropyloxy-1,4-dioxo-(E)-but-2-en)oxy-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.120 | 3-Hydroxy-2,2-dimethyl-Propionyl-oxy | S-[4-(3-Hydroxy-2,2-dimethyl-propionyl-oxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.121 | OCO—CH=CH$_2$ | S-(4-Acryloyloxy-but-2-ynyl) 6α,9α-difluoro-17α-[(2-furanylcarbonyl)oxy]-11β-hydroxy-16α-methyl-3-oxoandrosta-1,4-diene-17β-carbothioate. |
| IB.122 | OCOC(OH)—(C$_2$H$_5$)$_2$ | S-[4-(1-Ethyl-1-hydroxypropylcarbonyl-oxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.123 | OCOOCH$_2$-cyclopropyl | S-[4-(Cyclopropylmethyloxycarbonyl-oxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.124 | OCOC≡C—COOCH$_3$ | S-[4-(4-Methoxybut-2-yne-1,4-dione)oxy-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.125 | OCOO-cyclopentyl | S-[4-(Cyclopentyloxycarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.126 | OCOO—CH$_2$-cyclopentyl | S-[4-(Cyclopentylmethyloxycarbonyl-oxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.127 | OCOO—CH$_2$—CH(CH$_3$)$_2$ | S-[4-(2-Methylpropyloxycarbonyloxy)-but-2-ynyl] 9α-chloro-17α-[(2-furanyl- |

TABLE 4-continued

Lists the compound of formula I-B which have been synthesized

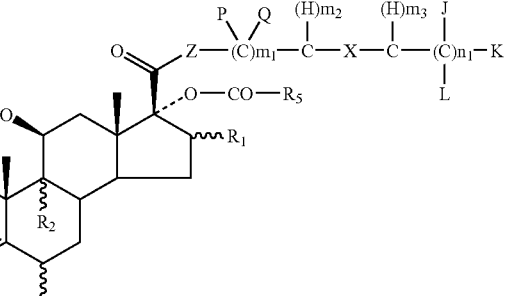

Formula I-B

| | | |
|---|---|---|
| IB.128 | 2,2-Dimethyl-1,3-dioxolan-4-yl-methoxy-carbonyloxy | carbonyl)oxy]-11β-hydroxy-16β-methyl-3-oxoandrosta-1,4-diene-17βcarbothioate. S-[4-(2,2-Dimethyl-1,3-dioxolan-4-yl-methoxycarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.129 | OCON(C$_2$H$_5$)$_2$ | S-[4-(N,N-Diethylaminocarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.130 | Piperidin-1-ylcarbonyloxy | S-[4-(Piperidin-1-ylcarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.131 | 4-Methyl-piperazin-1-yl-carbonyloxy | S-[4-(4-Methyl-piperazine-1-yl-carbonyl-oxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.132 | OH | S-(4-Hydroxy-but-2-ynyl) 6α,9α-difluoro-17α-[(2-furanylcarbonyl)-oxy]-11β-hydroxy-16β-methyl-3-oxoandrosta-1,4-diene-17β-carbothioate. |
| IB.133 | OCOCH—(CH$_3$)$_2$ | S-[4-(2-Methylpropionyloxy)-but-2-ynyl] 6α,9α-difluoro-17α-[(2-furanylcarbonyl)-oxy]-11β-hydroxy-16β-methyl-3-oxoandrosta-1,4-diene-17β-carbothioate. |
| IB.134 | OCCOOCH$_2$—CH(CH$_3$)$_2$ | S-[4-(2-Methylpropyloxycarbonyloxy)-but-2-ynyl] 6α,9α-difluoro-17α-[(2-furanyl-carbonyl)oxy]-11β-hydroxy-16β-methyl-3-oxoandrosta-1,4-diene-17β-carbothioate. |
| IB.135 | OCOCCl$_2$—CH$_3$ | S-[4-(2,2-Dichloropropionyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.136 | N(C$_2$H$_5$)$_2$ | S-[4-(N,N-Diethylamino)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.137 | OCOOCH—(CH$_3$)$_2$ | S-[4-(Isopropyloxycarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.138 | OCOOCH$_3$—CH═C(CH$_3$)$_2$ | S-[4-(3-Methylbut-2-enoxycarbonyl-oxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.139 | OCOO—(CH$_2$)$_5$—CH$_3$ | S-[4-(n-Hexyloxycarbonyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.140 | OCOOCH$_2$-cyclohexyl | S-[4-(Cyclohexylmethyloxycarbonyl-oxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.141 | OCOO-cyclohexyl | S-[4-(Cyclohexyloxycarbonyloxy)-but-2-ynyl] 6α,9α-difluoro-17α-[(2-furanyl- |

TABLE 4-continued

Lists the compound of formula I-B which have been synthesized

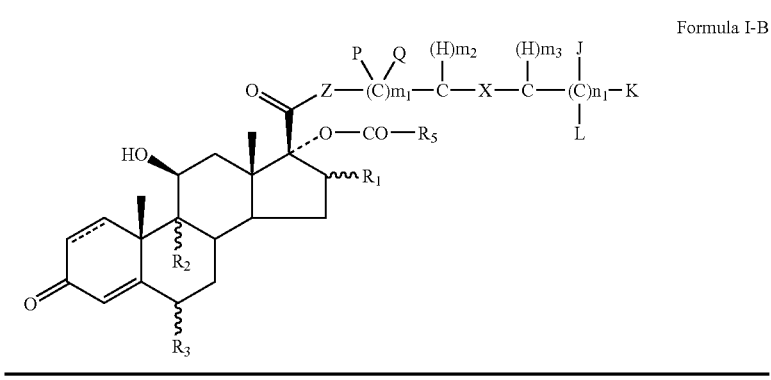

Formula I-B

| | | |
|---|---|---|
| | | carbonyl)oxy]-11β-hydroxy-16α-methyl-3-oxoandrosta-1,4-diene-17β-carbothioate. |
| IB.142 | OCOO—(CH$_2$)$_8$CH$_3$ | S-[4-(n-Nonanyloxycarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.143 | OCOOCH$_2$—C(CH$_3$)$_3$ | S-[4-(2,2-Dimethylpropyloxycarbonyl-oxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.144 | OCOOCH$_2$-cyclobutyl | S-[4-(Cyclobutylmethyoxycarbonyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.145 | OCOOCH$_2$-(furan-2-yl) | S-[4-(2-Methylfuryloxycarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.146 | OCOO—(CH$_2$)$_3$CH$_3$ | S-[4-(n-Butyloxycarbonyloxy)-but-2-ynyl] 6α,9α-difluoro-17α-[(2-furanylcarbonyl)-oxy]-11β-hydroxy-16α-methyl-3-oxoandrosta-1,4-diene-17β-carbothioate. |
| IB.147 | OCOO—(CH$_2$)$_4$CH$_3$ | S-[4-(n-Pentyloxycarbonyloxy)-but-2-ynyl] 6α,9α-difluoro-17α-[(2-furanyl-carbonyl)oxy]-11β-hydroxy-16α-methyl-3-oxoandrosta-1,4-diene-17β-carbothioate. |
| IB.148 | 2,2-Dimethyl-fluoro-propionyl-oxy | S-[4-(2,2-Dimethyl-3-fluoro-propionyl-oxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.149 | (S)-2,2-Dimethyl-1,3-dioxolan-4-yl-methoxy-carbonyloxy | S-[4-((S)-2,2-Dimethyl-1,3-dioxolan-4-yl-methoxycarbonyloxy)-but-2-ynyl] 6α,9α-difluoro-17α-[(2-furanylcarbonyl)oxy]-carbonyloxy-11β-hydroxy-16α-methyl-3-oxoandrosta-1,4-diene-17β-carbothioate. |
| IB.150 | (R)-2,2-Dimethyl-1,3-dioxolan-4-yl-methoxy-carbonyloxy | S-[4-((R)-2,2-Dimethyl-1,3-dioxolan-4-yl-methoxy-carbonyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.151 | (Morpholin-4-yl)-carbonyloxy | S-[4-(Morpholin-4-yl)carbonyloxy-but-2-ynyl] 6α,9α-difluoro-17α-[(2-furanyl-carbonyl)oxy]-11β-hydroxy-16α-methyl-3-oxoandrosta-1,4-diene-17β-carbothioate |
| IB.152 | 2,2-Dimethyl-1,3-dioxolan-4-ylmethyl carbamoyl-oxy | S-[4-(2,2-Dimethyl-1,3-dioxolan-4-yl-methylcarbamoyloxy)-but-2-ynyl] 6α,9α-difluoro-17α-[(2-furanylcarbonyl)oxy]-11β-hydroxy-16α-methyl-3-oxoandroasta-1,4-diene-17β-carbothioate. |

TABLE 4-continued

Lists the compound of formula I-B which have been synthesized

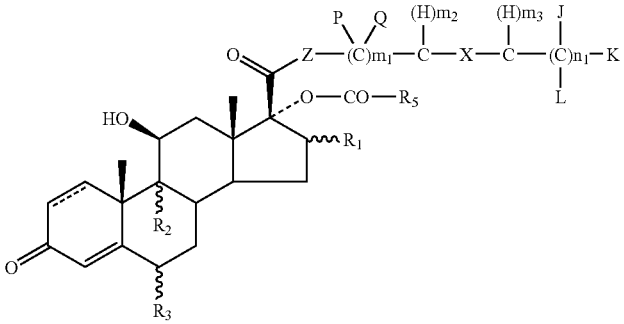

Formula I-B

| | | |
|---|---|---|
| IB.153 | OCOO(CH$_2$)$_2$-cyclopentyl | S-[4-(2-Cyclopentylethoxycarbonyloxy)-but-2-ynyl] 6α,9α-difluoro-17α-[(2-furanylcarbonyl)oxy]-11β-hydroxy-16α-methyl-3-oxoandrosta-1,4-diene-17β-carbothioate. |
| IB.154 | OCOO—(CH$_2$)$_2$—CH(CH$_3$)$_2$ | S-[4-(Isoamyloxycarbonyloxy)-but-2-ynyl] 6α,9α-difluoro-17α-[(2-furanylcarbonyl)-oxy]-11β-hydroxy-16α-methyl-3-oxoandroasta-1,4-diene-17β-carbothioate. |
| IB.155 | OCO(CH$_2$)$_3$—ONO$_2$ | S-[4-(3-Nitroxypropylcarbonyloxy)-but-2-ynyl] 6α,9α-difluoro-17α-[(2-furanyl-carbonyl)oxy]-11β-hydroxy-16α-methyl-3-oxoandroasta-1,4-diene-17β-carbothioate. |
| IB.156 | 2,2,7,7-Tetramethyl tetrahydro-bis [1,3]dioxolo [4,5-b; 4',5'-d]pyran-5-yl methoxy carbonyloxy | S-[4-(2,2,7,7-Tetramethyltetrahydro-bis[1,3]dioxolo[4,5-b; 4',5'-d]pyran-5-yl methoxycarbonyloxy)-but-2-ynyl] 6α,9α-difluoro-17α-[(2-furanylcarbonyl)oxy]-11β-hydroxy-16α-methyl-3-oxoandroasta-1,4-diene-17β-carbothioate. |
| IB.157 | OCO(CH$_2$)$_4$—ONO$_2$ | S-[4-(4-Nitroxybutylcarbonyloxy)-but-2-ynyl] 6α,9α-difluoro-17α-[(2-furanyl-carbonyl)oxy]-11β-hydroxy-16α-methyl-3-oxoandroasta-1,4-diene-17β-carbothioate. |
| IB.158 | OCH$_3$ | S-(4-Methoxy-but-2-ynyl) 6α,9α-difluoro-17α-[(2-furanylcarbonyl)oxy]-11β-hydroxy-16α-methyl-3-oxoandroasta-1,4-diene-17β-carbothioate. |
| IB.159 | OCH$_2$CH$_3$ | S-(4-Ethoxy-but-2-ynyl) 6α,9α-difluoro-17α-[(2-furanylcarbonyl)oxy]-11β-hydroxy-16α-methyl-3-oxoandroasta-1,4-diene-17β-carbothioate. |
| IB.160 | OCH$_2$CH—(CH$_3$)$_2$ | S-[4-Isobutoxy-but-2-ynyl] 6α,9α-difluoro-17α-[(2-furanylcarbonyl)oxy]-11β-hydroxy-16α-methyl-3-oxoandroasta-1,4-diene-17β-carbothioate. |

TABLE 5

Lists the compound of formula I-C which have been synthesized

Formula I-C

| Sr. No | $R_1$ | $R_2$ | $R_3$ | $R_5$ | $m_1$ | $R_7$ | P | Q | Chemical Name |
|---|---|---|---|---|---|---|---|---|---|
| IC.1 | α-$CH_3$ | F | F | Ethyl | 1 | 4-Fluoro-phenyl | H | H | 6α,9α-Difluoro-11β-hydroxy-16α-methyl-3-oxo-17α-propionyloxyandrosta-1,4-diene-17β-carbonylsulfenic acid(4-fluorophenyl)methyl ester. |
| IC.2 | α-$CH_3$ | F | F | Ethyl | 1 | 3,4-Dichloro-phenyl | H | H | 6α,9α-Difluoro-11β-hydroxy-16α-methyl-3-oxo-17α-propionyloxyandrosta-1,4-diene-17β-carbonylsulfenic acid (3,4-dichlorophenyl)methyl ester. |
| IC.3 | α-$CH_3$ | F | F | Ethyl | 1 | F | H | H | 6α,9α-Difluoro-11β-hydroxy-16α-methyl-3-oxo-17α-propionyloxyandrosta-1,4-diene-17β-carbonylsulfenic acid fluoromethyl ester. |
| IC.4 | α-$CH_3$ | F | F | 2-Furyl | 1 | F | H | H | 6α,9α-Difluoro-17α-[(2-furanylcarbonyl)oxy]-11β-hydroxy-16α-methyl-3-oxoandrosta-1,4-diene-17β-carbonylsulfenic acid fluoromethyl ester. |
| IC.5 | α-$CH_3$ | F | F | 2-Furyl | 1 | 4-Fluoro-phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (4-fluorophenyl)methyl ester. |
| IC.6 | α-$CH_3$ | F | F | 2-Furyl | 1 | 4-Trifluoro-methylphenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (4-trifluoromethylphenyl)methyl ester. |
| IC.7 | α-$CH_3$ | F | F | 2-Furyl | 1 | 4-Chloro-phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (4-chlorophenyl)methyl ester. |
| IC.8 | α-$CH_3$ | F | F | Ethyl | 1 | 4-Trifluoro-methylphenyl | H | H | 6α,9α-Difluoro-11β-hydroxy-16α-methyl-3-oxo-17α-propionyloxyandrosta-1,4-diene-17β-carbonylsulfenic acid (4-trifluoromethylphenyl)methyl eseter. |
| IC.9 | α-$CH_3$ | F | H | 2-Furyl | 1 | 4-Fluoro-phenyl | H | H | 9α-Fluoro-17α-[(2-furanylcarbonyl)oxy]-11β-hydroxy-16α-methyl-3-oxoandrosta-1,4-diene-17β-carbonylsulfenic acid (4-fluorophenyl)methyl ester. |
| IC.10 | α-$CH_3$ | F | F | Ethyl | 1 |  | H | H | 6α,9α-Difluoro-11β-hydroxy-16α-methyl-3-oxo-17α-propionyloxyandrosta-1,4-diene-17β-carbonylsulfenic acid [2-(4-chlorophenyl)-2-oxoethyl]ester. |
| IC.11 | α-$CH_3$ | F | H | 2-Furyl | 1 | F | H | H | 9α-Fluoro-17α-[(2-furanylcarbonyl)oxy]-11β-hydroxy-16α-methyl-3-oxoandrosta-1,4-diene-17β-carbonylsulfenic acid fluoromethyl ester. |
| IC.12 | α-$CH_3$ | F | F | n-$C_4H_9$ | 1 | F | H | H | 17α-n-Butylcarbonyloxy-6α,9α-difluoro-11β-hydroxy-16α-methyl-3-oxoandrosta-1,4-diene-17β-carbonylsulfenic acid fluoromethyl esteer. |
| IC.13 | α-$CH_3$ | F | F | Ethyl | 1 | H | H | H | 6α,9α-Difluoro-11β-hydroxy-16α-methyl-3-oxo-17α-propionyloxyandrosta-1,4-diene-17β-carbonylsulfenic acid methyl ester. |
| IC.14 | α-$CH_3$ | F | F | 2-Furyl | 1 | H | H | H | 6α,9α-Difluoro-17α-[(2-furanylcarbonyl)oxy]-11β-hydroxy-16α-methyl-3-oxoandrosta-1,4-diene-17β-carbonylsulfenic acid methyl ester |
| IC.15 | α-$CH_3$ | F | F | Ethyl | 1 | Phenyl | H | H | 6α,9α-Difluoro-11β-hydroxy-16α-methyl-3-oxo-17α-propionyloxyandrosta-1,4-diene-17β-carbonylsulfonic acid phenylmethyl ester. |
| IC.16 | α-$CH_3$ | F | F | 2-Furyl | 1 | Phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid phenylmethyl ester. |
| IC.17 | α-$CH_3$ | F | F | Ethyl | 1 | 2,4,6-Tri-methylphenyl-carbonyl | H | H | 6α,9α-Difluoro-11β-hydroxy-16α-methyl-3-oxo-17α-propionyloxyandrosta-1,4-diene-17β-carbonylsulfenic acid [2-(2,4,6-trimethylphenyl)-2-oxoethyl]ester. |
| IC.18 | α-$CH_3$ | F | F | Ethyl | 1 | 4-Chloro-phenyl | H | H | 6α,9α-Difluoro-11β-hydroxy-16α-methyl-3-oxo-17α-propionyloxyandrosta-1,4-diene-17β-carbonylsulfenic acid (4-chlorophenyl)methyl ester. |
| IC.19 | α-$CH_3$ | F | F | 2-Furyl | 1 | 3,4-Dichloro-phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (3,4-dichlorophenyl)methyl ester. |

TABLE 5-continued

Lists the compound of formula I-C which have been synthesized

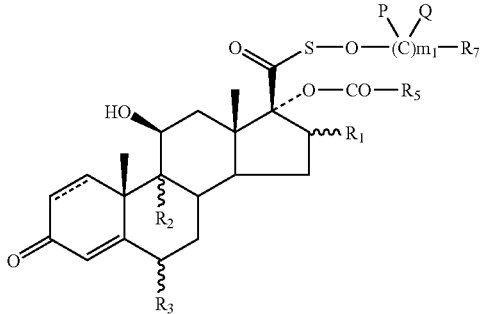

Formula I-C

| Sr. No | $R_1$ | $R_2$ | $R_3$ | $R_5$ | $m_1$ | $R_7$ | P | Q | Chemical Name |
|---|---|---|---|---|---|---|---|---|---|
| IC.20 | α-CH$_3$ | F | F | 2-Furyl | 1 | 2,4-Dichloro-phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (2,4-dichlorophenyl)methyl ester. |
| IC.21 | α-CH$_3$ | F | F | 2-Furyl | 1 | 3-Chloro-phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (3-chlorophenyl)methyl ester. |
| IC.22 | α-CH$_3$ | F | F | 2-Furyl | 1 | 2,4,6-Trifluoro-phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (2,4,6-trifluorophenyl)methyl ester. |
| IC.23 | α-CH$_3$ | F | F | 2-Furyl | 1 | 3-(Trifluoromethyl)phenyl | H | H | 6α,9α-Difluoro-17α-[(2-furanylcarbonyl)oxy]-11β-hydroxy-16α-methyl-3-oxoandrosta-1,4-diene-17β-carbonylsulfenic acid (3-trifluoromethylphenyl)methyl ester. |

TABLE 6

Spectral data for the synthesized compounds

| Comp. No | $^1$H-NMR (δ ppm), MASS (EI/ES+, m/z) |
|---|---|
| IA.1 | 1.19 (s, 3H), 1.29 (t, 3H, J = 7.1 Hz), 1.45 (s, 3H), 1.5-1.54 (m, 1H), 1.66-1.73 (m, 3H), 1.81-1.84 (m, 1H), 1.95-2.24 (m, 6H), 2.32-2.36 (m, 1H), 2.56-2.62 (m, 1H), 2.9-3.0 (m, 1H), 4.1-4.2 (q, 2h, J = 7.1), 4.51 (br, d, 1H, J = 2.51 Hz), 5.07 (d, 1H, J = 16.4 Hz), 5.62 (d, 1H, J = 16.4 Hz), 6.17 (s, 1H), 6.27 (dd, 1H, $J_1$ = 10.1 Hz, $J_2$ = 1.8 Hz), 7.27 (d, 1H, J = 10.4 Hz), 7.47 (d, 2H, J = 6.9 Hz), 7.84 (d, 2H, J = 6.9 Hz). MASS (ES+): 592.9 (M + Na)$^+$. |
| IA.2 | 0.96 (d, 3H, J = 7.16 Hz), 1.11-1.15 (m, 3H), 1.24 (s, 3H), 1.55 (s, 3H), 1.67 (s, 2H), 1.71-1.89 (m, 3H), 2.25-2.40 (m, 6H), 3.3-3.4 (m, 1H), 4.42 (br, 1H), 4.95 (d, 1H, J = 16.6 Hz), 5.69 (d, 1H, J = 16.6 Hz), 5.3-5.37 & 5.43-5.49 (m, 1H), 6.38 (dd, 1H, $J_1$ = 10.14 Hz, $J_2$ = 1.8 Hz), 6.45 (s, 1H), 7.16 (dd, 1H, $J_1$ = 10.1 Hz, $J_2$ = 1.8 Hz), 7.49 (d, 2H, J = 8.8 Hz), 7.56 (d, 2H, J = 8.6 Hz). MASS (ES+): 627.0 (M + Na)$^+$. |
| IA.3 | 0.99 (d, 3H, J = 7.14 Hz), 1.11-1.14 (m, 6H), 1.53 (s, 3H), 1.62 (s, 2H), 1.7-1.91 (m, 4H), 2.21-2.29 (m, 2H), 2.34-2.38 (m, 4H), 3.35-3.42 (m, 1H), 4.3 (d, 1H, J = 16.5 Hz), 4.41 (br, 1H), 4.48 (d, 1H, J = 16.5 Hz), 5.30-5.35 & 5.42-5.47 (m, 1H), 6.38 (dd, 1H, $J_1$ = 10.15 Hz, $J_2$ = 1.75 Hz), 6.43 (s, 1H), 7.12 (d, 1H, J = 10.15 Hz), 7.47 (d, 2H, J = 8.5 Hz), 7.9 (d, 2H, J = 8.5 Hz). MASS (ES+): 643.1 (M + Na)$^+$. |
| IA.4 | 1.16 (d, 1H, J = 3.30 Hz), 1.20 (s, 3H), 1.29 (t, 3H, J = 7.10 Hz), 1.48 (s, 3H), 1.54 (m, 2H), 1.70 (m, 1H), 1.83 (m, 2H), 1.96-2.22 (m, 5H), 2.34 (m, 1H), 2.59 (m, 1H), 2.95 (m, 1H), 4.16 (q, 2H, J = 7.00 Hz), 4.52 (br, 1H), 5.08 (d, 1H, J = 16.32 Hz), 5.63 (d, 1H, J = 16.32 Hz), 6.02 (s, 1H), 6.27 (dd, 1H, $J_1$ = 10.59 Hz, $J_2$ = 1.67 Hz), 7.17 (dd, 2H, $J_1$ = $J_2$ = 8.55 Hz), 7.28 (d, 1H, J = 10.19 Hz), 7.94 (dd, 2H, $J_1$ = 8.76, $J_2$ = 5.31). MASS (EI): 554 |
| IA.5 | 0.96 (s, 3H), 1.13 (t, 3H, J = 7.55 Hz), 1.24 (s, 3H), 1.30 (m, 1H), 1.55 (s, 3H), 1.82 (m, 2H), 2.05 (m, 2H), 2.20 (br, 1H), 2.25-2.50 (m, 6H), 3.35 (m, 1H), 4.41 (d, 1H, J = 8.52 Hz), 5.00 (d, 1h, J = 16.53), 5.33 & 5.46 (m, 1H), 5.69 (d, 1H, J = 16.53 Hz), 6.38 (1H, dd, $J_1$ = 10.15 Hz, $J_2$ = 1.64 Hz), 6.44 (s, 1H), 7.18 (dd, 2H, $J_1$ = $J_2$ = 8.50 Hz), 7.95 (dd, 2H, $J_1$ = 8.70 Hz, $J_2$ = 5.30 Hz). MASS (ES+): 611.1 (M + Na)$^+$. |
| IA.6 | 0.99 (d, 3H, J = 7.15 Hz), 1.13 (m, 6H), 1.25 (s, 1H), 1.33 (m, 1H), 1.53 (s, 3H), 1.86 (m, 3H), 2.26 (m, 2H), 2.39 (m, 4H), 3.39 (m, 1H), 4.32 (d, 1H, J = 16.48 Hz), 4.41 (d, 1H, J = 8.92 Hz), 4.48 (d, 1H, J = 16.49 Hz), 5.32 & 5.44 (m, 1H), 6.38 (dd, 1H, $J_1$ = 10.15 Hz, $J_2$ = 1.69 Hz), 6.44 (s, 1H), 7.12 (dd, 1H, $J_1$ = 10.19 Hz, $J_2$ = 0.95 Hz), 7.17 (dd, 2H, $J_1$ = $J_2$ = 8.50 Hz), 8.05 (dd, 2H, $J_1$ = 10.26 Hz, $J_2$ = 5.35 Hz). MASS (ES+): 627.1 (M + Na)$^+$. |
| IA.7 | 1.18 (dd, 2H, $J_1$ = 11.44 Hz, $J_2$ = 3.21 Hz), 1.21 (s, 3H), 1.29 (t, 3H, J = 7.11 Hz), 1.48 (s, 3H), 1.52 (m, 1H), 1.66-1.84 (m, 2H), 1.95-2.22 (m, 6H), 2.32-2.36 (m, 1H), 2.91-2.98 (m, 1H), 4.16 (q, 2H, J = 7.14 Hz), 4.52 (s, 1H), 5.00 (dd, 1H, $J_1$ = 17.35 Hz, $J_2$ = Hz3.61), 5.48 (dd, 1H, $J_1$ = 17.35 Hz, $J_2$ = 3.61 Hz), 6.02 (s, 1H), 6.22 (dd, 1H, $J_1$10.09 Hz, $J_2$ = 1.73 Hz), 6.92 (t, 1H, J = 6.67 Hz), 7.00 (1H, t, J = 6.67 Hz), 7.29 (1H, d, J = 10.15 Hz), 8.01 (dd, 1H, $J_1$ = 8.25 Hz, $J_2$ = 6.75 Hz). MASS (ES+): 595.1 (M + Na)$^+$. |

TABLE 6-continued

Spectral data for the synthesized compounds

| Comp. No | $^1$H-NMR ($\delta$ ppm), MASS (EI/ES+, m/z) |
|---|---|
| IA.8 | 1.13 (s, 3H), 1.16 (dd, 2H, $J_1$ = 11.37 Hz, $J_2$ = 3.2 Hz), 1.28 (t, 3H, J = 7.13 Hz), 1.47 (s, 3H), 1.50-1.52 (m, 1H), 1.64-1.68 (m, 1H), 1.80-1.83 (m, 1H), 1.91-2.20 (m, 6H), 2.33 (dd, 1H, $J_1$ = 13.36 Hz, $J_2$ = 2.80 Hz), 2.53-2.61 (m, 1H), 2.88-2.95 (m, 1H), 4.14 (q, 2H, J = 7.12 Hz), 4.51 (s, 1H), 5.00 (d, 1H, J = 16.75 Hz), 5.41 (d, 1H, J = 16.75 Hz), 6.02 (s, 1H), 6.26 (dd, 1H, $J_1$ = 10.01, $J_2$ = 1.78 Hz), 7.27 (d, 1H, J = 10.09 Hz), 7.36 (dd, 1H, $J_1$ = 8.38 Hz, $J_2$1.93 Hz), 7.47 (d, 1H, J = 1.89 Hz), 7.62 (d, 1H, J = 8.37 Hz). MASS (ES+): 627.0 (M + Na)$^+$. |
| IA.9 | 0.96 (d, 3H, J = 7.14 Hz), 1.14 (t, 3H, J = 7.57 Hz), 1.26 (s, 3H), 1.29-1.34 (m, 3H), 1.56 (s, 3H), 1.71-1.88 (m, 4H), 2.02-2.05 (m, 1H), 2.25-2.50 (m, 6H), 3.33-3.38 (m, 1H), 4.42 (d, 1H, J = 8.87 Hz), 4.92 (dd, 1H, $J_1$ = 17.59 Hz, $J_2$ = 3.07 Hz), 5.35 & 5.46 (m, 1H), 5.56 (dd, 1H, $J_1$ = 17.59 Hz, $J_2$ = 3.07 Hz), 6.38 ((dd, 1H, $J_1$ = 10.14 Hz, $J_2$ = 1.70 Hz), 6.44 (s, 1H), 6.90-7.04 (m, 1H), 7.15 (d, 1H, J = 10.12 Hz), 8.00 (dd, 1H, $J_1$ = 15.04 Hz, $J_2$ = 8.43 Hz). MASS (ES+): 629.0 (M + Na)$^+$. |
| IA.10 | 0.94 (d, 3H, J = 6.91 Hz), 1.12 (t, 3H, J = 7.51 Hz), 1.18 (s, 3H), 1.24-1.32 (m, 2H), 1.55 (s, 3H), 1.71-1.96 (m, 4H), 2.27-2.48 (m, 5H), 3.32 (s, 1H), 4.40 (d, 1H, J = 7.18 Hz), 4.90 (d, 1H, J = 16.85 Hz), 5.33 (m, 0.5H), 5.46 (d, 1.5H, J = 16.87 Hz), 6.38 (d, 1H, J = 10.07 Hz), 6.44 (s, 1H), 7.15 (d, 1H, J = 9.95 Hz), 7.37 (d, 1H, J = 8.30 Hz), 7.49 (s, 1H), 7.64 (d, 1H, J = 8.33). MASS (ES+): 661.0 (M + Na)$^+$. |
| IA.11 | 0.98 (d, 3H, J = 7.13 Hz), 1.10-1.13 (m, 6H), 1.26-1.35 (m, 2H), 1.54 (s, 3H), 1.72-2.01 (m, 4H), 2.23-2.46 (m, 5H), 3.37 (m, 1H), 4.92 (dd, 1H, $J_1$ = 17.43 Hz, $J_2$ = 2.69 Hz), 4.43 (dd, 2H, $J_1$ = 17.44 Hz, $J_2$2.76 Hz), 5.33 & 5.45 (m, 1H), 6.37 (dd, 1H, $J_1$ = 10.13 Hz, $J_2$ = 1.73 Hz), 6.43 (s, 1H), 6.89-7.01 (m, 2H), 7.16 (dd, 1H, $J_1$ = 10.14 Hz, $J_2$ = 1.05 Hz), 7.94 (dd, 1H, $J_1$ = 15.09 Hz, $J_2$ = 8.50 Hz). MASS (ES+): 645.0 (M + Na)$^+$. |
| IA.12 | 1.15 (d, 1H, J = 3.26 Hz), 1.17 (s, 4H), 1.29 (t, 3H, J = 7.13 Hz), 1.48 (s, 3H), 1.51-1.54 (m, 1H), 1.66-1.73 (m, 2H), 1.81-1.84 (m, 1H), 1.95-2.22 (m, 5H), 2.34 (dd, 1H, $J_1$ = 13.41 Hz, $J_2$ = 2.71 Hz), 2.56-2.62 (m, 1H), 2.90-2.97 (m, 1H), 4.15 (q, 2H, J = 7.15 Hz), 4.52 (s, 1H), 5.06 (d, 1H, J = 16.43 Hz), 5.56 (d, 1H, J = 16.43 Hz), 6.02 (s, 1H), 6.27 (dd, 1H, $J_1$ = 10.08 Hz, $J_2$ = 1.70 Hz), 7.29 (d, 1H, J = 10.08 Hz), 7.59 (d, 1H, J = 8.34 Hz), 7.73 (dd, 1H, $J_1$ = 8.35 Hz, $J_2$ = 1.92 Hz), 7.99 (d, 1H, J = 1.88 Hz). MASS (ES+): 627.0 (M + Na)$^+$. |
| IA.13 | 0.97 (d, 3H, J = 7.16 Hz), 1.05 (s, 3H), 1.12 (t, 3H, J = 7.58 Hz), 1.28-1.35 (m, 2H), 1.53 (s, 3H), 1.72-1.94 (m, 3H), 2.24-2.42 (m, 6H), 3.35 (m, 1H), 4.21 (d, 1H, J = 16.84 Hz), 4.34 (d, 1H, J = 6.84 Hz), 5.32 & 5.44 (m, 1H), 6.38 (dd, 1H, $J_1$ = 10.14 Hz, $J_2$ = 1.78 Hz), 6.43 (s, 1H), 7.11 (dd, 1H, $J_1$ = 10.12 Hz, $J_2$ = 1.22 Hz), 7.35 (dd, 1H, $J_1$ = 8.34 Hz, $J_2$ = 1.92 Hz), 7.46 (d, 1H, J = 8.33 Hz). MASS (ES+): 677.0 (M + Na)$^+$. |
| IA.14 | 0.99 (3H, d, J = 7.10 Hz), 1.10 (s, 3H), 1.12 (t, 3H, J = 7.57 Hz), 1.33 (m, 1H), 1.53 (s, 3H), 1.73-1.97 (m, 5H), 2.20-2.46 (m, 5H), 3.37 (m, 1H), 4.28 (d, 2H, J = 16.38 Hz), 4.41 (d, 2H, J = 15.93 Hz), 5.32 & 5.44 (m, 1H), 6.36 (d, 1H, J = 10.14 Hz), 6.43 (s, 1H), 7.13 (d, 1H, J = 10.14 Hz), 7.58 (d, 1H, J = 8.35 Hz), 7.83 (dd, 1H, $J_1$ = 8.23 Hz, $J_2$ = 1.66 Hz), 8.08 (d, 1H, J = 1.71 Hz). MASS (ES+): 677.0 (M + Na)$^+$. |
| IA.15 | 0.96 (d, 3H, J = 7.10 Hz), 1.13 (t, 3H, J = 7.56 Hz), 1.22 (s, 3H), 1.26-1.33 (m, 2H), 1.55 (s, 3H), 1.71-1.90 (m, 3H), 2.00 (d, 1H, J = 14.88 Hz), 2.27-2.50 (m, 5H), 3.34 (m, 1H), 4.41 (d, 1H, J = 8.73 Hz), 4.96 (d, 1H, J = 16.66 Hz), 5.33 & 5.45 (m, 1H), 5.64 (d, 1H, J = 16.59 Hz), 6.38 (d, 1H, J = 10.14 Hz), 6.44 (s, 1H), 7.14 (d, 1H, J = 10.14 Hz), 7.59 (d, 1H, J = 8.35 Hz), 8.01 (s, 1H). |
| IA.16 | 1.15 (m, 2H), 1.19 (s, 3H), 1.29 (t, 3H, J = 7.13 Hz), 1.61 (s, 3H), 1.66-1.84 (m, 2H), 1.95-2.22 (m, 6H), 2.32-2.36 (m, 1H), 2.55-2.63 (m, 2H), 2.92-2.98 (m, 1H), 4.15 (q, 2H, J = 7.04 Hz), 4.51 (br, 1H), 5.00 (d, 1H, J = 16.00 Hz), 5.58 (d, 1H, J = 16.00 Hz), 6.02 (s, 1H), 6.27 (dd, 1H, $J_1$ = 10.09 Hz, $J_2$ = 1.74 Hz), 7.18 (t, 1H, J = 3.94 Hz), 7.29 (s, 1H), 7.72 (d, 1H, J = 4.92 Hz), 7.75 (d, 1H, J = 3.82 Hz). MASS (ES+): 565.1 (M + Na)$^+$. |
| IA.17 | 1.16 (s, 3H), 1.19 (m, 2H), 1.28 (t, 3H, J = 7.13 Hz), 1.45 (m, 2H), 1.47 (s, 3H), 1.67-2.38 (m, 6H), 2.51-2.67 (m, 1H), 2.88-3.00 (m, 1H), 4.14 (q, 2H, $J_1$ = 14.24 Hz, $J_2$ = 7.11 Hz), 4.51 (br, 1H), 4.94 (d, 1H, J = 15.95 Hz), 5.49 (d, 1H, J = 15.98 Hz), 6.02 (s, 1H), 6.27 (dd, 1H, $J_1$ = 10.07 Hz, $J_2$ = 1.72 Hz), 7.00 (d, 1H, J = 4.08 Hz), 7.27 (d, 1H, J = 9.96 Hz), 7.54 (d, 1H, J = 4.09 Hz). MASS (ES+): 599.0 (M + Na)$^+$. |
| IA.18 | 0.95 (d, 3H, J = 7.14 Hz), 1.13 (t, 3H, J = 7.56 Hz), 1.20 (s, 3H), 1.26-1.36 (m, 1H), 1.54 (s, 3H), 1.77-2.04 (m, 4H), 2.25-2.43 (m, 6H), 3.30-3.37 (m, 1H), 4.40 (d, 1H, J = 9.64 Hz), 4.85 (d, 1H, J = 16.19 Hz), 5.28 & 5.51 (m, 1H), 5.56 (d, 1H, J = 16.17 Hz), 6.35-6.44 (m, 2H), 7.00 (d, 1H, J = 4.09 Hz), 7.14 (d, 1H, J = 10.02 Hz), 7.54 (d, 1H, J = 4.08 Hz). MASS (ES+): 633.0 (M + Na)$^+$. |
| IA.19 | 1.17 (m, 1H), 1.18 (s, 3H), 1.28 (t, 3H, J = 7.11 Hz), 1.47 (s, 3H), 1.70-2.38 (m, 8H), 2.41 (s, 3H), 2.51-2.66 (m, 1H), 2.88-3.01 (m, 1H), 4.15 (q, 2H, $J_1$ = 14.21 Hz, $J_2$ = 7.09 Hz), 4.49 (br, 1H), 4.89 (d, 1H, J = 16.20 Hz), 5.49 (d, 1H, J = 16.21 Hz), 6.02 (s, 1H), 6.21 (d, 1H, J = 3.51 Hz), 6.27 (dd, 1H, $J_1$ = 10.11 Hz, $J_2$ = 1.72 Hz), 7.19 (d, 1H, J = 3.46 Hz), 7.28 (d, 1H, J = 9.26 Hz). MASS (EI): 540 |
| IA.20 | 0.99 (d, 3H, J = 7.35 Hz), 1.10-1.16 (m, 6H), 1.21-1.38 (m, 1H), 1.53 (s, 3H), 1.69-2.02 (m, 4H), 2.16-2.49 (m, 6H), 3.34-3.46 (m, 1H), 4.17 (d, 1H, J = 16.03 Hz), 4.35 (d, 1H, J = 16.01 Hz), 4.43 (br, 1H), 5.28 & 5.51 (m, 1H), 6.37 (d, 1H, J = 10.33 Hz), 6.99 (d, 1H, J = 4.03 Hz), 7.16 (d, 1H, J = 10.03 Hz), 7.65 (d, 1H, J = 4.04 Hz). MASS (ES+): 649.0 (M + Na)$^+$. |
| IA.21 | 0.95 (d, 3H, J = 7.13 Hz), 1.13 (t, 3H, J = 7.56 Hz), 1.22 (s, 3H), 1.54 (s, 3H), 1.70-1.88 (m, 2H), 2.03-2.08 (m, 1H), 2.25-2.51 (m, 8H), 2.40 (s, 3H), 3.30-3.38 (m, 1H), 4.39 (d, 1H, J = 8.28 Hz), 4.80 (d, 1H, J = 16.31 Hz), 5.28 & 5.50 (m, 1H), 5.52 (d, 1H, J = 16.33 Hz), 6.21 (d, 1H, J = 2.99 Hz), 6.37 (dd, 1H, $J_1$ = 10.12 Hz, $J_2$ = 1.77 Hz), 6.43 (s, 1H), 7.15-7.20 (m, 2H). MASS (EI): 574 |
| IA.22 | 0.98 (d, 3H, J = 7.13 Hz), 1.09-1.16 (m, 6H), 1.22-1.37 (m, 1H), 1.53 (s, 3H), 1.69-2.56 (m, 10H), 2.41 (s, 3H), 3.36-3.43 (m, 1H), 4.12 (d, 1H, J = 16.31 Hz), 4.33 (d, 1H, J = 16.33 Hz), 4.43 (br, 1H), 5.28 & 5.52 (m, 1H), 6.21 (d, 1H, J = 3.12 Hz), 6.34-6.43 (m, 2H), 7.18 (dd, 1H, $J_1$ = 10.04 Hz, $J_2$ = 1.03 Hz), 7.27 (d, 1H, J = 3.60 Hz). MASS (ES+): 613.1 (M + Na)$^+$. |
| IA.23 | 1.17 (s, 3H), 1.20 (s, 1H), 1.21 (s, 9H), 1.28 (t, 3H, J = 7.12 Hz), 1.43 (s, 1H), 1.47 (s, 3H), 1.63-2.97 (m, 12H), 4.14 (q, 2H, $J_1$ = 14.26 Hz, $J_2$ = 7.12 Hz), 4.49 (br, 1H), 4.63 (d, 1H, J = 16.68 Hz), 5.23 (d, 1H, J = 16.69 Hz), 6.01 (s, 1H), 6.27 (dd, 1H, $J_1$ = 10.10 Hz, $J_2$ = 1.84 Hz), 7.27 (d, 1H, J = 9.73 Hz). MASS (EI): 516 |
| IA.24 | 1.13 (s, 3H), 1.18-1.25 (m, 3H), 1.28 (t, 3H, J = 7.12 Hz), 1.47 (s, 3H), 1.55-2.16 (m, 8H), 2.18 (s, 3H), 2.36-2.96 (m, 3H), 4.14 (q, 2H, J = 7.13 Hz), 4.50 (d, 1H, J = 16.83 Hz), 4.51 (m, 1H), 4.92 (d, 1H, J = |

TABLE 6-continued

Spectral data for the synthesized compounds

| Comp. No | $^1$H-NMR (δ ppm), MASS (EI/ES+, m/z) |
|---|---|
| | 16.84 Hz), 6.02 (s, 1H), 6.26 (dd, 1H, $J_1$ = 10.09 Hz, $J_2$ = 1.82 Hz), 7.28 (d, 1H, J = 10.10 Hz). MASS (EI): 474 |
| IA.25 | 0.94 (d, 3H, J = 7.17 Hz), 1.12 (t, 3H, J = 7.56 Hz), 1.21 (s, 12H), 1.26-1.29 (m, 1H), 1.54 (s, 3H), 1.77-2.41 (m, 10H), 3.28-3.35 (m, 1H), 4.38 (br, 1H), 4.54 (d, 1H, J = 16.98 Hz), 5.28 & 5.52 (m, 1H), 5.30 (d, 1H, J = 16.91 Hz), 6.38 (dd, 1H, $J_1$ = 10.10 Hz, $J_2$ = 1.73 Hz), 6.43 (s, 1H), 7.17 (dd, 1H, $J_1$ = 10.05 Hz, $J_2$ = 1.10 Hz). MASS (ES+): 573.2 (M + Na)$^+$. |
| IA.26 | 0.98 (d, 3H, J = 7.12 Hz), 1.12 (s, 3H), 1.12 (t, 3H, J = 7.54 Hz), 1.24 (s, 9H), 1.23-1.34 (m, 1H), 1.54 (s, 3H), 1.75-2.50 (m, 10H), 3.34-3.42 (m, 1H), 3.89 (d, 1H, J = 17.40 Hz), 4.14 (d, 1H, J = 17.38 Hz), 4.38-4.42 (br, 1H), 5.28 & 5.52 (m, 1H), 6.37 (dd, 1H, $J_1$ = 10.20 Hz, $J_2$ = 1.64 Hz), 6.43 (s, 1H), 7.17 (d, 1H, J = 9.96 Hz). MASS (ES+): 589.1 (M + Na)$^+$. |
| IA.27 | 0.99 (d, 3H, J = 7.13 Hz), 1.10 (s, 3H), 1.12 (t, 3H, J = 7.55 Hz), 1.20-1.39 (m, 2H), 1.53 (s, 3H), 1.69-1.97 (m, 4H), 2.22-2.42 (m, 8H), 3.33-3.40 (m, 1H), 3.72 (d, 1H, J = 16.52 Hz), 3.83 (d, 1H, J = 16.51 Hz), 4.40 (br, 1H), 5.28 & 5.50 (m, 1H), 6.38 (dd, 1H, $J_1$ = 10.08 Hz, $J_2$ = 1.28 Hz), 6.43 (s, 1H), 7.13 (dd, 1H, $J_1$ = 10.08 Hz, $J_2$ = 1.37 Hz). MASS (ES+): 547.1 (M + Na)$^+$. |
| IA.28 | 0.94 (d, 3H, J = 7.12 Hz), 1.12 (t, 3H, J = 7.58 Hz), 1.17 (s, 3H), 1.24-1.35 (m, 1H), 1.55 (s, 3H), 1.70-1.95 (m, 3H), 2.18 (s, 3H), 2.24-2.42 (m, 7H), 3.30 (m, 1H), 4.39 (br, 1H), 4.43 (d, 1H, J = 17.04 Hz), 4.96 (d, 1H, J = 17.04 Hz), 5.28 & 5.52 (m, 1H), 6.37 (dd, 1H, $J_1$ = 10.10 Hz, $J_2$ = 1.79 Hz), 6.42 (s, 1H), 7.17 (dd, 1H, $J_1$ = 10.07 Hz, $J_2$ = 1.11 Hz). MASS (ES+): 531.1 (M + Na)$^+$. |
| IA.29 | 1.15 (d, J = 3.312 Hz, 3H), 1.21 (s, 3H), 1.29 (t, J = 7.08, 3H), 1.48 (s, 3H), 1.71-2.38 (m, 6H), 2.58 (m, 1H), 2.97 (m, 1H), 3.89 (s, 3H), 4.16 (q, J = 7.07 Hz, 2H), 4.51 (d, 1H), 5.05 (d, J = 16.2 Hz, 1H), 5.60 (d, J = 16.2 Hz, 1H), 6.02 (s, 1H), 6.27 (dd, $J_1$ = 10.11 Hz, $J_2$ = 1.83 Hz, 1H), 6.96 (d, J = 8.9 Hz, 2H), 7.28 (d, J = 10.3 Hz, 1H), 7.88 (d, J = 8.9 Hz, 2H). |
| IA.30 | 0.96 (d, J = 7.1 Hz 3H), 1.13 (t, J = 7.5 Hz 3H), 1.25 (s, 3H), 1.55 (s, 3H), 1.70-1.88 (m, 2H), 2.08 (d, J = 15.9 Hz, 1H), 2.26-2.46 (m, 7H), 2.56 (m, 1H), 3.34 (m, 1H), 3.38 (s, 3H), 4.40 (d, J = 8.63 Hz, 1H), 4.97 (d, J = 16.4 Hz, 1H), 5.42 (m, 1H), 5.70 (d, J = 16.42, Hz, 1H), 6.37 (dd, $J_1$ = 10.1 Hz, $J_2$ = 1.76 Hz, 1H), 6.43 (s, 1H), 6.95 (d, J = 10.9 Hz, 2H), 7.175 (dd, $J_1$ = 10.1 Hz, $J_2$ = 1.03 Hz, 1H), 7.88 (d J = 8.89 Hz, 1H). MASS (ES+): 623.1 (M + Na)$^+$. |
| IA.31 | 0.98 (d, J = 6.2 Hz, 3H), 1.11 (s, 3H), 1.13 (t, J = 7.3 Hz, 3H), 1.22-1.37 (m, 2H), 1.53 (s, 3H), 1.69-2.27 (m, 3H), 2.37 (q, J = 7.52 Hz, 2H), 2.15-2.35 (m, 4H), 3.40 (m, 1H), 3.88 (s, 3H), 4.30 (d, J = 16.5 Hz, 1H), 4.39 (bd, 1H), 4.52 (d, J = 16.5 Hz, 1H), 5.25-5.60 (m, 1H), 6.38 (dd, $J_1$ = 10.10 Hz, $J_2$ = 1.7 Hz, 1H), 6.42 (s, 1H), 6.95 (d, J = 8.8 Hz, 2H), 7.16 (d, J = 10 Hz, 1H), 7.98 (d, J = 8.89 Hz, 2H). MASS (ES+): 639.1 (M + Na)$^+$. |
| IA.32 | 1.16 (s, 6H), 1.26 (t, J = 7.07 Hz, 3H), 1.47 (s, 3H), 1.54-2.36 (m, 24H), 2.57 (m, 1H), 2.90 (t, J = 11.31 Hz, 1H), 4.13 (q, J = 7.14 Hz, 2H), 4.49 (d, J = 1.39 Hz, 1H), 4.60 (d, J = 16.61 Hz, 1H), 5.21 (d, J = 16.70 Hz, 1H), 6.01 (s, 1H), 6.26 (dd, $J_1$ = 1.64 Hz, $J_2$ = 10.82 Hz, 1H), 7.27 (d, J = 3.22 Hz, 1H). MASS (ES+): 617.2 (M + Na)$^+$. |
| IA.33 | 0.935 (d, J = 7.11 Hz, 3H), 1.11 (t, J = 7.66 Hz, 3H), 1.20-1.34 (m, 3H), 1.54 (s, 3H), 1.66-1.94 (m, 14H), 2.05 (d, J = 4.87 Hz, 6H), 2.18-2.51 (m, 6H), 3.30 (m, 1H), 4.38 (d, J = 8.13 Hz, 1H), 4.51 (d, J = 16.91 Hz, 1H), 5.25 (d, J = 17.23 Hz, 1H), 5.40-5.60 (m, 1H), 6.37 (dd, $J_1$ = 1.73 Hz, $J_2$ = 10.09 Hz, 1H), 6.42 (s 1H), 7.15 (d, J = 9.011 Hz, 1H). MASS (ES+): 651.2 (M + Na)$^+$. |
| IA.34 | 0.97 (d, J = 7.14 Hz, 3H), 1.12 (t, J = 7.57 Hz, 6H), 1.22-1.36 (m, 2H), 1.52 (s, 3H), 1.71 (s, 6H), 1.82-1.91 (m, 9H), 2.06 (s, 3H), 2.21-2.26 (m, 4H), 2.35 (q, J = 7.15 Hz, 2H), 3.39 (m, 1H), 3.84 (d, J = 17.48 Hz, 1H), 4.11 (d, J = 17.49 Hz, 1H), 4.40 (d, J = 7.69 Hz, 1H), 5.40-5.60 (m 1H), 6.35 (d, J = 1.81 Hz, 1H), 6.41 (d, J = 6.48 Hz, 1H), 7.16 (dd $J_1$ = 1.21 Hz, $J_2$ = 10.06 Hz, 1H). MASS (ES+): 667.1 (M + Na)$^+$. |
| IA.35 | 0.99 (d, J = 7.06 Hz, 3H), 1.12 (t, J = 7.44 Hz, 6H), 1.22-1.38 (m, 2H), 1.53 (s, 3H), 1.69-2.02 (m, 3H), 2.16-2.38 (m, 6H), 3.38 (m, 1H), 4.30 (d, J = 16.50 Hz, 1H), 4.39 (d, 1H), 4.48 (d, J = 16.51 Hz, 1H), 5.20-5.50 (m, 1H), 6.345 (d, J = 1.69 Hz, 1H), 6.41 (d, J = 4.53 Hz, 1H), 7.16 (d, J = 10.03 Hz, 1H), 7.31 (d, J = 8.31 Hz, 2H), 8.06 (d, J = 8.87 Hz, 2H). MASS (ES+): 693.1 (M + Na)$^+$. |
| IA.36 | 0.96 (d, J = 7.02 Hz, 3H), 1.12 (t, J = 7.50 Hz, 3H), 1.24-1.36 (m, 4H), 1.55 (s, 3H), 1.64-2.07 (m, 3H), 2.26-2.58 (m, 6H), 3.31-3.38 (m, 1H), 4.41 (d, J = 8.22 Hz, 1H), 5.03 (d, J = 16.58 Hz, 1H), 5.40 (m, 1H), 5.65 (d, J = 16.59 Hz 1H), 6.35 (d, J = 1.62 Hz, 1H), 6.42 (d, J = 5.32 Hz, 1H), 7.17 (d, J = 9.99 Hz, 1H), 7.32 (d, J = 8.23 Hz, 2H), 7.97 (d, J = 8.76 Hz, 2H). MASS (ES+): 677.0 (M + Na)$^+$. |
| IA.37 | 0.88-1.32 (m, 10H), 1.48 (s, 3H), 1.53-2.37 (m, 7H), 2.51-3.01 (m, 2H), 4.15 (q, J = 7.13 Hz, 2H), 4.52 (d, J = 2.46 Hz, 1H), 5.08 (d, J = 16.41 Hz, 1H), 5.64 (d, J = 16.41 Hz, 1H), 6.02 (s, 1H), 6.28 (dd, $J_1$ = 1.78 Hz, $J_2$ = 10.07 Hz, 1H), 7.26 (s, 1H), 7.33 (d, J = 8.60 Hz, 2H), 7.97 (d, J = 8.84 Hz, 2H). MASS (ES+): 643.1 (M + Na)$^+$. |
| IA.38 | 1.00 (d, J = 7.18 Hz, 3H), 1.05-1.50 (m, 8H), 1.53 (s, 3H), 1.69-2.42 (m, 9H), 3.38 (m, 1H), 4.32 (d, J = 16.14 Hz, 1H), 4.40 (s, 1H), 4.50 (d, J = 16.10 Hz, 1H), 5.30 (m, 1H), 6.38 (dd, $J_1$ = 1.67 Hz, $J_2$ = 10.12 Hz, 1H), 6.43 (s, 1H), 7.12 (d, J = 10.05 Hz, 1H), 7.76 (d, J = 8.21 Hz, 2H), 8.12 (d, J = 8.08 Hz, 2H). MASS (ES+): 677.1 (M + Na)$^+$. |
| IA.39 | 1.06 (d, J = 7.12 Hz, 3H), 1.17 (s, 3H), 1.36-1.41 (m, 1H), 1.55 (s, 3H), 1.72-2.01 (m, 4H), 2.28-2.49 (m, 4H), 3.43-3.48 (m, 1H), 4.38 (d, J = 16.56 Hz, 1H), 4.47 (d, J = 10.79 Hz, 1H), 4.52 (d, J = 16.65 Hz, 1H), 5.32-5.49 (m, 1H), 6.41 (d, d $J_1$ = 10.13 Hz, $J_2$ = 1.79 Hz, 1H), 6.46 (s, 1H), 6.93 (d, J = 4.18 Hz, 1H), 7.14 (d, d $J_1$ = 10.19 Hz, $J_2$ = 1.16 Hz, 1H), 7.52 (d, J = 4.00 Hz, 1H), 7.77 (d, J = 8.24 Hz, 2H), 8.12 (d, J = 8.13 Hz, 2H). MASS (ES+): 743.5 |
| IA.40 | 1.05 (d, J = 7.15 Hz, 3H), 1.11 (s, 3H), 1.34-1.40 (m, 1H), 1.54 (s, 3H), 1.77-2.01 (m, 4H), 2.25 (s, 6H), 2.28 (s, 3H), 2.28-2.50 (m, 4H), 3.45-3.50 (m, 1H), 4.09 (d, J = 17.76 Hz, 1H), 4.29 (d, J = 17.83 Hz, 1H), 4.43 (d, J = 8.40 Hz, 1H), 5.32-5.48 (m, 1H), 6.40 (dd, $J_1$ = 10.15 Hz, $J_2$ = 1.79 Hz, 1H), 6.46 (s, 1H), 6.85 (s, 2H), 6.93 (d, J = 4.09 Hz, 1H), 7.14 (dd, $J_1$ = 10.11 Hz, $J_2$ = 1.00 Hz, 1H), 7.52 (d, J = 4.07 Hz, 1H). MASS (ES+): 717.5 |
| IA.41 | 1.06 (d, J = 7.16 Hz, 3H), 1.10 (s, 3H), 1.29-1.35 (m, 1H), 1.67 (s, 3H), 1.77-1.92 (m, 4H), 2.25 (s, 6H), 2.28 (s, 3H), 2.42-2.87 (m, 5H), 3.45-3.48 (m, 1H), 4.07 (d, J = 17.54 Hz, 1H), 4.31 (d, J = 17.68 Hz, 1H), 4.59 (s, 1H), 6.11 (s, 1H), 6.36 (dd, $J_1$ = 10.09 Hz, $J_2$ = 1.74 Hz, 1H), 6.49 (dd, $J_1$ = 3.45 Hz, $J_2$ = 1.67 Hz, 1H), 6.85 (s, 2H), 7.17 (d, J = 3.45 Hz, 1H), 7.20 (d, J = 10.13 Hz, 1H), 7.58 (d, J = 0.8 Hz, 1H). MASS (ES+): 687.5 (M + Na)$^+$. |

TABLE 6-continued

Spectral data for the synthesized compounds

| Comp. No | $^1$H-NMR (δ ppm), MASS (EI/ES+, m/z) |
|---|---|
| IA.42 | 0.96 (d, J = 7.10 Hz, 3H), 1.13 (t, J = 7.35 Hz, 2H), 1.22-1.34 (m, 4H), 1.55 (s, 3H), 1.64-2.04 (m, 7H), 2.17-2.51 (m, 4H), 3.10 (s, 3H), 3.34 (m, 1H), 4.41 (d, J = 8.44 Hz, 1H), 5.02 (d, J = 16.63 Hz, 1H), 5.44 (m, 1H), 5.70 (d, J = 16.73 Hz, 1H), 6.38 (d, J = 10.14 Hz, 1H), 6.44 (s, 1H), 7.14 (d, J = 10.14 Hz, 1H), 8.09 (s, 4H). MASS (ES+): 671.0 (M + Na)$^+$. |
| IA.43 | 0.99 (d, J = 7.11 Hz, 3H), 1.12 (t, J = 7.54 Hz, 3H), 1.24-1.52 (m, 4H), 1.72-1.90 (m, 8H), 2.23-2.43 (m, 6H), 3.10 (s, 3H), 3.35 (m, 1H), 4.36 (d, J = 16.36 Hz, 1H), 4.40 (d, 1H), 4.43 (d, J = 16.19 Hz, 1H), 5.40 (m, 1H), 6.37 (d, J = 10.14 Hz, 1H), 6.43 (s, 1H), 7.11 (d, J = 10.09 Hz, 1H), 8.04 (d, J = 8.32 Hz, 2H), 8.17 (d, J = 8.33 Hz, 2H). MASS (ES+): 687.0 (M + Na)$^+$. |
| IA.44 | 0.96 (d, J = 7.14 Hz, 3H), 1.13 (t, J = 7.56 Hz, 3H), 1.24-1.33 (m, 3H), 1.70-2.08 (m, 8H), 2.25-2.42 (m, 6H), 3.36 (m, 1H), 4.41 (d, J = 8.98 Hz, 1H), 5.02 (d, J = 16.63 Hz 1H), 5.40 (m, 1H), 5.75 (d, J = 16.64 Hz, 1H), 6.38 (dd, J$_1$ = 1.52 Hz, J$_2$ = 10.13 Hz, 1H), 6.44 (s, 1H), 7.12 (d, J = 10.09 Hz, 1H), 7.50 (t, J = 7.73 Hz, 2H), 7.63 (t, J = 7.38 Hz, 1H), 7.91 (d, J = 7.47 Hz, 2H). MASS (ES+): 593.1 (M + Na)$^+$. |
| IA.45 | 1.00 (d, J = 7.12 Hz, 3H), 1.13 (t, J = 7.67 Hz, 6H), 1.14-1.35 (m, 3H), 1.67-2.00 (m, 6H), 2.23-2.44 (m, 5H), 3.40 (m, 1H), 4.35 (d, J = 16.72 Hz, 1H), 4.40 (d, J = 9.27 Hz 1H), 4.53 (d, J = 16.82 Hz, 1H), 5.40 (m, 1H), 6.38 (dd, J$_1$ = 1.22 Hz, J$_2$ = 10.10 Hz, 1H), 6.43 (s, 1H), 7.12 (d, J = 10.05 Hz, 1H), 7.49 (t, J = 7.71 Hz, 2H), 7.61 (t, J = 7.43 Hz, 1H), 8.01 (d, J = Hz, 2H). MASS (ES+): 609.1 (M + Na)$^+$. |
| IA.46 | 0.96 (d, J = 7.11 Hz, 3H), 1.13 (t, J = 7.55 Hz, 3H), 1.24 (s, 3H), 1.27-2.09 (m, 8H), 2.24-2.40 (m, 6H), 2.43 (s, 3H), 3.36 (m, 1H), 4.41 (d, J = 8.93 Hz, 1H), 5.00 (d, J = 16.55 Hz, 1H), 5.40 (m, 1H), 5.73 (d, J = 16.56 Hz, 1H), 6.37 (dd, J$_1$ = 10.18 Hz, J$_2$ = 1.37 Hz, 1H), 6.44 (s, 1H), 7.15 (d, J = 10.15 Hz, 1H), 7.29 (d, J = 8.01 Hz, 2H), 7.80 (d, J = 8.08 Hz, 2H). MASS (ES+): 607.1 (M + Na)$^+$. |
| IA.47 | 0.99 (d, J = 7.15 Hz, 3H), 1.12 (t, J = 7.49 Hz, 6H), 1.29-2.00 (m, 8H), 2.20-2.42 (m, 6H), 2.42 (s, 3H), 3.40 (m, 1H), 4.34 (d, J = 16.63 Hz, 1H), 4.40 (d, J = 8.60 Hz 1H), 4.52 (d, J = 16.61 Hz, 1H), 5.40 (m, 1H), 6.37 (dd, J$_1$ = 10.17 Hz, J$_2$ = Hz, 1H), 6.43 (s, 1H), 7.13 (d, J = 10.15 Hz 1H), 7.28 (d, J = 8.05 Hz, 2H), 7.90 (d, J = 8.17 Hz, 2H). MASS (ES+): 623.1 (M + Na)$^+$. |
| IA.48 | 0.93 (d, J = 7.14 Hz, 3H), 1.11 (t, J = 7.56 Hz, 3H), 1.15 (s, 3H), 1.25-1.84 (m, 8H), 2.21-2.38 (m, 6H), 3.32 (m, 1H), 4.34 (d, J = 8.93 Hz, 1H), 4.81 (d, J = 17.90 Hz, 1H), 5.40 (m, 1H), 5.41 (d, J = 17.68 Hz, 1H), 6.38 (d, d J$_1$ = 10.17 Hz, J$_2$ = 1.49 Hz, 1H), 6.43 (s, 1H), 7.11 (d, J = 10.07 Hz, 1H), 7.36 (d, J = 2.95 Hz, 3H). MASS (ES+): 661.0 (M + Na)$^+$. |
| IA.49 | 0.98 (d, J = 7.13 Hz, 3H), 1.07 (s, 3H), 1.12 (t, J = 7.554 Hz, 3H), 1.25-2.01 (m, 8H), 2.23-2.43 (m, 6H), 3.40 (m, 1H), 4.25 (d, J = 17.50 Hz, 1H), 4.42 (d, J = 8.45 Hz, 1H), 4.45 (d, J = 17.57 Hz 1H), 5.40 (m, 1H), 6.39 (d, J = 10.15 Hz, 1H), 6.43 (s, 1H), 7.13 (d, J = 10.11 Hz, 1H), 7.26-7.36 (m, 3H). MASS (ES+): 677.0 (M + Na)$^+$. |
| IA.50 | 0.93 (d, J = 7.14 Hz, 3H), 1.08 (s, 3H), 1.12 (t, J = 7.53 Hz, 3H), 1.26-1.86 (m, 8H), 2.24-2.38 (m, 6H), 3.29 (m, 1H), 4.39 (d, J = 8.69 Hz, 1H), 4.85 (d, J = 19.97 Hz, 1H), 5.36 (d, J = 17.05 Hz, 1H), 5.40 (m, 1H), 6.38 (d, d J$_1$ = 10.10 Hz, J$_2$ = 1.50 Hz, 1H), 6.43 (s, 1H), 7.15 (d, J = 10.11 Hz, 1H), 7.33 (t, J = 7.90 Hz, 1H), 7.47 (d, d J$_1$ = 7.60 Hz, J$_2$ = 1.21 Hz, 1H), 7.62 (d, d J$_1$ = 7387 Hz, J$_2$ = 1.11 Hz, 1H). MASS (ES+): 661.0 (M + Na)$^+$. |
| IA.51 | 0.97 (d, J = 7.13 Hz, 3H), 1.01 (s, 3H), 1.12 (t, J = 7.55 Hz, 3H), 1.29-1.95 (m, 8H), 2.24-2.40 (m, 6H), 3.35 (m, 1H), 4.17 (d, J = 16.89 Hz, 1H), 4.32 (d, J = 16.88 Hz, 1H), 4.41 (d, J = 8.19 Hz, 1H), 5.40 (m, 1H), 6.38 (dd, J$_1$ = 10.04 Hz, J$_2$ = 1.50 Hz, 1H), 6.43 (s, 1H), 7.13 (d, J = 10.14 Hz 1H), 7.31 (d, J = 7.89 Hz, 1H), 7.53 (dd, J$_1$ = 7.62 Hz, J$_2$ = 1.15 Hz, 1H), 7.58 (dd, J$_1$ = 8.01 Hz, J$_2$ = 1.19 Hz, 1H). MASS (ES+): 677.0 (M + Na)$^+$. |
| IA.52 | 0.94 (d, J = 7.16 Hz, 3H), 1.12 (t, J = 7.55 Hz, 3H), 1.19 (s, 3H), 1.25-1.97 (m, 8H), 2.17-2.41 (m, 6H), 3.34 (m, 1H), 4.39 (d, J = 8.73 Hz, 1H), 4.81 (d, J = 17.22 Hz, 1H), 5.38 (m, 1H), 5.42 (d, J = 17.55 Hz 1H), 6.38 (d, d J$_1$ = 10.13 Hz, J$_2$ = 1.37 Hz, 1H), 6.43 (s, 1H), 7.02 (d, J = 8.53 Hz, 2H), 7.15 (d, J = 10.17 Hz, 1H), 7.47-7.51 (m, 1H). MASS (ES+): 629.1 (M + Na)$^+$. |
| IA.53 | 0.97 (d, J = 7.13 Hz, 3H), 1.07 (s, 3H), 1.10 (t, J = 7.54 Hz, 3H), 1.16-1.95 (m, 8H), 2.22-2.44 (m, 6H), 3.36 (m, 1H), 4.17 (d, J = 16.90 Hz, 1H), 4.29 (d, J = 16.88 Hz, 1H), 4.40 (d, J = 8.72 Hz, 1H), 5.40 (m, 1H), 6.37 (dd, J$_1$ = 10.16 Hz, J$_2$ = 1.46 Hz, 1H), 6.43 (s, 1H), 6.98 (t, J = 8.34 Hz 2H), 7.13 (d, J = 9.90 Hz, 1H), 7.44 (t, J = 7.62 Hz, 1H). MASS (ES+): 645.0 (M + Na)$^+$. |
| IA.54 | 0.96 (d, J = 7.13 Hz, 3H), 1.13 (t, J = 7.55 Hz, 3H), 1.24 (s, 3H), 1.25-1.99 (m, 8H), 2.17-2.43 (m, 6H), 3.35 (m, 1H), 4.42 (d, J = 8.41 Hz, 1H), 4.95 (dd, J$_1$ = 17.53 Hz, J$_2$ = 2.75 Hz 1H), 5.40 (m, 1H), 5.57 (dd, J$_1$ = 17.55 Hz, J$_2$ = 2.80 Hz, 1H), 6.38 (d, d J$_1$ = 10.10 Hz, J$_2$ = 1.06 Hz, 1H), 6.44 (s, 1H), 7.15 (d, J = 10.15 Hz, 1H), 7.22 (d, d J$_1$ = 10.05 Hz, J$_2$ = 5.61 Hz, 1H), 7.43 (d, d J$_1$ = 16.25 Hz, J$_2$ = 8.85 Hz, 1H), 7.69 (t, J = 7.42 Hz, 1H). MASS (ES+): 629.1 (M + Na)$^+$. |
| IA.55 | 0.98 (d, J = 7.08 Hz, 3H), 1.10-1.14 (m, 6H), 1.24-1.99 (m, 8H), 2.23-2.43 (m, 6H), 3.36 (m, 1H), 4.29 (dd, J$_1$ = 17.37 Hz, J$_2$ = 1.85 Hz 1H), 4.43 (dd, J$_1$ = 17.25 Hz, J$_2$ = 2.03 Hz 2H), 5.40 (m, 1H), 6.38 (d, J = 10.14 Hz, 1H), 6.43 (s, 1H), 7.13 (d, J = 10.11 Hz, 1H), 7.21 (dd, J$_1$ = 12.35 Hz, J$_2$ = 7.93 Hz, 1H), 7.40 (d, J = 8.21 Hz, 1H), 7.63 (t, J = 6.40 Hz, 1H). MASS (ES+): 645.1 (M + Na)$^+$. |
| IA.56 | 1.06 (d, J = 7.11 Hz, 3H), 1.17 (s, 3H), 1.35-1.41 (m, 1H), 1.54 (s, 3H), 1.77-2.03 (m, 4H), 2.28-2.49 (m, 4H), 3.43-3.49 (m, 1H), 4.34 (d, 1H, J = 16.58 Hz), 4.47 (d, J = 6.32 Hz, 1H), 4.50 (d, J = 16.57 Hz, 1H), 5.32-5.49 (m, 1H), 6.40 (dd, J$_1$ = 10.19 Hz, J$_2$ = 1.84 Hz, 1H), 6.46 (s, 1H), 6.93 (d, J = 3.95 Hz, 1H), 7.14 (dd, J$_1$ = 10.12 Hz, J$_2$ = 1.10 Hz, 1H), 7.47 (d, J = 8.60 Hz, 2H), 7.52 (d, J = 4.06 Hz, 1H), 7.95 (d, J = 8.60 Hz, 2H). MASS (ES+): 731.5 (M + Na)$^+$. |
| IA.57 | 0.93 (d, J = 7.11 Hz, 3H), 1.07 (s, 3H), 1.11 (t, J = 7.54 Hz, 3H), 1.25-1.82 (m, 8H), 2.25 (s, 9H), 2.22-2.37 (m, 6H), 3.31 (m, 1H), 4.27 (d, J = 8.71 Hz, 1H), 4.55 (d, J = 17.82 Hz, 1H), 5.33 (d, J = 17.85 Hz, 1H), 5.40 (m, 1H), 6.38 (d, d J$_1$ = 10.14 Hz, J$_2$ = 1.44 Hz, 1H), 6.43 (s, 1H), 6.87 (s, 2H), 7.11 (d, J = 9.94 Hz, 1H). MASS (ES−): 611.3 (M − H)$^+$. |
| IA.58 | 0.98 (d, J = 7.07 Hz, 3H), 1.03 (s, 3H), 1.12 (t, J = 7.53 Hz, 3H), 1.25-1.95 (m, 8H), 2.25 (s, 9H), 2.22-2.41 (m, 6H), 3.40 (m, 1H), 4.05 (d, J = 17.72 Hz, 1H), 4.28 (d, J = 17.74 Hz, 1H), 4.38 (d, J = 8.06 Hz, 1H), 5.41 (m, 1H), 6.38 (d, J = 10.17 Hz, 1H), 6.43 (s, 1H), 6.85 (s, 2H), 7.12 (d, J = 10.13 Hz 1H). MASS (ES+): 651.1 (M + Na)$^+$. |
| IA.59 | 0.44 (s, 3H), 0.95 (d, J = 7.02 Hz, 3H), 1.08 (t, J = 7.53 Hz, 3H), 1.22-1.75 (m, 15H), 2.17-2.32 (m, 6H), 3.15 (m, 1H), 4.29 (d, J = 6.81 Hz, 1H), 5.40 (m, 1H), 6.35 (dd, J$_1$ = 10.11 Hz, J$_2$ = 1.43 Hz 1H), |

TABLE 6-continued

Spectral data for the synthesized compounds

| Comp. No | $^1$H-NMR (δ ppm), MASS (EI/ES+, m/z) |
|---|---|
| | 6.40 (s, 1H), 7.05 (d, J = 9.98 Hz 1H), 7.36 (t, J = 7.70 Hz, 2H), 7.46 (t, J = 7.20 Hz, 1H), 7.95 (d, J = 7.43 Hz, 2H). MASS (ES+): 637.1 (M + Na)⁺. |
| IA.60 | 0.96 (d, J = 7.10 Hz, 3H), 1.13 (t, J = 7.56 Hz, 3H), 1.23-2.06 (m, 11H), 2.17-2.49 (m, 6H), 3.35 (m, 1H), 4.40 (d, J = 8.55 Hz, 1H), 4.93 (d, J = 16.21 Hz, 1H), 5.39 (m, 1H), 5.64 (d, J = 16.21 Hz, 1H), 6.38 (d J₁ = 10.18 Hz, J₂ = 1.30 Hz, 1H), 6.43 (s, 1H), 7.15 (d, J = 10.22 Hz, 1H), 7.18 (t, J = 4.56 Hz, 1H), 7.73 (d, J = 4.96 Hz, 1H), 7.75 (d, J = 3.66 Hz, 1H). MASS (ES+): 599.2 (M + Na)⁺. |
| IA.61 | 0.99 (d, J = 7.11 Hz, 3H), 1.11-1.14 (m, 6H), 1.25-1.96 (m, 8H), 2.17-2.41 (m, 6H), 3.39 (m, 1H), 4.27 (d, J = 16.28 Hz, 1H), 4.41 (d, J = 13.26 Hz, 1H), 4.44 (d, J = 16.48 Hz, 1H), 5.42 (m, 1H), 6.38 (dd, J₁ = 10.16 Hz, J₂ = 1.46 Hz, 1H), 6.43 (s, 1H), 7.13 (d, J = 9.66 Hz 1H), 7.17 (t, J = 4.16 Hz, 1H), 7.71 (d, J = 4.90 Hz, 1H), 7.86 (d, J = 3.51 Hz, 1H). MASS (ES+): 615.2 (M + Na)⁺. |
| IA.62 | 0.96 (d, J = 7.11 Hz, 3H), 1.13 (t, J = 7.54 Hz, 3H), 1.23 (s, 3H), 1.25-2.03 (m, 8H), 2.24-2.42 (m, 6H), 3.34 (m, 1H), 4.40-4.42 (m, 1H), 4.97 (d, J = 16.57 Hz, 1H), 5.40 (m, 1H), 5.64 (d, J = 16.56 Hz, 1H), 6.37 (d, d J = 10.15 Hz, 1H), 6.44 (s, 1H), 7.14 (d, J = 10.11 Hz, 1H), 7.33-7.26 (m, 1H), 7.68-7.79 (m, 2H). MASS (ES+): 629.2 (M + Na)⁺. |
| IA.63 | 0.99 (d, J = 7.09 Hz, 3H), 1.11 (t, J = 7.80 Hz, 6H), 1.25-1.93 (m, 8H), 2.17-2.44 (m, 6H), 3.36 (m, 1H), 4.18-4.38 (m, 3H), 4.40 (d, J = 16.10 Hz, 1H), 5.38 (m, 1H), 6.33 (d, J = 10.07 Hz, 1H), 6.39 (s, 1H), 7.20 (d, J = 10.05 Hz 1H), 7.28-7.32 (m, 1H), 7.79-7.85 (m, 1H). MASS (ES+): 645.1 (M + Na)⁺. |
| IA.64 | 0.95 (d, J = 7.13 Hz, 3H), 1.13 (t, J = 7.56 Hz, 3H), 1.22 (s, 3H), 1.25-2.05 (m, 8H), 2.24-2.49 (m, 6H), 3.32-3.37 (m, 1H), 4.40 (d, J = 8.68 Hz, 1H), 4.86 (d, J = 16.63 Hz, 1H), 5.32-5.48 (m, 1H), 5.58 (d, J = 16.63 Hz, 1H), 6.38 (d, d J₁ = 10.13 Hz, J₂ = 1.29 Hz, 1H), 6.43 (s, 1H), 6.60 (d, d J₁ = 3.19 Hz, J₂ = 1.29 Hz, 1H), 7.14 (d, J = 10.16 Hz, 1H), 7.27 (d, J = 3.65 Hz, 1H), 7.63 (s, 1H). MASS (ES+): 583.2 (M + Na)⁺. |
| IA.65 | 1.03 (d, J = 7.10 Hz, 3H), 1.25-1.95 (m, 10H), 2.07 (d, J = 14.85 Hz, 1H) 2.28-2.51 (m, 4H), 3.41-3.44 (m, 1H), 4.44 (d, J = 8.26 Hz, 1H), 5.02 (d, J = 16.48 Hz, 1H), 5.32-5.49 (m, 1H), 5.73 (d, J = 16.48 Hz, 1H), 5.97 (s, 1H), 6.38 (d, J = 10.19 Hz, 1H), 6.44 (s, 1H), 7.13-7.21 (m, 3H), 7.95 (d, d J₁ = 8.18 Hz, J₂ = 5.45 Hz, 2H). MASS (ES−): 641.2 (M − H)⁺. |
| IA.66 | 1.03 (d, J = 7.12 Hz, 3H), 1.25-2.07 (m, 11H), 2.28-2.52 (m, 4H), 3.41-3.44 (m, 1H), 4.44 (d, J = 8.40 Hz, 1H), 4.93 (d, d J₁ = 17.51 Hz, J₂ = 3.47 Hz, 1H), 5.32-5.49 (m, 1H), 5.67 (d, d J₁ = 17.49 Hz, J₂ = 3.40 Hz, 1H), 5.96 (s, 1H), 6.38 (d, d J₁ = 10.16 Hz, J₂ = 1.38 Hz, 1H), 6.44 (s, 1H), 6.91-6.97 (m, 1H), 7.01-7.05 (m, 1H), 7.15 (d, J = 10.12 Hz 1H), 8.01 (d, d J₁ = 14.98 Hz, J₂ = 8.29 Hz, 1H). MASS (ES+): 683.1 (M + Na⁺). |
| IA.67 | 0.97 (d, J = 7.10 Hz, 3H), 1.14 (t, J = 7.53 Hz, 3H), 1.24-2.05 (m, 8H), 2.27-2.44 (m, 6H), 3.32-3.36 (m, 1H), 4.40 (d, J = 9.07 Hz, 1H), 5.00 (d, J = 16.85 Hz, 1H), 5.20-5.60 (m, 1H), 5.72 (d, J = 16.81 Hz, 1H), 6.38 (d, d J₁ = 10.11 Hz, J₂ = 1.74 Hz, 1H), 6.44 (s, 1H), 7.15 (d, J = 10.06 Hz, 1H), 7.31-7.39 (m, 1H), 7.49-7.59 (m, 3H), 7.74 (d, J = 7.85 Hz, 1H). MASS (ES+): 633.2 (M + Na⁺). |
| IA.68 | 0.99 (d, J = 7.11 Hz, 3H), 1.13 (d, J = 7.32 Hz, 6H), 1.25-1.99 (m, 8H), 2.23-2.45 (m, 6H), 3.38 (m, 1H), 4.19 (d, J = 16.55 Hz, 1H), 4.36 (d, J = 16.90 Hz, 1H), 4.40 (d, J = 13.09 Hz, 1H), 5.39 (m, 1H), 6.38 (dd, J₁ = 10.15 Hz, J₂ = 1.46 Hz, 1H), 6.43 (s, 1H), 7.13 (d, J = 10.16 Hz, 1H), 7.33 (d, J = 3.51 Hz, 1H), 7.64 (s, 1H). MASS (ES+): 599.1 (M + Na)⁺. |
| IA.69 | 0.99 (d, J = 7.07 Hz, 3H), 1.13 (t, J = 7.22 Hz, 6H), 1.25-1.93 (m, 8H), 2.00-2.48 (m, 6H), 3.35-3.42 (m, 1H), 4.27-4.52 (m, 3H), 5.25-5.52 (m, 1H), 6.34-6.40 (m, 1H), 6.43 (s, 1H), 7.13 (d, J = 9.96 Hz 1H), 7.33 (t, J = 6.94 Hz, 1H), 7.47-7.76 (m, 4H). MASS (ES+): 649.1 (M + Na)⁺. |
| IA.70 | 0.95 (d, J = 7.18 Hz, 3H), 1.09-1.16 (m, 6H), 1.25-1.30 (m, 2H), 1.34 (s, 9H), 1.42-1.95 (m, 6H), 2.17-2.43 (m, 6H), 3.37-3.44 (m, 1H), 4.28-4.49 (m, 2H), 4.53 (d, J = 16.72 Hz, 1H), 5.20-5.60 (m, 1H), 6.37 (dd, J₁ = 10.12 Hz, J₂ = 1.73 Hz, 1H), 6.43 (s, 1H), 7.13 (d, J = 10.19 Hz 1H), 7.50 (d, J = 8.52 Hz, 2H), 7.95 (d, J = 8.52 Hz, 2H). MASS (ES+): 665.2 (M + Na)⁺. |
| IA.71 | 0.96 (d, J = 7.11 Hz, 3H), 1.14 (t, J = 7.52 Hz, 3H), 1.24-1.36 (m, 5H), 1.55-2.07 (m, 6H), 2.20-2.46 (m, 6H), 3.32-3.39 (m, 1H), 4.02 (s, 3H), 4.40 (d, J = 9.33 Hz, 1H), 5.02 (d, J = 16.95 Hz, 1H), 5.20-5.60 (m, 1H), 5.74 (d, J = 16.94 Hz, 1H), 6.37 (d, d J₁ = 10.13 Hz, J₂ = 1.73 Hz, 1H), 6.44 (s, 1H), 6.97 (d, d J₁ = 6.86 Hz, J₂ = 1.97 Hz, 1H), 7.13-7.28 (m, 3H), 7.56 (s, 1H). MASS (ES+): 663.2 (M + Na)⁺. |
| IA.72 | 0.96 (d, J = 7.11 Hz, 3H), 1.14 (t, J = 7.52 Hz, 3H), 1.24-1.30 (m, 6H), 1.34 (s, 8H), 1.42-1.92 (m, 6H), 2.11-2.54 (m, 6H), 3.30-3.41 (m, 1H), 4.41 (d, J = 9.37 Hz, 1H), 5.00 (d, J = 16.55 Hz, 1H), 5.26-5.53 (m, 1H), 5.74 (d, J = 16.56 Hz, 1H), 6.38 (d, d J₁ = 10.12 Hz, J₂ = 1.67 Hz, 1H), 6.44 (s, 1H), 7.15 (d, J = 10.03 Hz, 1H), 7.50 (d, J = 8.48 Hz, 2H), 7.85 (d, J = 8.47 Hz, 2H). MASS (ES+): 649.2 (M + Na)⁺. |
| IA.73 | 1.00 (d, J = 7.18 Hz, 3H), 1.05-1.50 (m, 8H), 1.53 (s, 3H), 1.69-2.42 (m, 9H), 3.38 (m, 1H), 4.32 (d, J = 16.14 Hz, 1H), 4.40 (s, 1H), 4.50 (d, J = 16.10 Hz, 1H), 5.30 (m, 1H), 6.38 (dd, J₁ = 1.67 Hz, J₂ = 10.12 Hz, 1H), 6.43 (s, 1H), 7.12 (d, J = 10.05 Hz, 1H), 7.76 (d, J = 8.21 Hz, 2H), 8.12 (d, J = 8.08 Hz, 2H). MASS (ES+): 679.1 (M + Na)⁺. |
| IA.74 | 0.96 (d, J = 7.10 Hz, 3H), 1.13 (t, J = 7.54 Hz, 3H), 1.25-1.99 (m, 8H), 2.11-2.43 (m, 6H), 3.30-3.50 (m, 1H), 3.88 (s, 3H), 4.40 (d, J = 9.28 Hz, 1H), 4.85 (d, d J₁ = 17.50 Hz, J₂ = 3.72 Hz, 1H), 5.20-5.60 (m, 1H), 5.60 (d, d J₁ = 17.50 Hz, J₂ = 3.65 Hz, 1H), 6.37 (d, d J₁ = 10.11 Hz, J₂ = 1.74 Hz, 1H), 6.44 (s, 1H), 6.65 (d, d J₁ = 13.13 Hz, J₂ = 2.25 Hz, 1H), 6.79 (d, d J₁ = 8.90 Hz, J₂ = 2.35 Hz, 1H), 7.15 (d, d J₁ = 10.14 Hz, J₂ = 1.04 Hz, 1H), 7.91 (t, J = 8.54 Hz, 1H). MASS (ES+): 641.2 (M + Na)⁺. |
| IA.75 | 0.99 (d, J = 7.17 Hz, 3H), 1.09-1.16 (m, 6H), 1.25-1.97 (m, 8H), 2.05-2.44 (m, 6H), 3.30-3.50 (m, 1H), 3.87 (s, 3H), 4.25-4.54 (m, 3H), 5.20-5.60 (m, 1H), 6.38 (dd, J₁ = 10.09 Hz, J₂ = 1.73 Hz, 1H), 6.43 (s, 1H), 6.65 (dd, J₁ = 13.18 Hz, J₂ = 2.35 Hz, 1H), 6.77 (dd, J₁ = 8.40 Hz, J₂ = 2.38 Hz, 1H), 7.14 (d, J = 9.05 Hz, 1H), 7.89 (t, J = 8.67 Hz, 1H). MASS (ES+): 657.1 (M + Na)⁺. |
| IA.76 | 0.96 (d, J = 7.15 Hz, 3H), 1.15 (t, J = 7.60 Hz, 3H), 1.25-1.94 (m, 8H), 2.04-2.43 (m, 6H), 3.33-3.41 (m, 1H), 3.95 (s, 3H), 4.41 (d, J = 8.47 Hz, 1H), 4.97 (d, J = 17.66 Hz, 1H), 5.20-5.60 (m, 1H), 5.65 (d, J = 17.71 Hz, 1H), 6.34-6.44 (m, 2H), 6.98-7.08 (m, 2H), 7.15 (d, J = 10.01 Hz, 1H), 7.52 (t, J = 6.82 Hz, 1H), 7.89 (dd, J₁ = 7.79 Hz, J₂ = 1.66 Hz, 1H). MASS (ES+): 623.2 (M + Na)⁺. |
| IA.77 | 0.96 (d, J = 7.13 Hz, 3H), 1.13 (t, J = 7.55 Hz, 3H), 1.24-2.43 (m, 17H), 3.31-3.40 (m, 1H), 3.87 (s, 3H), 3.92 (s, 3H), 4.41 (d, J = 9.87 Hz, 1H), 4.88 (d, J = 17.64 Hz, 1H), 5.20-5.68 (m, 2H), 6.34-6.59 (m, 4H), 7.17 (d, d J₁ = 10.11 Hz, J₂ = 0.97 Hz, 1H), 7.92 (d, J = 8.80 Hz, 1H). MASS (ES+): 635.2 (M + Na)⁺. |

TABLE 6-continued

Spectral data for the synthesized compounds

| Comp. No | $^1$H-NMR (δ ppm), MASS (EI/ES+, m/z) |
|---|---|
| IA.78 | 0.98 (d, J = 7.16 Hz, 3H), 1.09-1.16 (m, 6H), 1.25-1.88 (m, 8H), 2.05-2.41 (m, 6H), 3.36-3.45 (m, 1H), 3.86 (s, 3H), 3.93 (s, 3H), 4.30-4.61 (m, 3H), 5.20-5.60 (m, 1H), 6.34-6.57 (m, 4H), 7.15 (dd, $J_1$ = 10.05 Hz, $J_2$ = 1.00 Hz, 1H), 7.85 (d, J = 8.73 Hz, 1H). MASS (ES+): 669.1 (M + Na)$^+$. |
| IA.79 | 0.97 (d, J = 7.16 Hz, 3H), 1.09-1.25 (m, 6H), 1.29-1.96 (m, 8H), 2.03-2.41 (m, 6H), 3.36-3.43 (m, 1H), 3.95 (s, 3H), 4.31-4.60 (m, 3H), 5.20-5.6 (m, 1H), 6.35-6.45 (m, 2H), 6.97-7.05 (m, 2H), 7.14 (d, J = 9.89 Hz, 1H), 7.46-7.55 (m, 1H), 7.77 (dd, $J_1$ = 7.71 Hz, $J_2$ = 1.58 Hz, 1H). MASS (ES+): 639.1 (M + Na)$^+$. |
| IA.80 | 0.95 (d, J = 7.16 Hz, 3H), 1.08-1.18 (m, 6H), 1.22-1.93 (m, 8H), 2.19-2.41 (m, 6H), 3.28-3.37 (m, 1H), 4.39 (d, J = 8.09 Hz, 1H), 4.73 (d, J = 17.18 Hz, 1H), 5.22-5.53 (m, 2H), 6.38 (d, d $J_1$ = 10.09 Hz, $J_2$ = 1.78 Hz, 1H), 6.43 (s, 1H), 7.14 (d, d $J_1$ = 10.07 Hz, $J_2$ = 1.16 Hz, 1H), 7.63-7.88 (m, 4H). MASS (ES+): 661.1 (M + Na)$^+$. |
| IA.81 | 0.99 (d, J = 7.15 Hz, 3H), 1.09-1.17 (m, 6H), 1.25-2.02 (m, 8H), 2.17-2.44 (m, 6H), 3.34-3.41 (m, 1H), 4.11 (d, J = 17.43 Hz, 1H), 4.30 (d, J = 17.42 Hz, 1H), 4.41 (d, J = 9.75 Hz, 1H), 5.20-5.60 (m, 1H), 6.38 (dd, $J_1$ = 10.11 Hz, $J_2$ = 1.74 Hz, 1H), 6.43 (s, 1H), 7.13 (dd, $J_1$ = 10.13 Hz, $J_2$ = 1.07 Hz, 1H), 7.60-7.88 (m, 4H). MASS (ES+): 677.1 (M + Na)$^+$. |
| IA.82 | 1.03 (d, J = 7.07 Hz, 3H), 1.25-1.79 (m, 7H), 1.79-2.55 (m, 8H), 3.41-3.45 (m, 1H), 4.45 (d, J = 8.28 Hz, 1H), 4.98 (d, J = 16.58 Hz, 1H), 5.34-5.50 (m, 1H), 5.79 (d, J = 16.48 Hz, 1H), 6.40 (d, d $J_1$ = 10.16 Hz, $J_2$ = 1.38 Hz, 1H), 6.46 (s, 1H), 6.51 (s, 1H), 7.14-7.19 (m, 4H), 7.60 (s, 1H), 7.93 (d, d $J_1$ = 8.55 Hz, $J_2$ = 5.35 Hz, 2H). MASS (ES+): 649.1 (M + Na)$^+$. |
| IA.83 | 1.07 (d, J = 6.86 Hz, 3H), 1.17 (s, 3H), 1.38-1.92 (m, 6H), 1.95-2.54 (m, 6H), 3.47 (m, 1H), 4.31 (d, J = 16.60 Hz, 1H), 4.45-4.67 (m, 2H), 5.32-5.49 (m, 1H), 6.39-6.51 (m, 3H), 7.14-7.19 (m, 4H), 7.59 (s, 1H), 8.05 (dd, $J_1$ = 8.14 Hz, $J_2$ = 5.42 Hz 2H). MASS (ES+): 665.1 (M + Na)$^+$. |
| IA.84 | 1.03 (d, J = 7.08 Hz, 3H), 1.25-1.66 (m, 7H), 1.76-2.56 (m, 8H), 3.41-3.45 (m, 1H), 4.45 (d, J = 8.26 Hz, 1H), 4.90 (d, d $J_1$ = 17.59 Hz, $J_2$ = 3.07 Hz, 1H), 5.34-5.51 (m, 1H), 5.65 (d, d $J_1$ = 17.61 Hz, $J_2$ = 3.17 Hz, 1H), 6.41 (d, d $J_1$ = 10.05 Hz, $J_2$ = 1.50 Hz, 1H), 6.46 (s, 1H), 6.51 (d, d $J_1$ = 3.20 Hz, $J_2$ = 1.52 Hz, 1H), 6.90-7.04 (m, 2H), 7.13-7.19 (m, 2H), 7.59 (s, 1H), 7.99 (d, d $J_1$ = 15.08 Hz, $J_2$ = 8.28 Hz, 1H). MASS (ES+): 683.1 (M + Na)$^+$. |
| IA.85 | 1.06 (d, J = 7.02 Hz, 3H), 1.19 (s, 3H), 1.36-1.66 (m, 6H), 1.71-2.55 (m, 6H), 3.44-3.48 (m, 1H), 4.31 (d, J = 17.67 Hz, 1H), 4.46-4.50 (m, 2H), 5.33-5.66 (m, 1H), 6.41 (dd, $J_1$ = 10.18 Hz, $J_2$ = 0.81 Hz, 1H), 6.45 (s, 1H), 6.50 (d, J = 1.54 Hz, 1H), 6.89-7.01 (m, 2H), 7.12-7.17 (m, 2H), 7.59 (s, 1H), 7.95 (dd, $J_1$ = 15.16 Hz, $J_2$ = 8.35 Hz, 1H). MASS (ES+): 683.1 (M + Na)$^+$. |
| IA.86 | 0.96 (d, J = 7.14 Hz, 3H), 1.11 (s, 3H), 1.12 (t, J = 7.53 Hz, 3H), 1.24-1.34 (m, 1H), 1.54 (s, 3H), 1.59-1.64 (m, 1H), 1.75-1.98 (m, 4H), 2.13-2.61 (m, 7H), 3.37 (m, 1H), 4.36 (d, J = 11.18, 1H), .4.42 (d, J = 8.7, 1H), 4.49 (d, J = 16.46, 1H), 6.34 (s, 1H), 6.34 (d, d $J_1$ = 10.12 Hz, $J_2$ = 1.79 Hz, 1H), 7.11-7.23 (m, 3H), 8.01 (m,, 2H). MASS (ES+): 609.1 (M + Na)$^+$. |
| IA.87 | 0.94 (d, J = 7.09 Hz, 3H), 1.12 (t, J = 7.54 Hz, 3H), 1.24 (s, 3H), 1.27-1.31 (m, 1H), 1.57 (s, 3H), 1.59-1.62 (m, 1H), 1.81-1.87 (m, 2H), 1.97-2.03 (m, 2H), 2.15-2.23 (m, 1H), 2.34-2.46 (m, 6H), 2.60-2.66 (m, 1H), 3.30-3.36 (m, 1H), 4.41 (d, J = 8.85 Hz, 1H), 4.98 (d, J = 16.51 Hz, 1H), 5.69 (d, J = 16.54 Hz, 1H), 6.13 (s, 1H), 6.34 (d, d $J_1$ = 9.98 Hz, $J_2$ = 1.40 Hz, 1H), 7.17 (t, J = 8.50 Hz, 2H), 7.23 (d, J = 10.14 Hz, 1H), 7.95 (dd, $J_1$ = 8.58 Hz, $J_2$ = 5.36 Hz, 2H). MASS (ES+): 593.2 (M + Na)$^+$. |
| IA.88 | 0.98 (d, J = 6.7 Hz, 3H); 1.09 (m, 6H); 1.31-1.35 (m, 2H); 1.54 (s, 3H); 1.71-1.84 (m, 1H); 1.87-2.00 (m, 2H); 2.20-2.33 (m, 6H); 2.88 (s, 1H); 3.36 (m, 1H); 4.39 (d, 1H, J = 31.8 Hz); 4.47 (d, 1H, J = 31.7 Hz); 5.31-5.48 (m, 1H); 6.36 (d, 1H, J = 10.1 Hz); 6.41 (s, 1H); 7.21 (d, 1H, J = 10.0); 8.10 (s, 1H); 8.44 (s, 1H). MASS (ES+): 745.1 (M + Na)$^+$. |
| IA.89 | 0.99 (d, J = 6.91 Hz, 3H); 1.10 (m, 5H); 1.32 (m, 1H); 1.54 (s, 3H); 1.80 (m, 2H); 2.20-2.48 (m, 7H); 3.21 (m, 1H); 3.38 (m, 1H); 4.36-4.47 (m, 3H); 5.32-5.48 (m, 1H); 6.36 (d, 1H, J = 10.0 Hz); 6.41 (s, 1H); 7.22 (d, 1H, J = 10.0 Hz); 7.65 (t, 1H,, J = 7.7 Hz); 7.85 (d, 1H, J = 7.6 Hz); 8.19 (d, 1H, J = 7.8 Hz); 8.24 (s, 1H). MASS (ES+): 677.1 (M + Na)$^+$ |
| IA.90 | 0.90 (d, J = 6.4 Hz, 6H), 0.99 (d, 3H, J = 6.7 Hz); 1.12 (s, 3H), 1.30-1.34 (m, 1H), 1.52 (s, 3H), 1.72-1.89 (m, 3H), 1.91-2.19 (m, 4H), 2.25-2.47 (m, 7H), 2.53 (m, 3H), 3.40 (m, 1H), 4.36 (d, 1H, J = 17.0 Hz), 4.51 (d, 1H, J = 16.5 Hz), 5.30-5.50 (m, 1H), 6.37 (d, 1H, J = 10.0 Hz, 6.43 (s, 1H), 7.17 (d, 1H) J = 10.0 Hz), 7.25 (d, 2H, J = 7.8 Hz), 7.91 (d, 2H, J = 7.8 Hz). MASS (ES+): 665.2 (M + Na)$^+$ |
| IA.91 | 1.11 (t, J = 7.57 Hz, 3H), 1.18 (s, 3H), 1.23-1.25 (m, 1H), 1.43 (d, J = 7.34 Hz, 3H), 1.58 (s, 3H), 1.61-1.64 (m, 1H), 1.91-2.07 (m, 4H), 2.13-2.22 (m, 2H), 2.29-2.55 (m, 7H), 2.61-2.66 (m, 1H), 4.43 (d, J = 8.38 Hz, 1H), 4.88 (d, J = 16.49 Hz, 1H), 5.68 (d, J = 16.4 Hz, 1H), 6.14 (s, 1H), 6.35 (d, d $J_1$ = 10.12 Hz, $J_2$ = 1.44 Hz, 1H), 7.17 (t, J = 8.52 Hz, 2H), 7.25 (d, J = 9.93 Hz, 1H), 7.92 (dd, $J_1$ = 8.67 Hz, $J_2$ = 5.31 Hz, 2H). MASS (ES+): 593.2 (M + Na)$^+$ |
| IA.92 | 0.99 (d, 3H, J = 6.95 Hz); 1.06-1.14 (m, 6H); 1.26 (t, 3H, J = 7.52); 1.30-1.34 (m, 1H); 1.52 (s, 3H), 1.72-1.96 (m, 4H), 2.0-2.28 (m, 2H), 2.34-2.44 (m, 4H), 2.72 (q, 2H, $J_1$ = 15.05 Hz, $J_2$ = 7.51 Hz), 3.39-3.42 (m, 1H), 4.33-4.41 (m, 2H), 4.52 (1H, d, J = 16.60 Hz), 5.25-5.50 (m, 1H), 6.37 (1H, d, J = 10.09 Hz), 6.43 (s, 1H), 7.13 (d, 1H, J = 10.07 Hz), 7.31 (d, 2H, J = 7.92 Hz), 7.93 (d, 2H, J = 8.00 Hz). MASS (ES+): 637.1 (M + Na)$^+$ |
| IA.93 | 0.99 (d, J = 7.0 Hz, 3H); 1.11-1.50 (m, 5H); 1.26-1.48 (m, 7H); 1.52 (s, 3H); 1.67 (s, 3H); 1.70-1.80 (m, 2H), 1.87-2.00 (m, 6H); 2.20-2.45 (m, 3H); 2.57 (m, 1H); 3.38-3.42 (m, 1H); 4.32 (d, 1H, J = 16.7 Hz); 4.40 (d, 1H, J = 8.01 Hz); 4.54 (d, 1H, J = 16.7 Hz); 5.30-5.47 (m, 1H); 6.38 (dd, 1H, $J_1$ = 10.01 Hz, $J_1$ = 1.09 Hz); 6.43 (s, 1H); 7.13 (d, 1H, J = 5.05 Hz); 7.32 (d, 2H, J = 8.13 Hz); 7.94 (d, 2H, J = 8.12 Hz). MASS (ES+): 691.2 (M + Na)$^+$ |
| IA.94 | 0.99 (s, 3H), 1.14 (t, J = 7.53 Hz, 3H), 1.22-1.29 (m, 1H), 1.36 (d, J = 7.31 Hz, 3H), 1.56 (s, 3H), 1.63-2.11 (m, 6H), 2.25-2.65 (m, 7H), 4.01 (d, d, $J_1$ = 17.65 Hz, $J_2$ = 3.11 Hz, 1H), 4.47 (d, d, $J_1$ = 17.62 Hz, $J_2$ = 3.11 Hz, 1H), 4.49 (d, J = 7.05 Hz, 1H), 6.13 (s, 1H), 6.34 (d d $J_1$ = 10.11 Hz, $J_2$ = 1.81 Hz, 1H), 6.86-7.04 (m, 2H), 7.22 (d, J = 10.18 Hz, 1H), 7.87-7.98 (m, 1H). MASS (ES+): 627.1 (M + Na)$^+$ |
| IA.95 | 0.99 (d, J = 7.08 Hz, 6H), 1.11-1.15 (m, 5H), 1.27 (d, 6H, J = 6.8 Hz), 1.52 (s, 3H), 1.67 (s, 3H), 1.72-1.89 (m, 3H), 1.99 (d, 1H, J = 14.47 Hz), 2.37 (q, 2H), 2.96-2.99 (m, 1H), 3.39-3.42 (m, 1H), 4.32 (d, 1H, J = 16.63 Hz), 4.40 (d, 1H, J = 8.64 Hz), 4.54 (d, 1H, J = 16.7 Hz), 5.30-5.47 (m, 1H), 6.37 (d, 1H, J = 10.0 Hz), 6.43 (s, 1H), 7.14 (d, 1H, J = 10.0 Hz), 7.34 (d, 2H, J = 8.17 Hz), 7.94 (d, 2H, J = 8.1 Hz). MASS (ES+): 651.1 (M + Na)$^+$ |
| IA.96 | 0.83-0.95 (m, 1H), 0.99 (d, 3H, J = 7.0 Hz), 1.11 (d, 3H, J = 4.13 Hz), 1.26-1.34 (m, 2H), 1.65-1.69 (m, 2H), 1.72-2.08 (m, 11H), 2.14-2.32 (m, 2H), 2.36 (q, 2H, $J_1$ = 15.04, $J_2$ = 7.58), 3.39-3.42 (m, 1H), 4.32 (d, 1H, J = 16.43 Hz), 4.40 (1H, d, J = 8.26 Hz), 4.49 (d, 1H, J = 16.4 Hz), 5.30-5.46 (m, 1H), |

TABLE 6-continued

Spectral data for the synthesized compounds

| Comp. No | $^1$H-NMR (δ ppm), MASS (EI/ES+, m/z) |
|---|---|
| | 6.37 (d, 1H, J = 9.92 Hz), 6.43 (s, 1H), 6.90 (d, 2H, J = 8.71 Hz), 7.13 (d, 1H, J = 10.04 Hz), 7.95 (d, 2H, J = 8.71 Hz). MASS (ES+): 693.1 (M + Na)$^+$ |
| IA.97 | 0.94 (d, J = 7.11 Hz, 3H), 1.04 (s, 3H), 1.11 (t, J = 7.55 Hz, 3H), 1.21-1.44 (m, 1H), 1.54 (s, 3H), 1.75-2.04 (m, 4H), 2.12-2.41 (m, 7H), 3.1 (s, 3H), 3.29-3.33 (m, 1H), 4.34 (d, J = 16.23, 1H), 4.44 (d, J = 16.35, 1H), 6.12 (s, 1H), 6.34 (d, d J$_1$ = 10.12 Hz, J$_2$ = 1.77 Hz, 1H), 7.19 (d, J = 10.15 Hz, 1H), 8.06 (d, J = 8.59 Hz, 2H), 8.18 (d, J = 8.62 Hz, 2H). MASS (ES+): 669.1 (M + Na)$^+$ |
| IA.98 | 0.97 (d, J = 7.14 Hz, 3H), 1.11 (t, J = 7.54 Hz, 3H), 1.13 (s, 3H), 1.21-1.45 (m, 1H), 1.55 (s, 3H), 1.60-2.07 (m, 5H), 2.17-2.68 (m, 7H), 3.31-3.41 (m, 1H), 4.22 (dd, J$_1$ = 17.96 Hz, J$_2$ = 3.50 Hz, 1H), 4.40-4.42 (d, 1H), 4.43 (dd, J$_1$ = 17.47 Hz, J$_2$ = 2.98 Hz, 1H), 6.13 (s, 1H), 6.34 (d d J$_1$ = 10.13 Hz, J$_2$ = 1.83 Hz, 1H), 6.86-7.03 (m, 2H), 7.21 (d, J = 10.16 Hz, 1H), 7.89-8.01 (m, 1H). MASS (ES+): 627.1 (M + Na)$^+$ |
| IA.99 | 0.94 (s, 3H), 1.12 (t, J = 7.54 Hz, 3H), 1.20-1.29 (m, 1H), 1.37 (d, J = 7.28 Hz, 3H), 1.55 (s, 3H), 1.60-1.95 (m, 6H), 2.25-2.46 (m, 7H), 3.1 (s, 3H), 4.00 (d, J = 16.59 Hz, 1H), 4.42 (d, J = 9.05 Hz, 1H), 4.53 (d, J = 16.61 Hz, 1H), 6.12 (s, 1H), 6.35 (d, d J$_1$ = 10.12 Hz, J$_2$ = 1.75 Hz, 1H), 7.19 (d, J = 10.15 Hz, 1H), 8.07 (d, J = 6.69 Hz, 2H), 8.13 (d, J = 8.73 Hz, 2H). MASS (ES+): 669.0 (M + Na)$^+$ |
| IA.100 | 0.98 (d, J = 7.10 Hz, 3H), 1.11 (s, 3H), 1.11 (t, J = 7.46 Hz, 3H), 1.27-1.33 (m, 1H), 1.54 (s, 3H), 1.57-1.65 (m, 4H), 2.14-2.41 (m, 7H), 2.61-2.63 (m, 1H), 3.35-3.37 (m, 1H), 4.30 (d, J = 16.48 Hz), 4.40 (d, 1H, J = 8.83 Hz), 4.47 (d, 1H, J = 16.47 Hz), 6.13 (s, 1H), 6.34 (d, d J$_1$ = 10.13 Hz, J$_2$ = 1.45 Hz, 1H), 7.20 (d, J = 10.15 Hz, 1H), 7.47 (d, J = 8.5 Hz, 2H), 7.95 (d, J = 8.5 Hz, 2H). MASS (ES+): 625.1 (M + Na)$^+$ |
| IA.101 | 0.97 (s, 3H), 1.14 (t, J = 7.50 Hz, 3H), 1.18-1.27 (m, 1H), 1.38 (d, J = 7.26 Hz, 3H), 1.56 (s, 3H), 1.60-1.64 (m, 1H), 1.89-2.29 (m, 6H), 2.35-2.47 (m, 5H), 2.59-2.64 (m, 1H), 3.97 (d, J = 16.8 Hz, 1H), 4.45 (d, J = 8.17 Hz, 1H), 4.55 (d, J = 16.82 Hz, 1H), 6.13 (s, 1H), 6.35 (d, J = 10.18 Hz, 1H), 7.22 (d, J = 10.13 Hz, 1H), 7.47 (d, J = 8.37 Hz, 2H), 7.92 (d, J = 8.38 Hz, 2H). MASS (ES+): 625.1 (M + Na)$^+$ |
| IA.102 | 1.05-1.15 (m, 6H), 1.22-1.52 (m, 9H), 1.76-2.47 (m, 8H), 3.34-3.41 (m, 1H), 4.07-4.16 (m, 2H), 4.16-4.56 (m, 3H), 5.23-5.48 (m, 1H), 6.36 (d, J = 11.36 Hz, 1H), 6.42 (s, 1H), 7.11 (d, J = 9.95 Hz, 1H), 7.76 (d, J = 8.11 Hz, 2H), 8.11 (d, J = 8.12 Hz, 2H). MASS (ES+): 693.5 (M + Na)$^+$ |
| IA.103 | 0.87 (m, 4H), 0.96 (d, J = 6.88 Hz, 3H), 1.24 (s, 3H), 1.29-1.35 (m, 1H), 1.55 (s, 3H), 1.61-1.66 (m, 1H), 1.81-2.09 (m, 2H), 2.28-2.50 (m, 6H), 3.31-3.36 (m, 1H), 4.42 (d, J = 8.86 Hz, 1H), 4.97 (d, J = 16.53 Hz, 1H), 5.32-5.48 (m, 1H), 5.69 (d, J = 16.53 Hz, 1H), 6.38 (d, d J$_1$ = 10.17 Hz, J$_2$ = 1.46 Hz, 1H), 6.44 (s, 1H), 7.16 (d, J = 8.50 Hz, 2H), 7.23 (t, J = 8.64 Hz, 3H), 7.94 (dd, J$_1$ = 8.60 Hz, J$_2$ = 5.35 Hz, 2H). MASS (ES+): 623.0 (M + Na)$^+$ |
| IA.104 | 0.86-0.96 (m, 4H), 0.98 (d, J = 7.35 Hz, 3H), 1.12 (s, 3H), 1.31-1.36 (m, 1H), 1.53 (s, 3H), 1.60-1.65 (m, 1H), 1.70-2.03 (m, 5H), 2.22-2.29 (m, 2H), 2.39-2.45 (m, 2H), 3.35-3.39 (m, 1H), 4.26 (d, J = 17.62 Hz, 1H), 4.42 (d, J = 8.24 Hz, 1H), 4.43 (d, J = 17.30 Hz, 1H), 5.31-5.47 (m, 1H), 6.38 (d, d, J$_1$ = 10.11 Hz, J$_2$ = 1.09 Hz, 1H), 6.43 (s, 1H), 6.89-6.94 (m, 1H), 6.96-7.01 (m, 1H), 7.14 (d, J = 10.14 Hz, 1H), 7.95 (dd, J$_1$ = 15.13 Hz, J$_2$ = 8.38 Hz, 1H). MASS (ES+): 657.5 (M + Na)$^+$ |
| IA.105 | 1.07 (d, J = 7.14 Hz, 3H), 1.10 (s, 3H), 1.27 (t, J = 7.60 Hz, 3H), 1.32-1.97 (m, 8H), 2.23-2.44 (m, 4H), 3.36-3.42 (m, 1H), 4.09-4.14 (m, 2H), 4.30 (d, J = 16.57 Hz, 1H), 4.43 (d, J = 8.43 Hz, 1H), 4.51 (d, J = 16.58 Hz, 1H), 5.20-5.60 (m, 1H), 6.36 (dd J$_1$ = 10.15 Hz, J$_2$ = 1.20 Hz, 1H), 6.42 (s, 1H), 7.12 (d, J = 10.14 Hz, 1H), 7.47 (d, J = 8.52 Hz, 2H), 7.95 (d, J = 8.54 Hz, 2H). MASS (ES+): 659.4 (M + Na)$^+$ |
| IA.106 | 0.87-0.97 (m, 4H), 0.99 (d, J = 7.12 Hz, 3H), 1.00 (s, 3H), 1.31-1.36 (m, 1H), 1.53 (s, 3H), 1.62-1.66 (m, 1H), 1.77-2.01 (m, 3H), 2.25-2.42 (m, 4H), 3.36-3.39 (m, 1H), 4.28 (d, J = 16.54 Hz, 1H), 4.42 (d, J = 14.05 Hz, 1H), 4.46 (d, J = 16.73 Hz, 1H), 5.30-5.48 (m, 1H), 6.38 (d, d, J$_1$ = 9.63 Hz, J$_2$ = 1.85 Hz, 1H), 6.43 (s, 1H), 7.14 (d, J = 10.10 Hz, 1H), 7.46 (d, J = 8.51 Hz, 2H), 7.94 (d, J = 8.53 Hz, 2H). MASS (ES+): 655.2 (M + Na)$^+$. |
| IA.107 | 0.98 (s, 3H), 1.14 (t, J = 7.56 Hz, 3H), 1.20-1.27 (m, 1H), 1.38 (d, J = 7.23 Hz, 3H), 1.56 (s, 3H), 1.60-1.65 (m, 1H), 1.91-1.98 (m, 3H), 2.04-2.30 (m, 2H), 2.36-2.66 (m, 7H), 3.88 (s, 3H), 3.97 (d, 1H, J = 16.74 Hz), 4.44 (d, 1H, J = 8.41 Hz), 4.58 (d, 1H, J = 16.74 Hz), 6.13 (s, 1H), 6.35 (d, J = 10.07 Hz, 1H), 6.95 (d, J = 8.74 Hz, 2H), 7.24 (d, J = 10.33 Hz, 1H), 7.97 (d, J = 8.74 Hz, 2H). MASS (ES+): 621.3 (M + Na)$^+$. |
| IA.108 | 0.98 (d, J = 7.15 Hz, 3H), 1.11 (s, 3H), 1.11 (t, J = 7.56 Hz, 3H), 1.27-1.33 (m, 1H), 1.54 (s, 3H), 1.57-1.94 (m, 5H), 2.13-2.17 (m, 1H), 2.32-2.41 (m, 5H), 2.62-2.63 (m, 1H), 3.33-3.38 (m, 1H), 4.33 (d, 1H, J = 16.52 Hz), 4.41 (d, 1H, J = 9.09 Hz), 4.49 (d, 1H, J = 16.49 Hz), 6.13 (s, 1H), 6.34 (d, d J$_1$ = 10.12 Hz, J$_2$ = 1.81 Hz, 1H), 7.21 (d, J = 10.12 Hz, 1H), 7.76 (d, J = 8.25 Hz, 2H), 8.12 (d, J = 8.14 Hz, 2H). MASS (ES+): 659.3 (M + Na)$^+$. |
| IA.109 | 0.53 (s, 3H), 0.93 (d, J = 6.88 Hz, 3H), 1.07 (t, J = 7.52 Hz, 3H), 1.12-1.90 (m, 14H), 2.07-2.42 (m, 6H), 3.14-3.17 (m, 1H), 3.84 (s, 3H), 4.28 (d, J = 7.12 Hz, 1H), 5.25-5.42 (m, 1H), 6.34 (dd, J$_1$ = 10.14 Hz, J$_2$ = 1.19 Hz 1H), 6.40 (s, 1H), 6.87 (d, J = 8.84 Hz, 2H), 7.03 (d, J = 10.07 Hz, 1H), 8.02 (d, J = 8.80 Hz, 2H). MASS (ES+): 667.3 (M + Na)$^+$. |
| IA.110 | 1.07 (d, J = 7.20 Hz, 3H), 1.11 (s, 3H), 1.27 (t, J = 7.12 Hz, 3H), 1.33-1.39 (m, 1H), 1.52 (s, 3H), 1.74-1.98 (m, 6H), 2.33-2.45 (m, 4H), 3.36-3.42 (m, 1H), 4.08-4.14 (m, 2H), 4.31 (d, J = 16.55 Hz, 1H), 4.41 (d, J = 8.80 Hz, 1H), 4.52 (d, J = 16.55 Hz, 1H), 5.29-5.46 (m, 1H), 6.37 (dd J$_1$ = 10.15 Hz, J$_2$ = 1.75 Hz, 1H), 6.42 (s, 1H), 7.13 (dd J$_1$ = 10.15 Hz, J$_2$ = 1.05 Hz, 1H), 7.17-7.19 (m, 2H), 8.03-8.07 (m, 2H). MASS (ES+): 643.2 (M + Na)$^+$. |
| IA.111 | 0.97 (s, 3H), 1.13 (t, J = 7.55 Hz, 3H), 1.15-1.29 (m, 1H), 1.38 (d, J = 7.33 Hz, 3H), 1.56 (s, 3H), 1.58-1.66 (m, 1H), 1.88-2.14 (m, 5H), 2.17-2.30 (m, 1H), 2.35-2.64 (m, 5H), 4.01 (d, J = 16.84 Hz, 1H), 4.45 (d, J = 8.23 Hz, 1H), 4.57 (d, J = 16.84 Hz, 1H), 6.13 (s, 1H), 6.35 (d, d J$_1$ = 10.12 Hz, J$_2$ = 1.77 Hz, 1H), 7.22 (d, J = 10.13 Hz, 1H), 7.77 (d, J = 8.24 Hz, 2H), 8.09 (d, J = 8.14 Hz, 2H). MASS (ES+): 659.2 (M + Na)$^+$. |
| IA.112 | 0.97 (d, J = 7.05 Hz, 3H), 1.10 (s, 3H), 1.12-1.48 (m, 7H), 1.53 (s, 3H), 1.71-2.01 (m, 8H), 2.20-2.43 (m, 5H), 3.36-3.39 (m, 1H), 4.30 (d, J = 16.59 Hz, 1H), 4.43 (d, J = 8.27 Hz, 1H), 4.51 (d, J = 16.56 Hz, 1H), 5.31-5.47 (m, 1H), 6.38 (d, d J$_1$ = 10.12 Hz, J$_2$ = 1.33 Hz, 1H), 6.44 (s, 1H), 7.16 (d, J = 10.07 Hz, 1H), 7.76 (d, J = 8.15 Hz, 1H), 8.11 (d, J = 8.08 Hz, 1H). MASS (ES+): 731.2 (M + Na)$^+$. |
| IA.113 | 0.97 (d, J = 7.06 Hz, 3H), 1.10 (s, 3H), 1.15-1.45 (m, 6H), 1.53 (s, 3H), 1.58-1.66 (m, 1H), 1.72-2.0 (m, 8H), 2.20-2.44 (m, 5H), 3.36-3.40 (m, 1H), 4.28 (d, J = 16.54 Hz, 1H), 4.43 (d, J = 8.81 Hz, 1H), 4.48 (d, J = 16.56 Hz, 1H), 5.31-5.47 (m, 1H), 6.38 (d, d J$_1$ = 10.15 Hz, J$_2$ = 1.46 Hz, 1H), 6.44 (s, 1H), |

TABLE 6-continued

Spectral data for the synthesized compounds

| Comp. No | $^1$H-NMR (δ ppm), MASS (EI/ES+, m/z) |
|---|---|
| | 7.14 (d, J = 10.06 Hz, 1H), 7.46 (d, J = 8.53 Hz, 2H), 7.94 (d, J = 8.54 Hz, 2H). MASS (ES+): 697.2 (M + Na)$^+$. |
| IA.114 | 0.96 (d, J = 7.05 Hz, 3H), 1.12 (s, 3H), 1.17-1.48 (m, 6H), 1.53 (s, 3H), 1.58-1.65 (m, 1H), 1.71-2.06 (m, 8H), 2.20-2.43 (m, 5H), 3.36-3.39 (m, 1H), 4.27 (d, J = 17.51 Hz, 1H), 4.24-4.45 (m, 2H), 5.31-5.47 (m, 1H), 6.38 (dd, J$_1$ = 10.12 Hz, J$_2$ = 1.43 Hz, 1H), 6.44 (s, 1H), 6.89-7.01 (m, 2H), 7.14 (d, J = 10.11 Hz, 1H), 7.94 (dd, J$_1$ = 15.1 Hz, J$_2$ = 8.41 Hz, 1H). MASS (ES+): 699.2 (M + Na)$^+$. |
| IA.115 | 0.94 (d, J = 7.07 Hz, 3H), 1.24 (s, 3H), 1.28-1.46 (m, 5H), 1.55 (s, 3H), 1.61-2.06 (m, 10H), 2.24-2.50 (m, 5H), 3.32-3.37 (m, 1H), 4.42 (d, J = 8.32 Hz, 1H), 4.96 (d, J = 16.52 Hz, 1H), 5.32-5.48 (m, 1H), 5.68 (d, J = 16.53 Hz, 1H), 6.38 (d, d J$_1$ = 10.12 Hz, J$_2$ = 1.30 Hz, 1H), 6.44 (s, 1H), 7.17 (d, J = 9.9 Hz, 1H), 7.16-7.19 (m, 2H), 7.94 (dd, J$_1$ = 8.62 Hz, J$_2$ = 5.31 Hz, 2H). MASS (ES+): 665.5 (M + Na)$^+$. |
| IA.116 | 0.96 (d, J = 7.14 Hz, 3H), 1.10 (s, 3H), 1.14-1.43 (m, 6H), 1.53 (s, 3H), 1.62-2.06 (m, 10H), 2.23-2.45 (m, 4H), 3.38-3.42 (m, 1H), 3.88 (s, 3H), 4.27 (d, J = 16.51 Hz, 1H), 4.42 (d, J = 8.73 Hz, 1H), 4.53 (d, J = 16.53 Hz, 1H), 5.31-5.47 (m, 1H), 6.38 (d, d J$_1$ = 10.11 Hz, J$_2$ = 1.66 Hz, 1H), 6.44 (s, 1H), 6.95 (d, J = 8.90 Hz, 2H), 7.15 (d, J = 10.10 Hz, 1H), 7.99 (d, J$_1$ = 8.89 Hz, 2H). MASS (ES+): 693.2 (M + Na)$^+$ |
| IA.117 | 0.98 (d, J = 7.03 Hz, 3H), 1.10 (s, 3H), 1.24-1.34 (m, 1H), 1.53 (s, 3H), 1.55-1.68 (m, 2H), 1.73-2.04 (m, 9H), 2.20-2.41 (m, 4H), 2.74-2.78 (m, 1H), 3.36-3.40 (m, 1H), 4.27 (d, J = 16.55 Hz, 1H), 4.41 (d, J = 7.75 Hz, 1H), 4.49 (d, J = 16.55 Hz, 1H), 5.30-5.47 (s, 1H), 6.37 (d, d J = 10.15 Hz, 1H), 6.43 (s, 1H), 7.13 (d, J = 10.12 Hz, 1H), 7.47 (d, J = 8.36 Hz, 1H), 7.95 (d, J = 8.36 Hz, 2H). MASS (ES+): 661.2 |
| IA.118 | 0.96 (d, J = 7.08 Hz, 3H), 1.24 (s, 3H), 1.24-1.33 (m, 1H), 1.55 (s, 3H), 1.56-1.92 (m, 9H), 2.02-2.50 (m, 5H), 2.73-2.81 (m, 1H), 3.32-3.36 (m, 1H), 4.42 (d, J = 7.77 Hz, 1H), 4.97 (d, J = 16.51 Hz, 1H), 5.32-5.48 (m, 1H), 5.68 (d, J = 16.56 Hz, 1H), 6.38 (d, d J$_1$ = 10.08 Hz, J$_2$ = 1.22 Hz, 1H), 6.44 (s, 1H), 7.14-7.19 (m, 3H), 7.93-7.96 (m, 2H). MASS (ES+): 629.3 |
| IA.119 | 0.98 (d, J = 6.93 Hz, 3H), 1.10 (s, 3H), 1.16 (t, J = 6.88 Hz, 6H), 1.31-1.35 (m, 1H), 1.53 (s, 3H), 1.58-2.01 (m, 4H), 2.21-2.62 (m, 5H), 3.36-3.38 (m, 1H), 4.31 (d, J = 16.58 Hz), 4.42 (d, J = 7.40 Hz, 1H), 4.51 (d, J = 16.58 Hz, 1H), 5.30-5.47 (m, 1H), 6.38 (d, J = 10.15 Hz, 1H), 6.43 (s, 1H), 7.13 (d, J = 10.11 Hz, 1H), 7.76 (d, J = 7.98 Hz, 2H), 8.11 (d, J = 7.91 Hz, 2H). MASS (ES+): 669.2 |
| IA.120 | 0.98 (d, J = 7.12 Hz, 3H), 1.12 (s, 3H), 1.29-1.35 (m, 1H), 1.53 (s, 3H), 1.56-1.66 (m, 5H), 1.70-2.00 (m, 7H), 2.20-2.40 (m, 4H), 2.73-2.77 (m, 1H), 3.35-3.40 (m, 1H), 4.26 (d, d J$_1$ = 17.47 Hz, J$_2$ = 2.37 Hz, 1H), 4.42 (d, J = 5.81 Hz, 1H), 4.54 (d, d J$_1$ = 17.35 Hz, J$_2$ = 2.61 Hz, 1H), 5.31-5.47 (m, 1H), 6.38 (d, d J$_1$ = 10.14 Hz, J$_2$ = 1.38 Hz, 1H), 6.43 (s, 1H), 6.89-7.01 (m, 1H), 7.13 (d, J = 10.09 Hz, 1H), 7.94 (dd, J$_1$ = 15.10 Hz, J$_2$ = 8.46 Hz, 2H). MASS (ES+): 663.3 |
| IA.121 | 0.95 (d, J = 7.14 Hz, 3H), 1.16 (d, J = 7.00 Hz, 6H), 1.22 (s, 3H), 1.28-1.34 (m, 1H), 1.55 (s, 3H), 1.74-2.18 (m, 4H), 2.28-2.57 (m, 4H), 2.58-2.62 (m, 1H), 2.30-2.38 (m, 1H), 3.30-3.38 (m, 1H), 4.42 (d, J = 8.92 Hz, 1H), 4.97 (d, J = 16.51 Hz, 1H), 5.32-5.49 (m, 1H), 5.69 (d, J = 16.53 Hz, 1H), 6.38 (d, d J$_1$ = 10.13 Hz, J$_2$ = 1.75 Hz, 1H), 6.44 (s, 1H), 7.14-7.20 (m, 3H), 7.93-7.97 (m, 2H). MASS (ES+): 603.3 |
| IA.122 | 0.98 (d, J = 7.14 Hz, 3H), 1.11 (s, 3H), 1.16 (d, J = 2.98 Hz, 3H), 1.17 (d, J = 3.00 Hz, 3H), 1.31-1.34 (m, 1H), 1.53 (s, 3H), 1.71-2.03 (m, 4H), 2.24-2.42 (m, 4H), 2.57-2.61 (m, 1H), 3.40-3.43 (m, 1H), 3.88 (s, 3H), 4.28 (d, J = 16.49 Hz, 1H), 4.42 (d, J = 8.74 Hz, 1H), 4.54 (d, J = 16.50 Hz, 1H), 5.30-5.47 (m, 1H), 6.37 (d, d J$_1$ = 10.13 Hz, J$_2$ = 1.77 Hz, 1H), 6.43 (s, 1H), 6.95 (d, J = 8.89 Hz, 2H), 7.14 (dd, J$_1$ = 10.18 Hz, J$_2$ = 1.12 Hz, 2H), 7.99 (d, J = 8.87 Hz, 2H). MASS (ES+): 653.3 |
| IA.123 | 0.97 (d, J = 7.14 Hz, 3H), 1.13 (s, 3H), 1.16 (d, d, J$_1$ = 6.99 Hz, J$_2$ = 3.08 Hz, 6H), 1.29-1.33 (m, 3H), 1.53 (s, 3H), 1.73-2.02 (m, 4H), 2.23-2.47 (m, 4H), 2.55-2.62 (m, 1H), 3.36-3.41 (m, 1H), 4.28 (d, d, J$_1$ = 17.54 Hz, J$_2$ = 2.63 Hz, 1H), 4.42 (d, 1H), 4.44 (d, d, J$_1$ = 17.54 Hz, J$_2$ = 2.90 Hz, 1H), 5.31-5.48 (m, 1H), 6.38 (d, d, J$_1$ = 10.13 Hz, J$_2$ = 1.79 Hz, 1H), 6.44 (s, 1H), 6.89-7.01 (m, 2H), 7.13 (d, d, J$_1$ = 10.10 Hz, J$_2$ = 1.16 Hz, 1H), 7.92-7.98 (m, 1H). MASS (ES+): 637.3 |
| IA.124 | 1.07 (d, J = 7.13 Hz, 3H), 1.17 (s, 3H), 1.33-1.41 (m, 1H), 1.55 (s, 3H), 1.73-2.04 (m, 3H), 2.28-2.54 (m, 5H), 3.43-3.48 (m, 1H), 4.35 (d, J = 16.65 Hz, 1H), 4.46 (d, J = 8.34 Hz, 1H), 4.54 (d, J = 16.65 Hz, 1H), 5.33-5.49 (m, 1H), 6.41 (dd, J$_1$ = 10.12 Hz, J$_2$ = 1.69 Hz 1H), 6.42 (s, 1H), 6.51 (dd, J$_1$ = 3.46 Hz, J$_2$ = 1.69 Hz, 1H), 7.09-7.21 (m, 2H), 7.59 (d, J = 0.72 Hz, 1H), 7.77 (d, J = 8.25 Hz, 2H), 8.72 (d, J = 8.18 Hz 2H). MASS (ES+): 693.3 |
| IA.125 | 0.59 (s, 3H), 0.93 (d, J = 6.99 Hz, 3H), 1.07 (t, J = 7.54 Hz, 3H), 1.21-1.88 (m, 14H), 2.09-2.36 (m, 6H), 3.13-3.17 (m, 1H), 4.31 (d, J = 7.52 Hz, 1H), 5.27-5.42 (m, 1H), 6.35 (dd, J$_1$ = 10.08 Hz, J$_2$ = 1.16 Hz 1H), 6.41 (s, 1H), 7.07 (d, J = 10.11 Hz, 1H), 7.36 (d, J = 8.47 Hz, 2H), 7.29 (d, J = 8.49 Hz, 2H). MASS (ES+): 649.2 |
| IA.126 | 1.07 (d, J = 7.12 Hz, 3H), 1.11 (s, 3H), 1.16-1.87 (m, 11H), 1.90-2.09 (m, 2H), 2.13-2.44 (m, 4H), 3.38-3.42 (m, 1H), 4.06-4.19 (m, 2H), 4.31 (d, J = 16.58 Hz, 1H), 4.40 (d, J = 8.68.Hz, 1H), 4.55 (d, J = 16.55 Hz, 1H), 5.29-5.47 (m, 1H), 6.37 (dd J$_1$ = 10.17 Hz, J$_2$ = 1.45 Hz, 1H), 6.42 (s, 1H), 6.96 (d, J = 8.81 Hz, 2H), 7.13 (d, J = 10.19 Hz, 1H), 8.00 (d, J = 8.83 Hz, 2H). MASS (ES+): 633 |
| IA.127 | 1.07 (d, J = 7.06 Hz, 3H), 1.17 (s, 3H), 1.23-2.10 (m, 8H), 2.17-2.53 (m, 4H), 3.46-3.50 (m, 1H), 3.88 (s, 3H), 4.31 (d, J = 16.63 Hz, 1H), 4.45 (d, J = 8.39 Hz, 1H), 4.57 (d, J = 16.60 Hz, 1H), 5.32-5.49 (m, 1H), 6.40 (dd, J$_1$ = 10.14 Hz, J$_2$ = 1.36 Hz 1H), 6.45 (s, 1H), 6.50 (dd, J$_1$ = 3.1 Hz, J$_2$ = 1.47 Hz 1H), 6.96 (d, J = 8.82 Hz, 2H), 7.13-7.21 (m, 2H), 7.59 (s, 1H), 8.00 (d, J = 8.80 Hz 2H). MASS (ES+): 655.2 |
| IA.128 | 0.88 (t, J = Hz, 3H), 0.99 (d, J = Hz, 3H), 1.11 (s, 3H), 1.22-1.32 (m, 4H), 1.53-1.97 (m, 8H), 2.20-2.46 (m, 6H), 3.36-3.40 (m, 1H), 4.33 (d, J = Hz, 1H), 4.41 (d, J = Hz, 1H), 4.49 (d, J = Hz, 1H), 5.30-5.47 (m, 1H), 6.38 (dd J$_1$ = Hz, J$_2$ = Hz, 1H), 6.43 (s, 1H), 7.13 (dd J$_1$ = Hz, J$_2$ = Hz, 1H), 7.76 (d, J = Hz, 2H), 8.12 (d, J = Hz, 2H). MASS (ES+): 683.2 |
| IA.129 | 0.88 (t, J = 7.32 Hz, 3H), 0.99 (d, J = 7.10 Hz, 3H), 1.11 (s, 3H), 1.19-1.32 (m, 4H), 1.48-1.97 (m, 8H), 2.20-2.48 (m, 6H), 3.36-3.40 (m, 1H), 4.30 (d, J = 16.53 Hz, 1H), 4.41 (d, J = 7.86 Hz, 1H), 4.47 (d, J = 16.56 Hz, 1H), 5.30-5.47 (m, 1H), 6.38 (dd J$_1$ = 10.12 Hz, J$_2$ = 1.53 Hz, 1H), 6.43 (s, 1H), 7.13 (d, J = 10.02 Hz, 1H), 7.47 (d, J = 8.48 Hz, 2H), 7.95 (d, J = 8.48 Hz, 2H). MASS (ES+): 649.3 |
| IA.130 | 0.88 (t, J = 7.32 Hz, 3H), 0.98 (d, J = 7.11 Hz, 3H), 1.13 (s, 3H), 1.18-1.42 (m, 4H), 1.45-1.99 (m, 8H), 2.20-2.46 (m, 6H), 3.36-3.39 (m, 1H), 4.30 (d, J = 17.38 Hz, 1H), 4.41-4.46 (m, 2H), 5.30-5.47 (m, 1H), 6.38 (dd J$_1$ = 10.13 Hz, J$_2$ = 1.55 Hz, 1H), 6.43 (s, 1H), 6.89-6.95 (m, 1H), 6.97-7.01 (m, 1H), 7.13 (d, J = 9.99 Hz, 1H), 7.92-7.98 (m, 1H). MASS (ES+): 651.4 |

TABLE 6-continued

Spectral data for the synthesized compounds

| Comp. No | $^1$H-NMR (δ ppm), MASS (EI/ES+, m/z) |
|---|---|
| IA.131 | 0.88 (t, J = 7.35 Hz, 3H), 0.99 (d, J = 7.12 Hz, 3H), 1.11 (s, 3H), 1.21-1.38 (m, 3H), 1.45-1.99 (m, 9H), 2.20-2.46 (m, 6H), 3.36-3.40 (m, 1H), 4.31 (d, J = 16.51 Hz, 1H), 4.41 (d, J = 7.65 Hz, 1H), 4.49 (d, J = 16.50 Hz, 1H), 5.30-5.47 (m, 1H), 6.38 (dd $J_1$ = 10.12 Hz, $J_2$ = 1.69 Hz, 1H), 6.43 (s, 1H), 7.12-7.18 (m, 3H), 8.03-8.06 (m, 2H). MASS (ES+): 633.4 |
| IA.132 | 0.98 (d, J = 7.04 Hz, 3H), 1.11 (s, 3H), 1.16 (d, J = 5.6 Hz, 6H), 1.30-1.35 (m, 1H), 1.53 (s, 3H), 1.73-2.01 (m, 4H), 2.21-2.60 (m, 5H), 3.37-3.40 (m, 1H), 4.28 (d, J = 16.48 Hz, 1H), 4.42 (d, J = 7.47 Hz, 1H), 4.48 (d, J = 16.59 Hz, 1H), 5.30-5.47 (m, 1H), 6.38 (d, J = 10.17 Hz, 1H), 6.43 (s, 1H), 7.13 (d, J = 10.11 Hz, 1H), 7.473 (d, J = 8.33 Hz, 2H), 7.95 (d, J = 8.39 Hz, 2H). MASS (ES+): 635.2 |
| IA.133 | 0.96 (d, J = 7.13 Hz, 3H), 1.24 (s, 3H), 1.27-1.33 (m, 1H), 1.55 (s, 3H), 1.75-2.06 (m, 6H), 2.19-2.38 (m, 8H), 3.13-3.19 (m, 1H), 3.33-3.37 (m, 1H), 4.41 (d, J = 9.04 Hz, 1H), 5.00 (d, J = 16.54 Hz, 1H), 5.31-5.48 (m, 1H), 5.71 (d, J = 16.57 Hz, 1H), 6.38 (d, d $J_1$ = 10.15 Hz, $J_2$ = 1.70 Hz, 1H), 6.44 (s, 1H), 7.15 (d, d $J_1$ = 9.99 Hz, $J_2$ = 1.10 Hz, 1H), 7.18 (t, J = 8.54 Hz, 2H), 7.94-7.97 (m, 2H). MASS (ES+): 615.1 |
| IA.134 | 0.98 (d, J = 7.16 Hz, 3H), 1.10 (s, 3H), 1.30-1.36 (m, 1H), 1.53 (s, 3H), 1.53-1.98 (m, 12H), 2.23-2.42 (m, 4H), 2.72-2.80 (m, 1H), 3.36-3.40 (m, 1H), 4.33 (d, J = 16.54 Hz, 1H), 4.42 (d, J = 8.83 Hz, 1H), 4.49 (d, J = 16.53 Hz, 1H), 5.30-5.47 (m, 1H), 6.38 (d, d $J_1$ = 10.14 Hz, $J_2$ = 1.80 Hz, 1H), 6.43 (s, 1H), 7.12 (d, d $J_1$ = 10.19 Hz, $J_2$ = 1.24 Hz, 1H), 7.76 (d, J = 8.27 Hz, 2H), 8.11 (d, J = 8.14 Hz, 2H). MASS (ES+): 695.3 |
| IA.135 | 0.99 (d, J = 7.13 Hz, 3H), 1.11 (s, 3H), 1.25-1.32 (m, 1H), 1.52 (s, 3H), 1.72-2.04 (m, 6H), 2.18-2.40 (m, 8H), 3.14-3.16 (m, 1H), 4.31 (d, J = 16.5 Hz, 1H), 4.40 (d, J = 8.48 Hz, 1H), 4.48 (d, J = 16.52 Hz, 1H), 6.37 (d, d $J_1$ = 10.12 Hz, $J_2$ = 1.72 Hz, 1H), 6.43 (s, 1H), 7.12 (d, d $J_1$ = 10.12 Hz, $J_2$ = 0.8 Hz, 1H), 7.47 (d, J = 8.57 Hz, 2H), 7.95 (d, J = 8.59 Hz, 2H). MASS (ES+): 647.2 |
| IA.136 | 0.99 (d, J = 7.12 Hz, 3H), 1.10 (s, 3H), 1.29-1.35 (m, 1H), 1.53 (s, 3H), 1.76-1.99 (m, 6H), 2.17-2.45 (m, 8H), 3.12-3.21 (m, 1H), 3.35-3.41 (m, 1H), 4.33 (d, 1H, J = 16.59 Hz), 4.41 (d, J = 8.63 Hz, 1H), 4.51 (d, 1H, J = 16.56 Hz), 5.30-5.47 (m, 1H), 6.37 (d, d $J_1$ = 10.16 Hz, $J_2$ = 1.61 Hz, 1H), 6.43 (s, 1H), 7.13 (d, d $J_1$ = 10.18 Hz, $J_2$ = 0.73 Hz, 1H), 7.77 (d, J = 8.24 Hz, 2H), 8.12 (d, J = 8.14 Hz, 2H). MASS (ES+): 681.2 |
| IA.137 | 0.98 (d, J = 7.13 Hz, 3H), 1.12 (s, 3H), 1.29-1.35 (m, 1H), 1.53 (s, 3H), 1.70-2.00 (m, 5H), 2.16-2.45 (m, 7H), 3.13-3.18 (m, 1H), 3.36-3.41 (m, 1H), 4.29 (d, d, $J_1$ = 17.52 Hz, $J_2$ = 2.62 Hz, 1H), 4.41 (d, J = 9.87 Hz, 1H), 4.45 (d, d, $J_1$ = 17.67 Hz, $J_2$ = 2.71 Hz, 1H), 5.31-5.47 (m, 1H), 6.38 (d, $J_1$ = 10.12 Hz, $J_2$ = 1.71 Hz, 1H), 6.43 (s, 1H), 6.89-7.02 (m, 2H), 7.14 (d, J = 10.13 Hz, 1H), 7.92-7.98 (m, 1H). MASS (ES+): 649.3 |
| IA.138 | 0.96 (d, J = 7.16 Hz, 3H), 1.11 (s, 3H), 1.29-1.34 (m, 1H), 1.52 (s, 3H), 1.84-2.04 (m, 5H), 2.17-2.39 (m, 8H), 3.14-3.19 (m, 1H), 3.38-3.43 (m, 1H), 3.88 (s, 3H), 4.30 (d, J = 16.51 Hz, 1H), 4.40 (d, J = 8.92 Hz, 1H), 4.53 (d, J = 16.51 Hz, 1H), 5.30-5.47 (m, 1H), 6.37 (d, d $J_1$ = 10.13 Hz, $J_2$ = 1.74 Hz, 1H), 6.43 (s, 1H), 6.96 (d, J = 8.85 Hz, 2H), 7.14 (d, J = 10.11 Hz, 1H), 7.99 (d, J = 8.85 Hz, 2H). MASS (ES+): 643.3 |
| IA.139 | 1.06 (d, J = 7.12 Hz, 3H), 1.17 (s, 3H), 1.33-1.38 (m, 1H), 1.56 (s, 3H), 1.60-1.99 (m, 5H), 2.29-2.65 (m, 4H), 3.41-3.46 (m, 1H), 4.35 (d, 1H, J = 16.58 Hz), 4.46 (d, J = 8.88 Hz, 1H), 4.53 (d, 1H, J = 16.55 Hz), 6.15 (s, 1H), 6.37 (d, d $J_1$ = 10.13 Hz, $J_2$ = 1.68 Hz, 1H), 6.49 (d, d $J_1$ = 3.42 Hz, $J_2$ = 1.65 Hz, 1H), 7.12 (d, J = 3.47 Hz, 1H), 7.22 (d, J = 10.12 Hz, 1H), 7.58 (d, J = 1.48 Hz, 1H), 7.76 (d, J = 8.35 Hz, 2H), 8.12 (d, J = 8.26 Hz, 2H). MASS (ES+): 675.3 |
| IA.140 | 1.05 (d, J = 7.1 Hz, 3H), 1.19 (s, 3H), 1.32-1.37 (m, 1H), 1.55 (s, 3H), 1.60-2.02 (m, 5H), 2.29-2.67 (m, 5H), 3.42-3.47 (m, 1H), 4.31 (dd, $J_1$ = 17.52 Hz, $J_2$ = 2.24 Hz, 1H), 4.46 (d, J = 8.89 Hz, 1H), 4.47 (dd, 1H), 6.15 (s, 1H), 6.37 (d, d $J_1$ = 10.11 Hz, $J_2$ = 1.09 Hz, 1H), 6.48 (d, d $J_1$ = 3.04 Hz, $J_2$ = 1.33 Hz, 1H), 6.88-7.01 (m, 2H), 7.12 (d, J = 3.45 Hz, 1H), 7.23 (d J = 10.12 Hz, 1H), 7.58 (d), 7.95 (d, d $J_1$ = 15.1 Hz, $J_2$ = 8.46 Hz, 1H). MASS (ES+): 643.2 |
| IA.141 | 1.05 (d, J = 7.09 Hz, 3H), 1.17 (s, 3H), 1.25-1.38 (m, 1H), 1.56 (s, 3H), 1.60-2.00 (m, 5H), 2.29-2.65 (m, 4H), 3.43-3.45 (m, 1H), 4.32 (d, 1H, J = 16.52 Hz), 4.45 (d, 1H, J = 9.02 Hz), 4.50 (d, 1H, J = 16.61 Hz), 6.15 (s, 1H), 6.37 (d, d $J_1$ = 10.07 Hz, $J_2$ = 0.81 Hz, 1H), 6.49 (d, J = 3.33 Hz, 1H), 7.12 (d, J = 3.43 Hz, 1H), 7.22 (d, J = 10.12 Hz, 1H), 7.47 (d, J = 8.40 Hz, 2H), 7.58 (s, 1H), 7.95 (d, J = 8.45 Hz, 2H). MASS (ES+): 641.3 |
| IA.142 | 1.06 (d, J = 7.12 Hz, 3H), 1.18 (s, 3H), 1.31-1.37 (m, 1H), 1.56 (s, 3H), 1.60-2.04 (m, 4H), 2.29-2.65 (m, 5H), 3.44-3.48 (m, 1H), 3.88 (s, 3H), 4.33 (d, J = 16.64 Hz, 1H), 4.45 (d, J = 8.94 Hz, 1H), 4.54 (d, J = 16.50 Hz, 1H), 6.15 (s, 1H), 6.36 (d, d $J_1$ = 10.11 Hz, $J_2$ = 1.73 Hz, 1H), 6.49 (d, d $J_1$ = 3.46 Hz, $J_2$ = 1.70 Hz, 1H), 6.95 (d, J = 8.89 Hz, 2H), 7.12 (d J = 13.39 Hz, 1H), 7.23 (d, J = 10.15 Hz, 1H), 7.58 (s, 1H), 7.99 (d, $J_1$ = 8.66 Hz, 2H). MASS (ES+): 637.4 |
| IA.143 | 1.05 (d, J = 7.12 Hz, 3H), 1.18 (s, 3H), 1.25-1.35 (m, 1H), 1.57 (s, 3H), 1.63-1.99 (m, 5H), 2.03-2.64 (m, 5H), 3.45 (m, 1H), 4.32 (d, J = 16.52 Hz, 1H), 4.45 (d, J = 9.01 Hz, 1H), 4.53 (d, J = 16.54 Hz, 1H), 6.15 (s, 1H), 6.37 (d, d $J_1$ = 10.11 Hz, $J_2$ = 1.75 Hz, 1H), 6.49 (d, d $J_1$ = 3.47 Hz, $J_2$ = 1.71 Hz, 1H), 7.13-7.25 (m, 4H), 7.58 (d, J = 0.81 Hz, 1H), 8.03-8.07 (m, 2H). MASS (ES+): 647.2 (M + Na)$^+$ |
| IA.144 | 0.96 (d, J = 7.17 Hz, 3H), 1.04 (s, 3H), 1.15 (d, J = 3.84 Hz, 3H), 1.17 (d, J = 3.86 Hz, 3H), 1.28-1.34 (m, 1H), 1.52 (s, 3H), 1.76-1.89 (m, 4H), 2.25 (s, 6H), 2.28 (s, 3H), 2.22-2.41 (m, 4H), 2.55-2.62 (m, 1H), 3.38-3.43 (m, 1H), 4.03 (d, J = 17.76 Hz, 1H), 4.30 (d, J = 17.79 Hz, 1H), 4.37 (d, J = 8.81 Hz, 1H), 5.30-5.47 (m, 1H), 6.37 (dd, $J_1$ = 10.14 Hz, $J_2$ = 1.86 Hz, 1H), 6.43 (s, 1H), 6.85 (s, 2H), 7.12 (dd, $J_1$ = 10.13 Hz, $J_1$ = 1.29 Hz, 1H). MASS (ES+): 643.5 |
| IA.145 | 0.95 (d, J = 7.15 Hz, 3H), 1.02 (s, 3H), 1.20-1.42 (m, 8H), 1.52 (s, 3H), 1.72-1.89 (m, 6H), 2.25 (s, 6H), 2.28 (s, 3H), 2.25-2.41 (m, 5H), 3.37-3.43 (m, 1H), 4.02 (d, J = 17.62 Hz, 1H), 4.30 (d, J = 17.83 Hz, 1H), 4.38 (d, J = 8.83 Hz, 1H), 5.30-5.47 (m, 1H), 6.38 (dd, $J_1$ = 10.14 Hz, $J_2$ = 1.86 Hz, 1H), 6.44 (s, 1H), 6.85 (s, 2H), 7.13 (dd, $J_1$ = 10.14 Hz, $J_2$ = 1.39 Hz, 1H). MASS (ES+): 705.3 (M + Na)$^+$. |
| IA.146 | 0.96 (d, J = 7.16 Hz, 3H), 1.03 (s, 3H), 1.25-1.34 (m, 1H), 1.52 (s, 3H), 1.76-1.89 (m, 7H), 2.25 (s, 6H), 2.28 (s, 3H), 2.27-2.80 (m, 1H), 3.37-3.43 (m, 1H), 4.03 (d, J = 17.77 Hz, 1H), 4.30 (d, J = 17.77 Hz, 1H), 4.37 (d, J = 8.7 Hz, 1H), 5.30-5.47 (m, 1H), 6.37 (dd, $J_1$ = 10.14 Hz, $J_2$ = 1.82 Hz, 1H), 6.43 (s, 1H), 6.85 (s, 2H), 7.12 (dd, $J_1$ = 10.14 Hz, $J_2$ = 1.12 Hz, 1H). MASS (ES+): 669.4 |
| IA.147 | 0.97 (d, J = 7.17 Hz, 3H), 1.02 (s, 3H), 1.28-1.34 (m, 1H), 1.52 (s, 3H), 1.72-1.97 (m, 6H), 2.18-2.23 (m, 5H), 2.26 (s, 6H), 2.28 (s, 3H), 2.30-2.43 (m, 2H), 3.12-3.20 (m, 1H), 3.38-3.43 (m, 1H), 4.06 (d, J = 17.72 Hz, 1H), 4.29 (d, |

TABLE 6-continued

Spectral data for the synthesized compounds

| Comp. No | $^1$H-NMR ($\delta$ ppm), MASS (EI/ES+, m/z) |
|---|---|
| | J = 17.72 Hz, 1H), 4.37 (d, J = 8.92 Hz, 1H), 5.30-5.47 (m, 1H), 6.38 (dd, J$_1$ = 10.15 Hz, J$_2$ = 1.87 Hz, 1H), 6.43 (s, 1H), 6.85 (s, 2H), 7.11 (dd, J$_1$ = 10.13 Hz, J$_2$ = 1.27 Hz, 1H). MASS (ES+): 655.4 |
| IA.148 | 0.91-0.94 (m, 2H), 0.98 (d, J = 7.11 Hz, 3H), 1.03 (s, 3H), 1.09-1.26 (m, 5H), 1.52-(s, 3H), 1.65-1.75 (m, 8H), 1.83-1.93 (m, 2H), 2.17-2.22 (m, 3H), 2.25 (s, 6H), 2.28 (s, 3H), 2.34-2.38 (m, 1H), 3.37-3.41 (m, 1H), 4.06 (d, J = 17.78 Hz, 1H), 4.27 (d, J = 17.79 Hz, 1H), 4.27 (d,, J = 9.08 Hz, 1H), 5.30-5.46 (m, 1H), 6.38 (d, d, J$_1$ = 10.14 Hz, J$_2$ = 1.85 Hz, 1H), 6.43 (s, 1H), 6.85 (s, 2H), 7.12 (d, d, J$_1$ = 10.12 Hz, J$_2$ = 1.20 Hz, 1H). MASS (ES+): 719.4 (M + Na)$^+$ |
| IA.149 | 1.07 (d, J = 7.13 Hz, 3H), 1.20 (s, 3H), 1.35-1.40 (m, 1H), 1.56 (s, 3H), 1.72-1.98 (m, 3H), 2.25 (s, 6H), 2.28 (s, 3H), 2.32-2.44 (m, 4H), 3.44-3.49 (m, 1H), 4.13 (d, J = 17.69 Hz, 1H), 4.23 (d, J = 17.69 Hz, 1H), 4.40 (d, J = 8.86 Hz, 1H), 4.53-4.55 (m, 1H), 5.34-5.51 (m, 1H), 6.36 (dd, J$_1$ = 10.10 Hz, J$_2$ = 1.79 Hz, 1H), 6.41 (s, 1H), 6.86 (s, 2H), 7.10 (dd, J$_1$ = 4.94 Hz, J$_2$ = 3.81 Hz, 1H), 7.25 (dd, J$_1$ = 10.12 Hz, J$_2$ = 1.05 Hz, 1H), 7.58 (dd, J$_1$ = 4.98 Hz, J$_2$ = 1.15 Hz, 1H), 7.73 (dd, J$_1$ = 3.65 Hz, J$_2$ = 1.16 Hz, 1H). MASS (ES+): 683.9 |
| IA.150 | 0.88-0.94 (m, 2H), 0.99 (d, J = 7.10 Hz, 3H), 1.13 (s, 3H), 1.17-1.35 (m, 4H), 1.53 (s, 3H), 1.64-1.98 (m, 10H), 2.17-2.46 (m, 6H), 3.35-3.39 (m, 1H), 4.30 (d, d, J$_1$ = 15.16 Hz, J$_2$ = 2.50 Hz, 1H), 4.40 (d, 1H), 4.42 (d, d, J$_1$ = 17.58 Hz, J$_2$ = 2.47 Hz, 1H), 5.31-5.45 (m, 1H), 6.38 (d, d, J$_1$ = 10.13 Hz, J$_2$ = 1.65 Hz, 1H), 6.43 (s, 1H), 6.89-7.01 (m, 2H), 7.13 (d, d, J$_1$ = 10.11 Hz, J$_2$ = 1.11 Hz, 1H), 7.92-7.98 (m, 1H). MASS (ES+): 691.5 |
| IA.151 | 0.91-0.97 (m, 2H), 0.99 (d, J = 7.15 Hz, 3H), 1.11 (s, 3H), 1.13-1.35 (m, 4H), 1.52 (s, 3H), 1.61-1.95 (m, 9H), 2.19-2.40 (m, 6H), 3.35-3.40 (m, 1H), 4.33 (d, J = 16.4 Hz, 1H), 4.41 (d, J = 12.88 Hz, 1H), 4.45 (d, J = 16.53 Hz, 1H), 5.30-5.47 (m, 1H), 6.38 (d, d J$_1$ = 10.12 Hz, J$_2$ = 1.80 Hz, 1H), 6.43 (s, 1H), 7.13 (d, d J$_1$ = 10.14 Hz, J$_2$ = 1.27 Hz, 1H), 7.46 (d, J = 8.55 Hz, 2H), 7.94 (d, J = 8.61 Hz, 2H). MASS (ES+): 711.3 (M + Na)$^+$ |
| IA.152 | 0.91-0.97 (m, 2H), 1.00 (d, J = 7.13 Hz, 3H), 1.11 (s, 3H), 1.13-1.36 (m, 4H), 1.53 (s, 3H), 1.61-1.91 (m, 10H), 2.20-2.45 (m, 6H), 3.34-3.40 (m, 1H), 4.35 (d, J = 16.56 Hz, 1H), 4.41 (d, J = 8.94 Hz, 1H), 4.48 (d, J = 16.54 Hz, 1H), 5.30-5.47 (m, 1H), 6.38 (d d J$_1$ = 10.15 Hz, J$_2$ = 1.87 Hz, 1H), 6.43 (s, 1H), 7.12 (d, d, J$_1$ = 10.13 Hz, J$_2$ = 1.26 Hz, 1H), 7.76 (d, J = 8.28 Hz, 2H), 8.11 (d, J = 8.16 Hz, 2H). MASS (ES+): 723.1 |
| IA.153 | 0.91-0.97 (m, 2H), 1.00 (d, J = 7.11 Hz, 3H), 1.12 (s, 3H), 1.09-1.36 (m, 4H), 1.52 (s, 3H), 1.61-1.87 (m, 10H), 2.20-2.39 (m, 6H), 3.37-3.42 (m, 1H), 3.88 (s, 3H), 4.34 (d, J = 16.49 Hz, 1H), 4.40 (d, J = 9.19 Hz, 1H), 4.48 (d, J = 16.43 Hz, 1H), 5.30-5.47 (m, 1H), 6.37 (d, d J$_1$ = 10.14 Hz, J$_2$ = 1.76 Hz, 1H), 6.43 (s, 1H), 6.95 (d, J = 8.87 Hz, 2H), 7.13 (d, d, J$_1$ = 10.13 Hz, J$_2$ = 1.02 Hz, 1H), 7.99 (d, J = 8.89 Hz, 2H). MASS (ES+): 707.3 (M + Na)$^+$ |
| IA.154 | 0.89 (t, J = 7.34 Hz, 3H), 0.97 (d, J = 7.10 Hz, 3H), 1.03 (s, 3H), 1.25-1.96 (m, 8H), 2.09-2.40 (m, 15H), 3.38-3.42 (m, 1H), 4.05 (d, J = 17.80 Hz, 1H), 4.29 (d, J = 17.72 Hz, 1H), 4.39 (d, J = 7.99 Hz, 1H), 5.30-5.47 (m, 1H), 6.39 (dd J$_1$ = 10.10 Hz, J$_2$ = 1.65 Hz, 1H), 6.43 (s, 1H), 6.85 (s, 2H), 7.13 (d, J = 10.07 Hz, 1H). MASS (ES+): 657.3 |
| IA.155 | 1.03 (s, 3H), 1.06 (d, J = 7.19 Hz, 3H), 1.26 (t, J = 7.09 Hz, 3H), 1.32-1.94 (m, 10H), 2.22-2.44 (m, 12H), 3.37-3.42 (m, 1H), 4.04-4.18 (m, 3H), 4.30 (d, J = 17.74 Hz, 1H), 4.36-4.38 (m, 1H), 5.30-5.45 (m, 1H), 6.37 (dd, J$_1$ = 10.14 Hz, J$_2$ = 1.67 Hz, 1H), 6.42 (s, 1H), 6.86 (s, 2H), 7.12 (d, J = 10.21 Hz, 1H). MASS (ES+): 645.1 |
| IA.156 | 1.06 (d, J = 7.19 Hz, 3H), 1.11 (s, 3H), 1.25-1.97 (m, 8H), 2.25 (s, 6H), 2.28 (s, 3H), 2.30-2.53 (m, 3H), 3.46-3.51 (m, 1H), 4.07 (d, J = 17.84 Hz, 1H), 4.31 (d, J = 17.82 Hz, 1H), 5.34-5.46 (m, 1H), 6.41 (dd, J$_1$ = 10.14 Hz, J$_2$ = 1.87 Hz, 1H), 6.51 (dd, J$_1$ = 3.50 Hz, J$_2$ = 1.73 Hz, 1H), 6.85 (s, 2H), 7.12-7.16 (m, 2H), 7.59 (d, J = 1.01 Hz, 1H). MASS (ES+): 667.3 |
| IA.157 | 1.07 (d, J = 7.10 Hz, 3H), 1.17 (s, 3H), 1.21-2.03 (m, 8H), 2.17-2.55 (m, 4H), 3.45-3.48 (m, 1H), 4.32 (d, J = 16.56 Hz, 1H), 4.46 (d, J = 8.46 Hz, 1H), 4.51 (d, J = 15.90 Hz, 1H), 5.7-5.49 (m, 1H), 6.40 (dd, J$_1$ = 10.14 Hz, J$_2$ = 1.70 Hz 1H), 6.45 (s, 1H), 6.51 (dd, J$_1$ = 3.44 Hz, J$_2$ = 1.67 Hz 1H), 7.13-7.16 (m, 2H), 7.47 (d, J = 8.56 Hz, 2H), 7.59 (s, 1H), 7.96 (d, J = 8.59 Hz 2H). MASS (ES+): 659.5 |
| IA.158 | 0.97 (s, 3H), 1.14 (t, J = 7.54 Hz, 3H), 1.19-1.25 (m, 1H), 1.38 (d, J = 7.35 Hz, 3H), 1.54 (s, 3H), 1.92-2.14 (m, 4H), 2.26-2.48 (m, 5H), 3.97 (d, J = 16.90 Hz, 1H), 4.45 (d, J = 8.33 Hz, 1H), 4.56 (d, J = 16.89 Hz, 1H), 5.31-5.48 (m, 1H), 6.38 (dd J$_1$ = 10.14 Hz, J$_2$ = 1.85 Hz 1H), 6.44 (s, 1H), 7.14 (dd J$_1$ = 10.12 Hz, J$_2$ = 1.22 Hz, 1H), 7.47 (d, J = 8.60 Hz, 2H), 7.93 (d, J = 8.59 Hz, 2H). MASS (ES+): 643.3 (M + Na)$^+$ |
| IA.159 | 1.08 (d, J = 7.14 Hz, 3H), 1.17 (s, 3H), 1.37-1.42 (m, 1H), 1.55 (s, 3H), 1.78-1.94 (m, 4H), 2.00-2.57 (m, 4H), 3.44-3.49 (m, 1H), 4.37 (d, J = 16.62 Hz, 1H), 4.47 (d, J = 6.55 Hz, 1H), 4.53 (d, J = 16.57 Hz, 1H), 5.33-5.55 (m, 1H), 6.40 (d, d J$_1$ = 10.15 Hz, J$_2$ = 1.80 Hz, 1H), 6.46 (s, 1H), 7.11 (d, d J$_1$ = 4.95 Hz, J$_2$ = 3.87 Hz, 1H), 7.15 (d, J = 10.14 Hz, 1H), 7.58 (d, d J$_1$ = 5.02 Hz, J$_2$ = 1.10 Hz, 1H), 7.74 (d, d J$_1$ = 3.85 Hz, J$_2$ = 1.12 Hz, 1H), 7.76 (d, J = 8.39 Hz, 2H), 8.10 (d, J = 8.23 Hz, 2H). MASS (ES+): 709.3 |
| IA.160 | 0.99 (d, J = 7.10 Hz, 3H), 1.09 (s, 3H), 1.11 (t, J = 7.59 Hz, 3H), 1.31-1.36 (m, 1H), 1.53 (s, 3H), 1.72-1.97 (m, 4H), 2.23-2.44 (m, 6H), 3.32-3.37 (m, 1H), 4.38-4.48 (m, 3H), 5.30-5.47 (m, 1H), 6.38 (d, J$_1$ = 10.14 Hz, J$_2$ = 1.5 Hz, 1H), 6.43 (s, 1H), 7.13 (d, J = 10.08 Hz, 1H), 7.72 (t, J = 7.99 Hz, 1H), 8.34 (d, J = 7.78 Hz, 1H), 8.46 (d, J$_1$ = 8.17 Hz, J$_2$ = 1.14 Hz, 1H), 8.82 (s, 1H). MASS (ES+): 654.3 (M + Na)$^+$ |
| IA.161 | 0.99 (d, J = 7.16 Hz, 3H), 1.12 (t, J = 7.58 Hz, 3H), 1.13 (s, 3H), 1.31-1.35 (m, 1H), 1.52 (s, 3H), 1.76-2.01 (m, 3H), 2.23-2.45 (m, 6H), 2.32 (s, 3H), 2.33 (s, 3H), 3.38-3.43 (m, 1H), 4.34 (d, J = 16.65 Hz, 1H), 4.39-4.41 (m, 1H), 4.52 (d, J = 16.66 Hz, 1H), 5.30-5.47 (m, 1H), 6.37 (dd, J$_1$ = 10.14 Hz, J$_2$ = 1.81 Hz, 1H), 6.43 (s, 1H), 7.13 (dd, J$_1$ = 10.13 Hz, J$_2$ = 1.23 Hz, 1H), 7.24 (d, J = 7.86 Hz, 1H), 7.74 (dd, J$_1$ = 8.51 Hz, J$_2$ = 1.38 Hz, 1H), 7.77 (s, 1H). MASS (ES+): 615.4 |
| IA.162 | 0.97 (s, 3H), 1.14 (t, J = 7.51 Hz, 3H), 1.21-1.27 (m, 1H), 1.38 (d, J = 7.37 Hz, 3H), 1.54 (s, 3H), 1.73-2.12 (m, 5H), 2.26-2.50 (m, 6H), 4.01 (d, 1H, J = 16.98 Hz), 4.46 (d, J = 8.09 Hz, 1H), 4.58 (d, J = 16.98 Hz, 1H), 5.31-5.48 (m, 1H), 6.38 (dd, J$_1$ = 10.11 Hz, J$_2$ = 1.78 Hz, 1H), 6.44 (s, 1H), 7.13 (dd, J$_1$ = 10.17 Hz, J$_2$ = 1.27 Hz, 1H), 7.77 (d, J = 8.35 Hz, 2H), 8.09 (d, J = 8.05 Hz, 2H). MASS (ES+): 655.4 |

TABLE 6-continued

Spectral data for the synthesized compounds

| Comp. No | $^1$H-NMR (δ ppm), MASS (EI/ES+, m/z) |
|---|---|
| IA.163 | 0.93 (t, J = 7.36 Hz, 3H), 1.00 (d, J = 7.20 Hz, 3H), 1.11 (s, 3H), 1.25-1.97 (m, 10H), 2.20-2.41 (m, 6H), 3.35-3.39 (m, 1H), 4.33 (d, J = 16.58 Hz, 1H), 4.41 (d, J = 8.84 Hz, 1H), 4.50 (d, J = 16.57 Hz, 1H), 5.30-5.47 (m, 1H), 6.38 (dd $J_1$ = 10.14 Hz, $J_2$ = 1.81 Hz, 1H), 6.43 (s, 1H), 7.12 (dd $J_1$ = 10.12 Hz, $J_2$ = 1.17 Hz, 1H), 7.76 (d, J = 8.29 Hz, 2H), 8.12 (d, J = 8.12 Hz, 2H). MASS (ES+): 669.3 |
| IA.164 | 0.94 (t, J = 7.40 Hz, 3H), 0.99 (d, J = 7.15 Hz, 3H), 1.11 (s, 3H), 1.24-1.98 (m, 10H), 2.22-2.41 (m, 6H), 3.36-3.40 (m, 1H), 4.29 (d, J = 16.51 Hz, 1H), 4.41 (d, J = 8.74 Hz, 1H), 4.47 (d, J = 16.54 Hz, 1H), 5.30-5.47 (m, 1H), 6.37 (dd $J_1$ = 10.12 Hz, $J_2$ = 1.75 Hz, 1H), 6.43 (s, 1H), 7.13 (dd $J_1$ = 10.12 Hz, $J_2$ = 1.14 Hz, 1H), 7.46-7.48 (m, 2H), 7.95 (d, J = 8.61 Hz, 2H). MASS (ES+): 635.3 |
| IA.165 | 0.94 (t, J = 7.39 Hz, 3H), 0.99 (d, J = 7.16 Hz, 3H), 1.13 (s, 3H), 1.22-2.01 (m, 10H), 2.20-2.45 (m, 6H), 3.36-3.40 (m, 1H), 4.30 (d, J = 16.52 Hz, 1H), 4.28 (dd $J_1$ = 17.53 Hz, $J_2$ = 2.68 Hz), 4.42-4.47 (m, 2H), 5.30-5.47 (m, 1H), 6.38 (dd $J_1$ = 10.14 Hz, $J_2$ = 1.76 Hz, 1H), 6.43 (s, 1H), 6.89-7.01 (m, 2H), 7.12-7.15 (m, 1H), 7.92-7.98 (m, 1H). MASS (ES+): 637.3 |
| IA.166 | 0.94 (t, J = 7.36 Hz, 3H), 0.99 (d, J = 7.16 Hz, 3H), 1.11 (s, 3H), 1.24-1.99 (m, 10H), 2.20-2.41 (m, 6H), 3.37-3.41 (m, 1H), 4.30 (d, J = 16.52 Hz, 1H), 4.41 (d, J = 8.86 Hz, 1H), 4.49 (d, J = 16.51 Hz, 1H), 5.30-5.47 (m, 1H), 6.38 (dd $J_1$ = 10.14 Hz, $J_2$ = 1.74 Hz, 1H), 6.43 (s, 1H), 7.12-7.18 (m, 3H), 8.03-8.06 (m, 2H). MASS (ES+): 619.4 |
| IA.167 | 0.94 (t, J = 7.40 Hz, 3H), 0.99 (d, J = 7.15 Hz, 3H), 1.20 (s, 3H), 1.17-1.87 (m, 10H), 2.20-2.45 (m, 6H), 3.38-3.43 (m, 1H), 3.88 (s, 3H), 4.30 (d, J = 16.44 Hz, 1H), 4.41 (d, J = 9.06 Hz, 1H), 4.52 (d, J = 16.51 Hz, 1H), 5.30-5.47 (m, 1H), 6.38 (dd $J_1$ = 10.15 Hz, $J_2$ = 1.85 Hz, 1H), 6.43 (s, 1H), 6.94-6.97 (m, 2H), 7.13 (dd $J_1$ = 10.12 Hz, $J_2$ = 1.21 Hz 1H), 7.98-8.00 (m, 2H). MASS (ES+): 631.3 |
| IA.168 | 1.07 (d, J = 7.15 Hz, 3H), 1.16 (s, 3H), 1.35-1.41 (m, 1H), 1.55 (s, 3H), 1.74-2.03 (m, 4H), 2.28-2.55 (m, 1H), 3.43-3.48 (m, 1H), 4.33 (d, J = 16.67 Hz, 1H), 4.46 (d, J = 11.14 Hz, 1H), 4.49 (d, J = 16.89 Hz, 1H), 5.32-5.49 (m, 1H), 6.40 (dd, $J_1$ = 10.14 Hz, $J_2$ = 1.69 Hz 1H), 6.45 (s, 1H), 6.50 (dd, $J_1$ = 3.47 Hz, $J_2$ = 1.69 Hz, 1H), 7.13 (d, J = 2.81 Hz, 1H), 7.14 (dd, $J_1$ = 9.98 Hz, $J_2$ = 1.20 Hz 1H), 7.45 (t, J = 7.89 Hz, 1H), 7.57 (dd, $J_1$ = 1.86 Hz, $J_2$ = 0.89 Hz, 1H), 7.59 (m, 1H), 7.88-7.91 (m, 1H), 7.98 (t, J = 1.75 Hz, 1H). MASS (ES+): 681.3 (M + Na)$^+$ |
| IA.169 | 1.03 (s, 3H), 1.13-1.36 (m, 1H), 1.43 (d, J = 7.23 Hz, 3H), 1.56 (s, 3H), 1.77-2.23 (m, 5H), 2.31-2.67 (m, 4H), 3.97 (d, 1H, J = 17.00 Hz), 4.53 (d, J = 7.38 Hz, 1H), 4.62 (d, J = 17.03 Hz, 1H), 5.24-5.57 (m, 1H), 6.41 (d, J = 10.09 Hz, 1H), 6.44 (s, 1H), 6.53 (dd $J_1$ = 3.24 Hz, $J_2$ = 1.49 Hz, 1H), 7.17 (d, J = 9.71 Hz, 1H), 7.20 (d, J = 3.03 Hz, 1H), 7.62 (s, 1H), 7.76 (d, J = 8.15 Hz, 2H), 8.09 (d, J = 8.09 Hz, 2H). MASS (ES+): 693.2 |
| IA.170 | 1.07 (d, J = 7.13 Hz, 3H), 1.17 (s, 3H), 1.35-1.41 (m, 1H), 1.54 (s, 3H), 1.76-2.04 (m, 4H), 2.28-2.54 (m, 4H), 3.45-3.50 (m, 1H), 3.83 (s, 3H), 4.36 (d, 1H, J = 16.61 Hz), 4.45 (d, J = 8.19 Hz, 1H), 4.51 (d, J = 16.68 Hz, 1H), 5.32-5.49 (m, 1H), 6.39 (dd, $J_1$ = 10.15 Hz, $J_2$ = 1.84 Hz, 1H), 6.45 (s, 1H), 6.50 (dd, $J_1$ = 3.50 Hz, $J_2$ = 1.70 Hz, 1H), 6.68 (t, J = 2.27 Hz, 1H), 7.13-7.17 (m, 4H), 7.59 (m, 1H). MASS (ES+): 685.2 |
| IA.171 | 1.07 (d, J = 7.12 Hz, 3H), 1.17 (s, 3H), 1.34-1.42 (m, 1H), 1.55 (s, 3H), 1.73-1.99 (m, 4H), 2.28-2.55 (m, 4H), 3.41-3.47 (m, 1H), 4.35 (d, 1H, J = 16.49 Hz), 4.46 (d, J = 8.61 Hz, 1H), 4.52 (d, J = 16.49 Hz, 1H), 5.33-5.49 (m, 1H), 6.40 (dd, $J_1$ = 10.12 Hz, $J_2$ = 1.73 Hz, 1H), 6.45 (s, 1H), 6.51 (dd, $J_1$ = 3.47 Hz, $J_2$ = 1.71 Hz, 1H), 7.13 (d, J = 3.46 Hz, 1H), 7.14 (d, J = 10.8 Hz, 1H), 7.59-7.60 (m, 1H), 8.17 (d, J = 8.8 Hz, 2H), 8.34 (d, J = 8.72 Hz, 2H). MASS (ES+): 692.3 (M + Na)$^+$ |
| IA.172 | 1.03 (d, J = 7.16 Hz, 3H), 1.13 (s, 3H), 1.33-1.38 (m, 1H), 1.52 (s, 3H), 1.66-1.96 (m, 4H), 2.18-2.38 (m, 4H), 3.36-3.43 (m, 1H), 3.41 (s, 3H), 4.05 (s, 2H), 4.35 (d, 1H, J = 16.67 Hz), 4.40 (d, J = 9.01 Hz, 1H), 4.49 (d, J = 16.66 Hz, 1H), 5.30-5.47 (m, 1H), 6.37 (dd, $J_1$ = 10.12 Hz, $J_2$ = 1.73 Hz, 1H), 6.43 (s, 1H), 7.11 (dd, $J_1$ = 10.11 Hz, $J_2$ = 1.01 Hz, 1H), 7.77 (d, J = 8.33 Hz, 2H), 8.11 (d, J = 8.18 Hz, 2H). MASS (ES+): 693.3 (M + Na)$^+$ |
| IA.173 | 1.01 (d, J = 7.14 Hz, 3H), 1.07 (s, 3H), 1.31-1.35 (m, 1H), 1.52 (s, 3H), 1.75-1.95 (m, 4H), 2.19-2.35 (m, 4H), 2.25 (s, 6H), 2.28 (s, 3H), 3.41 (s, 3H), 3.41-3.49 (m, 1H), 4.05 (s, 3H), 4.07 (d, J = 13.34 Hz, 1H), 4.27 (d, J = 17.85 Hz, 1H), 4.37 (d, J = 8.64 Hz, 1H), 5.30-5.46 (m, 1H), 6.37 (dd, $J_1$ = 10.13 Hz, $J_2$ = 1.65 Hz, 1H), 6.43 (s, 1H), 6.86 (s, 2H), 7.12 (d, $J_1$ = 10.09 Hz, 1H). MASS (ES+): 667.2 (M + Na)$^+$ |
| IA.174 | 0.99 (d, J = 7.00 Hz, 3H), 1.10-1.14 (m, 6H), 1.22-1.97 (m, 8H), 2.20-2.45 (m, 6H), 3.35-3.39 (m, 1H), 4.27 (d, J = 16.36 Hz, 1H), 4.40-4.45 (m, 2H), 5.30-5.47 (m, 1H), 6.37 (dd, $J_1$ = 10.14 Hz, $J_2$ = 1.74 Hz 1H), 6.43 (s, 1H), 7.13 (dd, $J_1$ = 10.15 Hz, $J_2$ = 0.90 Hz 1H), 7.24-7.28 (m, 1H), 7.91-7.95 (m, 1H), 8.08-8.10 (m, 1H). MASS (ES+): 639.4 |
| IA.175 | 0.91 (s, 3H), 1.25-1.27 (m, 1H), 1.44 (d, J = 7.23 Hz, 3H), 1.55 (s, 3H), 1.74-2.17 (m, 4H), 2.23 (s, 6H), 2.28 (s, 3H), 2.31-2.58 (m, 4H), 3.69 (d, J = 17.64 Hz, 1H), 4.43 (d, J = 17.63 Hz, 1H), 4.46 (d, J = 11.28 Hz, 1H), 5.32-5.48 (m, 1H), 6.40 (dd, $J_1$ = 10.11 Hz, $J_2$ = 1.68 Hz, 1H), 6.44 (s, 1H), 6.52 (dd, $J_1$ = 3.63 Hz, $J_1$ = 1.51 Hz, 1H), 6.85 (s, 2H), 7.16 (dd, $J_1$ = 10.15 Hz, J2 = 0.99 Hz, 1H), 7.19 (d, J = 3.31 Hz, 1H), 7.61 (d, J = 0.79 Hz, 1H). MASS (ES+): 667.1 |
| IA.176 | 1.01 (d, J = 7.14 Hz, 3H), 1.06 (s, 3H), 1.21 (d, J = 7.00 Hz, 3H), 1.32-1.36 (m, 1H), 1.52 (s, 3H), 1.75-1.94 (m, 4H), 2.25 (s, 6H), 2.28 (s, 3H), 2.20-2.36 (m, 4H), 3.35-3.45 (m, 1H), 3.54 (q, J = 7.02 Hz, 2H), 4.06 (d, J = 17.75 Hz, 1H), 4.09 (s, 2H), 4.26 (d, J = 17.82 Hz, 1H), 4.36 (d, J = 8.94 Hz, 1H), 5.29-5.47 (m, 1H), 6.37 (dd, $J_1$ = 10.14 Hz, $J_2$ = 1.78 Hz, 1H), 6.43 (s, 1H), 6.86 (s, 2H), 7.10 (dd, $J_1$ = 10.11 Hz, $J_2$ = 0.82 Hz, 1H). MASS (ES+): 659.1 |
| IA.177 | 1.03 (d, J = 7.13 Hz, 3H), 1.13 (s, 3H), 1.21 (t, J = 7.00 Hz, 3H), 1.32-1.37 (m, 1H), 1.52 (s, 3H), 1.68-1.95 (m, 4H), 2.20-2.45 (m, 4H), 3.38-3.43 (m, 1H), 3.54 (qd, $J_1$ = 6.98 Hz, $J_2$ = 1.49 Hz, 2H), 4.09 (s, 2H), 4.25 (d, J = 16.66 Hz, 1H), 4.40 (d, J = 10.48 Hz, 1H), 4.49 (d, J = 16.63 Hz, 1H), 5.30-5.46 (m, 1H), 6.37 (dd, $J_1$ = 10.15 Hz, $J_2$ = 1.72 Hz, 1H), 6.43 (s, 1H), 7.11 (dd, $J_1$ = 10.11 Hz, $J_2$ = 0.73 Hz, 1H), 7.77 (d, J = 8.28 Hz, 2H), 8.11 (d, J = 8.15 Hz, 2H). MASS (ES+): 685.1 |
| IA.178 | 1.07 (d, J = 7.12 Hz, 3H), 1.19 (s, 3H), 1.31-1.40 (m, 1H), 1.55 (s, 3H), 1.77-2.06 (m, 4H), 2.21-2.54 (m, 4H), 2.37 (s, 6H), 3.46-3.50 (m, 1H), 4.35 (d, J = 16.85 Hz, 1H), 4.45 (d, J = 8.6 Hz, 1H), 4.56 (d, J = 16.77 Hz, 1H), 5.32-5.49 (m, 1H), 6.39 (dd, $J_1$ = 10.15 Hz, $J_2$ = 1.7 Hz, 1H), 6.45 (s, 1H), 6.50 (dd, $J_1$ = 3.43 Hz, $J_2$ = 1.68 Hz, 1H), 7.13 (s, 1H), 7.14 (s, 1H), 7.16 (dd, $J_1$ = 11.79 Hz, $J_2$ = 0.67 Hz, 1H), 7.24 (s, 1H), 7.59 (s, 1H), 7.61 (s, 1H). MASS (ES+): 653.1 |

TABLE 6-continued

Spectral data for the synthesized compounds

| Comp. No | $^1$H-NMR (δ ppm), MASS (EI/ES+, m/z) |
|---|---|
| IA.179 | 1.08 (d, J = 7.11 Hz, 3H), 1.16 (s, 3H), 1.33-1.41 (s, 1H), 1.53 (s, 3H), 1.71-2.04 (m, 4H), 2.28-2.51 (m, 4H), 3.46-3.51 (m, 1H), 4.44 (d, J = 8.45 Hz, 1H), 4.53 (d, J = 16.43 Hz, 1H), 4.69 (d, J = 16.48 Hz, 1H), 5.31-5.48 (m, 1H), 6.39 (dd, $J_1$ = 10.15 Hz, $J_2$ = 1.84 Hz 1H), 6.45 (s, 1H), 6.50 (dd, $J_1$ = 3.48 Hz, $J_2$ = 1.69 Hz, 1H), 7.13 (s, 1H), 7.14 (dd, $J_1$ = 8.47 Hz, $J_2$ = 1.99 Hz 1H), 7.56-7.65 (m, 3H), 7.87-8.04 (m, 4H), 8.58 (s, 1H). MASS (ES+): 675.1 |
| IA.180 | 0.98 (s, 3H), 1.06 (d, J = 7.15 Hz, 3H), 1.33-1.39 (m, 1H), 1.51 (s, 3H), 1.71-1.93 (m, 4H), 2.35-2.49 (m, 4H), 3.42-3.47 (m, 1H), 4.37 (d, J = 13.12 Hz, 1H), 4.39 (d, J = 4.87 Hz, 1H), 4.59 (d, J = 16.48 Hz, 1H), 5.30-5.47 (m, 1H), 6.37 (dd, $J_1$ = 10.12 Hz, $J_2$ = 1.80 Hz 1H), 6.44 (s, 1H), 6.50 (dd, $J_1$ = 3.14 Hz, $J_2$ = 1.36 Hz, 1H), 7.11 (dd, $J_1$ = 6.33 Hz, $J_2$ = 1.21 Hz, 1H), 7.13 (s, 1H), 7.52-7.61 (m, 4H), 7.89 (dd, $J_1$ = 8.54 Hz, $J_2$ = 1.43 Hz 1H), 8.02 (d, J = 8.22 Hz, 1H), 8.07 (dd, $J_1$ = 7.22 Hz, $J_2$ = 0.94 Hz, 1H), 8.49 (d, J = 8.42 Hz, 1H). MASS (ES+): 674.9 |
| IA.181 | 1.06 (d, J = 7.10 Hz, 3H), 1.16 (s, 3H), 1.34-1.42 (m, 1H), 1.54 (s, 3H), 1.65-2.02 (m, 4H), 2.29 (s, 3H), 2.24-2.61 (m, 4H), 3.44-3.49 (m, 1H), 4.37 (d, 1H, J = 16.53 Hz), 4.44 (d, J = 8.48 Hz, 1H), 4.53 (d, J = 16.5 Hz, 1H), 5.31-5.48 (m, 1H), 6.34 (d, J = 1.44 Hz, 1H), 6.38 (dd $J_1$ = 10.12 Hz, $J_2$ = 1.75 Hz, 1H), 6.44 (s, 1H), 7.13 (dd $J_1$ = 10.11 Hz, $J_2$ = 1.05 Hz, 1H), 7.44 (d, J = 1.43 Hz, 1H), 7.76 (d, J = 8.26 Hz, 2H), 8.12 (d, J = 8.13 Hz, 2H). MASS (ES+): 707.2 |
| IA.182 | 1.05 (d, J = 7.13 Hz, 3H), 1.09 (s, 3H), 1.36-1.43 (m, 1H), 1.54 (s, 3H), 1.75-2.00 (m, 4H), 2.26 (s, 6H), 2.28 (s, 3H), 2.30 (s, 3H), 2.41-2.60 (m, 4H), 3.47-3.50 (m, 1H), 4.09 (d, J = 17.81 Hz, 1H), 4.32 (d, J = 17.76 Hz, 1H), 4.41 (d, J = 8.28 Hz, 1H), 5.32-5.48 (m, 1H), 6.34 (d, J = 1.21 Hz, 1H), 6.38 (dd, $J_1$ = 10.16 Hz, $J_2$ = 1.66 Hz, 1H), 6.44 (s, 1H), 6.85 (s, 2H), 7.14 (d, J = 10.11 Hz), 7.43 (d, J = 1.18 Hz, 1H). MASS (ES+): 681.1 |
| IA.183 | 1.07 (d, J = 7.10 Hz, 3H), 1.12 (s, 3H), 1.32-1.42 (m, 1H), 1.54 (s, 3H), 1.73-2.00 (m, 4H), 2.27-2.53 (m, 4H), 3.40-3.44 (m, 1H), 4.05 (s, 3H), 4.39 (s, 2H), 4.46 (d, J = 8.45 Hz, 1H), 5.32-5.48 (m, 1H), 6.40 (dd, $J_1$ = 10.12 Hz, $J_2$ = 1.68 Hz, 1H), 6.45 (s, 1H), 6.50 (dd, $J_1$ = 3.44 Hz, $J_2$ = 1.68 Hz, 1H), 7.13 (s, 1H), 7.15 (dd, $J_1$ = 11.15 Hz, $J_2$ = 0.94 Hz, 1H), 7.19 (d, J = 8.88 Hz, 1H), 7.59 (d, J = 0.69 Hz, 1H), 8.22 (dd, $J_1$ = 8.81 Hz, $J_2$ = 2.16 Hz, 1H), 8.49 (d, J = 2.15 Hz, 1H). MASS (ES+): 700.1 |
| IA.184 | 1.07 (d, J = 7.16 Hz, 3H), 1.18 (s, 3H), 1.32-1.40 (m, 1H), 1.55 (s, 3H), 1.73-2.08 (m, 4H), 2.25-2.43 (m, 4H), 2.32 (s, 3H), 2.32 (s, 3H), 3.46-3.51 (m, 1H), 4.34 (d, J = 16.73 Hz, 1H), 4.45 (d, J = 8.08 Hz, 1H), 4.57 (d, J = 16.76 Hz, 1H), 5.32-5.49 (m, 1H), 6.39 (dd $J_1$ = 10.14 Hz, $J_2$ = 1.82 Hz, 1H), 6.45 (s, 1H), 6.50 (dd, $J_1$ = 3.53 Hz, $J_2$ = 1.74 Hz, 1H), 7.13 (dd, $J_1$ = 3.63 Hz, $J_2$ = 0.62 Hz, 1H), 7.16 (dd, $J_1$ = 10.14 Hz, $J_2$ = 1.18 Hz, 1H), 7.24 (d, J = 7.87 Hz, 1H), 7.59 (m, 1H), 7.74 (dd, $J_1$ = 8.69 Hz, $J_2$ = 1.66 Hz, 1H), 7.77 (s, 1H). MASS (ES+): 653.5.(M + H)$^+$ |
| IA.185 | 1.05 (d, J = 7.17 Hz, 3H), 1.16 (s, 3H), 1.14-1.40 (m, 1H), 1.54 (s, 3H), 1.72-2.03 (m, 4H), 2.29-2.48 (m, 4H), 3.42-3.47 (m, 1H), 4.35 (d, 1H, J = 16.60 Hz), 4.46 (d, J = 8.55 Hz, 1H), 4.53 (d, J = 16.65 Hz, 1H), 5.32-5.49 (m, 1H), 6.39 (dd $J_1$ = 10.14 Hz, $J_2$ = 1.84 Hz, 1H), 6.45 (s, 1H), 6.65 (d, J = 1.52 Hz, 1H), 7.13 (dd $J_1$ = 10.12 Hz, $J_2$ = 1.21 Hz, 1H), 7.42 (t, J = 1.70 Hz, 1H), 7.76 (d, J = 8.27 Hz, 2H), 7.97 (d, J = 0.75 Hz, 1H), 8.12 (d, J = 8.08 Hz, 2H). MASS (ES+): 693.2.(M + H)$^+$ |
| IA.186 | 1.04 (d, J = 7.12 Hz, 3H), 1.10 (s, 3H), 1.33-1.38 (m, 1H), 1.54 (s, 3H), 1.75-2.04 (m, 4H), 2.25 (s, 6H), 2.28 (s, 3H), 2.17-2.46 (m, 4H), 3.46-3.49 (m, 1H), 4.09 (d, J = 17.58 Hz, 1H), 4.30 (d, J = 17.79 Hz, 1H), 4.42 (d, J = 7.85 Hz, 1H), 5.32-5.48 (m, 1H), 6.40 (dd, $J_1$ = 10.12 Hz, $J_2$ = 1.70 Hz, 1H), 6.45 (s, 1H), 6.65 (d, J = 1.50 Hz, 1H), 6.85 (s, 2H), 7.13 (dd, $J_1$ = 10.09 Hz, $J_1$ = 0.79 Hz, 1H), 7.42 (t, J = 1.40 Hz, 1H), 7.97 (s, 1H). MASS (ES+): 667.1 (M + H)$^+$ |
| IA.187 | 0.44 (s, 3H), 0.95 (d, J = 7.02 Hz, 3H), 1.08 (t, J = 7.53 Hz, 3H), 1.22-1.75 (m, 15H), 2.17-2.32 (m, 6H), 3.15 (m, 1H), 4.29 (d, J = 6.81 Hz, 1H), 5.40 (m, 1H), 6.35 (dd, $J_1$ = 10.11 Hz, $J_2$ = 1.43 Hz 1H), 6.40 (s, 1H), 7.05 (d, J = 9.98 Hz 1H), 7.36 (t, J = 7.70 Hz, 2H), 7.46 (t, J = 7.20 Hz, 1H), 7.95 (d, J = 7.43 Hz, 2H). MASS (ES+): 705.4 (M + Na)$^+$ |
| IA.188 | 0.60 (s, 3H), 0.93 (d, J = 7.04 Hz, 3H), 1.06 (t, J = 7.54 Hz, 3H), 1.10-1.89 (m, 14H), 2.09-2.36 (m, 6H), 3.14-3.17 (m, 1H), 4.30 (d, J = 7.66 Hz, 1H), 5.26-5.43 (m, 1H), 6.34 (dd, $J_1$ = 10.14 Hz, $J_2$ = 1.67 Hz 1H), 6.41 (s, 1H), 7.06 (m, 3H), 8.02-8.05 (m, 2H). MASS (ES+): 655.5 (M + Na)$^+$. |
| IA.199 | 0.42 (s, 3H), 0.93 (d, J = 7.1 Hz, 3H), 1.08 (t, J = 7.57 Hz, 3H), 1.20-1.25 (m, 1H), 1.49 (s, 3H), 1.51-1.79 (m, 4H), 1.75 (s, 6H), 1.80-2.37 (m, 7H), 3.31 (m, 1H), 4.28 (d, J = 8.59 Hz, 1H), 6.10 (s, 1H), 6.31 (d, d $J_1$ = 10.12 Hz, $J_2$ = 1.80 Hz, 1H), 7.13 (d, J = 10.14 Hz, 1H), 7.38 (t, J = 7.53 Hz, 2H), 7.45-7.47 (m, 1H), 7.95-7.97 (m, 1H). MASS (ES+): 619.6 (M + Na)$^+$. |
| IA.190 | 0.44 (s, 3H), 0.82-1.15 (m, 2H), 0.92 (d, J = 6.92 Hz, 3H), 1.21-1.42 (m, 8H), 1.48 (s, 3H), 1.52-1.84 (m, 6H), 1.71 (s, 6H), 2.10-2.29 (m, 5H), 3.14-3.17 (m, 1H), 4.40 (d, J = 7.44 Hz, 1H), 5.24-5.44 (m, 1H), 6.35 (d, J = 9.7 Hz, 1H), 6.41 (s, 1H), 7.07 (d, J = 10.1 Hz, 1H), 7.37 (t, J = 7.54 Hz, 2H), 7.46 (t, J = 7.28 Hz, 1H), 7.95 (d, J = 7.61 Hz, 2H). MASS (ES+): 691.6 (M + Na)$^+$. |
| IA.191 | 0.44 (s, 3H), 0.93 (d, J = 7.07 Hz, 3H), 1.23-1.25 (m, 1H), 1.47 (s, 3H), 1.52-1.83 (m, 12H), 1.74 (s, 6H), 2.19-2.25 (m, 4H), 2.67-2.71 (m, 1H), 3.13-3.17 (m, 1H), 4.30 (d, J = 7.27 Hz, 1H), 5.25-5.42 (m, 1H), 6.34 (d, d $J_1$ = 10.19 Hz, $J_2$ = 1.75 Hz, 1H), 6.41 (s, 1H), 7.06 (d, J = 10.22 Hz, 1H), 7.37 (t, J = 7.57 Hz, 2H), 7.46 (t, 1H, J = 7.34 Hz), 7.95 (d, 2H, J = 7.22 Hz). MASS (ES+): 655.2. |
| IA.192 | 0.45 (s, 3H), 0.93 (d, J = 7.14 Hz, 3H), 1.11 (d, J = 6.96 Hz, 3H), 1.21-1.26 (m, 1H), 1.48 (s, 3H), 1.55-1.75 (m, 4H), 1.75 (d, J = 1.51 Hz, 6H), 2.10-2.27 (m, 4H), 2.47-2.52 (m, 1H), 3.13-3.18 (m, 1H), 4.30 (d, J = 7.45 Hz, 1H), 5.25-5.42 (m, 1H), 6.34 (d, d $J_1$ = 10.13 Hz, $J_2$ = 1.77 Hz, 1H), 6.41 (s, 1H), 7.06 (dd, $J_1$ = 10.13 Hz, $J_2$ = 1.06 Hz, 1H), 7.37 (t, J = 7.59 Hz, 2H), 7.47 (t, J = 7.59 Hz, 2H), 7.47 (t, J = 7.35 Hz, 1H), 7.95 (d, J = 7.28 Hz, 2H). MASS (ES+): 629.2. |
| IA.193 | 0.45 (s, 3H), 0.94 (d, J = 7.06 Hz, 3H), 1.16-1.26 (m, 2H), 1.47 (s, 3H), 1.55-1.96 (m, 5H), 1.7 (Two s, 6H), 2.09-2.29 (m, 8H), 3.06-3.17 (m, 2H), 4.28 (d, J = 7.88 Hz, 1H), 5.25-5.43 (m, 1H), 6.33 (dd, $J_1$ = 10.13 Hz, $J_2$ = 1.66 Hz, 1H), 6.40 (s, 1H), 7.05 (d, J = 10.13 Hz, 1H), 7.38 (t, J = 7.58 Hz, 2H), 7.47 (t, J = 7.83 Hz, 1H), 7.96 (d, J = 8.66 Hz, 2H). MASS (ES+): 641.5. |
| IA.194 | 0.5 (s, 3H), 1.0 (d, J = 6.97 Hz, 3H), 1.22-1.28 (m, 1H), 1.51 (s, 3H), 1.41-1.74 (m, 5H), 1.77 (s, 3H), 1.78 (s, 3H), 2.15-2.60 (m, 5H), 3.19-3.33 (m, 1H), 4.33 (d, J = 8.07 Hz, 1H), 6.12 (s, 1H), 6.35 (d, J = 10.10 Hz, 1H), 6.46 (d, J = 3.25 Hz, 1H), 7.04 (d, J = 3.27 Hz, 1H), 7.16 (d, J = 1.10 Hz, 1H), 7.38 (t, J = 7.57 Hz, 2H), 7.47 (t, J = 7.30 Hz, 1H), 7.56 (s, 1H), 7.95 (d, J = 7.71 Hz, 2H). MASS (ES+): 635.4. |

TABLE 6-continued

Spectral data for the synthesized compounds

| Comp. No | $^1$H-NMR ($\delta$ ppm), MASS (EI/ES+, m/z) |
|---|---|
| IA.195 | 0.44 (s, 3H), 0.88-0.91 (m, 2H), 0.94 (d, J = 7.11 Hz, 3H), 1.09-1.36 (m, 5H), 1.47 (s, 3H), 1.52-1.73 (m, 8H), 1.74 (s, 6H), 2.12-2.22 (m, 6H), 3.13-3.16 (m, 1H), 5.29 (d, J = 8.09 Hz, 1H), 5.25-5.42 (m, 1H), 6.35 (dd, $J_1$ = 10.12 Hz, $J_2$ = 1.79 Hz, 1H), 6.40 (s, 3H), 7.06 (dd, $J_1$ = 10.14 Hz, $J_2$ = 1.36 Hz, 1H), 7.37 (t, J = 7.54 Hz, 2H), 7.44-7.47 (m, 1H), 7.95 (dd, $J_1$ = 8.31 Hz, $J_2$ = 1.23 Hz, 2H). MASS (ES+): 683.4. |
| IA.196 | 0.66 (s, 3H), 1.02 (d, J = 7.03 Hz, 3H), 1.10-1.43 (m, 2H), 1.50 (s, 3H), 1.54-1.82 (m, 9H), 2.22-2.41 (m, 4H), 3.22-3.25 (m, 1H), 4.34 (d, J = 6.85 Hz, 1H), 5.28-5.45 (m, 1H), 6.38 (dd, $J_1$ = 10.17 Hz, $J_2$ = 1.68 Hz 1H), 6.43 (s, 1H), 6.47 (dd, $J_1$ = 3.39 Hz, $J_2$ = 1.86 Hz 1H), 7.03-7.09 (m, 4H), 7.56 (s, 1H), 8.01-8.01 (m, 2H). MASS (ES+): 671.3. |
| IA.197 | 0.58 (s, 3H), 1.02 (d, J = 7.09 Hz, 3H), 1.08-1.37 (m, 3H), 1.50 (s, 3H), 1.61-1.80 (m, 8H), 2.22-2.38 (m, 4H), 3.20-3.25 (m, 1H), 4.34-4.36 (m, 1H), 5.28-5.48 (m, 1H), 6.39 (dd, $J_1$ = 10.12 Hz, $J_2$ = 1.77 Hz 1H), 6.43 (s, 1H), 6.48 (dd, $J_1$ = 3.47 Hz, $J_2$ = 1.71 Hz 1H), 7.05 (d, J = 3.34 Hz, 1H), 7.09 (dd, $J_1$ = 10.12 Hz, $J_2$ = 1.07 Hz 1H), 7.57 (t, J = 0.85 Hz, 1H), 7.65 (d, J = 8.33 Hz, 2H), 8.01 (d, J = 8.21 Hz, 2H). MASS (ES+): 721.2 |
| IA.198 | 1.05 (d, J = 7.15 Hz, 3H), 1.17 (s, 3H), 1.34-1.39 (m, 1H), 1.55 (s, 3H), 1.74-1.92 (m, 4H), 2.09-2.50 (m, 4H), 2.32 (s, 3H), 2.33 (s, 3H), 3.45-3.49 (m, 1H), 4.32 (d, J = 16.76 Hz, 1H), 4.46 (d, J = 8.58 Hz, 1H), 4.59 (d, J = 16.79 Hz, 1H), 5.32-5.49 (m, 1H), 6.40 (dd, $J_1$ = 10.12 Hz, $J_2$ = 1.65 Hz, 1H), 6.46 (s, 1H), 6.93 (d, J = 4.02 Hz, 1H), 7.17 (d, J = 10.13 Hz, 1H), 7.24 (d, J = 7.93 Hz, 1H), 7.53 (dd, J = 3.95 Hz, 1H), 7.75 (d, J = 7.93 Hz, 1H), 7.78 (s, 1H). MASS (ES+): 703.7 |
| IA-1.1 | 0.33 (s, 3H), 0.92 (d, J = 7.14 Hz, 3H), 1.07 (t, J = 7.55 Hz, 3H), 1.17-1.88 (m, 12H), 2.08-2.30 (m, 8H), 2.66-2.63 (m, 2H), 3.10-3.13 (m, 1H), 4.28-4.30 (m, 1H), 5.25-5.63 (m, 1H), 6.36 (dd, $J_1$ = 10.13 Hz, $J_2$ = 1.77 Hz 1H), 6.40 (s, 1H), 7.03-7.07 (m, 3H), 7.94-7.97 (m, 2H). MASS (ES+): 660.5 |
| IA-1.2 | 0.15 (s, 3H), 0.91 (d, J = 7.10 Hz, 3H), 1.08 (t, J = 7.68 Hz, 3H), 1.17-1.88 (m, 12H), 2.04-2.31 (m, 8H), 2.63-2.67 (m, 2H), 3.05-3.15 (m, 1H), 4.26 (d, J = 7.89 Hz, 1H), 5.23-5.39 (m, 1H), 6.35 (dd, $J_1$ = 10.11 Hz, $J_2$ = 1.47 Hz, 1H), 6.39 (s, 1H), 7.05 (d, J = 10.11 Hz, 2H), 7.36-7.39 (m, 2H), 7.45-7.49 (m, 2H), 7.90 (d, J = 7.49 Hz, 2H). MASS (ES+): 663.0 (M + Na)$^+$. |
| IB.1 | 0.94 (d, J = 7.16 Hz, 3H), 1.10 (s, 3H), 1.12 (t, J = 7.53 Hz, 3H), 1.23-1.35 (m, 1H), 1.53 (s, 3H), 1.69-1.85 (m, 3H), 2.17-2.49 (m, 7H), 3.29-3.36 (m, 1H), 4.30-4.40 (m, 3H), 4.55 (d, J = 15.48, 1H), 5.04 (d, J = 15.46, 1H), 5.27-5.52 (m, 1H), 6.37 (d, d $J_1$ = 10.11 Hz, $J_2$ = 1.69 Hz, 1H), 6.43 (s, 1H), 7.13 (d, J = 10.10 Hz, 1H). MASS (ES+): 543.5 (M + Na)$^+$. |
| IB.2 | 0.97 (d, J = 6.99 Hz, 3H), 1.11 (s, 3H), 1.12 (t, J = 7.33 Hz, 3H), 1.29-1.33 (m, 1H), 1.53 (s, 3H), 1.70-1.98 (m, 3H), 2.17-2.54 (m, 7H), 3.33-3.34 (m, 1H), 3.67 (d, J = 14.69 Hz, 1H), 3.74 (d, J = 16.44 Hz, 1H), 4.19 (s, 2H), 4.32 (d, J = 7.28 Hz, 1H), 4.59 (s, 1H), 5.31-5.48 (m, 1H), 6.33 (d, J = 10.16 Hz, 1H), 6.37 (s, 1H), 7.22 (d, J = 10.02 Hz, 1H). MASS (ES+): 559.5 (M + Na)$^+$. |
| IB.3 | 0.99 (d, J = 7.10 Hz, 3H), 1.10 (s, 3H), 1.12 (t, J = 7.59 Hz, 3H), 1.31-1.36 (m, 1H), 1.52 (s, 3H), 1.70-1.91 (m, 4H), 2.19-2.45 (m, 6H), 3.33-3.37 (m, 1H), 3.72-3.78 (m, 2H), 4.41 (d, J = 6.54 Hz, 1H), 4.94 (d, J = 47.47 Hz, 2H), 5.30-5.47 (m, 1H), 6.38 (d, J = 10.13 Hz, 1H), 6.43 (s, 1H), 7.12 (d, J = 10.13 Hz, 1H). MASS (ES+): 561.2 (M + Na)$^+$. |
| IB.4 | 1.02 (d, J = 7.08 Hz, 3H), 1.13 (s, 3H), 1.32-1.37 (m, 1H), 1.55 (s, 3H), 1.66-2.02 (m, 4H), 2.07-2.32 (m, 4H), 3.38-3.41 (m, 1H), 3.70 (d, J = 16.32 Hz, 1H), 3.78 (d, J = 16.35 Hz, 1H), 1.12-4.15 (m, 2H), 4.33 (d, J = 6.37, 1H), 4.88 (t, J = 5.92 Hz, 1H), 5.14 (m, 1H), 5.36-5.53 (m, 1H), 6.29-6.32 (m, 2H), 6.54 (dd, $J_1$ = 3.47 Hz, $J_2$ = 1.72 Hz 1H), 7.11 (d, J = 3.46 Hz, 1H), 7.25 (d, J = 10.45 Hz, 1H), 7.66 (m, 1H). MASS (ES+): 597.5 (M + Na)$^+$. |
| IB.5 | 0.98 (d, J = 7.03 Hz, 3H), 1.11 (s, 3H), 1.12 (t, J = 7.72 Hz, 3H), 1.27-1.33 (m, 1H), 1.54 (s, 3H), 1.78-1.88 (m, 5H), 2.04-2.31 (m, 2H), 2.33-2.63 (m, 6H), 3.31-3.34 (m, 1H), 3.66 (d, J = 16.48 Hz, 1H), 3.74 (d, J = 16.56 Hz, 1H), 4.24 (s, 2H), 4.40 (d, J = 8.44 Hz, 1H), 6.13 (s, 1H), 6.35 (d, J = 10.06 Hz, 1H), 7.20 (d, J = 10.07 Hz, 1H). MASS (ES+): 541.6 (M + Na)$^+$. |
| IB.6 | 1.07 (d, J = 7.08 Hz, 3H), 1.15 (s, 3H), 1.32-1.41 (m, 1H), 1.54 (s, 3H), 1.58-1.95 (m, 5H), 2.29-2.53 (m, 3H), 3.41-3.45 (m, 1H), 3.75 (dd, $J_1$ = 15.74 Hz, $J_2$ = 5.95 Hz, 1H), 3.83 (dd, $J_1$ = 16.61 Hz, $J_2$ = 6.93 Hz, 1H), 4.46 (d, J = 8.11 Hz, 1H), 4.94 (d, J = 47.67 Hz, 2H), 5.32-5.49 (m, 1H), 6.40 (dd, $J_1$ = 10.11 Hz, $J_2$ = 1.43 Hz, 1H), 6.45 (s, 1H), 6.50 (dd, $J_1$ = 3.14 Hz, $J_2$ = 1.5 Hz, 1H), 7.12 (s, 1H), 7.14 (d, J = 10.36 Hz, 1H), 7.59 (s, 1H). MASS (ES+): 599.5 (M + Na)$^+$. |
| IB.7 | 0.95 (d, J = 7.14 Hz, 3H), 1.10 (s, 3H), 1.14 (d, J = 4.89 Hz, 3H), 1.16 (d, J = 4.92 Hz, 3H), 1.23-1.33 (m, 1H), 1.53 (s, 3H), 1.68-2.00 (m, 3H), 2.16-2.29 (m, 2H), 2.54-2.62 (m, 3H), 3.32-3.36 (m, 1H), 3.64-3.78 (m, 2H), 4.15-4.17 (m, 2H), 4.30-4.33 (m, 1H), 4.72 (t, J = 5.89 Hz, 1H), 4.99 (d, J = 2.77, 1H), 5.34-5.50 (m, 1H), 6.31 (d, $J_1$ = 12.18 Hz, $J_2$ = 1.97 Hz, 1H), 6.32 (s, 1H), 7.24 (d, J = 10.03 Hz, 1H). MASS (ES+): 551.2 |
| IB.8 | 0.99 (d, J = 7.31 Hz, 3H), 1.11 (s, 3H), 1.27-1.35 (m, 1H), 1.52 (s, 3H), 1.72-1.99 (m, 7H), 2.04-2.37 (m, 8H), 3.14-3.18 (m, 1H), 3.33-3.36 (m, 1H), 3.65-3.77 (m, 2H), 4.24 (d, J = 2.11, 2H), 4.39 (d, J = 8.66 Hz, 1H), 5.28-5.48 (m, 1H), 6.37 (dd, $J_1$ = 10.12 Hz, $J_2$ = 1.60 Hz, 1H), 6.43 (s, 1H), 7.12 (d, J = 10.18 Hz, 1H). MASS (ES+): 564.3 |
| IB.9 | 1.02 (d, J = 7.10 Hz, 3H), 1.16 (s, 3H), 1.13-1.36 (m, 1H), 1.57 (s, 3H), 1.60-2.00 (m, 4H), 2.24-2.66 (m, 6H), 3.38-3.42 (m, 1H), 3.70 (d, J = 16.38 Hz, 1H), 3.78 (d, J = 16.39 Hz, 1H), 4.15-4.17 (m, 2H), 4.34-4.37 (m, 1H), 4.73 (t, J = 5.85 Hz, 1H), 4.78 (s, 1H), 6.09 (s, 1H), 6.29 (dd, $J_1$ = 10.10 Hz, $J_2$ = 1.45 Hz, 1H), 6.52 (dd, $J_1$ = 3.33 Hz, $J_2$ = 1.60 Hz, 1H), 7.11 (d, J = 3.43 Hz, 1H), 7.32 (d, J = 10.12 Hz, 1H), 7.63 (s, 1H). MASS (ES+): 557.3 |
| IB.10 | 1.03 (d, J = 6.98 Hz, 3H), 1.13 (s, 3H), 1.33-1.37 (m, 1H), 1.55 (s, 3H), 1.62-1.98 (m, 3H), 2.24-2.54 (m, 4H), 3.3-(m, 1H), 3.71 (d, J = 16.40 Hz, 1H), 3.79 (d, J = 16.39 Hz, 1H), 4.08 (d, J = 7.17 Hz, 1H), 4.12 (d, J = 5.83 Hz, 2H), 4.99 (t, J = 5.92 Hz, 1H), 5.27 (s, 1H), 5.40-5.56 (m, 1H), 6.28 (s, 1H), 6.29 (d, J = 13.05 Hz, 1H), 7.14 (t, J = 4.33 Hz, 1H), 7.27 (d, J = 10.03 Hz, 1H), 7.71 (m, 2H). MASS (ES+): 591.4 |
| IB.11 | 0.99 (d, J = 7.15 Hz, 3H), 1.09 (s, 3H), 1.12 (t, J = 7.66 Hz, 3H), 1.30-1.36 (m, 1H), 1.52 (s, 3H), 1.64-1.90 (m, 4H), 2.18-2.44 (m, 7H), 3.34-3.38 (m, 1H), 3.65 (dd, $J_1$ = 16.57 Hz, $J_2$ = 2.60 Hz, 1H), 3.71 (dd, $J_1$ = 16.58 Hz, $J_2$ = 2.58 Hz, 1H), 4.41 (d, J = 7.42 Hz, 1H), 5.30-5.47 (m, 1H), 6.37 (dd, $J_1$ = 10.14 Hz, $J_2$ = 1.54 Hz, 1H), 6.43 (s, 1H), 7.12 (d, J = 10.05 Hz, 1H). MASS (ES+): 507.3 |
| IB.12 | 1.06 (d, J = 7.11 Hz, 3H), 1.18 (s, 3H), 1.35-1.61 (m, 11H), 1.55 (s, 3H), 1.80-1.97 (m, 3H), 2.39-2.60 (m, 5H), 3.43-3.46 (m, 1H), 3.70-3.82 (m, 3H), 4.06-4.33 (m, 4H), 4.45 (d, J = 7.47 Hz, 1H), 4.69-4.71 (m, 2H), 5.32-5.49 (m, 1H), |

TABLE 6-continued

Spectral data for the synthesized compounds

| Comp. No | $^1$H-NMR (δ ppm), MASS (EI/ES+, m/z) |
|---|---|
| | 6.39 (d, J = 10.13 Hz, 1H), 6.45 (s, 1H), 6.50 (d, $J_1$ = 3.26 Hz, $J_2$ = 1.48 Hz, 1H), 7.13 (d, J = 3.42 Hz, 1H), 7.16 (d, J = 10.32 Hz, 1H), 7.59 (s, 1H). MASS (ES+): 773.2 |
| IB.13 | 0.70 (d, J = 7.16 Hz, 3H), 1.07 (s, 3H), 1.11 (t, J = 7.53 Hz, 3H), 1.25-1.35 (m, 1H), 1.53 (s, 3H), 1.70-2.03 (m, 3H), 2.18-2.60 (m, 7H), 3.34-3.37 (m, 1H), 4.04 (d, J = 3.79 Hz, 2H), 4.28 (d, J = 9.37 Hz, 1H), 4.93 (s, 1H), 5.32-5.51 (m, 1H), 5.63-5.81 (m, 1H), 5.80-5.88 (m, 1H), 6.30 (dd, $J_1$ = 10.12 Hz, $J_2$ = 1.88 Hz, 1H), 6.33 (s, 1H), 7.24 (d, J = 9.87 Hz, 1H). MASS (ES+): 539.2 |
| IB.14 | 1.04 (d, J = 7.10 Hz, 3H), 1.12 (s, 3H), 1.12-1.37 (m, 1H), 1.55 (s, 3H), 1.70-1.95 (m, 4H), 2.29-2.59 (m, 4H), 3.40-3.44 (m, 1H), 3.55-3.68 (m, 2H), 4.02 (d, J = 4.19 Hz, 1H), 4.23 (br-s, 1H), 4.33 (br-d, J = 10.86 Hz, 1H), 5.07-5.09 (m, 1H), 5.36-5.53 (m, 1H), 5.65-5.71 (m, 1H), 6.31 (dd, $J_1$ = 10.68 Hz, $J_2$ = 1.76 Hz, 1H), 6.33 (s, 1H), 6.53 (dd, $J_1$ = 3.46 Hz, $J_2$ = 1.75 Hz, 1H), 7.10 (d, J = 3.47 Hz, 1H), 7.26 (d, J = 10.00 Hz, 1H), 7.64 (d, J = 1.37 Hz, 1H). MASS (ES+): 599.3 (M + Na)$^+$ |
| IB.15 | 1.02 (d, J = 7.10 Hz, 3H), 1.10 (s, 3H), 1.31-1.38 (m, 1H), 1.54 (s, 3H), 1.65-1.96 (m, 3H), 2.26-2.53 (m, 4H), 3.38-3.41 (m, 1H), 3.64 (d, J = 7.8 Hz, 2H), 4.16 (m, 2H), 4.29 (b, d, 1H), 4.48 (bs, 1H), 5.27 (m, 1H), 5.40-5.57 (m, 2H), 5.62-5.69 (m, 1H), 6.26 (s, 1H), 6.28 (dd, $J_1$ = 10.12 Hz, $J_2$ = 1.79 Hz, 1H), 6.56 (dd, $J_1$ = 3.47 Hz, $J_2$ = 1.72 Hz, 1H), 7.10 (d, J = 3.48 Hz, 1H), 7.26 (d, J = 10.10 Hz, 1H), 7.72 (d, J = 1.51 Hz, 1H). MASS (ES+): 599.3 (M + Na)$^+$ |
| IB.16 | 1.03 (d, J = 7.09 Hz, 3H), 1.11 (s, 3H), 1.31-1.37 (m, 1H), 1.55 (s, 3H), 1.65-2.01 (m, 4H), 2.28-2.58 (m, 4H), 3.36-3.41 (m, 1H), 3.64 (d, J = 7.76 Hz, 2H), 4.16 (m, 2H), 3.31 (d, J = 6.77 Hz, 1H), 4.49 (t, J = 5.37 Hz, 1H), 5.28 (m, 1H), 5.41-5.57 (m, 2H), 5.64-5.69 (m, 1H), 6.26 (s, 1H), 6.29 (dd, $J_1$ = 10.11 Hz, $J_2$ = 1.82 Hz, 1H), 7.14 (t, J = 4.36 Hz, 1H), 7.27 (dd, $J_1$ = 10.11 Hz, $J_2$ = 0.74 Hz, 1H), 7.70-7.71 (m, 2H). MASS (ES+): 615.0 (M + Na)$^+$ |
| IB.17 | 1.04 (d, J = 7.11 Hz, 3H), 1.12 (s, 3H), 1.32-1.38 (m, 1H), 1.55 (s, 3H), 1.60-1.99 (m, 4H), 2.29-2.59 (m, 4H), 3.39-3.43 (m, 1H), 3.56-3.67 (m, 2H), 4.00 (d, J = 5.11 Hz, 1H), 4.22 (dd, $J_1$ = 4.85 Hz, $J_2$ = 0.81 Hz, 1H), 4.32 (d, J = 6.73 Hz, 1H), 4.43 (t, J = 5.49 Hz, 1H), 5.21-5.22 (m, 1H), 5.39-5.56 (m, 1H), 5.63-5.70 (m, 1H), 5.83 (d, t, $J_1$ = 15.27 Hz, $J_2$ = 5.03 Hz, 1H), 6.29 (s, 1H), 6.30 (dd, $J_1$ = 10.58 Hz, $J_2$ = 1.77 Hz, 1H), 7.13 (dd, $J_1$ = 4.87 Hz, $J_2$ = 3.87 Hz, 1H), 7.27 (d, J = 9.68 Hz, 1H), 7.67 (dd, $J_1$ = 4.97 Hz, $J_2$ = 0.99 Hz, 1H), 7.70 (dd, $J_1$ = 3.70 Hz, $J_2$ = 1.05 Hz, 1H). MASS (ES+): 592.7 |
| IB.18 | 1.06 (d, J = 7.11 Hz, 3H), 1.18 (s, 3H), 1.35-1.41 (m, 1H), 1.55 (s, 3H), 1.67-1.97 (m, 11), 2.28-2.56 (m, 5H), 3.44 (m, 1H), 3.66-3.81 (m, 3H), 3.99-4.31 (m, 4H), 4.45 (d, J = 7.88 Hz, 1H), 4.65-4.75 (m, 2H), 5.32-5.49 (m, 1H), 6.39 (dd, $J_1$ = 10.15 Hz, $J_2$ = 1.29 Hz, 1H), 6.45 (s, 1H), 6.50 (dd, $J_1$ = 3.34 Hz, $J_2$ = 1.69 Hz, 1H), 7.13 (d, J = 3.45 Hz, 1H), 7.16 (d, J = 10.13 Hz, 1H), 7.59 (d, J = 0.66 Hz, 1H). MASS (ES+): 759.1 |
| IB.19 | 1.06 (d, J = 7.05 Hz, 3H), 1.18 (s, 3H), 1.36-1.41 (m, 1H), 1.54 (s, 3H), 1.74-1.97 (m, 7H), 2.29-2.50 (m, 5H), 3.42-3.45 (m, 1H), 3.72-3.74 (m, 2H), 4.20 (t, J = 5.74 Hz, 2H), 4.44-4.47 (m, 1H), 4.48 (t, J = 5.90 Hz, 2H), 4.65-4.74 (m,, 2H), 5.33-5.50 (m, 1H), 6.40 (dd, $J_1$ = 10.14 Hz, $J_2$ = 1.52 Hz, 1H), 6.45 (s, 1H), 6.50 (dd, $J_1$ = 3.22 Hz, $J_2$ = 1.48 Hz, 1H), 7.13-7.16 (m, 2H), 7.59 (s, 1H). MASS (ES+): 736.1 |
| IB.20 | 1.03 (d, J = 7.10 Hz, 3H), 1.15 (s, 3H), 1.33-1.39 (m, 1H), 1.55 (s, 3H), 1.60-2.00 (m, 4H), 2.25-2.60 (m, 4H), 3.30-3.42 (m, 1H), 3.71 (d, J = 16.35 Hz, 1H), 3.78 (d, t, $J_1$ = 16.38 Hz, $J_2$ = 1.86 Hz, 1H), 4.15-4.17 (m, 2H), 4.36 (d, J = 9.1 Hz, 1H), 4.71 (t, J = 5.90 Hz, 1H), 5.03 (d, J = 2.42 Hz, 1H), 5.16-5.52 (m, 1H), 6.34 (dd $J_1$ = 10.97 Hz, $J_2$ = 1.70 Hz, 1H), 6.36 (s, 1H), 6.97 (d, J = 13.05 Hz, 1H), 7.26 (d, J = 10.17 Hz, 1H), 7.52 (s, 1H). MASS (ES+): 647.0 (M + Na)$^+$ |
| IB.21 | 1.06 (d, J = 7.13 Hz, 3H), 1.14 (s, 3H), 1.35-1.40 (m, 1H), 1.54 (s, 3H), 1.79 (t, J = 2.34 Hz, 3H), 1.73-1.96 (m, 4H), 2.28-2.54 (m, 4H), 3.41-3.46 (m, 1H), 3.66 (dd, $J_1$ = 16.08 Hz, $J_2$ = 2.46 Hz, 1H), 3.73 (dd, $J_1$ = 16.12 Hz, $J_2$ = 2.45 Hz 1H), 4.45 (d, J = 8.43 Hz, 1H), 5.32-5.48 (m, 1H), 6.40 (d, J = 10.71 Hz, 1H), 6.45 (s, 1H), 6.50 (dd, $J_1$ = 3.21 Hz, $J_2$ = 1.11 Hz, 1H), 7.11 (d, J = 3.39, 1H), 7.13 (d, J = 9.96 Hz, 1H), 7.58 (m, 1H). MASS (ES+): 559.5 |
| IB.22 | 1.06 (d, J = 7.10 Hz, 3H), 1.17 (s, 3H), 1.36-1.43 (m, 1H), 1.53 (s, 3H), 1.56-1.96 (m, 4H), 2.30 (s, 3H), 2.38-2.58 (m, 4H), 3.41-3.45 (m, 1H), 3.70 (d, J = 16.56 Hz, 1H), 3.79 (d, J = 16.56 Hz, 1H), 4.22 (d, J = 14.06, 1H), 4.27 (d, J = 15.99 Hz, 1H), 4.42 (d, J = 8.53 Hz, 1H), 5.31-5.48 (m, 1H), 6.34 (d, J = 0.96 Hz, 1H), 6.38 (dd, $J_1$ = 10.16 Hz, $J_2$ = 1.43 Hz 1H), 6.44 (s, 1H), 7.14 (d, J = 10.2, 1H), 7.44 (s, 1H). MASS (ES+): 589.3 |
| IB.23 | 1.03 (d, J = 7.10 Hz, 3H), 1.12 (s, 3H), 1.21 (t, J = 6.99 Hz, 3H), 1.32-1.37 (m, 1H), 1.52 (s, 3H), 1.66-1.92 (m, 4H), 2.17-2.45 (m, 5H), 3.35-3.38 (m, 1H), 3.54 (q, J = 6.98 Hz, 2H), 3.69 (d, J = 14.78 Hz, 1H), 3.73 (d, J = 14.72 Hz, 1H), 4.09 (s, 2H), 4.19-4.28 (m, 2H), 4.39 (d, J = 8.39 Hz, 1H), 5.30-5.46 (m, 1H), 6.37 (dd, $J_1$ = 10.13 Hz, $J_2$ = 1.65 Hz, 1H), 6.43 (s, 1H), 7.13 (dd, $J_1$ = 10.07 Hz, $J_2$ = 0.65 Hz, 1H). MASS (ES+): 567.1 |
| IB.24 | 1.03 (d, J = 7.11 Hz, 3H), 1.12 (s, 3H), 1.32-1.38 (m, 1H), 1.52 (s, 3H), 1.68-1.93 (m, 5H), 2.16-2.32 (m, 4H), 3.35-3.39 (m, 1H), 3.41 (s, 3H), 3.71-3.73 (m, 2H), 4.05 (q, 2H), 4.23 (t, J = 2.22 Hz, 1H), 4.25 (t, J = 2.23, 1H), 4.39 (d, J = 8.92, 1H), 5.30-5.47 (m, 1H), 6.37 (dd, $J_1$ = 10.17 Hz, $J_2$ = 1.78 Hz, 1H), 6.43 (s, 1H), 7.14 (d, J = 10.13 Hz, 1H). MASS (ES+): 553.2 |
| IB.25 | 1.07 (d, J = 7.15 Hz, 3H), 1.18 (s, 3H), 1.28-1.42 (m, 1H), 1.46-1.67 (m, 10H), 1.54 (s, 3H), 1.74-2.02 (m, 9H), 2.28-2.50 (m, 1H), 3.40-3.46 (m, 1H), 3.70 (d, J = 16.45 Hz, 1H), 3.78 (d, J = 16.43 Hz, 1H), 4.44 (d, J = 8.82 Hz, 1H), 5.32-5.49 (m, 1H), 6.39 (dd, $J_1$ = 10.13 Hz, $J_2$ = 1.66 Hz, 1H), 6.45 (s, 1H), 6.49 (dd, $J_1$ = 3.42 Hz, $J_2$ = 1.66 Hz, 1H), 7.12 (d, J = 3.71 Hz, 1H), 7.14 (d, J = 12.28 Hz, 1H), 7.59 (s, 1H). MASS (ES+): 643.3 |
| IB.26 | 0.89-0.94 (m, 2H), 1.0 (d, J = 7.14 Hz, 3H), 1.12 (s, 3H), 1.08-1.36 (m, 4H), 1.52 (s, 3H), 1.61-1.91 (m, 10H), 2.16-2.44 (m, 7H), 3.31-3.35 (m, 1H), 3.65-3.76 (m, 2H), 4.19-4.28 (m, 2H), 4.40 (d, J = 8.88 Hz, 1H), 5.30-5.47 (m, 1H), 6.38 (d, d, $J_1$ = 10.12 Hz, $J_2$ = 1.78 Hz, 1H), 6.43 (s, 1H), 7.14 (d, d, $J_1$ = 10.12 Hz, $J_2$ = 1.31 Hz, 1H). MASS (ES+): 605.5 |
| IB.27 | 0.89 (t, J = 7.32 Hz, 3H), 0.99 (d, J = 7.11 Hz, 3H), 1.11 (s, 3H), 1.34 (q, J = 7.53 Hz, 2H), 1.52 (s, 3H), 1.55-1.59 (m, 2H), 1.73-2.04 (m, 4H), 2.22-2.37 (m, 7H), 3.34 (m, 1H), 3.69-3.73 (m, 2H), 4.24 (d, J = 1.36 Hz, 2H), 4.40 (d, J = 8.57 Hz, 1H), 5.30-5.48 (m, 1H), 6.38 (dd, $J_1$ = 10.13 Hz, $J_2$ = 1.70 Hz 1H), 6.43 (s, 1H), 7.13 (d, J = 10.12 Hz, 1H). MASS (ES+): 565.3 |
| IB.28 | 0.94 (d, J = 7.17 Hz, 3H), 1.08 (s, 3H), 1.12 (t, J = 7.58 Hz, 3H), 1.27-1.32 (m, 1H), 1.53 (s, 3H), 1.64-1.83 (m, 4H), 2.22-2.48 (m, 7H), 3.30-3.34 (m, 1H), 4.40 (d, J = 7.59 Hz, 1H), 4.60 (d, d $J_1$ = 15.58 Hz, |

TABLE 6-continued

Spectral data for the synthesized compounds

| Comp. No | $^1$H-NMR (δ ppm), MASS (EI/ES+, m/z) |
|---|---|
| | $J_2$ = 1.63 Hz, 1H), 4.84 (d, d $J_1$ = 15.60 Hz, $J_2$ = 2.18 Hz, 1H), 5.30-5.47 (m, 1H), 6.37 (d, d $J_1$ = 10.17 Hz, $J_2$ = 1.46 Hz, 1H), 6.43 (s, 1H), 7.12 (d, J = 10.10 Hz, 1H). MASS (ES+): 491.2 |
| IB.29 | 0.99 (d, J = 7.12 Hz, 3H), 1.12 (s, 3H), 1.31-1.36 (m, 1H), 1.52 (s, 3H), 1.54-1.70 (m, 5H), 1.73-1.92 (m, 6H), 2.18-2.38 (m, 6H), 2.72-2.80 (m, 1H), 3.32-3.37 (m, 1H), 3.64-3.76 (m, 2H), 4.24 (s, 2H), 4.41 (d, J = 8.75, 1H), 5.31-5.47 (m, 1H), 6.38 (d, d, $J_1$ = 10.16 Hz, $J_2$ = 164 Hz, 1H), 6.44 (s, 1H), 7.14 (d, J = 10.17 Hz, 1H). MASS (ES+): 577.2 |
| IB.30 | 0.99 (d, J = 7.13 Hz, 3H), 1.06 (s, 3H), 1.11 (t, J = 7.59 Hz, 3H), 1.30-1.35 (m, 1H), 1.52 (s, 3H), 1.72-2.04 (m, 4H), 2.17-2.43 (m, 7H), 3.31-3.36 (m, 1H), 3.57 (dd, $J_1$ = 13.64 Hz, $J_2$ = 7.49 Hz, 1H), 3.73 (dd, $J_1$ = 13.86 Hz, $J_2$ = 8.50 Hz, 1H), 4.21 (dd, $J_1$ = 12.64 Hz, $J_2$ = 6.89 Hz, 1H), 4.33 (dd, $J_1$ = 12.89 Hz, $J_2$ = 8.13 Hz, 1H), 4.37 (d, J = 10.81 Hz, 1H), 5.30-5.46 (m, 1H), 5.52-5.59 (m, 1H), 5.73-5.79 (m, 1H), 6.37 (dd, $J_1$ = 10.14 Hz, $J_2$ = 1.74 Hz, 1H), 6.43 (s, 1H), 7.22 (dd, $J_1$ = 10.10 Hz, $J_2$ = 1.03 Hz, 1H). MASS (ES+): 539.3 |
| IB.31 | 0.98 (d, J = 7.11 Hz, 3H), 1.10-1.17 (m, 6H), 1.15 (s, 3H), 1.30-1.36 (m, 1H), 1.54 (s, 3H), 1.73-1.90 (m, 3H), 2.20-2.44 (m, 8H), 3.03 (d, J = 2.56 Hz, 1H), 3.34-3.38 (m, 1H), 3.68 (dd, 2H), 4.40 (d, J = 8.47, 1H), 4.55 (d, J = 15.4 Hz, 1H), 7.72 (d, J = 15.4 Hz, 1H), 5.31-5.49 (m, 1H), 6.36 (dd, $J_1$ = 10.11 Hz, $J_2$ = 1.1.62 Hz 1H), 6.43 (s, 1H), 7.16 (d, J = 10.11 Hz, 1H). MASS (ES+): 615.5 (M + H)$^+$. |
| IB.32 | 0.98 (d, J = 7.1 Hz, 3H), 1.12 (t, J = 7.49 Hz, 3H), 1.13 (s, 3H), 1.20-1.36 (m, 1H), 1.54 (s, 3H), 1.70-1.93 (m, 3H), 2.10 (s, 3H), 2.19-2.42 (m, 6H), 2.88 (s, 1H), 3.34-3.37 (m, 1H), 3.64 (d, J = 16.77, 1H), 3.72 (d, J = 16.82, 1H), 4.411.12 (d, J = 8.07 Hz, 1H), 4.56 (d, J = 15.4 Hz, 1H), 4.691.12 (d, J = 15.4 Hz, 1H), 5.30-5.47 (m, 1H), 6.38 (dd, $J_1$ = 10.12 Hz, $J_2$ = 1.50 Hz, 1H), 6.43 (s, 1H), 7.17 (d, J = 10.15 Hz, 1H). MASS (ES+): 601.0 (M + Na)$^+$. |
| IB.33 | 0.97 (t, J = 7.7.47 Hz, 3H), 0.98 (d, J = 7.44 Hz, 3H), 1.12 (t, J = 7.64 Hz, 3H), 1.15 (s, 3H), 1.30-1.36 (m, 1H), 1.54 (s, 3H), 1.66 (q, J = 7.42 Hz, 2H), 1.70-1.94 (m, 4H), 2.19-2.46 (m, 8H), 3.01 (d, J = 2.63 Hz, 1H), 3.33-3.38 (m, 1H), 3.64 (d, J = 16.88 Hz, 1H), 3.72 (d, J = 16.75 Hz, 1H), 4.40 (d, J = 8.68 Hz, 1H), 4.53 (t, d, $J_1$ = 15.38 Hz, $J_2$ = 1.70 Hz, 1H), 4.72 (dd, J = 15.39 Hz, $J_2$ = 1.62 Hz, 1H), 5.31-5.48 (m, 1H), 6.37 (dd, $J_1$ = 10.12 Hz, $J_2$ = 1.77 Hz, 1H), 6.43 (s, 1H), 7.16 (dd, $J_1$ = 10.15 Hz, $J_2$ = 1.26 Hz 1H). MASS (ES+): 607.5 |
| IB.34 | 0.98 (d, J = 7.15 Hz, 3H), 1.12 (t, J = 7.59 Hz, 3H), 1.16 (s, 3H), 1.18 (d, J = 7.00 Hz, 3H), 1.19 (d, J = 6.96 Hz, 3H), 1.30-1.36 (m, 1H), 1.54 (s, 3H), 1.70-1.94 (m, 4H), 2.19-2.48 (m, 4H), 2.36 (q, J = 7.55 Hz, 2H), 2.56-2.63 (m, 1H), 3.11 (d, J = 3.05 Hz, 1H), 3.33-3.37 (m, 1H), 3.65 (d, J = 16.93 Hz, 1H), 3.71 (d, J = 17.26 Hz, 1H), 4.40 (d, J = 8.83 Hz, 1H), 4.53 (t, d, $J_1$ = 15.38 Hz, $J_2$ = 1.72 Hz 1H), 4.73 (dd, $J_1$ = 15.36 Hz, $J_2$ = 1.61 Hz, 1H), 5.31-5.48 (m, 1H), 6.37 (dd, $J_1$ = 10.12 Hz, $J_2$ = 1.79 Hz, 1H), 6.43 (s, 1H), 7.16 (dd, $J_1$ = 10.12 Hz, $J_2$ = 1.17 Hz 1H). MASS (ES+): 607.7 |
| IB.35 | 0.93 (t, J = 7.31 Hz, 3H), 0.98 (d, J = 7.15 Hz, 3H), 1.12 (t, J = 7.71 Hz, 3H), 1.15 (s, 3H), 1.25-1.41 (m, 3H), 1.54 (s, 3H), 1.55-1.94 (m, 6H), 2.19-2.46 (m, 8H), 3.03 (d, J = 2.91 Hz, 1H), 3.33-3.38 (m, 1H), 3.64 (d, J = 16.76 Hz, 1H), 3.72 (d, J = 16.71 Hz, 1H), 4.40 (d, J = 8.90 Hz, 1H), 4.53 (t, d, $J_1$ = 15.40 Hz, $J_2$ = 1.75 Hz, 1H), 4.71 (dd, $J_1$ = 15.41 Hz, $J_2$ = 1.43 Hz, 1H), 5.31-5.48 (m, 1H), 6.37 (dd, $J_1$ = 10.13 Hz, $J_2$ = 1.78 Hz, 1H), 6.43 (s, 1H), 7.16 (dd, $J_1$ = 10.11 Hz, $J_2$ = 1.19 Hz 1H). MASS (ES+): 621.5 |
| IB.36 | 0.98 (d, J = 7.18 Hz, 3H), 1.12 (t, J = 7.59 Hz, 3H), 1.15 (s, 3H), 1.25-1.36 (m, 1H), 1.55 (s, 3H), 1.73-2.04 (m, 6H), 2.20-2.47 (m, 10H), 3.16-3.20 (m, 2H), 3.34-3.37 (m, 1H), 3.68 (Two d, 2H), 4.41 (d, J = 8.64 Hz, 1H), 4.54 (t, d, $J_1$ = 15.38 Hz, $J_2$ = 1.74 Hz 1H), 4.72 (t, d, $J_1$ = 15.37 Hz, $J_2$ = 1.66 Hz, 1H), 5.33-5.45 (m, 1H), 6.37 (dd, $J_1$ = 10.16 Hz, $J_2$ = 1.81 Hz, 1H), 6.43 (s, 1H), 7.16 (dd, $J_1$ = 10.10 Hz, $J_2$ = 1.26 Hz, 1H). MASS (ES+): 619.7 |
| IB.37 | 0.91 (t, J = 6.86 Hz, 3H), 0.98 (d, J = 7.15 Hz, 3H), 1.12 (t, J = 7.59 Hz, 3H), 1.15 (s, 3H), 1.25-1.36 (m, 3H), 1.54 (s, 3H), 1.61-1.94 (m, 6H), 2.19-2.38 (m, 8H), 3.05 (d, J = 3.03 Hz, 1H), 3.34-3.38 (m, 1H), 3.64 (d, J = 16.70 Hz, 1H), 3.72 (d, J = 16.93 Hz, 1H), 4.40 (d, J = 8.58 Hz, 1H), 4.52 (d, J = 15.37 Hz, 1H), 4.72 (d, J = 15.39 Hz, 1H), 5.31-5.47 (m, 1H), 6.37 (dd, $J_1$ = 10.14 Hz, $J_2$ = 1.75 Hz, 1H), 6.43 (s, 1H), 7.16 (dd, $J_1$ = 10.63 Hz, $J_2$ = 1.04 Hz, 1H). MASS (ES+): 634.8 |
| IB.38 | 1.07 (s, 3H), 1.14 (t, J = 7.53 Hz, 3H), 1.21-1.28 (m, 1H), 1.42 (d, J = 7.27 Hz, 3H), 1.55 (s, 3H), 1.60-1.65 (m, 1H), 1.90-2.00 (m, 5H), 2.26-2.42 (m, 7H), 2.61-2.71 (m, 1H), 3.36 (d, J = 16.65 Hz, 1H), 3.80 (d, J = 16.65 Hz, 1H), 4.26 (m, 2H), 4.40 (d, J = 8.38, 1H), 6.14 (s, 1H), 6.35 (dd, $J_1$ = 10.06 Hz, $J_2$ = 1.39 Hz, 1H), 7.24 (d, J = 10.23 Hz, 1H). MASS (ES+): 541.6 (M + Na)$^+$. |
| IB.39 | 1.06 (s, 3H), 1.15 (t, J = 7.54 Hz, 3H), 1.21-1.29 (m, 1H), 1.43 (d, J = 7.35 Hz, 3H), 1.53 (s, 3H), 1.70-2.06 (m, 6H), 2.27-2.41 (m, 6H), 3.35 (d, t, $J_1$ = 16.67 Hz, $J_2$ = 2.34 1H), 3.81 (d, t, $J_1$ = 16.67 Hz, $J_2$ = 2.08 Hz, 1H), 4.25-4.28 (m, 2H), 4.40 (d, J = 8.32 Hz, 1H), 5.31-5.48 (m, 1H), 6.37 (dd, $J_1$ = 10.12 Hz, $J_2$ = 1.77 Hz, 1H), 6.44 (s, 1H), 7.16 (dd, $J_1$ = 10.12 Hz, $J_2$ = 1.16 Hz, 1H). MASS (ES+): 559.2 (M + Na)$^+$ |
| IB.40 | 1.04 (d, J = 7.13 Hz, 3H), 1.16 (s, 3H), 1.25-1.39 (m, 2H), 1.43 (s, 3H), 1.44 (s, 3H), 1.55 (s, 3H), 1.72-1.94 (m, 3H), 2.28-2.51 (m, 4H), 3.39-3.44 (m, 1H), 3.67 (d, J = 16.29 Hz, 1H), 3.75 (d, J = 16.24 Hz, 1H), 4.60 (s, 1H), 4.98-4.99 (m, 1H), 5.37-5.50 (m, 1H), 6.32-6.35 (m, 2H), 6.53 (dd, $J_1$ = 3.41 Hz, $J_2$ = 1.65 Hz, 1H), 7.12 (d, J = 3.48 Hz, 1H), 7.26 (d, J = 10.03 Hz, 1H), 7.64 (d, 1H). MASS (ES+): 625.0 (M + Na)$^+$ |
| IB.41 | 0.96 (d, 3H, J = 7.16 Hz), 1.06 (s, 3H), 1.12 (t, J = 7.57 Hz), 1.26-1.34 (m, 1H), 1.53 (s, 3H), 1.71-1.91 (m, 3H), 2.24-2.39 (m, 6H), 3.30-3.35 (m, 1H), 3.76 (s, 3H), 4.41 (m, 1H), 4.71 (1H, ddd, $J_1$ = 15.93 Hz, $J_2$ = 4.75 Hz, $J_3$ = 1.81 Hz), 4.84 (ddd, 1H, $J_1$ = 16.00 Hz, $J_2$ = 4.75 Hz, $J_3$ = 1.82 Hz), 5.34 & 5.46 (m, 1H), 6.03 (d, 1H, J = 15.77 Hz), 6.37 (dd, 1H, $J_1$ = 10.15 Hz, $J_2$ = 1.78 Hz), 6.44 (s, 1H), 6.93-6.97 (m, 1H), 7.12 (dd, 1H, $J_1$ = 10.13 Hz, $J_2$ = 1.18 Hz). MASS (ES+): 573.1 (M + Na)$^+$. |
| IB.42 | 1.00 (d, 3H, J = 7.15 Hz), 1.06 (s, 3H), 1.12 (t, 3H, J = 7.56 Hz), 1.30-1.35 (m, 1H), 1.52 (s, 3H), 1.73-1.87 (m, 4H), 2.22-2.40 (m, 6H), 3.34-3.36 (m, 1H), 3.71 (d, 2H, J = 7.09 Hz), 3.74 (s, 3H), 4.40 (d, 1H, J = 8.85 Hz), 5.32 & 5.44 (m, 1H), 6.02 (d, 1H, J = 15.46 Hz), 6.38 (dd, 1H, $J_1$ = 10.15 Hz, $J_2$ = 1.79 Hz), 6.43 (s, 1H), 6.85-6.89 (m, 1H), 7.12 (dd, 1H, $J_1$ = 10.15 Hz, $J_2$ = 1.18 Hz). MASS (ES+): 589.1 (M + Na)$^+$. |

TABLE 6-continued

Spectral data for the synthesized compounds

| Comp. No | $^1$H-NMR (δ ppm), MASS (EI/ES+, m/z) |
|---|---|
| IB.43 | 1.03 (s, 3H), 1.15-1.23 (m, 3H), 1.27 (t, 3H, J = 7.12 Hz), 1.45 (s, 3H), 1.47-1.55 (m, 1H), 1.63-1.70 (m, 2H), 1.80-1.87 (m, 1H), 1.93-2.00 (m, 1H), 2.09-2.16 (m, 3H), 2.32-2.36 (m, 1H), 2.53-2.61 (m, 1H), 2.91-2.98 (m, 1H), 3.76 (s, 3H), 4.13 (d of q, 2H, $J_1$ = 14.22 Hz, $J_2$ = 7.10 Hz, $J_3$ = 2.13 Hz), 4.51 (s, 1H), 4.79 (d, 1H, J = 1.62 Hz), 4.80 (d, 1H, J = 1.62 Hz), 6.02 (s, 1H), 6.06 (d, 1H, J = 15.77 Hz), 6.27 (dd, 1H, $J_1$ = 10.09 Hz, $J_2$ = 1.75 Hz), 6.94 (d of t, 1H, $J_1$ = 15.76 Hz, $J_2$ = 4.71 Hz), 7.23 (d, 1H, J = 10.11 Hz). MASS (EI): 516 |
| IB.44 | 0.99 (d, J = 7.13 Hz, 3H), 1.09 (s, 3H), 1.11 (t, J = 7.38 Hz, 3H), 1.29-1.35 (m, 1H), 1.39 (t, J = 7.18 Hz, 3H) 1.53 (s, 3H), 1.72-1.89 (m, 3H), 2.20-2.50 (m, 6H), 3.32-3.37 (m, 1H), 3.52 (d, J = 13.42 Hz, 1H), 3.62 (dd, $J_1$ = 15.97 Hz, $J_2$ = 4.53 Hz, 1H), 4.37 (q, J = 7.15 Hz, 2H), 4.38-4.40 (m, 1H), 4.70-4.82 (m, 1H), 5.30-5.47 (m, 1H), 5.82-5.83 (m, 2H), 6.37 (dd, $J_1$ = 10.13 Hz, $J_2$ = 1.77 Hz, 1H), 6.43 (s, 1H), 7.15 (dd, $J_1$ = 10.12 Hz, $J_2$ = 1.18 Hz, 1H). |
| IB.45 | 1.04 (d, J = 7.06 Hz, 3H), 1.16 (s, 3H), 1.29-1.34 (m, 1H), 1.68 (s, 3H), 1.71-1.97 (m, 4H), 2.37-2.70 (m, 5H), 3.38-3.41 (m, 1H), 3.70 (d, J = 16.35 Hz, 1H), 3.79 (d, J = 16.32 Hz, 1H), 4.15-4.16 (m, 2H), 4.53 (d, J = 2.4 Hz, 1H), 4.74 (t, J = 5.94 Hz, 1H), 5.03 (d, J = 3.67 Hz, 1H), 6.05 (s, 1H), 6.28 (dd, $J_1$ = 10.07 Hz, $J_2$ = 1.27 Hz, 1H), 6.53 (dd, $J_1$ = 3.15 Hz, $J_2$ = 1.47 Hz, 1H), 7.18 (d, J = 3.35 Hz, 1H), 7.31 (d, J = 10.11 Hz, 1H), 7.63 (br-s, 1H). MASS (ES+): 595.4 (M + Na)$^+$. |
| IB.46 | 1.07 (d, J = 7.16 Hz, 3H), 1.15 (s, 3H), 1.35-1.38 (m, 1H), 1.39 (t, J = 7.14 Hz, 3H), 1.56 (s, 3H), 1.76-1.97 (m, 3H), 2.28-2.50 (m, 5H), 3.40-3.44 (m, 1H), 3.55 (dd, $J_1$ = 14.06 Hz, $J_2$ = 2.91 Hz, 1H), 3.65 (dd, $J_1$ = 15.79 Hz, $J_2$ = 4.86 Hz, 1H), 4.36 (q, J = 7.17 Hz, 2H), 4.43 (d, J = 9.21 Hz, 1H), 4.70-4.83 (m, 1H), 5.32-5.49 (m, 1H), 5.83-5.85 (m, 2H), 6.39 (dd, $J_1$ = 10.13 Hz, $J_2$ = 1.82 Hz, 1H), 6.45 (s, 1H), 6.48 (dd, $J_1$ = 3.49 Hz, $J_2$ = 1.73 Hz, 1H), 7.11 (dd, $J_1$ = 3.49 Hz, $J_2$ = 0.64 Hz, 1H), 7.18 (dd, $J_1$ = 10.11 Hz, $J_2$ = 1.20 Hz, 1H), 7.57 (dd, $J_1$ = 1.6 Hz, $J_2$ = 0.70 Hz, 1H). |
| IB.47 | 1.06 (d, J = 7.13 Hz, 3H), 1.12 (s, 3H), 1.34-1.38 (m, 1H), 1.38 (t, J = 7.16 Hz, 3H), 1.55 (s, 3H), 1.77-1.98 (m, 3H), 2.25-2.48 (m, 5H), 3.42-3.45 (m, 1H), 3.63 (d, $J_1$ = 13.76 Hz, $J_2$ = 7.57 Hz, 1H), 3.76 (dd, $J_1$ = 13.79 Hz, $J_2$ = 8.48 Hz, 1H), 4.36 (q, J = 7.17 Hz, 2H), 4.43 (d, J = 8.99 Hz, 1H), 4.95-5.05 (m, 2H), 5.31-5.50 (m, 1H), 5.67-5.71 (m, 1H), 5.77-5.81 (m, 1H), 6.39 (dd, $J_1$ = 10.14 Hz, $J_2$ = 1.55 Hz, 1H), 6.45 (s, 1H), 6.49 (dd, $J_1$ = 3.32 Hz, $J_2$ = 1.55 Hz, 1H), 7.11 (dd, J = 3.48 Hz, 1H), 7.16 (d, J = 10.14 Hz, 1H), 7.58 (s, 1H). |
| IB.48 | 1.05 (d, J = 7.15 Hz, 3H), 1.17 (s, 3H), 1.37-1.40 (m, 1H), 1.49 (d, J = 7.07 Hz, 3H), 1.55 (s, 3H), 1.77-1.99 (m, 4H), 2.13 (s, 3H), 2.17-2.48 (m, 4H), 3.42-3.46 (m, 1H), 3.67 (d, J = 16.90 Hz, 1H), 3.77 (d, J = 16.82 Hz, 1H), 4.44 (d, J = 8.50 Hz, 1H), 4.64 (t, d, $J_1$ = 15.4 Hz, $J_2$ = 1.87 Hz, 1H), 4.78 (t, d, $J_1$ = 15.41 Hz, $J_2$ = 1.86 Hz, 1H), 5.09 (q, J = 6.37 Hz, 1H), 5.32-5.51 (m, 1H), 6.39 (dd, $J_1$ = 10.12 Hz, $J_2$ = 1.78 Hz, 1H), 6.45 (s, 1H), 6.50 (dd, $J_1$ = 3.49 Hz, $J_2$ = 1.73 Hz, 1H), 7.12 (dd, $J_1$ = 3.47 Hz, $J_2$ = 0.49 Hz, 1H), 7.16 (dd, $J_1$ = 10.14 Hz, $J_2$ = 1.31 Hz, 1H), 7.59 (d, J = 0.75 Hz, 1H). MASS (ES+): 689.0 |
| IB.49 | 0.97 (t, J = 7.7.47 Hz, 3H), 0.98 (d, J = 7.44 Hz, 3H), 1.12 (t, J = 7.64 Hz, 3H), 1.15 (s, 3H), 1.30-1.36 (m, 1H), 1.54 (s, 3H), 1.66 (q, J = 7.42 Hz, 2H), 1.70-1.94 (m, 4H), 2.19-2.46 (m, 8H), 3.01 (d, J = 2.63 Hz, 1H), 3.33-3.38 (m, 1H), 3.64 (d, J = 16.88 Hz, 1H), 3.72 (d, J = 16.75 Hz, 1H), 4.40 (d, J = 8.68 Hz, 1H), 4.53 (t, d, $J_1$ = 15.38 Hz, $J_2$ = 1.70 Hz, 1H), 4.72 (dd, $J_1$ = 15.39 Hz, $J_2$ = 1.62 Hz, 1H), 5.31-5.48 (m, 1H), 6.37 (dd, $J_1$ = 10.12 Hz, $J_2$ = 1.77 Hz, 1H), 6.43 (s, 1H), 7.16 (dd, $J_1$ = 10.15 Hz, $J_2$ = 1.26 Hz 1H). MASS (ES+): 607.5 |
| IB.50 | 1.06 (d, J = 7.16 Hz, 3H), 1.17 (d, J = 2.39 Hz, 3H), 1.18 (d, J = 2.37 Hz, 3H), 1.21 (s, 3H), 1.35-1.41 (m, 1H), 1.56 (s, 3H), 1.77-2.00 (m, 3H), 2.29-2.62 (m, 5H), 3.21 (d, J = 2.62 Hz, 1H), 3.42-3.49 (m, 1H), 3.67 (d, J = 16.86 Hz, 1H), 3.75 (d, J = 16.81 Hz, 1H), 4.45 (d, J = 8.59 Hz, 1H), 4.52 (d, J = 15.45 Hz, 1H), 4.74 (d, J = 15.33 Hz, 1H), 5.33-5.50 (m, 1H), 6.40 (dd, $J_1$ = 10.05 Hz, $J_2$ = 1.65 Hz, 1H), 6.45 (s, 1H), 6.50 (dd, $J_1$ = 3.50 Hz, $J_2$ = 1.69 Hz, 1H), 7.13 (dd, $J_1$ = 3.56 Hz, $J_2$ = 0.57 Hz, 1H), 7.19 (dd, $J_1$ = 0.75 Hz, $J_2$ = 0.22 Hz, 1H), 7.58 (s, 1H). MASS (ES+): 667.0 (M + Na)$^+$ |
| IB.51 | 1.06 (d, J = 7.16 Hz, 3H), 1.21 (s, 9H), 1.22 (s, 3H), 1.35-1.41 (m, 1H), 1.56 (s, 3H), 1.77-2.00 (m, 1H), 2.29-2.53 (m, 1H), 3.27 (d, J = 3.09 Hz, 1H), 3.42-3.47 (m, 1H), 3.67 (d, J = 16.88 Hz, 1H), 3.74 (d, J = 16.89 Hz, 1H), 4.45 (d, J = 8.56 Hz, 1H), 4.50 (d, J = 15.35 Hz, 1H), 4.75 (d, J = 15.40 Hz, 1H), 5.33-5.40 (m, 1H), 6.40 (dd, $J_1$ = 10.19 Hz, $J_2$ = 1.84 Hz, 1H), 6.45 (s, 1H), 6.50 (dd, $J_1$ = 3.51 Hz, $J_2$ = 1.68 Hz, 1H), 7.14 (d, J = 3.43 Hz, 1H), 7.17 (dd, $J_1$ = 15.12 Hz, $J_2$ = 0.99 Hz, 1H), 7.58 (d, J = 0.98 Hz, 1H). MASS (ES+): 680.9 (M + Na)$^+$ |
| IB.52 | 0.98 (d, J = 7.14 Hz, 3H), 1.12 (t, J = 7.56 Hz, 3H), 1.17 (s, 3H), 1.22 (s, 9H), 1.30-1.36 (m, 1H), 1.54 (s, 3H), 1.73-1.95 (m, 3H), 2.21-2.40 (m, 6H), 3.20 (d, J = 3.29 Hz, 1H), 3.34-3.38 (m, 1H), 3.68 (br-s, 2H), 4.40 (d, J = 8.77 Hz, 1H), 4.50 (d, J = 14.59 Hz, 1H), 4.74 (d, J = 15.33 Hz, 1H), 5.30-5.50 (m, 1H), 6.37 (dd, $J_1$ = 10.12 Hz, $J_2$ = 1.77 Hz, 1H), 6.43 (s, 1H), 7.15 (dd, $J_1$ = 10.09 Hz, $J_2$ = 1.04 Hz, 1H), MASS (ES+): 643.0 (M + Na)$^+$ |
| IB.53 | 0.94 (d, J = 7.45 Hz, 3H), 1.06 (d, J = 7.18 Hz, 3H), 1.12 (s, 3H), 1.34-1.40 (m, 1H), 1.55 (s, 3H), 1.66 (t, J = 7.41 Hz, 2H), 1.77-2.05 (m, 3H), 2.30 (t, J = 7.45 Hz, 2H), 2.35-2.48 (m, 4H), 3.43-3.47 (m, 1H), 3.66 (d, J = 7.79 Hz, 1H), 3.43 (d, J = 9.05 Hz, 1H), 4.76-4.79 (m, 2H), 5.59-5.72 (m, 1H), 6.39 (dd, $J_1$ = 10.17 Hz, $J_2$ = 1.80 Hz, 1H), 6.45 (s, 1H), 6.49 (dd, $J_1$ = 3.48 Hz, $J_2$ = 1.81 Hz, 1H), 7.12 (d, J = 3.42 Hz, 1H), 7.17 (dd, $J_1$ = 10.08 Hz, $J_2$ = 1.02 Hz, 1H), 7.58 (d, J = 0.93 Hz, 1H). MASS (ES+): 669.0 (M + Na)$^+$ |
| IB.54 | 1.06 (d, 3H, J = 7.14 Hz), 1.21 (s, 3H), 1.38-1.41 (m, 1H), 1.39 (t, 3H, J = 7.15 Hz), 1.56 (s, 3H), 1.77-1.96 (m, 3H), 2.28-2.64 (m, 5H), 3.37-3.45 (m, 1H), 3.72 (br-s, 2H), 4.38 (q, J = 7.12 Hz, 2H), 4.46 (d, J = 8.96 Hz, 1H), 4.79 (d, J = 15.27 Hz, 1H), 4.89 (d, J = 15.31 Hz, 1H), 5.32-5.51 (m, 1H), 6.40 (dd, $J_1$ = 10.14 Hz, $J_2$ = 1.77 Hz, 1H), 6.45 (s, 1H), 6.50 (dd, $J_1$ = 3.47 Hz, $J_2$ = 1.69 Hz, 1H), 7.12 (d, J = 3.25 Hz, 1H), 7.19 (dd, $J_1$ = 10.11 Hz, $J_2$ = 0.85 Hz, 1H), 7.58 (d, J = 0.72 Hz, 1H). |
| IB.55 | 0.96 (t, J = 7.42 Hz, 3H), 1.07 (d, J = 7.18 Hz, 3H), 1.21 (s, 3H), 1.36-1.42 (m, 1H), 1.56 (s, 3H), 1.65 (q, J = 7.43 Hz, 2H), 1.70-2.02 (m, 3H), 2.29-2.53 (m, 6H), 3.09 (d, J = 2.87 Hz, 1H), 3.43-3.47 (m, 1H), 3.67 (d, J = 16.68 Hz, 1H), 3.77 (d, J = 16.66 Hz, 1H), 4.46 (d, J = 8.60 Hz, 1H), 4.53 (d, J = 18.41 Hz, 1H), 4.73 (d, J = 15.35 Hz, 1H), 5.33-5.50 (m, 1H), 6.40 (dd, $J_1$ = 10.17 Hz, $J_2$ = 1.81 Hz, 1H), |

TABLE 6-continued

Spectral data for the synthesized compounds

| Comp. No | $^1$H-NMR ($\delta$ ppm), MASS (EI/ES+, m/z) |
|---|---|
| | 6.46 (s, 1H), 7.10 (dd, $J_1$ = 4.83 Hz, $J_2$ = 3.94 Hz, 1H), 7.19 (dd, $J_1$ = 10.10 Hz, $J_2$ = 1.02 Hz, 1H), 7.57 (dd, $J_1$ = 5.01 Hz, $J_2$ = 1.05 Hz, 1H), 7.75 (dd, $J_1$ = 3.71 Hz, $J_2$ = 1.03 Hz, 1H). MASS (ES+): 682.9 (M + Na)$^+$ |
| IB.56 | 0.96 (t, J = 7.40 Hz, 3H), 1.05 (d, J = 7.16 Hz, 3H), 1.21 (s, 3H), 1.37-1.40 (m, 1H), 1.56 (s, 3H), 1.66 (q, J = 7.42 Hz, 2H), 1.78-2.0 (m, 3H), 2.28-2.41 (m, 6H), 3.11 (d, J = 3.03 Hz, 1H), 3.38-3.45 (m, 1H), 3.71 (d, J = 11.09 Hz, 1H), 4.46 (d, J = 8.70 Hz, 1H), 4.52 (d, J = 15.37 Hz, 1H), 4.74 (d, J = 15.34 Hz, 1H), 6.42 (dd, $J_1$ = 10.18 Hz, $J_2$ = 1.82 Hz, 1H), 6.46 (s, 1H), 6.94 (d, J = 4.09 Hz, 1H), 7.19 (dd, $J_1$ = 10.09 Hz, $J_2$ = 1.06 Hz, 1H), 7.54 (d, J = 4.07 Hz, 1H). MASS (ES+): 716.9 (M + Na)$^+$ |
| IB.57 | 0.92-1.03 (m, 4H), 1.05 (d, J = 7.26 Hz, 3H), 1.19 (s, 3H), 1.35-1.40 (m, 1H), 1.56 (s, 3H), 1.61-1.98 (m, 4H), 2.28-2.51 (m, 4H), 3.06 (d, J = 2.41 Hz, 1H), 3.43-3.46 (m, 1H), 3.66 (d, J = 16.84 Hz, 1H), 3.77 (d, J = 16.84 Hz, 1H), 4.44 (d, J = 8.44 Hz, 1H), 4.55 (d, J = 16.23 Hz, 1H), 4.70 (d, J = 14.68 Hz, 1H), 5.33-5.50 (m, 1H), 6.40 (dd, $J_1$ = 10.15 Hz, $J_2$ = 1.79 Hz, 1H), 6.45 (s, 1H), 6.50 (dd, $J_1$ = 3.47 Hz, $J_2$ = 1.65 Hz, 1H), 7.13 (d, J = 3.3 Hz, 1H), 7.18 (dd, $J_1$ = 10.10 Hz, $J_2$ = 1.04 Hz, 1H), 7.59 (d, J = 0.83 Hz, 1H). MASS (ES+): 693.0 (M + Na)$^+$ |
| IB.58 | 1.06 (d, J = 7.14 Hz, 3H), 1.21 (s, 3H), 1.35-1.41 (m, 1H), 1.57 (s, 3H), 1.77-2.04 (m, 5H), 2.21-2.53 (m, 8H), 3.15-3.21 (m, 2H), 3.42-3.47 (m, 1H), 3.67 (d, J = 16.81 Hz, 1H), 3.75 (d, J = 17.06 Hz, 1H), 4.45 (d, J = 8.61 Hz, 1H), 4.43 (d, J = 15.33 Hz, 1H), 4.73 (d, J = 15.39 Hz, 1H), 5.33-5.50 (m, 1H), 6.40 (dd, $J_1$ = 10.14 Hz, $J_2$ = 1.82 Hz, 1H), 6.45 (s, 1H), 6.50 (dd, $J_1$ = 3.47 Hz, $J_2$ = 1.60 Hz, 1H), 7.13 (d, $J_1$ = 3.26 Hz, 1H), 7.18 (dd, $J_1$ = 10.18 Hz, $J_2$ = 1.26 Hz, 1H), 7.58 (d, J = 1.71 Hz, 1H). MASS (ES+): 678.9 (M + Na)$^+$ |
| IB.59 | 1.06 (d, J = 7.16 Hz, 3H), 1.21 (s, 3H), 1.35-1.41 (m, 1H), 1.56 (s, 3H), 1.62-1.9 (m, 11H), 2.28-2.51 (m, 4H), 2.73-2.81 (m, 1H), 3.17 (d, J = 2.84 Hz, 1H), 3.42-3.49 (m, 1H), 3.66 (d, J = 16.87 Hz, 1H), 3.75 (d, J = 16.86 Hz, 1H), 4.44 (d, J = 8.46 Hz, 1H), 4.51 (d, J = 15.31 Hz, 1H), 4.74 (d, J = 15.33 Hz, 1H), 5.33-5.50 (m, 1H), 6.40 (dd, $J_1$ = 10.18 Hz, $J_2$ = 1.82 Hz, 1H), 6.45 (s, 1H), 6.50 (dd, $J_1$ = 3.48 Hz, $J_2$ = 1.79 Hz, 1H), 7.13 (d, $J_1$ = 3.41 Hz, 1H), 7.17 (dd, $J_1$ = 10.08 Hz, $J_2$ = 1.08 Hz, 1H), 7.59 (d, J = 1.89 Hz, 1H). MASS (ES+): 693.0 (M + Na)$^+$ |
| IB.60 | 0.95 (t, J = 7.38 Hz, 3H), 1.06 (d, J = 7.18 Hz, 3H), 1.12 (s, 3H), 1.34-1.40 (m, 1H), 1.55 (s, 3H), 1.64 (q, J = 7.44 Hz, 2H), 1.74-1.94 (m, 3H), 2.30 (t, J = 7.46 Hz, 2H), 2.36-2.50 (m, 4H), 2.72 (s, 1H), 3.42-3.47 (m, 1H), 3.53 (dd, $J_1$ = 14.08 Hz, $J_2$ = 6.92 Hz, 1H), 3.67 (dd, $J_1$ = 14.01 Hz, $J_2$ = 5.33 Hz, 1H), 4.42 (d, J = 8.53 Hz, 1H), 4.50 (dd, $J_1$ = 13.23 Hz, $J_2$ = 4.74 Hz, 1H), 4.62 (dd, $J_1$ = 13.20 Hz, $J_2$ = 5.70 Hz, 1H), 5.32-5.49 (m, 1H), 5.67-5.81 (m, 2H), 6.39 (dd, $J_1$ = 10.19 Hz, $J_2$ = 1.80 Hz, 1H), 6.45 (s, 1H), 6.49 (dd, $J_1$ = 3.49 Hz, $J_2$ = 1.56 Hz, 1H), 7.12 (d, J = 3.42 Hz, 1H), 7.16 (dd, $J_1$ = 10.15 Hz, $J_2$ = 1.02 Hz, 1H), 7.58 (d, J = 0.79 Hz, 1H). MASS (ES+): 669.0 (M + Na)$^+$ |
| IB.61 | 1.03 (d, J = 7.12 Hz, 3H), 1.19 (s, 3H), 1.25-1.42 (m, 2H), 1.55 (s, 3H), 1.65-1.96 (m, 3H), 2.21-2.46 (m, 4H), 3.45 (m, 1H), 3.71 (d, J = 16.51 Hz, 1H), 3.79 (d, J = 16.46 Hz, 1H), 4.20-4.30 (m, 2H), 4.46 (d, J = 8.42 Hz, 1H), 5.30-5.50 (m, 1H), 6.42 (dd, $J_1$ = 10.05 Hz, $J_2$ = 1.80 Hz, 1H), 6.47 (s, 1H), 7.15 (dd, $J_1$ = 10.15 Hz, $J_2$ = 1.21 Hz, 1H), 7.43 (d, J = 8.59 Hz, 2H), 7.86 (d, J = 8.55 Hz, 2H). MASS (ES+): 640.9 (M + Na)$^+$ |
| IB.62 | 1.03 (d, J = 7.05 Hz, 3H), 1.20 (s, 3H), 1.22-1.93 (m, 8H), 2.29-2.51 (m, 4H), 3.44-3.50 (m, 1H), 3.71 (d, J = 16.42 Hz, 1H), 3.80 (d, J = 16.52 Hz, 1H), 4.26-4.32 (m, 2H), 4.46 (d, J = 8.81 Hz, 1H), 5.33-5.50 (m, 1H), 6.40-6.42 (m, 1H), 6.46 (s, 1H), 7.16 (dd, J = 10.15 Hz, 1H), 7.39 (d, J = 7.91 Hz, 1H), 7.55 (d, J = 7.56 Hz, 1H) 7.79 (d, J = 7.76 Hz, 1H), 7.91 (s, 1H). MASS (ES+): 640.9 (M + Na)$^+$ |
| IB.63 | 1.06 (d, J = 7.14 Hz, 3H), 1.19 (s, 3H), 1.36-1.41 (m, 1H), 1.55 (s, 3H), 1.74-1.99 (m, 3H), 2.17-2.51 (m, 5H), 3.42-3.46 (m, 1H), 3.69 (d, J = 16.73 Hz, 1H), 3.76 (d, J = 16.91 Hz, 1H), 3.81 (s, 3H), 4.45 (d, J = 8.63 Hz, 1H), 4.66 (td, $J_1$ = 15.52 Hz, $J_2$ = 1.70 Hz, 1H), 4.73 (td, $J_1$ = 15.49 Hz, $J_2$ = 1.71 Hz, 1H), 5.33-5.49 (m, 1H), 6.40 (dd, $J_1$ = 10.12 Hz, $J_2$ = 1.72 Hz, 1H), 6.45 (s, 1H), 6.50 (dd, $J_1$ = 3.48 Hz, $J_2$ = 1.68 Hz, 1H), 7.14 (d, J = 3.43 Hz, 1H), 7.16 (dd, $J_1$ = 10.09 Hz, $J_2$ = 0.99 Hz, 1H), 7.59 (d, J = 0.92 Hz, 1H). MASS (ES+): 654.9 (M + Na)$^+$. |
| IB.64 | 1.06 (d, J = 7.16 Hz, 3H), 1.19 (s, 3H), 1.33 (t, J = 7.05 Hz, 3H), 1.36-1.41 (m, 1H), 1.55 (s, 3H), 1.74-1.99 (m, 3H), 2.28-2.50 (m, 4H), 2.56 (d, J = 1.85 Hz, 1H), 3.42-3.47 (m, 1H), 3.69 (d, J = 16.88 Hz, 1H), 3.76 (d, J = 16.88 Hz, 1H), 4.22 (q, J = 7.13 Hz, 2H), 4.44 (d, J = 8.65 Hz, 1H), 4.65 (d, J = 15.49 Hz, 1H), 4.72 (d, J = 15.41 Hz, 1H), 5.33-5.49 (m, 1H), 6.40 (dd, $J_1$ = 10.13 Hz, $J_2$ = 1.63 Hz, 1H), 6.45 (s, 1H), 6.51 (dd, $J_1$ = 3.44 Hz, $J_2$ = 1.69 Hz, 1H), 7.14 (d, J = 3.50 Hz, 1H), 7.16 (d, J = 10.20 Hz, 1H), 7.59 (d, J = 0.87 Hz, 1H). MASS (ES+): 669.1 (M + Na)$^+$. |
| IB.65 | 1.06 (d, J = 7.19 Hz, 3H), 1.20 (s, 3H), 1.34-1.43 (m, 1H), 1.50 (s, 9H), 1.55 (s, 3H), 1.62-1.99 (m, 3H), 2.28-2.54 (m, 5H), 3.43-3.48 (m, 1H), 3.68 (d, J = 16.70 Hz, 1H), 3.77 (d, J = 16.65 Hz, 1H), 4.44 (d, J = 8.51 Hz, 1H), 4.57-4.68 (m, 2H), 5.33-5.49 (m, 1H), 6.40 (dd, $J_1$ = 10.06 Hz, $J_2$ = 1.79 Hz, 1H), 6.45 (s, 1H), 6.50 (dd, $J_1$ = 3.48 Hz, $J_2$ = 1.78 Hz, 1H), 7.11-7.14 (m, 2H), 7.59 (d, J = 1.00 Hz, 1H). MASS (ES+): 697.0 (M + Na)$^+$. |
| IB.66 | 0.96 (d, J = 6.74 Hz, 6H), 1.06 (d, J = 7.13 Hz, 3H), 1.19 (s, 3H), 1.35-1.41 (m, 1H), 1.55 (s, 3H), 1.74-2.00 (m, 4H), 2.28-2.52 (m, 5H), 3.43-3.46 (m, 1H), 3.68 (d, J = 16.80 Hz, 1H), 3.77 (d, J = 16.79 Hz, 1H), 3.93 (d, J = 6.72 Hz, 2H), 4.44 (d, J = 8.62 Hz, 1H), 4.66 (d, J = 15.49 Hz, 1H), 4.71 (d, J = 15.48 Hz, 1H), 5.33-5.49 (m, 1H), 6.40 (dd, $J_1$ = 10.18 Hz, $J_2$ = 1.48 Hz, 1H), 6.45 (s, 1H), 6.50 (dd, $J_1$ = 3.36 Hz, $J_2$ = 1.59 Hz, 1H), 7.13-7.16 (m, 2H), 7.59 (s, 1H). MASS (ES+): 697.0 (M + Na)$^+$. |
| IB.67 | 1.06 (d, J = 7.14 Hz, 3H), 1.19 (s, 3H), 1.35-1.41 (m, 1H), 1.55 (s, 3H), 1.77-2.14 (m, 5H), 2.28-2.72 (m, 5H), 2.55 (t, J = 7.26 Hz, 2H), 3.42-3.47 (m, 1H), 3.59 (t, J = 6.37 Hz, 2H), 3.64 (d, J = 16.76 Hz, 1H), 3.76 (d, J = 16.58 Hz, 1H), 4.46 (d, J = 8.65 Hz, 1H), 4.58 (d, J = 15.39 Hz, 1H), 4.73 (d, J = 15.40 Hz, 1H), 5.33-5.49 (m, 1H), 6.40 (dd, $J_1$ = 10.14 Hz, $J_2$ = 1.64 Hz, 1H), 6.45 (s, 1H), 6.50 (dd, $J_1$ = 3.4 Hz, $J_2$ = 1.57 Hz, 1H), 7.13 (d, J = 3.45 Hz, 1H), 7.18 (d, J = 9.98 Hz, 1H), 7.59 (d, J = 0.75 Hz, 1H). MASS (ES+): 679.0 |
| IB.68 | 1.05 (d, J = 7.14 Hz, 3H), 1.12 (s, 3H), 1.19 (s, 9H), 1.34-1.40 (m, 1H), 1.55 (s, 3H), 1.71-2.06 (m, 3H), 2.27-2.52 (m, 4H), 3.42-3.47 (m, 1H), 3.63 (d, J = 11.76 Hz, 1H), 3.68 (d, J = 11.84 Hz, 1H), 4.43 (d, J = 9.20 Hz, 1H), 4.74 (dd, $J_1$ = 13.06 Hz, $J_2$ = 6.26 Hz, 1H), 4.79 (dd, $J_1$ = 13.58 Hz, |

TABLE 6-continued

Spectral data for the synthesized compounds

| Comp. No | $^1$H-NMR (δ ppm), MASS (EI/ES+, m/z) |
|---|---|
| | $J_2$ = 6.06 Hz, 1H), 5.32-5.49 (m, 1H), 5.55-5.74 (m, 1H), 6.39 (dd, $J_1$ = 10.19 Hz, $J_2$ = 1.41 Hz, 1H), 6.45 (s, 2H), 6.49 (dd, $J_1$ = 3.34 Hz, $J_2$ = 1.53 Hz, 1H), 7.12 (d, J = 3.45 Hz, 1H), 7.15 (d, J = 10.17 Hz, 1H), 7.58 (s, 1H). MASS (ES+): 683.0 (M + Na)$^+$ |
| IB.69 | 1.06 (d, J = 7.15 Hz, 3H), 1.13 (s, 3H), 1.20 (s, 9H), 1.34-1.42 (m, 1H), 1.55 (s, 3H), 1.71-1.95 (m, 3H), 2.17-2.53 (m, 4H), 2.81 (s, 1H), 3.42-3.49 (m, 1H), 3.54 (dd, $J_1$ = 14.17 Hz, $J_2$ = 7.36 Hz, 1H), 3.67 (dd, $J_1$ = 14.01 Hz, $J_2$ = 5.52 Hz, 1H), 4.42 (d, J = 8.46 Hz, 1H), 4.50 (dd, $J_1$ = 13.61 Hz, $J_2$ = 4.34 Hz, 1H), 4.62 (dd, $J_1$ = 13.51 Hz, $J_2$ = 5.59 Hz, 1H), 5.32-5.49 (m, 1H), 5.64-5.80 (m, 2H), 6.39 (dd, $J_1$ = 10.18 Hz, $J_2$ = 1.77 Hz, 1H), 6.45 (s, 1H), 6.49 (dd, $J_1$ = 3.43 Hz, $J_2$ = 1.80 Hz, 1H), 7.12 (d, J = 3.31 Hz, 1H), 7.15 (dd, J = 10.24 Hz, $J_2$ = 0.78 Hz, 1H), 7.58 (d, J = 0.85 Hz, 1H). MASS (ES+): 683.1 (M + Na)$^+$ |
| IB.70 | 1.06 (d, 3H, J = 7.16 Hz), 1.19 (s, 3H), 1.36-1.42 (m, 1H), 1.56 (s, 3H), 1.77-1.96 (m, 3H), 2.29-2.52 (m, 5H), 3.41-3.45 (m, 1H), 3.70 (d, 1H, J = 16.78 Hz), 3.77 (d, J = 16.93 Hz, 1H), 4.46 (d, J = 8.62 Hz, 1H), 4.77 (d, J = 15.30 Hz, 1H), 4.89 (d, J = 15.31 Hz, 1H), 5.33-5.50 (m, 1H), 5.99 (s, 1H), 6.40 (dd, $J_1$ = 10.16 Hz, $J_2$ = 1.75 Hz, 1H), 6.45 (s, 1H), 6.50 (dd, $J_1$ = 3.47 Hz, $J_2$ = 1.67 Hz, 1H), 7.12 (d, J = 3.41 Hz, 1H), 7.17 (d, J = 10.19 Hz, 1H), 7.59 (s, 1H). MASS (ES+): 597.2[(M + Na)$^+$ of IB.4] |
| IB.71 | 0.92 (q, J = 4.52 Hz, 3H), 1.06 (d, J = 7.11 Hz, 3H), 1.15 (dd, 3H), 1.22 (s, 3H), 1.22 (s, 3H), 1.35-1.41 (m, 1H), 1.56 (s, 3H), 1.46-2.00 (m, 5H), 2.29-2.53 (m, 5H), 3.22-3.26 (dd, 1H), 3.40-3.50 (m, 1H), 3.66 (d, J = 16.58 Hz, 1H), 3.75 (d, J = 16.83 Hz, 1H), 4.45 (d, J = 8.39 Hz, 1H), 4.48-4.53 (m, 1H), 5.33-5.50 (m, 1H), 6.40 (dd, $J_1$ = 10.15 Hz, $J_2$ = 1.71 Hz, 1H), 6.45 (s, 1H), 6.50 (dd, $J_1$ = 3.39 Hz, $J_2$ = 1.67 Hz, 1H), 7.13 (d, J = 3.49 Hz, 1H), 7.19 (d, J = 10.13 Hz, 1H), 7.58 (s, 1H). MASS (ES+): 659.3 |
| IB.72 | 1.03 (s, 9H), 1.05 (d, J = 7.35 Hz, 3H), 1.20 (s, 3H), 1.35-1.40 (m, 1H), 1.56 (s, 3H), 1.72-2.03 (m, 3H), 2.20 (d, J = 13.11 Hz, 1H), 2.24 (d, J = 13.16 Hz, 1H), 2.29-2.54 (m, 4H), 3.07 (s, 1H), 3.44-3.48 (m, 1H), 3.63 (d, J = 16.81 Hz, 1H), 3.78 (d, J = 16.84 Hz, 1H), 4.44 (d, J = 8.47 Hz, 1H), 4.50 (d, J = 15.41 Hz, 1H), 4.73 (d, J = 15.35 Hz, 1H), 5.33-5.50 (m, 1H), 6.40 (dd, $J_1$ = 10.17 Hz, $J_2$ = 1.78 Hz, 1H), 6.45 (s, 1H), 6.50 (dd, $J_1$ = 3.45 Hz, $J_2$ = 1.78 Hz, 1H), 7.14 (d, J = 3.37 Hz, 1H), 7.18 (dd, $J_1$ = 9.63 Hz, $J_2$ = 1.07 Hz, 1H), 7.59 (s, 1H). MASS (ES+): 673.3 |
| IB.73 | 1.06 (d, J = 7.17 Hz, 3H), 1.15 (t, J = 7.57 Hz, 3H), 1.20 (s, 3H), 1.35-1.41 (m, 1H), 1.56 (s, 3H), 1.74-2.00 (m, 3H), 2.28-2.52 (m, 6H), 3.10 (d, J = 2.84 Hz, 1H), 3.42-3.46 (m, 1H), 3.66 (d, J = 16.80 Hz, 1H), 3.75 (d, J = 16.82 Hz, 1H), 4.45 (d, J = 8.54 Hz, 1H), 4.54 (d, J = 15.48 Hz, 1H), 4.73 (d, J = 15.38 Hz, 1H), 5.33-5.40 (m, 1H), 6.40 (dd, $J_1$ = 10.11 Hz, $J_2$ = 1.76 Hz, 1H), 6.45 (s, 1H), 6.50 (dd, $J_1$ = 3.49 Hz, $J_2$ = 1.65 Hz, 1H), 7.13 (d, J = 3.35 Hz, 1H), 7.18 (dd, $J_1$ = 10.06 Hz, $J_2$ = 1.04 Hz, 1H), 7.59 (d, J = 0.80 Hz, 1H). MASS (ES+): 631.3 |
| IB.74 | 0.98 (d, J = 7.10 Hz, 3H), 1.16 (s, 3H), 1.30-1.36 (m, 1H), 1.54 (s, 3H), 1.73-1.99 (m, 5H), 2.10-2.47 (m, 8H), 2.61 (m, 1H), 3.11-3.19 (m, 1H), 3.31-3.35 (m, 1H), 3.67 (d, J = 16.90 Hz, 1H), 3.73 (d, J = 16.78 Hz, 1H), 4.36-4.41 (m, 3H), 4.79 (d, J = 15.23 Hz, 1H), 4.88 (d, J = 15.28 Hz, 1H), 5.31-5.48 (m, 1H), 6.38 (d, $J_1$ = 10.17 Hz, 1H), 6.43 (s, 1H), 7.17 (d, J = 10.05 Hz, 1H). MASS (ES+): 585.22 [(M + Na)$^+$ of IB.08] |
| IB.75 | 0.98 (d, J = 7.18 Hz, 3H), 1.16 (s, 3H), 1.18 (d, J = 3.67 Hz, 3H), 1.20 (d, J = 3.71 Hz, 3H), 1.29-1.35 (m, 1H), 1.54 (s, 3H), 1.70-1.99 (m, 5H), 2.16-2.61 (m, 9H), 3.12 (d, J = 3.61 Hz, 1H), 3.12-3.20 (m, 1H), 3.33-3.38 (m, 1H), 3.65 (d, J = 16.64 Hz, 1H), 3.72 (d, J = 16.26 Hz, 1H), 4.40 (d, J = 8.93, 1H), 4.52 (d, J = 15.32, 1H), 4.73 (d, J = 15.33 Hz, 1H), 5.31-5.48 (m, 1H), 6.37 (dd, $J_1$ = 10.09 Hz, $J_2$ = 1.77 Hz, 1H), 6.43 (s, 1H), 7.16 (d, $J_1$ = 10.10 Hz, $J_2$ = 1.10 Hz, 1H). MASS (ES+): 633.25 |
| IB.76 | 1.06 (d, J = 7.17 Hz, 3H), 1.22 (s, 3H), 1.35-1.41 (m, 1H), 1.57 (s, 3H), 1.67-2.03 (m, 1H), 2.29-2.53 (m, 4H), 3.31 (d, J = 3.06 Hz, 1H), 3.45 (m, 1H), 3.67 (d, J = 16.78 Hz, 1H), 3.73 (d, J = 17.10 Hz, 1H), 4.45 (d, J = 7.42 Hz, 1H), 4.48 (d, J = 15.41 Hz, 1H), 4.73 (d, J = 15.40 Hz, 1H), 5.33-5.40 (m, 1H), 6.40 (dd, $J_1$ = 10.07 Hz, $J_2$ = 1.79 Hz, 1H), 6.45 (s, 1H), 6.50 (dd, $J_1$ = 3.47 Hz, $J_2$ = 1.81 Hz, 1H), 7.14 (d, J = 3.28 Hz, 1H), 7.18 (dd, $J_1$ = 10.07 Hz, $J_2$ = 1.07 Hz, 1H), 7.58 (d, J = 0.97 Hz, 1H). MASS (ES+): 737.4 |
| IB.77 | 1.06 (d, J = 7.12 Hz, 3H), 1.19 (s, 3H), 1.25-1.43 (m, 2H), 1.55 (s, 3H), 1.74-1.97 (m, 3H), 2.28-2.50 (m, 4H), 3.24 (q, J = 10.07 Hz, 2H), 3.42-3.45 (m, 1H), 3.68 (d, J = 16.80 Hz, 1H), 3.76 (d, J = 16.82 Hz, 1H), 4.45 (d, J = 8.56 Hz, 1H), 4.65 (d, J = 15.34 Hz, 1H), 4.83 (d, J = 15.37 Hz, 1H), 5.33-5.49 (m, 1H), 6.41 (dd, $J_1$ = 10.14 Hz, $J_2$ = 1.72 Hz, 1H), 6.41 (s, 1H), 6.51 (dd, $J_1$ = 3.42 Hz, $J_2$ = 1.62 Hz, 1H), 7.13 (d, J = 3.42 Hz, 1H), 7.16 (d, J = 10.14 Hz, 1H), 7.59 (s, 1H). MASS (ES+): 707.13 (M + Na)$^{++}$ |
| IB.78 | 1.06 (d, J = 7.14 Hz, 3H), 1.23 (s, 3H), 1.35-1.41 (m, 1H), 1.57 (s, 3H), 1.77-1.99 (m, 3H), 2.28-2.53 (m, 4H), 3.11 (s, 1H), 3.39-3.45 (m, 1H), 3.45 (s, 3H), 3.67 (d, J = 17.19 Hz, 1H), 3.73 (d, J = 16.96 Hz, 1H), 4.03 (d, J = 16.48 Hz, 1H), 4.10 (d, J = 16.55 Hz, 1H), 4.43 (d, J = 8.74 Hz, 1H), 4.58 (d, J = 15.30 Hz, 1H), 4.58 (d, J = 15.33 Hz, 1H), 5.33-5.50 (m, 1H), 6.39 (dd, $J_1$ = 10.14 Hz, $J_2$ = 1.71 Hz, 1H), 6.45 (s, 1H), 6.50 (dd, $J_1$ = 13.41 Hz, $J_2$ = 1.76 Hz, 1H), 7.12 (d, J = 3.55 Hz, 1H), 7.17 (dd, $J_1$ = 0.19 Hz, $J_2$ = 0.74 Hz, 1H), 7.58 (d, J = 0.71 Hz, 1H). MASS (ES+): 647.24 |
| IB.79 | 1.06 (d, J = 7.16 Hz, 3H), 1.23 (s, 3H), 1.27 (t, J = 7.04 Hz, 3H), 1.35-1.41 (m, 1H), 1.56 (s, 3H), 1.73-1.99 (m, 3H), 2.28-2.53 (m, 4H), 3.17 (s, 1H), 3.39-3.42 (m, 1H), 3.57 (dd, $J_1$ = 7.03 Hz, $J_2$ = 2.38 Hz, 1H), 3.60 (dd, $J_1$ = 4.44 Hz, $J_2$ = 2.44 Hz, 1H), 3.65 (d, J = 16.18 Hz, 1H), 3.73 (d, J = 16.94 Hz, 1H), 4.07 (d, J = 16.64 Hz, 1H), 4.14 (d, J = 16.63 Hz, 1H), 4.43 (d, J = 8.74 Hz, 1H), 4.56 (d, J = 15.41 Hz, 1H), 4.85 (d, J = 15.30 Hz, 1H), 5.33-5.50 (m, 1H), 6.38 (dd, $J_1$ = 10.11 Hz, $J_2$ = 1.72 Hz, 1H), 6.45 (s, 1H), 6.50 (dd, $J_1$ = 3.49 Hz, $J_2$ = 1.65 Hz, 1H), 7.12 (d, J = 3.37 Hz, 1H), 7.17 (d, J = 10.17 Hz, 1H), 7.58 (d, J = 1.57 Hz, 1H). MASS (ES+): 661.22 |
| IB.80 | 1.05 (d, J = 7.10 Hz, 3H), 1.18 (s, 3H), 1.25-1.42 (m, 2H), 1.55 (s, 3H), 1.71-2.00 (m, 3H), 2.17-2.51 (m, 4H), 2.62-2.68 (m, 4H), 3.43-3.49 (m, 1H), 3.68 (d, J = 16.72 Hz, 1H), 3.75 (d, J = 16.78 Hz, 1H), 4.45 (d, J = 8.41 Hz, 1H), 4.58 (d, J = 15.45 Hz, 1H), 4.74 (d, J = 15.45 Hz, 1H), 5.33-5.49 (m, 1H), 6.42 (dd, $J_1$ = 10.09 Hz, $J_2$ = 1.58 Hz, 1H), 6.45 (s, 1H), 6.51 (dd, $J_1$ = 3.41 Hz, $J_2$ = 1.69 Hz, 1H), 7.14 (d, J = 3.41 Hz, 1H), 7.22 (d, J = 10.04 Hz, 1H), 7.59 (s, 1H). MASS (ES+): 697.16 (M + Na)$^+$ |
| IB.81 | 1.06 (d, 3H, J = 7.17 Hz), 1.18 (s, 3H), 1.35-1.41 (m, 1H), 1.56 (s, 3H), 1.77-1.99 (m, 3H), 2.09 (s, 3H), 2.28-2.51 (m, 4H), 2.91 (d, 1H, J = 2.60 Hz), 3.42-3.47 (m, 1H), 3.66 (d, 1H, J = 16.74 Hz), 3.76 (d, J = 16.78 Hz, 1H), 4.46 (d, J = 8.63 Hz, 1H), 4.56 (d, t, $J_1$ = 15.46 Hz, $J_2$ = 1.78 Hz, 1H), 4.70 (d, |

TABLE 6-continued

Spectral data for the synthesized compounds

| Comp. No | $^1$H-NMR (δ ppm), MASS (EI/ES+, m/z) |
|---|---|
| | $J_1$ = 15.39 Hz, $J_2$ = 1.65 Hz, 1H), 5.32-5.50 (m, 1H), 6.39 (dd, $J_1$ = 10.07 Hz, $J_2$ = 1.79 Hz, 1H), 6.45 (s, 1H), 6.50 (dd, $J_1$ = 3.53 Hz, $J_2$ = 1.68 Hz, 1H), 7.14 (d, J = 3.37 Hz, 1H), 7.20 (dd, $J_1$ = 10.18 Hz, $J_2$ = 1.23 Hz, 1H), 7.59 (d, J = 0.86 Hz, 1H). MASS (ES+): 617.1 |
| IB.82 | 1.06 (d, J = 7.18 Hz, 3H), 1.13 (s, 3H), 1.16 (d, J = 1.26 Hz, 3H), 1.18 (d, J = 1.30 Hz, 3H), 1.34-1.43 (m, 1H), 1.55 (s, 3H), 1.77-1.95 (m, 3H), 2.28-2.53 (m, 4H), 2.53-2.80 (m, 1H), 2.81 (m, 1H), 3.43-3.48 (m, 1H), 3.54 (dd, $J_1$ = 14.12 Hz, $J_2$ = 7.29 Hz, 1H), 3.66 (dd, $J_1$ = 14.07 Hz, $J_2$ = 5.45 Hz, 1H), 4.43 (d, J = 8.57 Hz, 1H), 4.50 (dd, $J_1$ = 13.32 Hz, $J_2$ = 4.52 Hz, 1H), 4.62 (dd, $J_1$ = 13.25 Hz, $J_2$ = 5.69 Hz, 1H), 5.32-5.49 (m, 1H), 5.65-5.80 (m, 2H), 6.39 (dd, $J_1$ = 10.15 Hz, $J_2$ = 1.79 Hz, 1H), 6.45 (s, 1H), 6.50 (dd, $J_1$ = 3.46 Hz, $J_2$ = 1.64 Hz, 1H), 7.11 (d, J = 3.43 Hz, 1H), 7.16 (dd, $J_1$ = 10.03 Hz, $J_2$ = 0.93 Hz, 1H), 7.58 (d, J = 0.86 Hz, 1H). MASS (ES+): 647.1 |
| IB.83 | 1.06 (d, J = 7.17 Hz, 3H), 1.12 (s, 3H), 1.16 (d, J = 6.98 Hz, 6H), 1.34-1.40 (m, 1H), 1.55 (s, 3H), 1.77-2.06 (m, 3H), 2.28-2.59 (m, 5H), 3.42-3.47 (m, 1H), 3.66 (d, J = 7.82 Hz, 2H), 4.44 (d, J = 9.08 Hz, 1H), 4.75-4.79 (m, 2H), 5.34-5.47 (m, 1H), 5.58-5.72 (m, 2H), 6.39 (dd, $J_1$ = 10.16 Hz, $J_2$ = 1.79 Hz, 1H), 6.45 (s, 1H), 6.49 (dd, $J_1$ = 3.41 Hz, $J_2$ = 1.82 Hz, 1H), 7.12 (d, J = 3.19 Hz, 1H), 7.16 (dd, $J_1$ = 10.08 Hz, $J_2$ = 1.06 Hz, 1H), 7.58 (br-s, 1H). MASS (ES+): 647.1 |
| IB.84 | 0.98 (d, J = 7.15 Hz, 3H), 1.17 (s, 3H), 1.22 (s, 9H), 1.27-1.38 (m, 1H), 1.54 (s, 3H), 1.70-1.99 (m, 5H), 2.17-2.50 (m, 8H), 3.12-3.18 (m, 1H), 3.21 (d, J = 3.24 Hz, 1H), 3.35-3.38 (m, 1H), 3.65 (d, J = 16.86 Hz, 1H), 3.65 (d, J = 16.86 Hz, 1H), 3.72 (d, J = 17.02 Hz, 1H), 4.39 (d, J = 8.61 Hz, 1H), 4.51 (d, J = 15.31 Hz, 1H), 4.73 (d, J = 15.33 Hz, 1H), 5.31-5.48 (m, 1H), 6.37 (dd, $J_1$ = 10.11 Hz, $J_2$ = 1.61 Hz, 1H), 6.43 (s, 1H), 7.15 (d, J = 10.16 Hz, 1H). MASS (ES+): 647.1 |
| IB.85 | 0.86 (t, J = 7.46 Hz, 3H), 1.05 (d, J = 7.15 Hz, 3H), 1.17 (s, 6H), 1.23 (s, 3H), 1.35-1.41 (m, 1H), 1.56 (s, 3H), 1.73-2.01 (m, 3H), 2.29-2.56 (m, 4H), 3.36 (br-s, 1H), 3.43-3.49 (m, 1H), 4.40 (d, 1H), 4.48 (d, J = 15.37 Hz, 1H), 4.76 (d, J = 15.31 Hz, 1H), 5.34-5.50 (m, 1H), 6.40 (dd, $J_1$ = 10.17 Hz, $J_2$ = 1.72 Hz, 1H), 6.45 (s, 1H), 6.50 (dd, $J_1$ = 3.44 Hz, $J_2$ = 1.67 Hz, 1H), 7.13 (d, J = 3.37 Hz, 1H), 7.17 (dd, $J_1$ = 10.07 Hz, $J_2$ = 0.60 Hz, 1H), 7.58 (s, 1H). MASS (ES+): 673.26 |
| IB.86 | 0.96 (s, 3H), 1.06 (d, J = 5.33 Hz, 3H), 1.07 (s, 3H), 1.13 (s, 3H), 1.25 (s, 3H), 1.35-1.41 (m, 1H), 1.56 (s, 3H), 1.69-2.13 (m, 6H), 2.28-2.57 (m, 5H), 3.10 (s, 1H), 3.39-3.42 (m, 1H), 3.66 (d, J = 16.62 Hz, 1H), 3.73 (d, J = 17.10 Hz, 1H), 4.53 (d, J = 8.29 Hz, 1H), 4.64 (d, J = 15.20 Hz, 1H), 4.92 (d, J = 15.23 Hz, 1H), 5.33-5.50 (m, 1H), 6.41 (dd, $J_1$ = 10.07 Hz, $J_2$ = 1.78 Hz, 1H), 6.44 (s, 1H), 6.49 (dd, $J_1$ = 3.51 Hz, $J_2$ = 1.70 Hz, 1H), 7.12 (d, J = 3.41 Hz, 1H), 7.29 (dd, $J_1$ = 10.04 Hz, $J_2$ = 0.99 Hz, 1H), 7.58 (d, J = 0.95 Hz, 1H). MASS (ES+): 777.18 (M + Na)$^+$ |
| IB.87 | 1.06 (d, J = 7.15 Hz, 3H), 1.23 (s, 3H), 1.33 (s, 9H), 1.33-1.38 (m, 1H), 1.56 (s, 3H), 1.77-2.08 (m, 3H), 2.29-2.53 (m, 4H), 3.47 (m, 1H), 3.61 (d, J = 16.75 Hz, 1H), 3.80 (d, J = 16.80 Hz, 1H), 4.38 (d, J = 16.03 Hz, 1H), 4.44 (d, J = 8.47 Hz, 1H), 4.72 (d, J = 15.70 Hz, 1H), 4.78 (s, 1H), 5.33-5.49 (m, 1H), 6.39 (dd, $J_1$ = 10.09 Hz, $J_2$ = 1.72 Hz, 1H), 6.45 (s, 1H), 6.50 (dd, $J_1$ = 3.45 Hz, $J_2$ = 1.62 Hz, 1H), 7.14 (m, 2H), 7.59 (d, J = 0.74 Hz, 1H). MASS (ES+): 696.20 (M + Na)$^+$ |
| IB.88 | 1.06 (d, J = 7.17 Hz, 3H), 1.18 (s, 3H), 1.35-1.41 (m, 2H), 1.55 (s, 3H), 1.77-1.96 (m, 3H), 2.17-2.47 (m, 4H), 3.42-3.46 (m, 1H), 3.66 (d, J = 16.77 Hz, 1H), 3.76 (d, J = 16.80 Hz, 1H), 4.15 (q, J = 7.15 Hz, 2H), 4.45 (d, J = 8.67 Hz, 1H), 4.59 (d, J = 15.47 Hz, 1H), 4.73 (d, J = 15.36 Hz, 1H), 5.32-5.49 (m, 1H), 6.40 (dd, $J_1$ = 10.09 Hz, $J_2$ = 1.75 Hz, 1H), 6.41 (s, 1H), 6.51 (dd, $J_1$ = 3.46 Hz, $J_2$ = 1.81 Hz, 1H), 7.13 (d, J = 3.36 Hz, 1H), 7.20 (dd, $J_1$ = 10.14 Hz, $J_2$ = 1.08 Hz, 1H), 7.59 (s, 1H). MASS (ES+): 725.18 (M + Na)$^+$ |
| IB.89 | 0.78 (d, J = 6.98 Hz, 3H), 0.88 (d, J = 7.03 Hz, 3H), (d, J = 6.41 Hz, 3H), 1.02-1.10 (m, 5H), 1.20 (s, 3H), 1.30-1.49 (m, 3H), 1.55 (s, 3H), 1.69-2.00 (m, 7H), 2.28-2.51 (m, 4H), 2.59 (s, 1H), 3..42-3.46 (m, 1H), 3.69 (d, J = 16.56 Hz, 1H), 3.76 (d, J = 16.91 Hz, 1H), 4.42 (d, J = 8.58 Hz, 1H), 4.59 (td, $J_1$ = 10.91 Hz, $J_2$ = 4.39 Hz, 1H), 4.62 (d, J = 15.52 Hz, 1H), 4.72 (d, J = 15.41 Hz, 1H), 5.32-5.49 (m, 1H), 6.40 (dd, $J_1$ = 10.18 Hz, $J_2$ = 1.81 Hz, 1H), 6.45 (s, 1H), 6.50 (dd, $J_1$ = 3.47 Hz, $J_2$ = 1.78 Hz, 1H), 7.12-7.14 (m, 2H), 7.59 (s, 1H). MASS (ES+): 779.32 (M + Na)$^+$ |
| IB.90 | 1.06 (d, J = 7.14 Hz, 3H), 1.17 (s, 3H), 1.34-1.40 (m, 1H), 1.55 (s, 3H), 1.76-1.97 (m, 3H), 2.06 (s, 3H), 2.28-2.54 (m, 4H), 3.41-3.46 (m, 1H), 3.67-3.75 (m, 2H), 4.00 (dd, $J_1$ = 18.22 Hz, $J_2$ = 5.46 Hz, 1H), 4.09 (dd, $J_1$ = 18.22 Hz, $J_2$ = 5.84 Hz, 1H), 4.41 (d, J = 5.81 Hz, 1H), 4.71 (s, 2H), 5.32-5.49 (m, 1H), 6.11 (s, 1H), 6.39 (dd, $J_1$ = 10.16 Hz, $J_2$ = 1.79 Hz, 1H), 6.45 (s, 1H), 6.50 (dd, $J_1$ = 3.45 Hz, $J_2$ = 1.77 Hz, 1H), 7.12 (d, J = 3.51 Hz, 1H), 7.19 (dd, $J_1$ = 10.09 Hz, $J_2$ = 0.96 Hz, 1H), 7.58 (d, J = 0.90 Hz, 1H). MASS (ES+): 696.13 (M + Na)$^+$ |
| IB.91 | 0.96 (d, J = 6.72 Hz, 3H), 1.05 (d, J = 7.15 Hz, 3H), 1.19 (s, 3H), 1.35-1.41 (m, 1H), 1.55 (s, 3H), 1.78-2.02 (m, 4H), 2.30-2.63 (m, 5H), 3.41-3.45 (m, 1H), 3.70 (d, J = 16.81 Hz, 1H), 3.76 (d, J = 16.76 Hz, 1H), 3.93 (d, J = 6.80 Hz, 2H), 4.44-4.46 (m, 1H), 4.66 (d, J = 15.53 Hz, 1H), 4.71 (d, J = 15.50 Hz, 1H), 5.33-5.49 (m, 1H), 6.40 (dd, $J_1$ = 10.13 Hz, $J_2$ = 1.67 Hz, 1H), 6.46 (s, 1H), 6.94 (d, J = 4.00 Hz, 1H), 7.15 (d, J = 10.22 Hz, 1H), 7.53 (d, J = 4.01 Hz, 1H). MASS (ES+): 747.0 (M + Na)$^+$ |
| IB.92 | 1.05 (d, J = 7.14 Hz, 3H), 1.18 (d, J = 6.98 Hz, 3H), 1.19 (d, J = 7.13 Hz, 3H), 1.22 (s, 3H), 1.35-1.41 (m, 1H), 1.56 (s, 3H), 1.78-2.00 (m, 3H), 2.28-2.63 (m, 5H), 3.23 (d, J = 3.19 Hz, 1H), 3.40-3.45 (m, 1H), 3.67-3.75 (m, 2H), 3.45-3.47 (m, 1H), 3.49-3.77 (m, 2H), 5.33-5.50 (m, 1H), 6.41 (dd, $J_1$ = 10.15 Hz, $J_2$ = 1.79 Hz, 1H), 6.46 (s, 1H), 6.93 (d, J = 4.0 Hz, 1H), 7.18 (dd, $J_1$ = 10.14 Hz, $J_2$ = 1.08 Hz, 1H), 7.53 (d, J = 4.08 Hz, 1H). MASS (ES+): 717.12 (M + Na)$^+$ |
| IB.93 | 1.06 (d, J = 7.16 Hz, 3H), 1.17 (s, 3H), 1.33 (t, J = 7.12 Hz, 3H), 1.36-1.40 (m, 1H), 1.55 (s, 3H), 1.71-1.97 (m, 3H), 2.28-2.48 (m, 4H), 2.71 (s, 1H), 3.42-3.48 (m, 1H), 3.68 (d, J = 16.79 Hz, 1H), 3.77 (d, J = 16.60 Hz, 1H), 4.25-4.30 (m, 2H), 4.44 (m, 1H), 4.68 (d, J = 15.47 Hz, 1H), 4.81 (d, J = 15.45 Hz, 1H), 5.32-5.49 (m, 1H), 6.21 (d, J = 12.01 Hz, 1H), 6.32 (d, J = 11.98 Hz, 1H), 6.40 (dd, $J_1$ = 10.10 Hz, $J_2$ = 1.75 Hz, 1H), 6.45 (s, 1H), 6.50 (dd, $J_1$ = 3.47 Hz, $J_2$ = 1.75 Hz, 1H), 7.13 (d, J = 3.42 Hz, 1H), 7.19 (dd, $J_1$ = 10.25 Hz, $J_2$ = 0.81 Hz, 1H), 7.59 (d, J = 0.88 Hz, 1H). MASS (ES+): 723.22 (M + Na)$^+$ |
| IB.94 | 1.06 (d, J = 7.17 Hz, 3H), 1.18 (s, 3H), 1.35-1.41 (m, 1H), 1.56 (s, 3H), 1.74-1.99 (m, 3H), 2.28-2.47 (m, 4H), 2.63-2.69 (m, 4H), 2.93 (s, 1H), 3.43-3.47 (m, 1H), 3.66 (d, J = 16.86 Hz, 1H), 3.70 (s, 3H), 3.76 (d, J = 17.21 Hz, |

TABLE 6-continued

Spectral data for the synthesized compounds

| Comp. No | $^1$H-NMR (δ ppm), MASS (EI/ES+, m/z) |
|---|---|
| | 1H), 4.45 (d, J = 8.60 Hz, 1H), 4.59 (d, J = 15.38 Hz, 1H), 4.68 (d, J = 15.45 Hz, 1H), 5.33-5.50 (m, 1H), 6.41 (dd, $J_1$ = 10.15 Hz, $J_2$ = 1.76 Hz, 1H), 6.46 (s, 1H), 6.51 (dd, $J_1$ = 3.45 Hz, $J_2$ = 1.64 Hz, 1H), 7.13 (d, J = 3.43 Hz, 1H), 7.19 (d, J = 9.97 Hz, 1H), 7.59 (d, J = 0.73 Hz, 1H). MASS (ES+): 711.19 (M + Na)$^+$ |
| IB.95 | 1.06 (d, J = 7.07 Hz, 3H), 1.18 (s, 3H), 1.23 (d, J = 6.20 Hz, 3H), 1246 (d, J = 6.25 Hz, 3H), 1.35-1.41 (m, 1H), 1.56 (s, 3H), 1.74-2.00 (m, 3H), 2.28-2.51 (m, 4H), 2.58-2.67 (m, 4H), 3.00 (s, 1H), 3.43-3.47 (m, 1H), 3.65 (d, J = 16.97 Hz, 1H), 3.76 (d, J = 17.57 Hz, 1H), 4.46 (d, J = 8.05 Hz, 1H), 4.59 (d, J = 15.43 Hz, 1H), 4.72 (d, J = 15.40 Hz, 1H), 4.96-5.06 (m, 1H), 5.33-5.49 (m, 1H), 6.41 (dd, $J_1$ = 10.20 Hz, $J_2$ = 1.24 Hz, 1H), 6.46 (s, 1H), 6.51 (dd, $J_1$ = 3.13 Hz, $J_2$ = 1.24 Hz, 1H), 7.13 (d, J = 3.33 Hz, 1H), 7.19 (d, J = 10.11 Hz, 1H), 7.59 (s, 1H). MASS (ES+): 739.31 (M + Na)$^+$ |
| IB.96 | 0.92 (d, J = 6.64 Hz, 6H), 1.06 (d, J = 6.64 Hz, 3H), 1.18 (s, 3H), 1.36-1.41 (m, 1H), 1.56 (s, 3H), 1.74-2.06 (m, 4H), 2.29-2.51 (m, 4H), 2.66-2.69 (m, 4H), 2.99 (s, 1H), 3.43-3.45 (m, 1H), 3.66 (d, J = 16.76 Hz, 1H), 3.77 (d, J = 16.64 Hz, 1H), 3.88 (d, J = 6.57 Hz, 2H), 4.46 (d, J = 6.66 Hz, 1H), 4.59 (d, J = 15.40 Hz, 1H), 4.73 (d, J = 15.33 Hz, 1H), 5.33-5.49 (m, 1H), 6.41 (d, $J_1$ = 10.11 Hz, 1H), 6.45 (s, 1H), 6.50 (dd, $J_1$ = 2.62 Hz, $J_2$ = 1.21 Hz, 1H), 7.13 (d, J = 3.43 Hz, 1H), 7.19 (d, J = 10.11 Hz, 1H), 7.59 (s, 1H). MASS (ES+): 753.35 (M + Na)$^+$ |
| IB.97 | 0.92 (t, J = 7.32 Hz, 3H), 1.05 (d, J = 7.15 Hz, 3H), 1.18 (s, 3H), 1.20-1.38 (m, 5H), 1.40-1.62 (m, 4H), 1.77-2.00 (m, 3H), 2.25-2.50 (m, 4H), 2.61-2.69 (m, 4H), 2.97 (s, 1H), 3.42-3.47 (m, 1H), 3.65 (d, J = 16.71 Hz, 1H), 3.76 (d, J = 16.87 Hz, 1H), 4.10 (t, J = 6.71 Hz, 2H), 4.45 (d, J = 8.59 Hz, 1H), 4.59 (d, J = 15.45 Hz, 1H), 4.72 (d, J = 15.43 Hz, 1H), 5.32-5.49 (m, 1H), 6.39 (dd, $J_1$ = 10.16 Hz, $J_2$ = 1.78 Hz, 1H), 6.46 (s, 1H), 6.50 (dd, $J_1$ = 3.74 Hz, $J_2$ = 1.47 Hz, 1H), 7.13 (d, J = 3.44 Hz, 1H), 7.19 (dd, $J_1$ = 10.10 Hz, $J_2$ = 0.91 Hz, 1H), 7.59 (d, J = 1.08 Hz, 1H). MASS (ES+): 753.18 (M + Na)$^+$ |
| IB.98 | 1.06 (d, J = 7.12 Hz, 3H), 1.21 (s, 3H), 1.31 (s, 6H), 1.35-1.41 (m, 1H), 1.56 (s, 3H), 1.77-2.01 (m, 3H), 2.29-2.53 (m, 4H), 2.91 (d, J = 2.26 Hz, 1H), 3.43-3.47 (m, 1H), 3.58-3.64 (m, 2H), 3.66 (d, J = 17.24 Hz, 1H), 3.76 (d, J = 16.76 Hz, 1H), 4.45-4.47 (m, 1H), 4.57 (d, J = 15.36 Hz, 1H), 4.78 (d, J = 15.36 Hz, 1H), 5.34-5.50 (m, 1H), 6.40 (dd, $J_1$ = 10.15 Hz, $J_2$ = 1.46 Hz, 1H), 6.45 (s, 1H), 6.50 (dd, $J_1$ = 3.28 Hz, $J_2$ = 1.48 Hz, 1H), 7.14 (d, J = 3.49 Hz, 1H), 7.18 (dd, J = 10.12 Hz, 1H), 7.59 (s, 1H). MASS (ES+): 715.02 (M + Na)$^+$ |
| IB.99 | 0.94 (d, J = 6.70 Hz, 6H), 1.06 (d, J = 7.12 Hz, 3H), 1.17 (s, 3H), 1.25-1.40 (m, 1H), 1.55 (s, 3H), 1.73-1.99 (m, 4H), 2.28-2.46 (m, 4H), 2.73 (s, 1H), 3.43-3.47 (m, 1H), 3.67 (d, J = 16.91 Hz, 1H), 3.78 (d, J = 17.01 Hz, 1H), 3.99 (d, J = 6.69 Hz, 2H), 4.44 (d, J = 8.42 Hz, 1H), 4.67 (d, J = 15.51 Hz, 1H), 4.81 (d, J = 15.46 Hz, 1H), 5.32-5.49 (m, 1H), 6.22 (d, J = 12.05 Hz, 1H), 6.34 (d, J = 12.03 Hz, 1H), 6.39 (dd, $J_1$ = 10.13 Hz, $J_2$ = 1.65 Hz, 1H), 6.45 (s, 1H), 6.50 (dd, $J_1$ = 3.57 Hz, $J_2$ = 1.85 Hz, 1H), 7.13 (d, J = 3.44 Hz, 1H), 7.19 (d, J = 10.20 Hz, 1H), 7.59 (d, 10.67 Hz, 1H). MASS (ES+): 751.16 (M + Na)$^+$ |
| IB.100 | 1.06 (d, J = 7.15 Hz, 3H), 1.16 (s, 3H), 1.25-1.41 (m, 1H), 1.56 (s, 3H), 1.77-1.96 (m, 3H), 2.28-2.49 (m, 4H), 2.71 (s, 1H), 3.41-3.45 (m, 1H), 3.67 (d, J = 16.72 Hz, 1H), 3.77 (d, J = 16.87 Hz, 1H), 3.82 (s, 3H), 4.46 (m, 1H), 4.74 (d, J = 15.44 Hz, 1H), 4.80 (d, J = 15.44 Hz, 1H), 5.32-5.49 (m, 1H), 6.42 (dd, $J_1$ = 10.16 Hz, $J_2$ = 1.79 Hz, 1H), 6.46 (s, 1H), 6.50 (dd, $J_1$ = 3.45 Hz, $J_2$ = 1.76 Hz, 1H), 6.86 (d, J = 15.85 Hz, 1H), 6.90 (d, J = 15.82 Hz, 1H), 7.13 (d, J = 3.51 Hz, 1H), 7.20 (dd, $J_1$ = 10.00 Hz, $J_2$ = 1.00 Hz, 1H), 7.59 (d, J = 0.73 Hz, 1H). MASS (ES+): 709.11 (M + Na)$^+$ |
| IB.101 | 0.96 (d, J = 6.59 Hz, 6H), 1.05 (d, J = 7.115 Hz, 3H), 1.20 (s, 3H), 1.35-1.41 (m, 1H), 1.56 (s, 3H), 1.77-2.01 (m, 3H), 2.052.12 (m, 1H), 2.21-2.52 (m, 6H), 3.07 (d, J = 2.84 Hz, 1H), 3.43-3.47 (m, 1H), 3.65 (d, J = 16.86 Hz, 1H), 3.77 (d, J = 16.79 Hz, 1H), 4.45 (d, J = 8.63 Hz, 1H), 4.52 (d, J = 15.42 Hz, 1H), 4.73 (d, J = 15.34 Hz, 1H), 5.33-5.48 (m, 1H), 6.40 (dd, $J_1$ = 10.12 Hz, $J_2$ = 1.71 Hz, 1H), 6.45 (s, 1H), 6.50 (dd, $J_1$ = 3.43 Hz, $J_2$ = 1.61 Hz, 1H), 7.13 (d, J = 3.43 Hz, 1H), 7.19 (d, J = 10.19 Hz, 1H), 7.58 (d, J = 0.85 Hz, 1H). MASS (ES+): 681.0 (M + Na)$^+$ |
| IB.102 | 0.90 (q, J = 7.40 Hz, 3H), 1.05 (d, J = 7.14 Hz, 3H), 1.23 (s, 3H), 1.35-1.41 (m, 1H), 1.50-1.65 (m, 4H), 1.57 (s, 3H), 1.77-2.01 (m, 3H), 2.21-2.55 (m, 5H), 3.31 (d, J = 2.47 Hz, 1H), 3.44-3.47 (m, 1H), 3.64 (d, J = 16.73 Hz, 1H), 3.76 (d, J = 16.70 Hz, 1H), 4.43-4.46 (m, 1H), 4.49 (d, J = 15.39 Hz, 1H), 4.78 (d, J = 15.38 Hz, 1H), 5.34-5.50 (m, 1H), 6.40 (dd, $J_1$ = 10.08 Hz, $J_2$ = 1.62 Hz, 1H), 6.45 (s, 1H), 6.50 (dd, $J_1$ = 3.37 Hz, $J_2$ = 1.57 Hz, 1H), 7.13 (d, J = 3.45 Hz, 1H), 7.19 (dd, J = 10.16 Hz, 1H), 7.59 (s, 1H). MASS (ES+): 695.0 (M + Na)$^+$ |
| IB.103 | 1.05 (d, J = 7.18 Hz, 3H), 1.23 (s, 3H), 1.34-1.40 (m, 1H), 1.56 (s, 3H), 1.77-2.08 (m, 3H), 2.17-2.53 (m, 4H), 2.92 (s, 6H), 3.44-3.48 (m, 1H), 3.64 (d, J = 16.62 Hz, 1H), 3.76 (d, J = 16.16 Hz, 1H), 4.01 (d, J = 3.45 Hz, 1H), 4.41-4.43 (m, 1H), 4.49 (d, J = 15.61 Hz, 1H), 4.76 (d, J = 15.59 Hz, 1H), 5.33-5.50 (m, 1H), 6.39 (dd, $J_1$ = 10.11 Hz, $J_2$ = 1.75 Hz, 1H), 6.45 (s, 1H), 6.50 (dd, $J_1$ = 3.47 Hz, $J_2$ = 1.74 Hz, 1H), 7.14 (d, J = 3.40 Hz, 1H), 7.18 (dd, $J_1$ = 10.16 Hz, $J_2$ = 0.91 Hz, 1H), 7.59 (s, 1H). MASS (ES+): 668.0 (M + Na)$^+$ |
| IB.104 | 1.06 (d, J = 7.12 Hz, 3H), 1.21 (s, 3H), 1.35-1.41 (m, 1H), 1.56 (s, 3H), 1.79 (s, 3H), 1.80 (s, 3H), 1.80-1.98 (m, 3H), 2.28-2.52 (m, 4H), 2.70 (d, J = 2.16 Hz, 1H), 3.42-3.46 (m, 1H), 3.67-3.77 (m, 2H), 3.44-3.46 (m, 1H), 4.62-4.85 (m, 2H), 5.33-5.49 (m, 1H), 6.39 (dd, $J_1$ = 10.15 Hz, $J_2$ = 1.70 Hz, 1H), 6.45 (s, 1H), 6.50 (dd, $J_1$ = 3.44 Hz, $J_2$ = 1.71 Hz, 1H), 7.12 (d, J = 3.42 Hz, 1H), 7.16 (dd, $J_1$ = 10.07 Hz, $J_2$ = 0.93 Hz, 1H), 7.58 (s, 1H). MASS (ES+): 679.0 |
| IB.105 | 0.90 (d, J = 6.31 Hz, 3H), 0.91 (d, J = 6.24 Hz, 3H), 1.06 (d, J = 7.14 Hz, 3H), 1.20 (s, 3H), 1.35-1.41 (m, 1H), 1.47-1.59 (m, 3H), 1.56 (s, 3H), 1.77-2.00 (m, 3H), 2.29-2.52 (m, 4H), 2.35 (t, J = 7.72 Hz, 2H), 3.10 (d, J = 2.65 Hz, 1H), 3.43-3.46 (m, 1H), 3.65 (d, J = 16.80 Hz, 1H), 3.77 (d, J = 16.81 Hz, 1H), 4.44-4.46 (m, 1H), 4.53 (d, J = 15.38 Hz, 1H), 4.71 (d, J = 15.33 Hz, 1H), 5.33-5.50 (m, 1H), 6.39 (dd, $J_1$ = 10.16 Hz, $J_2$ = 1.74 Hz, 1H), 6.45 (s, 1H), 6.50 (dd, $J_1$ = 3.43 Hz, $J_2$ = 1.77 Hz, 1H), 7.13 (d, J = 3.60 Hz, 1H), 7.18 (dd, $J_1$ = 10.22 Hz, $J_2$ = 0.72 Hz, 1H), 7.59 (s, 1H). MASS (ES+): 673.0 |
| IB.106 | 1.06 (d, J = 7.18 Hz, 3H), 1.17 (s, 3H), 1.35-1.41 (m, 1H), 1.55 (s, 3H), 1.74-1.97 (m, 3H), 2.28-2.48 (m, 4H), 2.65 (s, 1H), 2.69-2.77 (m, 4H), 3.43-3.47 (m, 1H), 3.67 (d, J = 16.80 Hz, 1H), 3.76 (d, J = 16.76 Hz, 1H), 4.45 (d, J = 8.68 Hz, 1H), 4.61 (d, J = 15.48 Hz, 1H), 4.74 (d, J = 15.38 Hz, 1H), 5.32-5.49 (m, 1H), 5.71 (d, J = 50.60 Hz, 2H), 6.41 (dd, $J_1$ = 10.18 Hz, $J_2$ = 1.81 Hz, 1H), 6.45 (s, 1H), 6.51 (dd, |

TABLE 6-continued

Spectral data for the synthesized compounds

| Comp. No | $^1$H-NMR ($\delta$ ppm), MASS (EI/ES+, m/z) |
|---|---|
| | $J_1$ = 3.49 Hz, $J_2$ = 1.64 Hz, 1H), 7.13 (d, J = 3.29 Hz, 1H), 7.18 (dd, $J_1$ = 10.16 Hz, $J_2$ = 0.91 Hz, 1H), 7.59 (d, J = 0.79 Hz, 1H). MASS (ES+): 729.28 (M + Na)$^+$ |
| IB.107 | 1.06 (d, J = 7.17 Hz, 3H), 1.17 (s, 3H), 1.25-1.41 (m, 1H), 1.54 (s, 3H), 1.77-1.98 (m, 3H), 2.28-2.49 (m, 5H), 3.42-3.47 (m, 1H), 3.69 (d, J = 16.78 Hz, 1H), 3.78 (d, J = 16.84 Hz, 1H), 4.44 (d, J = 8.74 Hz, 1H), 4.66 (d, J = 17.09 Hz, 1H), 4.84 (d, J = 17.31 Hz, 1H), 5.32-5.49 (m, 1H), 5.78 (dd, $J_1$ = 50.72 Hz, $J_2$ = 1.89 Hz, 1H), 5.82 (dd, $J_1$ = 50.31 Hz, $J_2$ = 1.91 Hz, 1H), 6.34 (d, J = 12.00 Hz, 1H), 6.38 (d, J = 12.14 Hz, 1H), 6.39 (dd, $J_1$ = 3.46 Hz, $J_2$ = 1.60 Hz, 1H), 6.45 (s, 1H), 6.51 (dd, $J_1$ = 3.46 Hz, $J_2$ = 1.60 Hz, 1H), 7.13 (d, J = 3.42 Hz, 1H), 7.17 (d, J = 10.16 Hz, 1H), 7.59 (d, J = 0.84 Hz, 1H). MASS (ES+): 727.26 (M + Na)$^+$ |
| IB.108 | 1.06 (d, J = 7.15 Hz, 3H), 1.19 (s, 3H), 1.25-1.41 (m, 1H), 1.55 (s, 3H), 1.74-1.97 (m, 3H), 2.29-2.50 (m, 4H), 2.81 (s, 1H), 3.43 (m, 3H), 3.68 (d, J = 17.09 Hz, 1H), 3.75 (d, J = 16.15 Hz, 1H), 3.77 (s, 3H), 4.46 (d, J = 8.71 Hz, 1H), 4.62 (d, J = 15.45 Hz, 1H), 4.80 (d, J = 15.32 Hz, 1H), 5.33-5.50 (m, 1H), 6.41 (dd, $J_1$ = 10.09 Hz, $J_2$ = 1.69 Hz, 1H), 6.45 (s, 1H), 6.51 (dd, $J_1$ = 3.43 Hz, $J_2$ = 1.69 Hz, 1H), 7.13 (d, J = 3.39 Hz, 1H), 7.18 (d, J = 10.15 Hz, 1H), 7.59 (d, J = 0.88 Hz, 1H). MASS (ES+): 697.29 (M + Na)$^+$ |
| IB.109 | 1.06 (d, J = 7.15 Hz, 3H), 1.21 (s, 3H), 1.37-1.41 (m, 1H), 1.44 (s, 3H), 1.45 (s, 3H), 1.56 (s, 3H), 1.77-1.97 (m, 3H), 2.29-2.52 (m, 4H), 3.05 (d, J = 2.12 Hz, 1H), 3.42-3.47 (m, 3H), 2.71-3.75 (m, 5H), 4.46 (d, J = 8.69 Hz, 1H), 4.62 (d, J = 15.42 Hz, 1H), 4.74 (d, J = 15.43 Hz, 1H), 5.33-5.50 (m, 1H), 6.41 (dd, $J_1$ = 10.15 Hz, $J_2$ = 1.76 Hz, 1H), 6.45 (s, 1H), 6.50 (dd, $J_1$ = 3.48 Hz, $J_2$ = 1.64 Hz, 1H), 7.13 (d, J = 3.41 Hz, 1H), 7.18 (dd, $J_1$ = 10.12 Hz, $J_2$ = 0.95 Hz, 1H), 7.59 (d, J = 0.88 Hz, 1H). MASS (ES+): 725.30 (M + Na)$^+$ |
| IB.110 | 1.06 (d, J = 7.15 Hz, 3H), 1.18 (s, 1H), 1.35-1.42 (m, 1H), 1.15 (s, 3H), 1.47 (s, 3H), 1.55 (s, 3H), 1.59-1.98 (m, 3H), 2.17-2.51 (m, 4H), 3.88 (m, 1H), 2.97 (s, 1H), 3.39-3.45 (m, 1H), 3.72 (s, 2H), 4.43-4.45 (m, 1H), 4.64-4.81 (m, 2H), 5.33-5.49 (m, 1H), 6.39 (dd, $J_1$ = 10.16 Hz, $J_2$ = 1.75 Hz, 1H), 6.45 (s, 1H), 6.50 (dd, $J_1$ = 3.45 Hz, $J_2$ = 1.76 Hz, 1H), 7.13 (d, J = 3.44 Hz, 1H), 7.17 (dd, $J_1$ = 10.12 Hz, $J_2$ = 0.76 Hz, 1H), 7.58 (d, J = 0.90 Hz, 1H). MASS (ES+): 683.10 (M + Na)$^+$ |
| IB.111 | 1.06 (d, J = 7.13 Hz, 3H), 1.23 (s, 3H), 1.36-1.41 (m, 1H), 1.56 (d, J = 21.29 Hz, 3H), 1.62 (d, J = 21.37 Hz, 3H), 1.77-1.99 (m, 3H), 2.28-2.53 (m, 4H), 2.95 (s, 1H), 3.39-3.43 (m, 1H), 3.67 (d, J = 16.95 Hz, 1H), 3.74 (d, J = 16.49 Hz, 1H), 4.44 (d, J = 8.03 Hz, 1H), 4.60 (d, J = 15.23 Hz, 1H), 4.86 (d, J = 15.34 Hz, 1H), 5.33-5.50 (m, 1H), 6.39 (dd, $J_1$ = 10.11 Hz, $J_2$ = 1.63 Hz, 1H), 6.45 (s, 1H), 6.50 (dd, $J_1$ = 3.35 Hz, $J_2$ = 1.50 Hz, 1H), 7.12 (d, J = 3.42 Hz, 1H), 7.19 (d, J = 10.13 Hz, 1H), 7.58 (s, 1H). MASS (ES+): 685.10 (M + Na)$^+$ |
| IB.112 | 1.06 (d, J = 7.15 Hz, 3H), 1.17 (s, 3H), 1.35-1.40 (m, 1H), 1.55 (s, 3H), 1.76-1.97 (m, 3H), 2.28-2.47 (m, 4H), 2.71 (s, 1H), 3.42-3.47 (m, 1H), 3.69 (d, J = 16.76 Hz, 1H), 3.78 (d, J = 16.97 Hz, 1H), 3.82 (S, 3H), 4.44 (d, J = 8.22 Hz, 1H), 4.69 (d, J = 15.50 Hz, 1H), 4.82 (d, J = 15.54 Hz, 1H), 5.30-5.60 (m, 1H), 6.23 (d, J = 11.91 Hz, 1H), 6.33 (d, J = 12.06 Hz, 1H), 6.40 (dd, $J_1$ = 10.14 Hz, $J_2$ = 1.58 Hz, 1H), 6.45 (s, 1H), 6.50 (dd, $J_1$ = 3.31 Hz, $J_2$ = 1.51 Hz, 1H), 7.13 (d, J = 3.47 Hz, 1H), 7.19 (d, J = 10.14 Hz, 1H), 7.59 (s, 1H). MASS (ES+): 687.73 |
| IB.113 | 1.06 (d, J = 7.12 Hz, 3H), 1.16 (s, 3H), 1.32 (t, 3H), 1.35-1.42 (m, 2H), 1.56 (s, 3H), 1.72-1.97 (m, 3H), 2.28-2.48 (m, 4H), 2.86 (s, 1H), 3.42-3.45 (m, 1H), 3.68 (d, J = 16.77 Hz, 1H), 3.77 (d, J = 16.62 Hz, 1H), 4.26 (q, J = 7.07 Hz, 2H), 4.46 (d, J = 8.36 Hz, 1H), 4.75 (d, J = 15.39 Hz, 1H), 4.80 (d, J = 15.39 Hz, 1H), 5.30-5.49 (m, 1H), 6.41 (dd, $J_1$ = 10.14 Hz, $J_2$ = 1.76 Hz, 1H), 6.46 (s, 1H), 6.50 (dd, $J_1$ = 3.45 Hz, $J_2$ = 1.76 Hz, 1H), 6.85 (d, J = 15.75 Hz, 1H), 6.90 (d, J = 15.90 Hz, 1H), 7.13 (d, J = 3.74 Hz, 1H), 7.20 (dd, $J_1$ = 10.19 Hz, $J_2$ = 0.84 Hz, 1H), 7.59 (d, J = 0.87 Hz, 1H). MASS (ES+): 701.0 |
| IB.114 | 0.96 (d, J = 6.72 Hz, 6H), 1.06 (d, J = 7.13 Hz, 3H), 1.17 (s, 3H), 1.25-1.41 (m, 1H), 1.56 (s, 3H), 1.74-2.00 (m, 4H), 2.28-2.49 (m, 4H), 2.86 (s, 1H), 3.42-3.45 (m, 1H), 3.68 (d, J = 16.76 Hz, 1H), 3.78 (d, J = 16.83 Hz, 1H), 4.00 (d, J = 6.70 Hz, 2H), 4.46 (d, J = 8.56 Hz, 1H), 4.75 (d, J = 15.47 Hz, 1H), 4.80 (d, J = 15.38 Hz, 1H), 5.30-5.49 (m, 1H), 6.41 (dd, $J_1$ = 10.15 Hz, $J_2$ = 1.80 Hz, 1H), 6.46 (s, 1H), 6.50 (dd, $J_1$ = 3.50 Hz, $J_2$ = 1.73 Hz, 1H), 6.85 (d, J = 15.79 Hz, 1H), 6.92 (d, J = 15.93 Hz, 1H), 7.13 (d, J = 3.32 Hz, 1H), 7.20 (dd, $J_1$ = 10.12 Hz, $J_2$ = 0.96 Hz, 1H), 7.59 (d, J = 0.90 Hz, 1H). MASS (ES+): 729.1 |
| IB.115 | 0.95 (t, J = 7.37 Hz, 6H), 1.06 (d, J = 7.10 Hz, 3H), 1.17 (s, 3H), 1.36-1.45 (m, 3H), 1.56 (s, 3H), 1.67-1.97 (m, 7H), 2.28-2.51 (m, 4H), 2.82 (s, 1H), 3.42-3.45 (m, 1H), 3.72 (d, J = 16.78 Hz, 1H), 3.77 (d, J = 16.74 Hz, 1H), 4.22 (t, J = 6.67 Hz, 2H), 4.47 (d, J = 8.32 Hz, 1H), 4.75 (d, J = 15.54 Hz, 1H), 4.79 (d, J = 15.52 Hz, 1H), 5.33-5.49 (m, 1H), 6.41 (dd, $J_1$ = 10.13 Hz, $J_2$ = 1.66 Hz, 1H), 6.46 (s, 1H), 6.50 (dd, $J_1$ = 3.33 Hz, $J_2$ = 1.52 Hz, 1H), 6.84 (d, J = 15.81 Hz, 1H), 6.90 (d, J = 15.77 Hz, 1H), 7.13 (d, J = 3.40 Hz, 1H), 7.20 (d, J = 10.18 Hz, 1H), 7.59 (s, 1H). MASS (ES+): 729.1 |
| IB.116 | 1.06 (d, J = 7.16 Hz, 3H), 1.18 (s, 3H), 1.19 (d, J = 7.07 Hz, 3H), 1.23 (s, 3H), 1.31-1.36 (m, 1H), 1.62 (s, 3H), 1.75-2.04 (m, 4H), 2.17-2.82 (m, 6H), 3.19 (s, 1H), 3.41-3.45 (m, 1H), 3.65-3.75 (m, 1H), 4.53 (d, J = 15.43 Hz, 1H), 4.63 (s, 1H), 4.73 (d, J = 15.42 Hz, 1H), 6.11 (s, 1H), 6.38 (dd, $J_1$ = 10.04 Hz, $J_2$ = 1.72 Hz, 1H), 6.49 (dd, $J_1$ = 3.43 Hz, $J_2$ = 1.62 Hz, 1H), 7.18 (d, J = 3.35 Hz, 1H), 7.24 (d, J = 10.57 Hz, 1H), 7.58 (d, J = 0.75 Hz, 1H). MASS (ES+): 665.1 (M + Na)$^+$ |
| IB.117 | 0.91 (t, J = 7.48 Hz, 3H), 1.05 (d, J = 7.13 Hz, 3H), 1.15 (d, 3H, J = 7.02 Hz), 1.22 (s, 3H), 1.38-2.00 (m, 6H), 1.56 (s, 3H), 2.28-2.46 (m, 5H), 3.19 (d, 1H, J = 3.09 Hz), 3.45 (m, 1H), 3.68-3.73 (m, 2H), 4.44-4.46 (m, 1H), 4.51 (d, J = 15.29 Hz, 1H), 4.75 (d, J = 15.38 Hz, 1H), 5.33-5.52 (m, 1H), 6.40 (dd, $J_1$ = 10.18 Hz, $J_2$ = 1.78 Hz, 1H), 6.45 (s, 1H), 6.50 (dd, $J_1$ = 3.46 Hz, $J_2$ = 1.61 Hz, 1H), 7.13 (d, J = 3.32 Hz, 1H), 7.18 (d, $J_1$ = 10.03 Hz, $J_2$ = 0.94 Hz, 1H), 7.58 (d, J = 0.89 Hz, 1H). MASS (ES+): 659.1 |
| IB.118 | 1.05 (d, J = 7.15 Hz, 3H), 1.20 (s, 3H), 1.35-1.40 (m, 1H), 1.59 (s, 3H), 1.77-2.00 (m, 3H), 2.28-2.52 (m, 4H), 3.12 (d, J = 2.71 Hz, 1H), 3.41-3.45 (m, 1H), 3.68 (d, J = 16.77 Hz, 1H), 3.75 (d, J = 16.87 Hz, 1H), 4.48-4.50 (m, 1H), 4.75-4.96 (m, 2H), 5.33-5.50 (m, 1H), 6.41 (dd, $J_1$ = 10.08 Hz, $J_2$ = 1.70 Hz, 1H), 6.46 (s, 1H), 6.49 (dd, $J_1$ = 3.44 Hz, $J_2$ = 1.76 Hz, 1H), 6.55 (dd, $J_1$ = 3.51 Hz, $J_2$ = 1.65 Hz, 1H), 7.11 (d, J = 3.34 Hz, 1H), 7.22-7.25 (m, 2H), 7.57 (d, J = 0.83 Hz, 1H), 7.61 (d, J = 0.85 Hz, 1H). MASS (ES+): 669.1 |

TABLE 6-continued

Spectral data for the synthesized compounds

| Comp. No | $^1$H-NMR (δ ppm), MASS (EI/ES+, m/z) |
|---|---|
| IB.119 | 1.06 (d, J = 7.12 Hz, 3H), 1.17 (s, 3H), 1.30 (d, J = 6.20 Hz, 6H), 1.36-1.41 (m, 1H), 1.56 (s, 3H), 1.72-1.97 (m, 3H), 2.28-2.50 (m, 4H), 2.82 (s, 1H), 3.42-3.45 (m, 1H), 3.67 (d, J = 16.71 Hz, 1H), 3.76 (d, J = 16.51 Hz, 1H), 4.46 (d, J = 8.56 Hz, 1H), 4.74 (d, J = 15.47 Hz, 1H), 4.79 (d, J = 15.41 Hz, 1H), 5.08-5.13 (m, 1H), 5.33-5.49 (m, 1H), 6.41 (dd, $J_1$ = 10.16 Hz, $J_2$ = 1.58 Hz, 1H), 6.46 (s, 1H), 6.50 (dd, $J_1$ = 3.36 Hz, $J_2$ = 1.62 Hz, 1H), 6.83 (d, J = 15.87 Hz, 1H), 6.88 (d, J = 15.76 Hz, 1H), 7.13 (d, J = 3.39 Hz, 1H), 7.20 (d, J = 10.29 Hz, 1H), 7.58 (s, 1H). MASS (ES+): 715.1 |
| IB.120 | 1.03 (d, 3H, J = 7.05 Hz), 1.15 (s, 3H), 1.16 (s, 6H), 1.33-1.39 (m, 1H), 1.55 (s, 1H), 1.67-2.00 (m, 3H), 2.29-2.59 (m, 4H), 3.39-3.49 (m, 1H), 3.51 (d, 1H, J = 4.81 Hz), 3.54 (d, 1H, J = 11.65 Hz), 3.71 (d, 1H, J = 16.53 Hz), 3.77 (d, 1H, J = 16.53 Hz), 4.73 (t, 1H, J = 5.86 Hz), 4.33-4.35 (m, 1H), 4.64 (d, 1H, J = 15.64 Hz), 4.68 (d, 1H, J = 15.66 Hz), 5.07 (s, 1H), 5.37-5.53 (m, 1H), 6.31-6.33 (m, 1H), 6.33 (s, 1H), 6.54 (dd, 1H, $J_1$ = 3.41 Hz, $J_2$ = 1.58 Hz), 7.12 (d, 1H, J = 3.37 Hz), 7.26 (d, 1H, J = 10.30 Hz), 7.66 (s, 1H). MASS (ES+): 697.07 (M + Na)$^+$ |
| IB.121 | 1.05 (d, 3H, J = 7.11 Hz), 1.18 (s, 3H), 1.35-1.40 (m, 1H), 1.56 (s, 1H), 1.73-2.00 (m, 3H), 2.28-2.55 (m, 4H), 3.01 (d, 1H, J = 2.36 Hz), 3.42-3.46 (m, 1H), 3.66 (d, 1H, J = 16.75 Hz), 3.77 (d, 1H, J = 16.77 Hz), 4.46 (d, 1H, J = 8.20 Hz), 4.67 (d, 1H, J = 15.43 Hz), 4.78 (d, 1H, J = 15.43 Hz), 5.33-5.49 (m, 1H), 5.92 (d, 1H, J = 10.35 Hz), 6.12 (dd, 1H, $J_1$ = 17.32 Hz, $J_2$ = 10.52 Hz), 6.39-6.46 (m, 1H), 6.43 (d, 1H, J = 13.3 Hz), 6.50 (dd, 1H, $J_1$ = 3.27 Hz, $J_2$ = 1.52 Hz), 7.12 (d, 1H, J = 3.39 Hz), 7.19 (d, 1H, J = 10.12 Hz), 7.58 (s, 1H). MASS (ES+): 629.05 |
| IB.122 | 0.86 (t, J = 6.57 Hz, 6H), 1.06 (d, J = 7.13 Hz, 3H), 1.16 (s, 3H), 1.27-1.41 (m, 1H), 1.55 (s, 3H), 1.61-1.98 (m, 8H), 2.29-2.51 (m, 4H), 3.38-3.42 (m, 1H), 3.64-3.79 (m, 3H), 4.36 (d, J = 6.47 Hz, 1H), 4.68-4.82 (m, 3H), 5.35-5.51 (m, 1H), 6.35 (dd, $J_1$ = 10.15 Hz, $J_2$ = 1.67 Hz, 1H), 6.38 (s, 1H), 6.52 (dd, $J_1$ = 3.40 Hz, $J_2$ = 1.68 Hz, 1H), 7.12 (d, J = 3.46 Hz, 1H), 7.27 (d, J = 9.97 Hz, 1H), 7.62 (s, 1H). MASS (ES+): 689.1 |
| IB.123 | 0.30-0.34 (m, 2H), 0.60-0.64 (m, 2H), 1.06 (d, J = 7.15 Hz, 3H), 1.19 (s, 3H), 1.36-1.41 (m, 1H), 1.55 (s, 3H), 1.64-1.99 (m, 4H), 2.29-2.51 (m, 4H), 2.61 (s, 1H), 3.42-3.47 (m, 1H), 3.69 (d, J = 16.73 Hz, 1H), 3.77 (d, J = 16.72 Hz, 1H), 3.99 (d, J = 7.39 Hz, 2H), 4.44 (d, J = 8.47 Hz, 1H), 4.65-4.74 (m, 2H), 5.33-5.49 (m, 1H), 6.41 (dd, $J_1$ = 10.13 Hz, $J_2$ = 1.66 Hz, 1H), 6.46 (s, 1H), 6.51 (dd, $J_1$ = 3.43 Hz, $J_2$ = 1.68 Hz, 1H), 7.13-7.17 (m, 2H), 7.59 (s, 1H).. MASS (ES+): 673.0 |
| IB.124 | 1.05 (d, J = 7.07 Hz, 3H), 1.15 (s, 3H), 1.29-1.41 (m, 1H), 1.54 (s, 1H), 1.72-2.00 (m, 3H), 2.28-2.50 (m, 4H), 2.76 (s, 3H), 3.39-3.43 (m, 1H), 3.73 (d, J = 16.53 Hz, 1H), 3.79 (d, J = 16.54 Hz, 1H), 4.16 (m, 2H), 4.36 (d, J = 6.03 Hz, 1H), 4.93 (s, 1H), 5.35-5.51 (m, 1H), 6.35 (d, J = 10.19 Hz, 1H), 6.37 (s, 1H), 6.52 (dd, $J_1$ = 3.09 Hz, $J_2$ = 1.32 Hz, 1H), 7.12 (d, J = 3.40 Hz, 1H), 7.27 (d, J = 10.15 Hz, 1H), 7.62 (s, 1H). MASS (ES+): 707.1 (M + Na)$^+$ |
| IB.125 | 1.06 (d, J = 7.13 Hz, 3H), 1.20-1.42 (m, 8H), 1.55 (s, 3H), 1.71-2.00 (m, 7H), 2.28-2.49 (m, 4H), 2.66 (s, 1H), 3.43-3.47 (m, 1H), 3.69 (d, J = 17.44 Hz, 1H), 3.76 (d, J = 16.97 Hz, 1H), 4.44 (d, J = 8.32 Hz, 1H), 4.63 (d, J = 15.47 Hz, 1H), 4.70 (d, J = 15.45 Hz, 1H), 5.05-5.09 (m, 1H), 5.33-5.49 (m, 1H), 6.40 (dd, $J_1$ = 10.14 Hz, $J_2$ = 1.48 Hz, 1H), 6.46 (s, 1H), 6.51 (dd, $J_1$ = 3.32 Hz, $J_2$ = 1.53 Hz, 1H), 7.13-7.16 (m, 2H), 7.59 (s, 1H). MASS (ES+): 687.1 |
| IB.126 | 1.06 (d, J = 7.07 Hz, 3H), 1.20-1.99 (m, 15H), 2.20-2.49 (m, 5H), 2.60 (s, 1H), 3.44 (m, 1H), 3.69 (d, J = 16.73 Hz, 1H), 3.77 (d, J = 16.67 Hz, 1H), 4.04 (d, J = 7.15 Hz, 2H), 4.44 (d, J = 7.91 Hz, 1H), 4.64-4.73 (m, 2H), 5.33-5.49 (m, 1H), 6.40 (d, J = 10.02 Hz, 1H), 6.46 (s, 1H), 6.50 (m, 1H), 7.13-7.17 (m, 2H), 7.59 (s, 1H). MASS (ES+): 701.1 |
| IB.127 | 1.06 (d, J = 7.16 Hz, 3H), 1.17 (d, J = 2.39 Hz, 3H), 1.18 (d, J = 2.37 Hz, 3H), 1.21 (s, 3H), 1.35-1.41 (m, 1H), 1.56 (s, 3H), 1.77-2.00 (m, 3H), 2.29-2.62 (m, 5H), 3.21 (d, J = 2.62 Hz, 1H), 3.42-3.49 (m, 1H), 3.67 (d, J = 16.86 Hz, 1H), 3.75 (d, J = 16.81 Hz, 1H), 4.45 (d, J = 8.59 Hz, 1H), 4.52 (d, J = 15.45 Hz, 1H), 4.74 (d, J = 15.33 Hz, 1H), 5.33-5.50 (m, 1H), 6.40 (dd, $J_1$ = 10.05 Hz, $J_2$ = 1.65 Hz, 1H), 6.45 (s, 1H), 6.50 (dd, $J_1$ = 3.50 Hz, $J_2$ = 1.69 Hz, 1H), 7.13 (dd, $J_1$ = 3.56 Hz, $J_2$ = 0.57 Hz, 1H), 7.19 (dd, $J_1$ = 0.75 Hz, $J_2$ = 0.22 Hz, 1H), 7.58 (s, 1H). MASS (ES+): 673.1 |
| IB.128 | 1.06 (d, J = 7.12 Hz, 3H), 1.18 (s, 3H), 1.35 (s, 3H), 1.38-1.41 (m, 1H), 1.43 (s, 3H), 1.55 (s, 3H), 1.80-1.97 (m, 3H), 2.40-2.64 (m, 5H), 3.39-3.50 (m, 1H), 3.71-3.83 (m, 3H), 4.07-4.33 (m, 4H), 4.44 (d, J = 8.59 Hz, 1H), 4.69-4.72 (m, 2H), 5.31-5.51 (m, 1H), 6.40 (dd, $J_1$ = 10.17 Hz, $J_2$ = 1.73 Hz, 1H), 6.45 (s, 1H), 6.50 (dd, $J_1$ = 3.47 Hz, $J_2$ = 1.64 Hz, 1H), 7.13 (d, J = 3.43 Hz, 1H), 7.16 (d, J = 10.04 Hz, 1H), 7.59 (s, 1H). MASS (ES+): 733.0 |
| IB.129 | 1.05 (d, J = 7.13 Hz, 3H), 1.12-1.14 (m, 6H), 1.24 (s, 3H), 1.35-1.39 (m, 1H), 1.56 (s, 3H), 1.80-2.11 (m, 3H), 2.30-2.42 (m, 4H), 3.19-3.35 (m, 4H), 3.43-3.52 (m, 1H), 3.60-3.82 (m, 2H), 4.12 (d, J = 3.12 Hz, 1H), 4.42 (d, J = 8.25 Hz, 1H), 4.48 (d, J = 15.61 Hz, 1H), 4.76 (d, J = 15.96 Hz, 1H), 5.32-5.52 (m, 1H), 6.39 (dd, $J_1$ = 10.12 Hz, $J_2$ = 1.75 Hz, 1H), 6.45 (s, 1H), 6.50 (dd, $J_1$ = 3.47 Hz, $J_2$ = 1.67 Hz, 1H), 7.14 (d, J = 3.39 Hz, 1H), 7.16 (dd, $J_1$ = 10.13 Hz, $J_2$ = 0.97 Hz, 1H), 7.58 (d, J = 0.78 Hz, 1H). MASS (ES+): 674.1 |
| IB.130 | 1.05 (d, J = 7.17 Hz, 3H), 1.22 (s, 3H), 1.34-1.40 (m, 1H), 1.56 (s, 3H), 1.56-1.60 (m, 6H), 1.77-2.07 (m, 3H), 2.28-2.42 (m, 4H), 3.40-3.49 (m, 5H), 3.62-3.82 (m, 2H), 3.86 (d, J = 3.25 Hz, 1H), 3.42 (d, J = 8.41 Hz, 1H), 4.52 (d, J = 15.61 Hz, 1H), 4.74 (d, J = 15.58 Hz, 1H), 5.32-5.51 (m, 1H), 6.39 (dd, $J_1$ = 10.11 Hz, $J_2$ = 1.68 Hz, 1H), 6.45 (s, 1H), 6.50 (dd, $J_1$ = 3.41 Hz, $J_2$ = 1.58 Hz, 1H), 7.13 (d, J = 3.41 Hz, 1H), 7.18 (d, J = 10.00 Hz, 1H), 7.59 (d, J = 0.74 Hz, 1H). MASS (ES+): 686.1 |
| IB.131 | 1.05 (d, J = 7.11 Hz, 3H), 1.20 (s, 3H), 1.34-1.40 (m, 1H), 1.55 (s, 3H), 1.77-2.04 (m, 3H), 2.30 (s, 3H), 2.39-2.53 (m, 8H), 3.48 (m, 5H), 3.64 (d, J = 15.98 Hz, 1H), 3.66 (s, 1H), 3.77 (d, J = 17.39 Hz, 1H), 4.42 (d, J = 8.06 Hz, 1H), 4.57 (d, J = 15.59 Hz, 1H), 4.73 (d, J = 15.61 Hz, 1H), 5.32-5.49 (m, 1H), 6.39 (dd, $J_1$ = 10.15 Hz, $J_2$ = 1.22 Hz, 1H), 6.45 (s, 1H), 6.50 (dd, $J_1$ = 3.11 Hz, $J_2$ = 1.26 Hz, 1H), 7.14 (d, J = 3.49 Hz, 1H), 7.17 (d, J = 10.13 Hz, 1H), 7.59 (s, 1H). MASS (ES+): 701.1 |
| IB.132 | 1.12 (s, 3H), 1.29-1.34 (m, 1H), 1.48 (d, J = 7.34 Hz, 3H), 1.55 (s, 3H), 1.74-2.16 (m, 4H), 2.33-2.81 (m, 4H), 3.35 (t, d, $J_1$ = 16.65 Hz, $J_2$ = 2.31 Hz, 1H), 3.82 (t, d, $J_1$ = 16.66 Hz, $J_2$ = 1.98 Hz, 1H), 4.26 (m, 2H), 4.46 (d, J = 8.42 Hz, 1H), 5.32-5.49 (m, 1H), 6.39 (dd, $J_1$ = 10.13 Hz, $J_2$ = 1.75 Hz, 1H), 6.44 (s, 1H), 6.51 (dd, $J_1$ = 3.50 Hz, $J_2$ = 1.65 Hz 1H), 7.17-7.19 (m, 1H), 7.61 (s, 1H). MASS (ES+): 575.1 |

TABLE 6-continued

Spectral data for the synthesized compounds

| Comp. No | $^1$H-NMR (δ ppm), MASS (EI/ES+, m/z) |
|---|---|
| IB.133 | 1.14 (s, 3H), 1.19 (d, J = 6.97 Hz, 3H), 1.25-1.32 (m, 1H), 1.48 (d, J = 7.33 Hz, 3H), 1.58 (s, 3H), 1.75-2.15 (m, 4H), 2.33-2.62 (m, 5H), 3.20 (dd, J$_1$ = 17.13 Hz, J$_2$ = 0.74 Hz, 1H), 3.84-3.90 (m, 2H), 4.40 (m, 2H), 4.72 (dd, J$_1$ = 15.25 Hz, J$_2$ = 1.33 Hz, 1H), 5.33-5.51 (m, 1H), 6.40 (dd, J$_1$ = 10.13 Hz, J$_2$ = 1.69 Hz, 1H), 6.44 (s, 1H), 6.51 (dd, J$_1$ = 3.43 Hz, J$_2$ = 1.57 Hz, 1H), 7.18-7.20 (m, 2H), 7.61 (d, J = 0.73 Hz, 1H). MASS (ES+): 645.0 |
| IB.134 | 1.06 (d, J = 7.16 Hz, 3H), 1.17 (d, J = 2.39 Hz, 3H), 1.18 (d, J = 2.37 Hz, 3H), 1.21 (s, 3H), 1.35-1.41 (m, 1H), 1.56 (s, 3H), 1.77-2.00 (m, 3H), 2.29-2.62 (m, 5H) 3.21 (d, J = 2.62 Hz, 1H), 3.42-3.49 (m, 1H), 3.67 (d, J = 16.86 Hz, 1H), 3.75 (d, J = 16.81 Hz, 1H), 4.45 (d, J = 8.59 Hz, 1H), 4.52 (d, J = 15.45 Hz, 1H), 4.74 (d, J = 15.33 Hz, 1H), 5.33-5.50 (m, 1H), 6.40 (dd, J$_1$ = 10.05 Hz, J$_2$ = 1.65 Hz, 1H), 6.45 (s, 1H), 6.50 (dd, J$_1$ = 3.50 Hz, J$_2$ = 1.69 Hz, 1H), 7.13 (dd, J$_1$ = 3.56 Hz, J$_2$ = 0.57 Hz, 1H), 7.19 (dd, J$_1$ = 0.75 Hz, J$_2$ = 0.22 Hz, 1H), 7.58 (s, 1H). MASS (ES+): 675.0 |
| IB.135 | 1.06 (d, J = 7.12 Hz, 3H), 1.19 (s, 3H), 1.36-1.41 (m, 1H), 1.55 (s, 3H), 1.77-1.97 (m, 3H), 2.32 (s, 3H), 2.29-2.49 (m, 5H), 3.41-3.58 (m, 1H), 3.73-3.75 (m, 2H), 4.45 (d, J = 8.67 Hz, 1H), 4.77 (d, J = 15.28 Hz, 1H), 4.98 (d, J = 15.27 Hz, 1H), 5.31-5.50 (m, 1H), 6.40 (dd, J$_1$ = 10.15 Hz, J$_2$ = 1.65 Hz, 1H), 6.45 (s, 1H), 6.50 (dd, J$_1$ = 3.39 Hz, J$_2$ = 1.64 Hz, 1H), 7.12 (d, J = 3.45 Hz, 1H), 7.15 (dd, J = 9.90 Hz, 1H), 7.59 (s, 1H). MASS (ES+): 699.0 |
| IB.136 | 1.05 (t, J = 7.09 Hz, 6H), 1.05 (d, J = 6.67 Hz, 3H), 1.34-1.40 (m, 1H), 1.55 (s, 3H), 1.76-2.02 (m, 3H), 2.28-2.62 (m, 4H), 2.56 (q, J = 7.22 Hz, 2H), 3.26-3.39 (m, 3H), 3.44-3.47 (m, 1H), 3.63 (d, J = 16.46 Hz, 1H), 3.85 (d, J = 16.45 Hz, 1H), 4.42 (d, J = 8.63 Hz, 1H), 5.30-5.81 (m, 1H), 6.39 (dd, J$_1$ = 10.17 Hz, J$_2$ = 1.45 Hz, 1H), 6.45 (s, 1H), 6.50 (dd, J$_1$ = 3.30 Hz, J$_2$ = 1.61 Hz, 1H), 7.14 (d, J = 3.21 Hz, 1H), 7.15 (d, J = 9.85 Hz, 1H), 7.59 (s, 1H). MASS (ES+): 630.1 |
| IB.137 | 1.06 (d, J = 7.13 Hz, 3H), 1.20 (s, 3H), 1.32 (d, J = 6.25 Hz, 3H), 1.32 (d, J = 6.13 Hz, 3H), 1.35-1.39 (m, 1H), 1.55 (s, 3H), 1.71-1.99 (m, 3H), 2.28-2.49 (m, 4H), 2.53 (s, 1H), 3.42-3.46 (m, 1H), 3.69 (d, J = 16.80 Hz, 1H), 3.76 (d, J = 16.64 Hz, 1H), 4.44 (d, J = 8.28 Hz, 1H), 4.64 (d, J = 15.56 Hz, 1H), 4.70 (d, J = 15.45 Hz, 1H), 4.82-4.90 (m, 1'H), 5.33-5.49 (m, 1H), 6.41 (dd, J$_1$ = 10.17 Hz, J$_2$ = 1.38 Hz, 1H), 6.46 (s, 1H), 6.50 (dd, J$_1$ = 3.26 Hz, J$_2$ = 1.44 Hz, 1H), 7.13-7.16 (m, 2H), 7.59 (s, 1H). MASS (ES+): 661.1 |
| IB.138 | 1.06 (d, J = 7.13 Hz, 3H), 1.20 (s, 3H), 1.35-1.41 (m, 1H), 1.55 (s, 3H), 1.72 (s, 1H), 1.76 (s, 3H), 1.74-1.98 (m, 3H), 2.28-2.53 (m, 5H), 3.42-3.46 (m, 1H), 3.69 (d, J = 16.85 Hz, 1H), 3.76 (d, J = 16.94 Hz, 1H), 4.43 (d, J = 8.85 Hz, 1H), 4.64-4.68 (m, 3H), 5.33-5.49 (m, 1H), 6.39 (dd, J$_1$ = 10.11 Hz, J$_2$ = 1.71 Hz, 1H), 6.46 (s, 1H), 6.50 (dd, J$_1$ = 3.45 Hz, J$_2$ = 1.71 Hz, 1H), 7.13-7.16 (m,, 2H), 7.59 (d, J = 0.83 Hz, 1H). MASS (ES+): 687.1 |
| IB.139 | 0.87 (t, J = 6.15 Hz, 3H), 1.06 (d, J = 7.15 Hz, 3H), 1.19 (s, 3H), 1.28-1.40 (m, 1H), 1.55 (s, 3H), 1.64-1.99 (m, 5H), 2.28-2.59 (m, 5H), 3.43-3.46 (m, 1H), 3.69 (d, J = 16.84 Hz, 1H), 3.76 (d, J = 16.70 Hz, 1H), 4.14 (t, J = 6.75 Hz, 1H), 4.44 (d, J = 8.29 Hz, 1H), 4.65 (d, J = 15.47 Hz, 1H), 4.65 (d, J = 15.48 Hz, 1H), 5.32-5.49 (m, 1H), 6.40 (dd, J$_1$ = 10.13 Hz, J$_2$ = 1.66 Hz, 1H), 6.46 (s, 1H), 6.50 (dd, J$_1$ = 3.42 Hz, J$_2$ = 1.70 Hz, 1H), 7.13-7.16 (m,, 2H), 7.59 (s, 1H). MASS (ES+): 703.1 |
| IB.140 | 0.94-1.02 (m, 2H), 1.06 (d, J = 7.14 Hz, 3H), 1.19 (s, 3H), 1.23-1.41 (m, 3H), 1.55 (s, 3H), 1.66-1.99 (m, 9H), 2.29-2.49 (m, 4H), 2.58 (d, J = 2.05 Hz, 1H), 3.43-3.46 (m, 1H), 3.68 (d, J = 16.65 Hz, 1H), 3.77 (d, J = 16.93 Hz, 1H), 3.97 (d, J = 6.45 Hz, 2H), 4.44 (d, J = 8.23 Hz, 1H), 4.65 (d, J = 15.56 Hz, 1H), 4.71 (d, J = 15.48 Hz, 1H), 5.33-5.49 (m, 1H), 6.40 (dd, J$_1$ = 10.16 Hz, J$_2$ = 1.50 Hz, 1H), 6.46 (s, 1H), 6.51 (dd, J$_1$ = 3.33 Hz, J$_2$ = 1.61 Hz, 1H), 7.13-7.16 (m,, 2H), 7.59 (s, 1H). MASS (ES+): 715.2 |
| IB.141 | 1.06 (d, J = 7.13 Hz, 3H), 1.20 (s, 3H), 1.25-1.52 (m, 7H), 1.55 (s, 3H), 1.73-1.99 (m, 7H), 2.29-2.53 (m, 4H), 2.63 (s, 1H), 3.43-3.47 (m, 1H), 3.68 (d, J = 16.79 Hz, 1H), 3.77 (d, J = 16.71 Hz, 1H), 4.44 (d, J = 8.52 Hz, 1H), 4.56-4.62 (m, 1H), 4.64 (d, J = 15.48 Hz, 1H), 4.70 (d, J = 15.53 Hz, 1H), 5.33-5.50 (m, 1H), 6.40 (dd, J$_1$ = 10.11 Hz, J$_2$ = 1.71 Hz, 1H), 6.46 (s, 1H), 6.50 (dd, J$_1$ = 3.45 Hz, J$_2$ = 1.58 Hz, 1H), 7.13-7.16 (m, 2H), 7.59 (d, J = 0.9 Hz, 1H). MASS (ES+): 701.1 |
| IB.142 | 0.88 (m, 9H), 0.94-1.25 (m, 14H), 1.38-1.41 (m, 1H), 1.49-1.72 (m, 6H), 1.78-1.99 (m, 3H), 2.28-2.55 (m, 5H), 3.43-3.46 (m, 1H), 3.68 (d, J = 17.42 Hz, 1H), 3.76 (d, J = 16.72 Hz, 1H), 4.17 (m, 2H), 4.44 (d, J = 7.54 Hz, 1H), 4.64 (d, J = 15.74 Hz, 1H), 4.76 (d, J = 15.62 Hz, 1H), 5.33-5.49 (m, 1H), 6.40 (d, J = 10.10 Hz, 1H), 6.46 (s, 1H), 6.50 (m, 1H), 7.13-7.16 (m, 2H), 7.59 (m, 1H). MASS (ES+): 745.1 |
| IB.143 | 0.96 (s, 9H), 1.06 (d, J = 7.05 Hz, 3H), 1.19 (s, 3H), 1.25-1.40 (m, 7H), 1.55 (s, 3H), 1.74-1.99 (m, 3H), 2.30-2.56 (m, 5H), 3.44 (m, 1H), 3.68 (d, J = 16.89 Hz, 1H), 3.79 (d, J = 17.24 Hz, 1H), 3.85 (d, J = 2H), 4.45 (d, J = 7.73 Hz, 1H), 4.67 (d, J = 15.98 Hz, 1H), 4.71 (d, J = 15.98 Hz, 1H), 5.33-5.49 (m, 1H), 6.40 (d, J = 10.09 Hz, 1H), 6.46 (s, 1H), 6.50-6.51 (m, 1H), 7.13-7.16 (m, 2H), 7.59 (s, 1H). MASS (ES+): 689.1 |
| IB.144 | 1.06 (d, J = 7.16 Hz, 3H), 1.19 (s, 3H), 1.25-1.39 (m, 1H), 1.55 (s, 3H), 1.76-2.10 (m, 9H), 2.28-2.67 (m, 6H), 3.43-3.47 (m, 1H), 33.67-3.79 (m, 2H), 4.12 (d, J = 8.32 Hz, 1H), 4.65-4.75 (m, 2H), 5.33-5.50 (m, 1H), 6.40 (dd, J$_1$ = 10.11 Hz, J$_2$ = 1.64 Hz, 1H), 6.46 (s, 1H), 6.51 (dd, J$_1$ = 3.45 Hz, J$_2$ = 1.60 Hz, 1H), 7.13-7.17 (m, 2H), 7.59 (m, 1H). MASS (ES+): 687.1 |
| IB.145 | 1.06 (d, J = 7.07 Hz, 3H), 1.19 (s, 3H), 1.36-1.41 (m, 1H), 1.54 (s, 3H), 1.70-1.94 (m, 3H), 2.17-2.49 (m, 5H), 3.44 (m, 1H), 3.68 (d, J = 16.70 Hz, 1H), 3.76 (d, J = 16.66 Hz, 1H), 4.42 (d, J = 7.94 Hz, 1H), 4.70 (s, 2H), 5.13 (s, 2H), 5.32-5.49 (m, 1H), 6.38-6.50 (m, 5H), 7.12-7.14 (m, 1H), 7.43 (s, 1H), 7.59 (s, 1H). MASS (ES+): 699.1 |
| IB.146 | 0.94 (t, J = 7.29 Hz, 3H), 1.06 (d, J = 7.15 Hz, 3H), 1.19 (s, 3H), 1.25-1.43 (m, 3H), 1.55 (s, 3H), 1.61-1.99 (m, 5H), 2.28-2.49 (m, 4H), 2.59 (s, 1H), 3.44-3.47 (m, 1H), 3.68-.379 (m, 2H), 4.15 (t, J = 6.69 Hz, 1H), 4.44 (d, J = 8.63 Hz, 1H), 4.65 (d, J = 15.51 Hz, 1H), 4.71 (d, J = 15.47 Hz, 1H), 5.33-5.49 (m, 1H), 6.40 (dd, J$_1$ = 10.14 Hz, J$_2$ = 1.59 Hz, 1H), 6.46 (s, 1H), 6.50 (dd, J$_1$ = 3.39 Hz, J$_2$ = 1.60 Hz, 1H), 7.13-7.17 (m, 2H), 7.59 (s, 1H). MASS (ES+): 675.1 |
| IB.147 | 0.90 (t, J = 6.86 Hz, 3H), 1.06 (d, J = 7.11 Hz, 3H), 1.19 (s, 3H), 1.33-1.43 (m, 5H), 1.55 (s, 3H), 1.65-1.99 (m, 5H), 2.28-2.53 (m, 4H), 2.60 (s, 1H), 3.42-3.47 (m, 1H), 3.69 (d, J = 16.86 Hz, 1H), 3.76 (d, J = 16.62 Hz, 1H), 4.15 (t, J = 6.78 Hz, 2H), 4.44 (d, J = 8.38 Hz, 1H), 4.66 (d, J = 15.54 Hz, 1H), 4.71 (d, J = 15.39 Hz, 1H), 5.33-5.49 (m, 1H), 6.40 (dd, J$_1$ = 10.08 Hz, J$_2$ = 1.55 Hz, 1H), 6.46 (s, 1H), 6.50 (dd, J$_1$ = 3.36 Hz, J$_2$ = 1.74 Hz, 1H), 7.13-7.17 (m, 2H), 7.59 (s, 1H). MASS (ES+): 689.2 |
| IB.148 | 1.06 (d, J = 7.17 Hz, 3H), 1.20 (s, 3H), 1.24-1.25 (m, 6H), 1.35-1.41 (m, 1H), 1.56 (s, 3H), 1.77-1.98 (m, 3H), 2.28-2.52 (m, 4H), 2.82 (s, 1H), 3.42-3.46 (m, 1H), 3.67 (d, J = 16.93 Hz, 1H), 3.75 (d, J = 16.87 Hz, 1H), 4.33 (dd, J$_1$ = 13.35 Hz, J$_2$ = 8.87 Hz, 1H), 4.45 (dd, J$_1$ = 13.22 Hz, J$_2$ = |

TABLE 6-continued

Spectral data for the synthesized compounds

| Comp. No | ¹H-NMR (δ ppm), MASS (EI/ES+, m/z) |
|---|---|
| | 8.77 Hz, 1H), 4.42-4.48 (m, 1H), 4.58 (d, J = 15.35 Hz, 1H), 4.78 (d, J = 15.36 Hz, 1H), 5.31-5.49 (m, 1H), 6.40 (dd, $J_1$ = 10.12 Hz, $J_2$ = 1.68 Hz, 1H), 6.45 (s, 1H), 6.50 (dd, $J_1$ = 3.43 Hz, $J_2$ = 1.64 Hz, 1H), 7.12 (d, J = 3.44 Hz, 1H), 7.17 (dd, J = 10.21 Hz, 1H), 7.58 (d, J = 0.71 Hz, 1H). MASS (ES+): 677.1 |
| IB.149 | 1.06 (d, J = 7.10 Hz, 3H), 1.18 (s, 3H), 1.36 (s, 3H), 1.38-1.43 (m, 1H), 1.43 (s, 3H), 1.55 (s, 3H), 1.77-1.98 (m, 3H), 2.28-2.55 (m, 5H), 3.43-3.46 (m, 1H), 3.66-3.83 (m, 3H), 4.07-4.36 (m, 4H), 4.44 (d, J = 7.86 Hz, 1H), 4.67-(d, J = 15.48 Hz, 1H), 4.73 (d, J = 15.48 Hz, 1H), 5.32-5.49 (m, 1H), 6.39 (d, J = 10.08 Hz, 1H), 6.45 (s, 1H), 6.50 (d, J = 1.59 Hz, 1H), 7.13 (d, J = 3.39 Hz, 1H), 7.15 (d, J = 10.24 Hz, 1H), 7.59 (s, 1H). MASS (ES+): 733.1 |
| IB.150 | 1.06 (d, J = 7.08 Hz, 3H), 1.18 (s, 3H), 1.35 (s, 3H), 1.38-1.43 (m, 1H), 1.43 (s, 3H), 1.55 (s, 3H), 1.77-1.97 (m, 3H), 2.28-2.49 (m, 5H), 3.42-3.46 (m, 1H), 3.69 (d, J = 16.77 Hz, 1H), 3.77 (d, J = 15.45 Hz, 1H), 3.80 (d, J = 5.40 Hz, 1H), 3.82 (d, J = 5.56 Hz, 1H), 4.08 (d, J = 6.42 Hz, 1H), 4.10 (d, J = 6.85 Hz, 1H), 4.18 (d, J = 5.35 Hz, 2H), 4.32 (m, 1H), 4.45 (d, J = 7.55 Hz, 2H), 4.70 (m, 1H), 5.31-5.51 (m, 1H), 6.39 (d, J = 10.13 Hz, 1H), 6.45 (s, 1H), 6.50 (dd, $J_1$ = 3.47 Hz, $J_2$ = 1.52 Hz, 1H), 7.12 (d, J = 3.44 Hz, 1H), 7.14 (d, J = 10.15 Hz, 1H), 7.59 (s, 1H). MASS (ES+): 733.1 |
| IB.151 | 1.05 (d, J = 7.11 Hz, 3H), 1.20 (s, 3H), 1.35-1.40 (m, 1H), 1.54 (s, 3H), 1.77-2.03 (m, 3H), 2.28-2.52 (m, 4H), 3.39 (d, J = 72.79 Hz, 1H), 3.39-3.46 (m, 5H), 3.67-3.80 (m, 6H), 4.42 (d, J = 8.10 Hz, 1H), 4.59 (d, J = 15.59 Hz, 1H), 4.74 (d, J = 15.59 Hz, 1H), 5.32-5.49 (m, 1H), 6.39 (dd, $J_1$ = 10.16 Hz, $J_2$ = 1.48 Hz, 1H), 6.45 (s, 1H), 6.50 (dd, $J_1$ = 3.26 Hz, $J_2$ = 1.59 Hz, 1H), 7.14 (d, J = 2.57 Hz, 1H), 7.16 (d, J = 10.25 Hz, 1H), 7.59 (s, 1H). MASS (ES+): 688.1 |
| IB.152 | 1.05 (d, J = 7.10 Hz, 3H), 1.20 (s, 3H), 1.34 (s, 3H), 1.34-1.40 (m, 1H), 1.43 (s, 3H), 1.55 (s, 3H), 1.77-2.03 (m, 3H), 2.28-2.53 (m, 4H), 3.23-3.30 (m, 1H), 3.37-3.45 (m, 3H), 3.63-3.79 (m, 3H), 4.02-4.24 (m, 2H), 4.43 (d, J = 7.99 Hz, 1H), 4.53 (d, J = 15.80 Hz, 1H), 4.70 (d, J = 15.61 Hz, 1H), 5.15 (s, 1H), 5.33-5.49 (m, 1H), 6.39 (dd, $J_1$ = 10.16 Hz, $J_2$ = 1.42 Hz, 1H), 6.45 (s, 1H), 6.50 (d, $J_1$ = 3.31 Hz, $J_2$ = 1.54 Hz, 1H), 7.14 (d, J = 3.39 Hz, 1H), 7.18 (d, J = 9.90 Hz, 1H), 7.59 (s, 1H). MASS (ES+): 732.1 |
| IB.153 | 1.06 (d, J = 7.12 Hz, 3H), 1.09 (m, 2H), 1.20 (s, 3H), 1.36-1.41 (m, 1H), 1.51-1.99 (m, 15H), 2.29-2.49 (m, 4H), 2.64 (d, J = 1.80 Hz, 1H), 3.43-3.47 (m, 1H), 3.69 (d, J = 16.81 Hz, 1H), 3.76 (d, J = 16.88 Hz, 1H), 4.17 (t, J = 6.97 Hz, 2H), 4.44 (d, J = 8.65 Hz, 1H), 4.65 (d, J = 15.48 Hz, 1H), 4.71 (d, J = 15.44 Hz, 1H), 5.33-5.49 (m, 1H), 6.40 (dd, $J_1$ = 10.13 Hz, $J_2$ = 1.56 Hz, 1H), 6.45 (s, 1H), 6.51 (dd, $J_1$ = 3.37 Hz, $J_2$ = 1.53 Hz, 1H), 7.13-7.17 (m, 2H), 7.59 (d, J = 0.70 Hz, 1H). MASS (ES+): 715.1 |
| IB.154 | 0.93 (d, J = 6.53 Hz, 6H), 1.06 (d, J = 7.11 Hz, 3H), 1.20 (m, 2H), 1.35-1.41 (m, 1H), 1.55 (s, 3H), 1.57-1.66 (m, 2H), 1.66-1.99 (m, 4H), 2.29-2.49 (m, 4H), 2.57 (s, 1H), 3.43-3.46 (m, 1H), 3.69 (d, J = 16.54 Hz, 1H), 3.77 (d, J = 16.68 Hz, 1H), 4.19 (t, J = 6.87 Hz, 2H), 4.44 (d, J = 8.08 Hz, 1H), 4.65 (d, J = 15.53 Hz, 1H), 4.71 (d, J = 15.51 Hz, 1H), 5.33-5.49 (m, 1H), 6.40 (d, J = 10.11 Hz, 1H), 6.46 (s, 1H), 6.50 (dd, $J_1$ = 3.10 Hz, $J_2$ = 1.63 Hz, 1H), 7.13-7.17 (m, 2H), 7.59 (s, 1H). MASS (ES+): 689.1 |
| IB.155 | 1.06 (d, J = 7.08 Hz, 3H), 1.17 (s, 3H), 1.36-1.40 (m, 1H), 1.55 (s, 3H), 1.74-2.11 (m, 5H), 2.29-2.63 (m, 6H), 3.44 (m, 1H), 3.67 (d, J = 16.71 Hz, 1H), 3.76 (d, J = 16.62 Hz, 1H), 4.45 (d, J = 8.31 Hz, 1H), 4.51 (t, J = 6.24 Hz, 2H), 4.61 (d, J = 15.49 Hz, 1H), 4.73 (d, J = 15.42 Hz, 1H), 4.40 (d, J = 11.18 Hz, 1H), 5.33-5.50 (m, 1H), 6.40 (d, J = 11.18 Hz, 1H), 6.45 (s, 1H), 6.50 (m, 1H), 7.13 (d, J = 3.30 Hz, 1H), 7.17 (d, J = 10.24 Hz, 1H), 7.59 (s, 1H). MASS (ES+): 706.1 |
| IB.156 | 1.05 (d, J = 7.06 Hz, 3H), 1.19 (s, 3H), 1.31 (s, 3H), 1.33 (s, 3H), 1.37-1.41 (m, 1H), 1.44 (s, 3H), 1.50 (s, 3H), 1.55 (s, 3H), 1.77-2.00 (m, 3H), 2.28-2.50 (m, 4H), 2.68 (s, 1H), 3.45 (m, 1H), 3.66 (d, J = 13.96 Hz, 1H), 3.77 (d, J = 16.58 Hz, 1H), 4.05 (t, J = 5.83 Hz, 1H), 4.24-4.34 (m, 4H), 4.46 (d, J = 7.50 Hz, 1H), 4.62 (dd, $J_1$ = 7.80 Hz, $J_2$ = 2.15 Hz, 1H), 4.69 (s, 2H), 5.33-5.49 (m, 1H), 5.52 (d, J = 4.93 Hz, 1H), 6.38 (d, J = 10.13 Hz, 1H), 6.45 (s, 1H), 6.50 (dd, $J_1$ = 3.19 Hz, $J_2$ = 1.47 Hz, 1H), 7.13 (d, J = 3.18 Hz, 1H), 7.18 (d, J = 10.10 Hz, 1H), 7.59 (s, 1H). MASS (ES+): 861.1 |
| IB.157 | 1.06 (d, J = 7.08 Hz, 3H), 1.17 (s, 3H), 1.36-1.40 (m, 1H), 1.55 (s, 3H), 1.74-2.11 (m, 5H), 2.29-2.63 (m, 6H), 3.44 (m, 1H), 3.67 (d, J = 16.71 Hz, 1H), 3.76 (d, J = 16.62 Hz, 1H), 4.45 (d, J = 8.31 Hz, 1H), 4.51 (t, J = 6.24 Hz, 2H), 4.61 (d, J = 15.49 Hz, 1H), 4.73 (d, J = 15.42 Hz, 1H), 4.40 (d, J = 11.18 Hz, 1H), 5.33-5.50 (m, 1H), 6.40 (d, J = 11.18 Hz, 1H), 6.45 (s, 1H), 6.50 (m, 1H), 7.13 (d, J = 3.30 Hz, 1H), 7.17 (d, J = 10.24 Hz, 1H), 7.59 (s, 1H). MASS (ES+): 720.1 |
| IB.158 | 1.06 (d, J = 7.14 Hz, 3H), 1.16 (s, 3H), 1.35-1.41 (m, 1H), 1.55 (s, 3H), 1.77-1.97 (m, 3H), 2.12-2.51 (m, 5H), 3.36 (s, 3H), 3.43-3.47 (m, 1H), 3.71 (d, J = 16.48 Hz, 1H), 3.83 (d, J = 16.48 Hz, 1H), 4.05 (d, J = 15.61 Hz, 1H), 4.10 (d, J = 15.58 Hz, 1H), 4.44 (d, J = 8.60 Hz, 1H), 5.34-5.47 (m, 1H), 6.41 (dd, $J_1$ = 10.16 Hz, $J_2$ = 1.69 Hz, 1H), 6.46 (s, 1H), 6.51 (dd, $J_1$ = 3.44 Hz, $J_2$ = 1.75 Hz, 1H), 7.13 (d, J = 3.40 Hz, 1H), 7.15 (d, J = 10.20 Hz, 1H), 7.59 (d, J = 0.86 Hz, 1H). MASS (ES+): 589.1 |
| IB.159 | 1.06 (d, J = 7.16 Hz, 3H), 1.16 (s, 3H), 1.22 (t, J = 7.01 Hz, 3H), 1.36-1.41 (m, 1H), 1.54 (s, 3H), 1.71-2.00 (m, 3H), 2.28-2.51 (m, 4H), 3.42-3.46 (m, 1H), 3.46-3.59 (m, 2H), 3.70 (d, J = 16.51 Hz, 1H), 3.83 (d, J = 16.49 Hz, 1H), 4.07-4.17 (m, 2H), 4.44 (d, J = 8.80 Hz, 1H), 5.32-5.49 (m, 1H), 6.41 (dd, $J_1$ = 10.12 Hz, $J_2$ = 1.68 Hz, 1H), 6.46 (s, 1H), 6.51 (dd, $J_1$ = 3.43 Hz, $J_2$ = 1.63 Hz, 1H), 7.13-7.16 (m, 2H), 7.59 (s, 1H). MASS (ES+): 603.1 |
| IB.160 | 0.91 (d, J = 6.70 Hz, 6H), 1.06 (d, J = 7.07 Hz, 3H), 1.15 (s, 3H), 1.25-1.41 (m, 1H), 1.54 (s, 3H), 1.67-1.97 (m, 5H), 2.28-2.53 (m, 4H), 3.22-3.28 (m, 2H), 3.42-3.46 (m, 1H), 3.71 (d, J = 16.42 Hz, 1H), 3.84 (d, J = 16.45 Hz, 1H), 4.06-4.16 (m, 2H), 4.44 (d, J = 7.72 Hz, 1H), 5.32-5.49 (m, 1H), 6.39-6.41 (m, 1H), 6.46 (s, 1H), 6.51 (dd, $J_1$ = 3.19 Hz, $J_2$ = 1.44 Hz, 1H), 7.12-7.15 (m, 2H), 7.59 (s, 1H). MASS (ES+): 631.1 |
| IC.1 | 1.03 (d, J = 7.07 Hz, 3H), 1.13 (d, J = 7.68 Hz, 3H), 1.15 (s, 3H), 1.20-1.89 (m, 8H), 2.15-2.44 (m, 6H), 2.85-2.88 (m, 1H), 4.30-4.33 (m, 1H), 4.82 (s, 2H), 5.30-5.47 (m, 1H), 6.34 (dd, $J_1$ = 10.13 Hz, $J_2$ = 1.17 Hz, 2H). 6.38 (s, 1H), 7.05 (dd, J = 8.67 Hz, 2H), 7.21 (d, J = 10.17 Hz, 1H), 7.43-7.47 (m, 2H). MASS (ES+): 615.5 (M + Na⁺). |
| IC.2 | 1.03 (d, J = 7.01 Hz, 3H), 1.11-1.14 (m, 6H), 1.32-1.89 (m, 8H), 2.20-2.44 (m, 6H), 2.80-2.84 (m, 1H), 4.40 (d, J = 8.11 Hz, 1H), 4.78 (d, J = 11.17 Hz, 1H), 4.4.81 (d, J = 11.19 Hz, 1H), 5.32-5.49 (m, 1H), 6.37 (d, J = 10.14 Hz, 1H), 7.10 (d, J = 10.15 Hz, 1H), 7.29 (d, J = 8.19 Hz, 1H), 7.44 (d, J = 8.19 Hz, 1H) 7.57 (s, 1H). MASS (ES+): 665.4 (M + Na⁺). |
| IC.3 | 1.03 (d, J = 7.09 Hz, 3H), 1.12 (t, J = 7.50 Hz, 3H), 1.16 (s, 3H), 1.16-1.95 (m, 8H), 2.20-2.40 (m, 6H), 2.78-2.84 (m, 1H), 4.41 (d, J = 8.70 Hz, 1H), 5.28-5.48 (m, 1H), 5.39 (d, d $J_1$ = 50.31 Hz, $J_2$ = 2.66 Hz, 1H), 5.51 (d, d $J_1$ = 49.30 Hz, $J_2$ = 2.61 Hz, 1H), 6.37 (dd $J_1$ = 10.15 Hz, |

TABLE 6-continued

Spectral data for the synthesized compounds

| Comp. No | $^1$H-NMR ($\delta$ ppm), MASS (EI/ES+, m/z) |
|---|---|
| | $J_2$ = 1.74 Hz, 1H), 6.43 (s, 1H), 7.10 (dd $J_1$ = 10.12 Hz, $J_2$ = 1.11 Hz, 1H).<br>MASS (ES+): 517.2 |
| IC.4 | 1.11 (d, J = 7.09 Hz, 3H), 1.21 (s, 3H), 1.24-1.97 (m, 8H), 2.28-2.50 (m, 4H), 2.86-2.90 (m, 1H), 4.45-4.47 (m, 1H), 5.30-5.52 (m, 1H), 5.41 (d,d $J_1$ = 53.67 Hz, $J_2$ = 2.34 Hz 1H), 5.56 (d, d $J_1$ = 52.24 Hz, $J_2$ = 2.33 Hz, 1H), 6.39 (d $J_1$ = 10.13 Hz, $J_2$ = 1.77 Hz 1H) 7.60 (d, J = 0.88 Hz, 1H). MASS (ES+): 555.2 |
| IC.5 | 1.10 (d, J = 7.17 Hz, 3H), 1.21 (s, 1H), 1.25-1.38 (m, 2H), 1.55 (s, 1H), 1.85-1.99 (m, 3H), 2.16-2.59 (m, 4H), 2.88-2.93 (m, 1H), 4.83 (d, J = 10.67 Hz, 1H), 4.83 (d, J = 10.69 Hz, 1H), 5.03-5.09 (m, 1H), 6.31-6.35 (m, 2H), 6.54 (dd, $J_1$ = 3.47 Hz, $J_2$ = 1.71 Hz, 1H), 7.03-7.07 (m, 2H), 7.26 (d, J = 10.03 Hz, 1H), 7.45-7.49 (m, 2H), 7.65 (d, J = 0.82 Hz, 1H). MASS (ES+): 631.2 |
| IC.6 | 1.12 (d, J = 7.07 Hz, 3H), 1.21 (s, 3H), 1.26-1.48 (m, 1H), 1.53 (s, 1H), 1.59-1.96 (m, 4H), 2.28-2.52 (m, 4H), 2.82-2.86-2.89 (m, 1H), 4.44-4.46 (m, 1H), 4.93 (d, J = 11.263 Hz, 1H), 5.03 (d, J = 11.24 Hz, 1H), 5.32-5.48 (m, 1H), 6.39 (dd, $J_1$ = 10.11 Hz, $J_2$ = 1.68 Hz, 1H), 6.45 (s, 1H), 6.52 (dd $J_1$ = 3.41 Hz, $J_2$ = 1.70 Hz, 1H), 7.11 (d, J = 5.71 Hz, 1H), 7.13 (s, 1H), 7.58-7.64 (m, 4H). MASS (ES+): 681.3 |
| IC.7 | 1.09 (d, J = 6.89 Hz, 3H), 1.20 (s, 3H), 1.25-1.50 (m, 1H), 1.55 (s, 1H), 1.60-2.03 (m, 4H), 2.16-2.52 (m, 4H), 2.92-3.13 (m, 1H), 4.32 (m, 1H), 4.83 (d, J = 10.85 Hz, 1H), 4.87 (d, J = 10.88 Hz, 1H), 5.13-5.51 (m, 1H), 6.30-6.33 (m, 2H), 6.55 (s, 1H), 7.13 (s, 1H), 7.26 (d, J = 10.22 Hz, 1H), 7.33-7.58 (m, 4H), 7.58-7.77 (m, 1H).<br>MASS (ES+): 647.2 |
| IC.8 | 0.99 (d, J = 7.09 Hz, 3H), 1.09 (t, J = 7.52 Hz, 3H), 1.12 (s, 3H), 1.22-1.88 (m, 8H), 2.13-2.55 (m, 6H), 2.82-2.86 (m, 1H), 4.25-4.27 (m, 1H), 4.89 (s, 2H), 4.96-4.98 (m, 1H), 5.30-5.50 (m, 1H), 6.26-6.29 (m, 2H), 7.21 (dd, $J_1$ = 10.03 Hz, $J_2$ = 1.05 Hz, 1H), 7.56 (d, J = 8.26 Hz, 2H), 7.61 (d, J = 8.30 Hz, 2H).<br>MASS (ES+): 643.0 |
| IC.9 | 1.05 (d, J = 7.09 Hz, 3H), 1.18 (s, 1H), 1.20-1.87 (m, 8H), 2.19-2.56 (m, 4H), 2.58-2.70 (m, 1H), 2.86-2.90 (m, 1H), 4.30-4.32 (m, 1H), 4.80 (d, J = 10.70 Hz, 1H), 4.85 (d, J = 10.70 Hz, 1H), 4.92-4.94 (m, 1H), 6.05 (m, 1H), 6.25 (dd, $J_1$ = 10.13 Hz, $J_2$ = 1.77 Hz, 1H), 6.51 (dd, $J_1$ = 3.45 Hz, $J_2$ = 1.70 Hz, 1H), 7.00-7.02 (m, 2H), 7.29 (d, J = 10.11 Hz, 1H), 7.43-7.46 (m, 2H), 7.63 (d, J = 0.85 Hz, 1H).<br>MASS (ES+): 613.0 |
| IC.10 | 1.00 (d, J = 7.06 Hz, 3H), 1.07 (t, J = 7.54 Hz, 3H), 1.15 (s, 3H), 1.25-1.92 (m, 8H), 2.16-2.44 (m, 6H), 2.81-2.84 (m, 1H), 4.41 (d, J = 8.51 Hz, 1H), 5.10 (d, J = 16.55 Hz, 1H), 5.21 (d, J = 16.64 Hz, 1H), 5.30-5.46 (m, 1H), 6.38 (dd, $J_1$ = 10.13 Hz, $J_2$ = 1.69 Hz, 1H), 7.14 (d, J = 10.13 Hz, 1H), 7.46 (d, J = 8.54 Hz, 2H), 7.85 (d, J = 8.58 Hz, 2H). MASS (ES+): 637.1 |
| IC.11 | 1.10 (d, J = 7.08 Hz, 3H), 1.22 (s, 3H), 1.25-1.94 (m, 8H), 2.27-2.65 (m, 5H), 2.80-2.92 (m, 1H), 4.45-4.56 (m, 1H), 5.41 (dd $J_1$ = 52.28 Hz, $J_2$ = 2.31 Hz, 1H), 5.56 (dd $J_1$ = 53.72 Hz, $J_2$ = 2.34 Hz, 1H), 6.15 (s, 1H), 6.37 (dd $J_1$ = 10.13 Hz, $J_2$ = 1.82 Hz, 1H), 6.50 (dd $J_1$ = 3.48 Hz, $J_2$ = 1.70 Hz, 1H), 7.12 (d, J = 3.40 Hz, 1H), 7.21 (d, J = 10.12 Hz, 1H), 7.59 (d, J = 0.86 Hz 1H). MASS (ES+): 537.1 |
| IC.12 | 0.89 (t, J = 7.33 Hz, 3H), 1.03 (d, J = 7.07 Hz, 3H), 1.16 (s, 3H), 1.25-1.91 (m, 12H), 2.17-2.44 (m, 6H), 2.80-2.84 (m, 1H), 4.1-4.33 (m, 1H), 5.30-5.58 (m, 3H), 6.38 (dd, $J_1$ = 10.13 Hz, $J_2$ = 1.69 Hz, 1H).6.43 (s, 1H), 7.11 (dd, $J_1$ = 10.12 Hz, $J_2$ = 0.98 1H). MASS (ES+): 537.1 |
| IC.13 | 1.02 (d, J = 7.08 Hz, 3H), 1.12 (t, J = 7.70 Hz, 3H), 1.15 (s, 3H), 1.32-1.37 (m, 1H), 1.52 (s, 3H), 1.68-1.92 (m, 4H), 2.22-2.39 (m, 4H), 2.76-2.81 (m, 1H), 3.84 (s, 3H), 4.40-4.42 (m, 1H), 5.29-5.47 (m, 1H), 6.38 (dd $J_1$ = 10.12 Hz, $J_2$ = 1.79 Hz, 1H), 6.43 (s, 1H), 7.12 (dd $J_1$ = 10.14 Hz, $J_2$ = 1.32 Hz, 1H). MASS (ES+): 499.0 |
| IC.14 | 1.08 (d, J = 7.08 Hz, 3H), 1.20 (s, 3H), 1.29-1.40 (m, 1H), 1.55 (s, 1H), 1.59-2.00 (m, 4H), 2.27-2.51 (m, 4H), 2.88-2.92 (m, 1H), 3.85 (s, 3H), 4.33-4.35 (m, 1H), 4.95-4.97 (m, 1H), 5.34-5.51 (m, 3H), 6.33 (dd $J_1$ = 10.10 Hz, $J_2$ = 1.85 Hz, 1H), 6.36 (s, 1H), 6.52 (dd $J_1$ = 3.49 Hz, $J_2$ = 1.72 Hz, 1H), 7.11 (dd $J_1$ = 3.48 Hz, $J_2$ = 0.53 Hz, 1H), 7.26 (dd $J_1$ = 10.05 Hz, $J_2$ = 0.96 Hz, 1H), 7.62-7.63m, 1H). MASS (ES+): 537.0 |
| IC.15 | 1.04 (d, J = 7.09 Hz, 3H), 1.11-1.15 (m, 6H), 1.34-1.85 (m, 8H), 2.20-2.39 (m, 6H), 2.80-2.90 (m, 1H), 4.38 (d, J = 8.66 Hz, 1H), 4.86 (d, J = 10.78 Hz, 1H), 4.92 (d, J = 10.77 Hz, 1H), 5.27-5.49 (m, 1H), 6.36 (dd, $J_1$ = 10.14 Hz, $J_2$ = 1.80 Hz 1H), 6.43 (s, 1H), 7.09 (dd, $J_1$ = 10.13 Hz, $J_2$ = 1.20 Hz, 1H), 7.35-7.45 (m, 5H). MASS (ES+): 575.0 |
| IC.16 | 1.08 (d, J = 7.08 Hz, 3H), 1.20 (s, 3H), 1.22-1.97 (m, 8H), 2.26-2.54 (m, 4H), 2.91-2.95 (m, 1H), 4.31 (d, J = 6.59 Hz, 1H), 4.85 (d, J = 10.66 Hz, 1H), 4.88 (d, J = 10.66 Hz, 1H), 5.24-5.56 (m, 1H), 6.28-6.31 (m, 2H), 6.56 (dd, $J_1$ = 3.39 Hz, $J_2$ = 1.64 Hz 1H), 7.31 (d, J = 3.45 Hz, 1H), 7.18-7.46 (m, 6H), 7.72 (s, 1H). MASS (ES+): 613.0 |
| IC.17 | 0.99 (d, J = 7.07 Hz, 3H), 1.09 (t, J = 7.51 Hz, 3H), 1.14 (s, 3H), 1.19-1.96 (m, 8H), 2.09-2.47 (m, 12H), 2.77-2.81 (m, 1H), 4.40 (d, J = 6.30 Hz, 1H), 4.74 (d, J = 18.25 Hz, 1H), 4.82 (d, J = 18.27 Hz, 1H), 5.30-5.46 (m, 1H), 6.38 (dd, $J_1$ = 10.15 Hz, $J_2$ = 1.79 Hz, 1H), 6.43 (s, 1H), 6.84 (s, 2H), 7.12 (d, J = 9.89 Hz, 1H). MASS (ES+): 645.3 |
| IC.18 | 1.03 (d, J = 7.09 Hz, 3H), 1.14 (s, 3H), 1.13 (t, J = 7.54 Hz, 3H), 1.25-1.89 (m, 8H), 2.17-2.40 (m, 6H), 2.81-2.83 (m, 1H), 4.38-4.41 (m, 1H), 4.81 (d, J = 10.91 Hz, 1H), 4.88 (d, J = 10.91 Hz, 1H), 5.25-5.50 (m, 1H), 6.35 (d, d $J_1$ = 10.13 Hz, $J_2$ = 1.65 Hz), 6.43 (s, 1H), 7.10 (d, d $J_1$ = 10.10 Hz, $J_2$ = 0.67 Hz 1H), 7.34 (d, J = 8.40 Hz, 2H), 7.40 (d, J = 8.39 Hz, 2H). MASS (ES+): 609.0 |
| IC.19 | 1.10 (d, J = 7.04 Hz, 3H), 1.21 (s, 3H), 1.30-1.96 (m, 8H), 2.29-2.54 (m, 4H), 2.90-2.93 (m, 1H), 4.33-4.36 (m, 1H), 4.82 (d, J = 11.11 Hz, 1H), 4.87 (d, J = 11.10 Hz, 1H), 4.95-4.98 (m, 1H), 5.36-5.51 (m, 1H), 6.33 (dd, $J_1$ = 10.13 Hz, $J_2$ = 1.75 Hz, 1H), 7.14 (d, J = 3.45 Hz, 1H), 7.25 (d, J = 10.09 Hz, 1H), 7.32 (dd, $J_1$ = 8.22 Hz, $J_2$ = 1.89 Hz 1H), 7.44-7.46 (m, 1H), 7.64 (s, 1H). MASS (ES+): 680.9 |
| IC.20 | 1.09 (d, J = 7.00 Hz, 3H), 1.20 (s, 3H), 1.30-2.02 (m, 8H), 2.26-2.53 (m, 4H), 2.91-2.95 (m, 1H), 4.32 (d, J = 6.99 Hz, 1H), 4.97 (d, J = 11.64 Hz, 1H), 5.03 (d, J = 11.59 Hz, 1H), 5.37-5.54 (m, 1H), 6.31-6.32 (m, 2H), 6.56 (dd, $J_1$ = 3.28 Hz, $J_2$ = 1.56 Hz, 1H), 7.13 (d, J = 3.41 Hz, 1H), 7.18-7.31 (m, 2H), 7.42 (d, J = 1.43 Hz, 1H), 7.58 (d, J = 8.25 Hz, 1H), 7.70 (s, 1H). MASS (ES+): 681.5 |
| IC.21 | 1.11 (d, J = 6.97 Hz, 3H), 1.22 (s, 3H), 1.25-1.96 (m, 8H), 2.28-2.58 (m, 4H), 2.90-3.95 (m, 1H), 4.36 (m, 1H), 4.83-4.88 (m, 3H), 5.30-5.55 (m, 1H), 6.34 (d, d $J_1$ = 10.10 Hz, $J_2$ = 1.68 Hz, 1H), 6.38 (m, 1H), 6.53 (d, d $J_1$ = 3.39 Hz, $J_2$ = 1.65 Hz, 1H), 7.13 (d, J = 3.43 Hz, 1H), 7.124-7.42 (m, 4H), 7.50 (s, 1H), 7.63 (s, 1H). MASS (ES+): 647.7 |

TABLE 6-continued

Spectral data for the synthesized compounds

| Comp. No | ¹H-NMR (δ ppm), MASS (EI/ES+, m/z) |
|---|---|
| IC.22 | 1.09 (d, J = 7.04 Hz, 3H), 1.20 (s, 3H), 1.25-1.97 (m, 8H), 2.03-2.57 (m, 4H), 2.89-2.93 (m, 1H), 4.33 (d, J = 6.78 Hz, 1H), 4.95 (d, J = 10.92 Hz, 1H), 5.05 (d, J = 10.89 Hz, 1H), 5.12 (m, 1H), 5.30-5.30 (m, 1H), 6.30-6.33 (m, 2H), 6.54 (dd, $J_1$ = 3.39 Hz, $J_2$ = 1.63 Hz 1H), 6.74-6.78 (m, 2H), 7.11 (d, J = 3.36 Hz, 1H), 7.26 (d, J = 10.07 Hz, 1H), 7.66 (s, 1H). MASS (ES+): 667.0 |
| IC.23 | 1.10 (d, J = 7.05 Hz, 3H), 1.22 (s, 3H), 1.36-1.42 (m, 1H), 1.55 (s, 3H), 1.72-2.00 (m, 4H), 2.29-2.52 (m, 4H), 2.87-2.92 (m, 1H), 4.32-4.35 (m, 1H), 4.93 (d, J = 11.04 Hz, 1H), 4.97 (d, J = 11.07 Hz, 1H), 5.05-5.06 (m, 1H), 5.30-5.52 (m, 1H), 6.33 (dd, $J_1$ = 10.09 Hz, $J_2$ = 1.88 Hz 1H), 6.35 (s, 1H), 6.54 (dd, $J_1$ = 3.49 Hz, $J_2$ = 1.72 Hz 1H), 7.13 (d, J = 3.39 Hz 1H), 7.26 (dd, $J_1$ = 10.07 Hz, $J_2$ = 1.01 Hz 1H), 7.51-7.69 (m, 4H), 7.74 (s, 1H). MASS (ES+): 681.5 |

Example 30

Pharmacological Activity (a) Steroid Receptor Binding Assays:

The steroid receptor binding assay were performed by MDS Pharma Services at their Taipei (Taiwan) pharmacology laboratory.

(i) Glucocorticoid Receptor Binding Assay

The activity of test compounds on glucocorticoid receptor was assessed using radioligand binding assays. The Human HeLa cells transfected with glucocorticoid receptors were incubated with [³H]dexamethasone at 25° C. for 2 hrs in RPMI-1640, 10 nM HEPES, pH 7.2 incubation medium, in the absence or presence of test compounds at 3 nM and/or 10 nM concentration. Free [³H]dexamethasone was removed from the medium by centrifugation and concentration of receptor bound ligand was determined in the supernatant by liquid scintillation counting.

Dexamethasone as reference compound was tested concurrently as an integral part of each assay to ensure the validity of the results obtained. The % inhibition was evaluated using a single concentration of test compound and the corresponding radiolabeled ligand. Results are presented as the percent inhibition of specific binding. The values are average of duplicate determinations for each concentration.

TABLE 7

Glucocoticoid Receptor binding (in vitro) screen

| Compound No. | Glucocorticoid receptor binding % inhibition |
|---|---|
| IA.143 | 58[b] |
| IA.161 | 55[b] |
| IA.157 | 56[b] |
| IA.159 | 36[b] |
| IA.168 | 40[a] |
| IB.2 | 55[a] |
| IB.4 | 88[b] |
| IB.6 | 92[b] |
| IB.7 | 82[b] |
| IB.8 | 93[b] |
| IB.10 | 82[b] |
| IB.13 | 79[b] |
| IB.14 | 85[b] |
| IB.15 | 83[b] |
| IB.50 | 74[b] |
| IB.51 | 67[b] |
| IB.54 | 82[b] |
| IB.66 | 72[b] |
| IB.67 | 77[b] |
| IB.70 | 43[a] |
| IB.73 | 45[a] |
| IB.88 | 46[a] |
| IB.100 | 45[a] |

TABLE 7-continued

Glucocoticoid Receptor binding (in vitro) screen

| Compound No. | Glucocorticoid receptor binding % inhibition |
|---|---|
| IB.101 | 45[a] |
| IB.103 | 78[b] |
| IB.104 | 72[b] |
| IB.105 | 42[a] |
| IC.3 | 72[c] |
| IC.4 | 73[b] |
| IC.5 | 75[c] |
| IC.7 | 41[b] |
| Fluticasone propionate | 88[b] |
| Budesonide | 85[b] |

[a]% Inhibition at 3 nM:
[b]% Inhibition at 10 nM;
[c]% Inhibition at 100 nM.

(b) Croton Oil Ear Edema

Mice (male, CD-1) were made into different groups. Test compounds were dissolved in pyridine-water-acetone (4:2:14) solution 101 of compound or vehicle solution was applied to the left ear of the mice. The right ear of each mouse was applied simultaneously with 10 μl of pyridine:water:acetone (4:2:14) solution. After 2 hrs of compound or vehicle application, 10 μl of croton oil solution was applied to the left ear of all animals. After 6 hr of croton oil treatment the animals were sacrificed; ears were excised and weighed separately.

TABLE 8

Croton oil Ear Edema Screen

| Compound No. | Mean % Inhibition |
|---|---|
| IA.3 | 45.31[a] |
| IA.56 | 34.59[a] |
| IA.184 | 49.06[a] |
| IA.185 | 49.06[a] |
| IB.20 | 61.49[a] |
| IB.33 | 76.16[a] |
| IB.34 | 64.39[a] |
| IB.35 | 60.18[a] |
| IB.37 | 57.12[a] |
| IB.44 | 75.19[a] |
| IB.46 | 75.97[a] |
| IB.49 | 71.82[a] |
| IB.52 | 78.12[a] |
| IB.53 | 71.19[a] |
| IB.55 | 74.78[a] |
| IB.57 | 74.43[a] |
| IB.64 | 72.75[a] |
| IB.73 | 76.24[a] |
| IB.77 | 71.71[a] |
| IB.81 | 77.75[a] |
| IB.98 | 73.71[b] |
| IB.102 | 73.63[b] |

TABLE 8-continued

Croton oil Ear Edema Screen

| Compound No. | Mean % Inhibition |
| --- | --- |
| IB.112 | 66.94[b] |
| IB.138 | 72.48[b] |
| IB.150 | 77.76b |
| IB.159 | 66.02[b] |
| IC.13 | 41.79[a] |
| IC.14 | 61.46[a] |
| Fluticasone propionate | 81.09[a] |
| Dexamethasone | 50.05[a] |

[a]Inhibition at 1.6 μg:
[b]Inhibition at 0.5 μg (c) Cotton Pellet Granuloma

SD rats were used for assessing anti-inflammatory activity of test compound using cotton pellet granuloma method. Sterilized cotton pellets weighing 20 mg were prepared. Test compounds were dissolved in acetone so as to get the required quantity for each cotton pellet in 500 μl. Different pellets were impregnated with 500 μl of acetone to contain required quantity of test compounds and allowed to dry. Vehicle control pellets were impregnated with 500 μl acetone. Rats were made into different groups. Two cotton pellets were surgically implanted into the scapular region of each rat. On sixth day of such implantation, pellets along with granuloma were taken out. Thymus gland was also separated from each animal and weighed. The pellets with granuloma were dried for 20 hrs at 60° C. and weighed. Mean weights of dry granuloma and thymus, body weight gain/100 g body weights were calculated.

TABLE 9

Cotton pellet granuloma test

| Compound No. | Dose (mcg) | Mean % Inhibition of Granuloma | Thymus wt.* (% Decrease) |
| --- | --- | --- | --- |
| IA.3 | 1000 | 74.76 | −11.72 |
| IA.6 | 1000 | 61.25 | −6.95 |
| IA.11 | 1000 | 61.36 | −4.72 |
| IA.13 | 1000 | 62.52 | 6.46 |
| IA.14 | 1000 | 70.74 | −13.26 |
| IA.20 | 1000 | 67.57 | 0.73 |
| IA.27 | 10 | 31.28 | 8.71 |
|  | 1000 | 69.84 | 11.74 |
| IA.28 | 1000 | 73.73 | 13.5 |
| IA.35 | 1000 | 67.16 | −11.43 |
| IA.36 | 1000 | 70.74 | −13.26 |
| IA.38 | 10 | 67.17 | −1.28 |
| IA.42 | 1000 | 65.63 | −1.33 |
| IA.43 | 10 | 27.72 | −0.55 |
|  | 1000 | 72.03 | 1.47 |
| IA.44 | 1000 | 71.79 | 4.58 |
| IA.45 | 1000 | 80.06 | −4.46 |
| IA.58 | 10 | 59.00 | 6.00 |
| IA.59 | 1000 | 76.86 | −2.51 |
| IA.122 | 3 | 37.29 | 2.25 |
| IA.136 | 10 | 37.74 | 4.44 |
|  | 1000 | 67.79 | 2.14 |
| IA.137 | 1000 | 65.58 | 1.59 |
| IA.138 | 1000 | 66.16 | 15.45 |
| IA.140 | 1000 | 62.54 | −36.16 |
| IA.141 | 1000 | 63.1 | −18.26 |
| IA.142 | 10 | 45.36 | −8.43 |
| IA.197 | 1000 | 79.04 | −8.89 |
| IB.5 | 10 | 39.79 | −0.39 |
| IB.7 | 1000 | 78.82 | 14.89 |
| IB.16 | 3 | 68.92 | −11.06 |
|  | 1000 | 77.36 | −11.65 |
| IB.163 | 3 | 45.8 | −5.44 |
|  | 10 | 76.13 | 13.77 |

TABLE 9-continued

Cotton pellet granuloma test

| Compound No. | Dose (mcg) | Mean % Inhibition of Granuloma | Thymus wt.* (% Decrease) |
| --- | --- | --- | --- |
| IC.6 | 1000 | 84.96 | 10.96 |
| IC.8 | 3 | 45.15 | 3.38 |
| IC.9 | 3 | 34.3 | 2.51 |
| Fluticasone propionate | 1000 | 75.03 | 82.36 |
| Dexamethasone | 1000 | 44.73 | 68.66 |

*In all the compounds (other than the reference compounds) the thymus weight change and the body weight gain were statistically insignificant when compared with vehicle control (d) Sephadex-Induced Lung Edema in the SD Rat Sephadex G-200 was prepared in sterile saline (10 mg/ml) and allowed to swell for at least 3 days at room temperature. Test compounds were prepared as suspensions by grinding and sonicating the solid in chilled saline. All the compounds were administered intratracheally at 24 hrs and 2 hrs prior to intratracheal administration of Sephadex (5 mg/kg) under light ether anesthesia. Vehicle control animals were administered vehicle instead of Sephadex. At 24 hr after Sephadex instillation, lung and thymus were excised from individual animals and weighed. Wet weight of lung and thymus was corrected for 100 g of initial body weight. The percentage increase in lung weight caused by Sephadex and its inhibitions by the compounds, were calculated. The percentage inhibitions of thymus compared to vehicle control group were also calculated.

TABLE 10

Sephadex-Induced Lung Edema in the SD Rat

| Compound No. | Dose (mcg/kg) | Mean % inhibition* Lung edema | Mean % inhibition* Thymus |
| --- | --- | --- | --- |
| IA.168 | 3000 | 95.3 | 9.2 |
| IB.15 | 1000 | 70.3 | 4.5 |
| IB.15 | 3000 | 71.1 | 6.4 |
| IB.51 | 3000 | 120.5 | 29.8 |
| IB.54 | 3000 | 110.4 | 29.7 |
| IB.64 | 1000 | 86.4 | 2.0 |
| IB.64 | 3000 | 104.6 | 20.0 |
| IB.67 | 3000 | 121.8 | 33.4 |
| IB.79 | 3000 | 99.3 | 15.2 |
| IB.94 | 3000 | 99.7 | 8.1 |
| IB.100 | 3000 | 120.8 | 36.0 |
| IB.101 | 3000 | 114.8 | 8.9 |
| IB.150 | 3000 | 106.2 | 18.0 |
| Budesonide | 3000 | 119.38 | 67.08 |

*In all the compounds (other than the reference compounds) the body weight gain was statistically insignificant when compared with vehicle control

TABLE 10a

Therapeutic Index for Compounds in Sephadex Lung Edema model in SD Rat

| Comp No. | ED50 Lung edema (mg/kg, i.t.) | ED$_{50}$ Thymus (mg/kg, i.t.) | Therapeutic index ED$_{50}$ Thymus involution/ ED$_{50}$ Lung edema |
| --- | --- | --- | --- |
| IB.51 | 0.641 | 13.31 | 20.76 |
| IB.67 | 0.232 | 8.84 | 38.10 |
| IB.70 | 0.323 | 7.67 | 23.75 |
| IB.88 | 0.300 | 4.09 | 13.63 |
| Budesonide | 0.101 | 0.68 | 6.73 |
| Fluticasone propionate | 0.086 | 0.36 | 4.18 |

(e) Liver Glycogen Deposition in Rats

Male Sprague Dawley rats, weighing 190-220 g were bilaterally adrenalectomized and maintained on 0.9% saline solution throughout the experiment. On day 5th and 6th of adrenalectomy, animals were made into different groups, test compounds prepared in cold saline (sonicated for 30 min) were instilled intratracheally 2 doses@3 mg/kg, 24 hrs apart. At 15 hrs after the last treatment, animals were sacrificed and livers were excised and weighed. The glycogen content of the livers was determined by anthrone method. Briefly, a weighed quantity of liver tissue was homogenized with 5% trichloroacetic acid, supernatant mixed with ethanol and kept overnight for precipitation. The glycogen thus extracted was estimated as glucose generated after acid hydrolysis by addition of anthrone reagent at 620 nm. Glycogen content was expressed as mg/100 g liver.

TABLE 11

Liver Glycogen Deposition in Rats

| Comp No. | Dose (mg/kg) | Glycogen content (mg/100 g liver) | % Inhibition of thymus |
|---|---|---|---|
| IA.3 | 3 | −13.6 | −2.42 |
| IB.4 | 3 | −5.77 | −9.68 |
| IB.50 | 3 | 6.67 | 5.48 |
| IC.3 | 3 | −11.34 | −2.43 |
| Fluticasone propionate | 3 | 1514.65 | 70.17 |
| Mometasone furoate | 3 | 1117.32 | 43.51 |
| Budesonide | 3 | 552.77 | 65.02 |

(f) Assessment of Systemic Activity by i.v. Route of Administration

For assessing systemic side effect on i.v. administration, cotton pellet granuloma assay (blank cotton pellet) in male SD rats was undertaken. Sterilized cotton pellets weighing 20 mg were surgically implanted into the scapular region on both sides. Starting from next day of implantation, compounds dissolved in Pharmasove (Pharmasolve 66.67% in saline) or vehicle were administered intravenously at 1.6 mg/kg dose for 3 successive days. On fifth day of implantation, pellets along with granuloma were taken out. The thymus gland was also separated from each animal and weighed. The pellets with granuloma were dried for 20 hrs at 60° C. and weighed. Mean weights of dry granuloma and thymus and body weight gain/100 g body weights were compared with vehicle control groups.

The compounds of formula I of present invention did not induce any significant thymus and body weight gain suppression by i.v. administration. Further, there was no significant cotton pellet granuloma inhibition by i.v. route of administration, thus clearly indicating lack of systemic activity and hence excellent systemic safety profile for the compounds of formula I.

TABLE 12

Activity by i.v. Routes of Administration

| Comp No. | Dose mcg (for 3 days), i.v. | Mean Inhibition of Granuloma (%) | Mean Thymus wt. Decrease (%)* |
|---|---|---|---|
| IA.3 | 1600 | 3.98 | 6.37 |
| IA.11 | 1600 | 16.65 | −17.88 |
| IA.89 | 1600 | 15.90 | 6.54 |
| IC.3 | 1600 | 12.09 | −10.38 |
| IC.5 | 1600 | −22.20 | 1.67 |

TABLE 12-continued

Activity by i.v. Routes of Administration

| Comp No. | Dose mcg (for 3 days), i.v. | Mean Inhibition of Granuloma (%) | Mean Thymus wt. Decrease (%)* |
|---|---|---|---|
| IA.143 | 1600 | −3.01 | 5.51 |
| Fluticasone propionate | 1600 | 55.62 | 75.71 |

*The body weight gain in all the compounds was statistically not significant when compared with vehicle control

CONCLUSION

The compounds of formula I of the present invention have potent binding to the glucocorticoid receptor in vitro. In the in vivo models, which include croton oil induced ear edema, cotton pellet induced granuloma, and Sephadex induced lung edema screens, the compounds of the present invention exhibit significant anti-inflammatory activity. In the cotton pellet granuloma, the thymus involution and the body weight gain due to the compounds was either absent or insignificant even at dose levels as high as 100-1000 mcg per pellet. Similar behaviour was once again observed in the case Sephadex induced lung edema models even when the compounds were administered at very high doses, clearly demonstrating that these compounds do not cause any adverse systemic effects following local administration. The absence or non-significance of the systemic side effects was further confirmed by measurement of hepatic glycogen deposition in rats after intratracheal administration, and by measurement of thymus and body weight gain suppression following i.v. administration.

Thus the compounds of formula I described in the present invention are potent anti-inflammatory glucocorticoids having insignificant or no noteworthy systemic activity even at doses significantly higher than therapeutic doses. Due to non-significant systemic effects, the compounds of the present invention have high therapeutic index for anti-inflammatory activity vs systemic side effects, a property which is highly desirable for therapies using glucocorticoids.

The insignificant or no noteworthy adverse systemic activity of the compounds and compositions of the invention can refer to effects having only a limited duration of adverse systemic effects or to a limited severity of such effects. The duration of any such effects can be, for example, less than about one hour, less than about one day, or less than about one week. The severity can refer to minimal severity, such as an amount of the effect that does not limit the use of the treatment. In some embodiments, minimal or no noteworthy systemic side effects are observed even at multiples of the efficacious dose.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An 11β-hydroxyandrosta-4-ene-3-one compound of formula I, or a physiologically acceptable salt thereof:

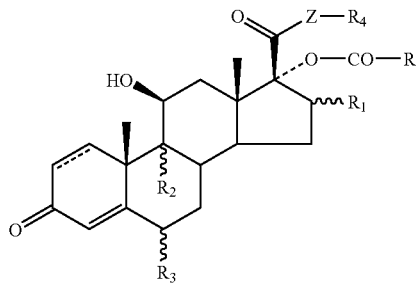

Formula I wherein
------ represents double bond and ∿∿∿ represents α or β-configuration;
Z represents O or S;
$R_1$ represents hydrogen or methyl which may be either in α or β-configuration;
$R_2$ and $R_3$ are the same or different and each independently represents hydrogen, halogen, or methyl;
$R_5$ is independently selected from the group consisting of $(C_1-C_4)$-alkyl, $(C_3-C_6)$-cycloalkyl, —O—$(C_1-C_4)$-alkyl, and a phenyl ring or heterocyclic ring selected from the group consisting of thienyl and furyl, wherein the ring or ring system is unsubstituted or substituted by one or more of halogen, —OH, and $(C_1-C_3)$-alkyl, wherein the alkyl or cycloalkyl groups are optionally substituted by one or more of halogen, $(C_1-C_3)$-alkyl, —O—$(C_1-C_3)$-alkyl, and $(C_3-C_6)$-cycloalkyl;
$R_4$ represents moiety:

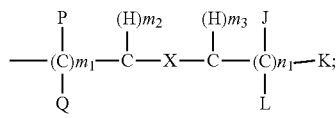

(B)

wherein
$m_1$ is 1;
$m_2$ is 0 or 1;
$m_3$ is 0 or 1;
$n_1$ is 0, 1 or 2;
P and Q are hydrogen;
X represents either a double bond or a triple bond;
J and K are independently selected from the group consisting of hydrogen and $(C_1-C_3)$-alkyl; and
L is selected from the group consisting of halogen, —OH, —O—$(C_1-C_4)$-alkyl, —OCO—$(C_1-C_6)$-alkyl, —OCO—$(C_3-C_{13})$-cycloalkyl, —OCO—CO—O—$(C_1-C_4)$-alkyl, —OCO—O—$(C_1-C_{10})$-alkyl, —OCO—O—$(C_3-C_6)$-cycloalkyl, —OCO—NH—$(C_1-C_4)$-alkyl, —OCO—N—$[(C_1-C_4)$-alkyl$]_2$, and —N—$[(C_1-C_8)$-alkyl$]_2$; wherein
the alkyl or cycloalkyl groups of J, K or L are optionally substituted by one or more of halogen, —OH, $(C_1-C_3)$-alkyl, —O—$(C_1-C_3)$-alkyl, —OCO—$(C_1-C_3)$-alkyl, —COOH, —COO—$(C_1-C_5)$-alkyl, —COO—$(C_1-C_5)$-haloalkyl, —NHCO—$(C_1-C_8)$-alkyl, —ONO$_2$, and $(C_3-C_6)$-cycloalkyl;

J and K are optionally joined together with the carbon atom to which they are attached to represent a $(C_3-C_6)$-cycloalkyl or —CO— group and L is selected from hydroxyl and O$(C_1-C_3)$alkyl; and
J, K and L are absent when $n_1$ is 0.

2. The compound of claim 1 wherein $R_1$ is methyl; $R_2$ is hydrogen, fluoro, or chloro; and $R_3$ is hydrogen or fluoro.

3. The compound of claim 1 wherein $R_5$ is $(C_1-C_4)$-alkyl, $(C_3-C_6)$-cycloalkyl, —O—$(C_1-C_4)$-alkyl, a phenyl ring, a furyl ring, or a thienyl ring, wherein the ring is unsubstituted or substituted by one or more of halogen, $(C_1-C_3)$-alkyl, and —O—$(C_1-C_3)$-alkyl; wherein the alkyl or cycloalkyl groups are optionally substituted by halogen, —OH, $(C_1-C_3)$-alkyl, —O—$(C_1-C_3)$-alkyl, $(C_3-C_6)$-cycloalkyl, or a combination thereof.

4. The compound of claim 1 wherein $R_5$ is methyl, ethyl, propyl, isopropyl, n-butyl, dichloromethyl, cyclopropyl, cyclobutyl, cyclopentyl, cyclohexyl, cyclohexylmethyl, methoxy, ethoxy, methoxymethyl, ethoxymethyl, 2-furyl, 3-furyl, 3-methyl-2-furyl, 2-thienyl, or 5-chloro-2-thienyl.

5. An 11β-hydroxyandrosta-4-ene-3-one compound of formula I-B, or a physiologically acceptable salt thereof:

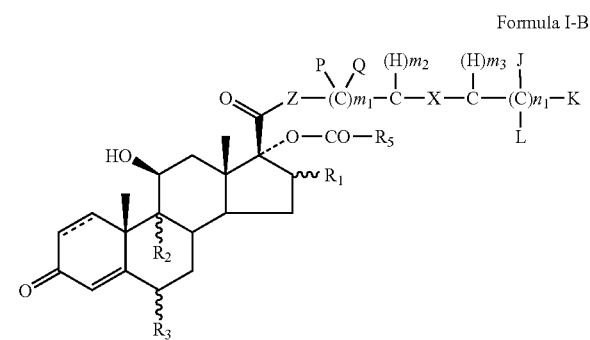

Formula I-B wherein
------ represents double bond and ∿∿∿ represents α or β-configuration;
Z represents O or S;
$R_1$ represents hydrogen or methyl which may be either in α or β-configuration;
$R_2$ and $R_3$ are the same or different and each independently represents hydrogen, halogen, or a methyl group;
$R_5$ is independently selected from the group consisting of $(C_1-C_4)$-alkyl, $(C_3-C_6)$-cycloalkyl, —O—$(C_1-C_4)$-alkyl, and a phenyl ring or heterocyclic ring selected from the group consisting of thienyl and furl, wherein the ring or ring system is unsubstituted or substituted by one or more of halogen, —OH, and $(C_1-C_3)$-alkyl, wherein the alkyl or cycloalkyl groups are optionally substituted by one or more of halogen, $(C_1-C_3)$-alkyl, —O—$(C_1-C_3)$-alkyl, and $(C_3-C_6)$-cycloalkyl;
$m_1$ is 1;
$m_2$ is 0 or 1;
$m_3$ is 0 or 1;
$n_1$ is 0, 1 or 2;
P and Q are hydrogen;
X represents either a double bond or a triple bond;
J and K are independently selected from the group consisting of hydrogen and methyl; and
L is selected from the group consisting of halogen, —OH, —O—$(C_1-C_4)$-alkyl, —OCO—$(C_1-C_6)$-alkyl, —OCO—$(C_3-C_{13})$-cycloalkyl, —OCO—CO—O—$(C_1-C_4)$-alkyl, —OCO—O—$(C_1-C_{10})$-alkyl, —OCO—

O—($C_3$-$C_6$)-cycloalkyl, —OCO—NH—($C_1$-$C_4$)-alkyl, —OCO—N—[($C_1$-$C_4$)-alkyl]$_2$, and —N—[($C_1$-$C_8$)-alkyl]$_2$; wherein the alkyl or cycloalkyl groups of J, K or L are optionally substituted by one or more of halogen, —OH, ($C_1$-$C_3$)-alkyl, —O—($C_1$-$C_3$)-alkyl, —OCO—($C_1$-$C_3$)-alkyl, —COOH, —COO—($C_1$-$C_5$)-alkyl, —COO—($C_1$-$C_5$)-haloalkyl, —NHCO—($C_1$-$C_8$)-alkyl, —ONO$_2$, and ($C_3$-$C_6$)-cycloalkyl;

J and K are optionally joined together with the carbon atom to which they are attached to represent a ($C_3$-$C_6$)-cycloalkyl or —CO— group and L is selected from hydroxyl and methoxy; and J, K and L are absent when n$_1$ is 0.

6. The compound of claim 5, wherein Z represents S.

7. The 11β-Hydroxyandrosta-4-ene-3-one as claimed in claim 1 selected from the group consisting of S-(4-Hydroxy-but-2-ynyl) 6α,9α-difluoro-17α-[(2-furanylcarbonyl)oxy]-11β-hydroxy-16α-methyl-3-oxoandrosta-1,4-diene-17β-carbothioate, S-(4-n-Propylcarbonyloxy-but-2-ynyl) 6α,9α-difluoro-11β-hydroxy-16α-methyl-3-oxo-17α-propionyloxyandrosta-1,4-diene-17β-carbothioate, S-[4-(2-Ethoxy-1,2-dioxoethyl-(E)-but-2-enyl]6α,9α-difluoro-11β-hydroxy-16α-methyl-3-oxo-17α-propionyloxyandrosta-1,4-diene-17β-carbothioate, S-[4-(2-Ethoxy-1,2-dioxoethyl)oxy-(E)-but-2-enyl]6α,9α-difluoro-17α-[(2-furanyl-carbonyl)oxy]-11β-hydroxy-16α-methyl-3-oxoandrosta-1,4-diene-17β-carbothioate, S-[4-n-Propylcarbonyloxy-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(2-Methylpropionyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(2,2-Dimethylpropionyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(2,2-Dimethylpropionyloxy)-but-2-ynyl]6α,9α-difluoro-11β-hydroxy-16α-methyl-3-oxo-17α-propionyloxyandrosta-1,4-diene-17β-carbothioate, S-[4-n-Propylcarbonyloxy-(Z)-but-2-enyl]6α,9α-difluoro-17α-[(2-furanylcarbonyl)oxy]-11β-hydroxy-16α-methyl-3-oxoandrosta-1,4-diene-17β-carbothioate, S-[4-(2-Ethoxy-1,2-dioxoethyl)oxy-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-n-Propylcarbonyloxy-but-2-ynyl]6α,9α-difluoro-11β-hydroxy-16α-methyl-3-oxo-17α-[(2-thienylcarbonyl)oxy]androsta-1,4-diene-17β-carbothioate, S-[(4-Cyclopropylcarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[(4-Cyclobutylcarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[(4-Cyclopentylcarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-n-Propylcarbonyloxy-(E)-but-2-enyl]6α,9α-difluoro-17α-[(2-furanylcarbonyl)oxy]-11β-hydroxy-16α-methyl-3-oxoandrosta-1,4-diene-17β-carbothioate, S-[(4-Methoxycarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[(4-Ethoxycarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(2,2-Dimethylethyloxycarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(2-Methylpropyloxycarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(3-Chloropropylcarbonyloxy)-but-2-ynyl]6α,9α-difluoro-17α-[(2-furanylcarbonyl)-oxy]-11β-hydroxy-16α-methyl-3-oxoandrosta-1,4-diene-17β-carbothioate, S-[4-Dichloroacetoxy-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(2-Methylpropylcarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(3,3-Dimethylpropylcarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-(4-Propionyloxy-but-2-ynyl) 6α,9α-difluoro-17α-[(2-furanylcarbonyl)oxy]-11β-hydroxy-16α-methyl-3-oxoandrosta-1,4-diene-17β-carbothioate, S-[4-(3,3,3-Trifluoropropionyloxy)-but-2-ynyl]6α,9α-difluoro-17α-[(2-furanylcarbonyl)-oxy]-11β-hydroxy-16α-methyl-3-oxoandrosta-1,4-diene-17β-carbothioate, S-[4-(Methoxyacetyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(Ethoxyacetyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-(4-Acetoxy-but-2-ynyl) 6α,9α-difluoro-17α-[(2-furanylcarbonyl)oxy]-11β-hydroxy-16α-methyl-3-oxoandrosta-1,4-diene-17β-carbothioate, S-[4-(2,2-Dimethylbutylcarbonyloxy)-but-2-ynyl]6α,9α-difluoro-17α-[(2-furanylcarbonyl)-oxy]-11β-hydroxy-16α-methyl-3-oxoandrosta-1,4-diene-17β-carbothioate, S-[4-((1S)-Camphanylcarbonyloxy)-but-2-ynyl]6α,9α-difluoro-17α-[(2-furanylcarbonyl)-oxy]-11β-hydroxy-16α-methyl-3-oxoandrosta-1,4-diene-17β-carbothioate, S-[4-(4-Ethoxybutyl-1,4-dione)oxy-but-2-ynyl]6α,9α-difluoro-17α-[(2-furanylcarbonyl)-oxy]-11β-hydroxy-16α-methyl-3-oxoandrosta-1,4-diene-17β-carbothioate, S-[4-(4-Ethyloxy-(Z)-but-2-en-1,4-dione)oxy-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(4-Methoxybutyl-1,4-dione)oxy-but-2-ynyl]6α,9α-difluoro-17α-[(2-furanylcarbonyl)-oxy]-11β-hydroxy-16α-methyl-3-oxoandrosta-1,4-diene-17β-carbothioate, S-[4-(4-Isopropyloxybutyl-1,4-dione)oxy-but-2-ynyl]6α,9α-difluoro-11β-hydroxy-16α-methyl-17α-[(2-furanylcarbonyl)oxy]-3-oxoandrosta-1,4-diene-17β-carbothioate, S-[4-(4-Isobutyloxybutyl-1,4-dione)oxy-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(4-n-Butyloxybutyl-1,4-dione)oxy-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(3-Chloro-2,2-dimethylpropionyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(4-Methoxy-(E)-but-2-en-1,4-dione)oxy-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(3-Methyl-1-oxobutyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(2-Ethyl-1-oxobutyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(N,N-Dimethylaminocarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(2-Chloro-2-methylpropionyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(4-Methyl-1-oxopentyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(2-Hydroxy-2-methylpropionyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(2-Fluoro-2-methylpropionyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(4-Methoxy-(Z)-but-2-en-1,4-dione)oxy-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(4-Ethoxy-(E)-but-2-en-1,4-dione)oxy-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(4-Isobutyloxy-(E)-but-2-en-1,4-dione)oxy-but-2-ynyl]6α,9α-difluoro-17α-[(2-furanylcarbonyl)oxy]-11β-hydroxy-16α-methyl-3-oxoandrosta-1,4-diene-17β-carbothioate, S-(4-Acryloyloxy-but-2-ynyl) 6α,9α-difluoro-17α-[(2-furanylcarbonyl)oxy]-11β-hydroxy-16α-methyl-3-oxoandrosta-1,4-diene-17β-carbothioate, S-[4-(Cyclopentylmethyloxycarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(3-Methylbut-2-enoxycarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(n-Pentyloxycarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(2,2-Dimethyl-3-fluoropropionyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-((S)-2,2-Dimethyl-1,3-dioxolan-4-yl-methoxycarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-[4-(R)-2,2-Dimethyl-1,3-dioxolan-4-yl-methoxycarbonyloxy)-but-2-ynyl]6α,9α-difluoro-17α-[(2-furanyl-carbonyl)oxy]-11β-hydroxy-16α-methyl-3-oxoandrosta-1,4-diene-17β-carbothioate, S-[4-(Isoamyloxycarbonyloxy)-but-2-ynyl]6α,9α-difluoro-17α-[(2-furanylcarbonyl)oxy]-11β-hydroxy-16α-methyl-3-oxoandrosta-1,4-diene-17β-carbothioate, S-(4-Ethoxy-but-2-ynyl)6α,9α-difluoro-17α-[(2-furanyl-carbonyl)oxy]-11β-hydroxy-16α-methyl-3-oxoandrosta-1,4-diene-17β-carbothioate.

8. A pharmaceutical composition comprising a compound of claim 1 and a pharmaceutically acceptable diluent or carrier.

9. A method of inhibiting a glucocorticoid receptor comprising contacting the receptor with an effective inhibitory amount of a compound of claim 1.

10. The method of claim 9 wherein the contacting is in vitro.

11. The method of claim 9 wherein the contacting is in vivo.

12. A method of treating inflammation comprising administering to a mammal in need of such treatment an effective anti-inflammatory amount of a composition of claim 8.

13. The method of claim 12 wherein the treatment comprises topical or parenteral administration of the composition.

14. The method of claim 12 wherein the administering causes insignificant or no adverse systemic effects.

\* \* \* \* \*

UNITED STATES PATENT AND TRADEMARK OFFICE
CERTIFICATE OF CORRECTION

| | |
|---|---|
| PATENT NO. | : 8,785,425 B2 |
| APPLICATION NO. | : 12/180257 |
| DATED | : July 22, 2014 |
| INVENTOR(S) | : Jiten Ranchhodbhai Patel et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1241 days.

Signed and Sealed this
Twenty-fourth Day of November, 2015

Michelle K. Lee
*Director of the United States Patent and Trademark Office*